US012140593B2

(12) United States Patent
Hughes et al.

(10) Patent No.: US 12,140,593 B2
(45) Date of Patent: Nov. 12, 2024

(54) GENETICALLY ENCODED FLUORESCENT SENSORS FOR DETECTING LIGAND BIAS AND INTRACELLULAR SIGNALING THROUGH cAMP PATHWAYS

(71) Applicant: Montana Molecular LLC, Bozeman, MT (US)

(72) Inventors: Thomas E. Hughes, Bozeman, MT (US); Paul H. Tewson, Bozeman, MT (US); Anne Marie Quinn, Bozeman, MT (US)

(73) Assignee: Montana Molecular LLC, Bozeman, MT (US)

( * ) Notice: Subject to any disclaimer, the term of this patent is extended or adjusted under 35 U.S.C. 154(b) by 0 days.

(21) Appl. No.: 17/824,643

(22) Filed: May 25, 2022

(65) Prior Publication Data

US 2022/0404357 A1 Dec. 22, 2022

Related U.S. Application Data

(62) Division of application No. 15/033,147, filed as application No. PCT/US2014/063916 on Nov. 4, 2014, now Pat. No. 11,366,114.

(60) Provisional application No. 61/899,611, filed on Nov. 4, 2013.

(51) Int. Cl.

| | |
|---|---|
| ***G01N 33/566*** | (2006.01) |
| ***C07K 14/00*** | (2006.01) |
| ***G01N 33/542*** | (2006.01) |
| ***G01N 33/58*** | (2006.01) |

(52) U.S. Cl.

CPC ........... *G01N 33/566* (2013.01); *C07K 14/00* (2013.01); *G01N 33/542* (2013.01); *G01N 33/582* (2013.01); *C07K 2319/60* (2013.01)

(58) Field of Classification Search

CPC .. G01N 33/566; G01N 33/542; G01N 33/582; C07K 14/00; C07K 2319/60

See application file for complete search history.

(56) References Cited

U.S. PATENT DOCUMENTS

| | | | |
|---|---|---|---|
| 5,519,163 | A | 5/1996 | Gibbs et al. |
| 6,469,154 | B1 | 10/2002 | Tsien et al. |
| 7,060,793 | B2 | 6/2006 | Tsien et al. |
| 11,366,114 | B2 | 6/2022 | Hughes et al. |
| 2005/0026234 | A1 | 2/2005 | Violin et al. |
| 2007/0111270 | A1 | 5/2007 | Zhang et al. |
| 2007/0172850 | A1 | 7/2007 | Lukyanov et al. |
| 2010/0015701 | A1 | 1/2010 | Lukyanov et al. |
| 2012/0022092 | A1 | 1/2012 | Holland et al. |
| 2012/0034691 | A1 | 2/2012 | Looger et al. |
| 2016/0003854 | A1 | 1/2016 | Hughes et al. |
| 2017/0198364 | A1 | 7/2017 | Hughes et al. |
| 2017/0247769 | A1 | 8/2017 | Ast et al. |

FOREIGN PATENT DOCUMENTS

| | | | |
|---|---|---|---|
| CA | 2286293 | A1 | 10/1998 |
| WO | WO-2006054167 | A2 | 5/2006 |
| WO | WO-2009142735 | A2 | 11/2009 |
| WO | WO-2013138684 | A1 | 9/2013 |

OTHER PUBLICATIONS

UniProt database, Accession No. Q8WZA2, Jun. 2003.

Adachi et al., "A technique for monitoring multiple signals with a combination of prism-based total internal reflection fluorescence microscopy and epifluorescence microscopy," Pflugers Arch—Eur. J. Physiol., 2009, vol. 459, pp. 227-234.

Akerboom et al., "Crystal Structures of the GCaMP Calcium Sensor Reveal the Mechanism of Fluorescence Signal Change and Aid Rational Design," The Journal of Biological Chemistry, 2009, vol. 284(10), pp. 6455-6464.

Akerboom et al., "Optimization of a GCaMP calcium indicator for neural activity imaging," J. Neuroscience, 2012, vol. 32(40), 43 pages.

Alford et al., "A Fluorogenic Red Fluorescent Protein Heterodimer," Chemical Biology, 2012, vol. 19(3), 16 pages.

Alford et al. "Dimerization-Dependent Green and Yellow Fluorescent Proteins," ACS Synthetic Biology, Dec. 2012, vol. 1, No. 12, pp. 569-575 (Abstract Only).

Almholt et al. "Changes in intracellular cAMP reported by a Redistribution@ assay using a cAMP-dependent protein kinase—green fluorescent protein chimera," Cellular Signalling, Aug. 2004, No. 16, No. 8, pp. 907-920 (Abstract Only).

Altschul et al., "Gapped BLAST and PSI-BLAST: a new generation of protein database search programs," Nucleic Acids Research, 1997, vol. 25(17), pp. 3389-3402.

Baird et al., "Circular permutation and receptor insertion within green fluorescent proteins," Proc. Natl. Acad. Sci. USA, 1999, vol. 96, pp. 11241-11246.

Barak et al. "Pharmacological Characterization of Membrane-Expressed Human Trace Amine-Associated Receptor 1 (TAAR1) by a Bioluminescence Resonance Energy Transfer cAMP Biosensor," Molecular Pharmacology, Sep. 2008, vol. 74, No. 3, pp. 585-594.

Barnett et al., "A Fluorescent, Genetically-Encoded Voltage Probe Capable of Resolving Action Potentials," PLOS One, 2012, vol. 7(9), 7 pages.

Berkner et al., "Abundant Expression of Polyomavirus Middle T Antigen and Dihydrofolate Reductase in an Adenovirus Recombinant," J. Virology, 1987, vol. 61(4), pp. 1213-1220.

(Continued)

*Primary Examiner* — Maryam Monshipouri

(74) *Attorney, Agent, or Firm* — Dechert LLP

(57) ABSTRACT

Described herein are novel fluorescent sensors for cyclic adenosine monophosphate (cAMP) that are based on single fluorescent proteins. These sensors use less visible spectrum than FRET-based sensors, produce robust changes in fluorescence, and can be combined with one another, or with other sensors, in a multiplex assay on standard fluorescent plate readers or live cell imaging systems.

17 Claims, 8 Drawing Sheets

Specification includes a Sequence Listing.

(56) References Cited

OTHER PUBLICATIONS

Binkowski et al. "A Luminescent Biosensor with Increased Dynamic Range for Intracellular cAMP." ACS Chemical Biology, Nov. 2011, vol. 6, No. 11, pp. 1193-1197 (Abstract Only).
Carlson et al., "Circularly permuted monomeric red fluorescent proteins with new termini in the ß-sheet," Protein Science, 2010, vol. 19, pp. 1490-1499.
Cifuentes et al., "Proteolytic fragments of phosphoinositide-specific phospholipase C-delta 1. Catalytic and membrane binding properties," Journal of Biological Chemistry, 1993, vol. 268(16), pp. 11586-11593.
Davidson et al., "Overproduction of Polyomavirus Middle T Antigen in Mammalian Cells through the Use of an Adenovirus Vector," Journal of Virology, 1987, vol. 61(4), pp. 1226-1239.
Depry et al., "Multiplexed visualization of dynamic signaling networks using genetically encoded fluorescent protein-based biosensors," Pflugers Arch., 2013, vol. 465(3), 15 pages.
Falkenburger et al., "Kinetics of M1 muscarinic receptor and G protein signaling to phospholipase C in living cells," J. General Physiology, 2010, vol. 135(2), pp. 81-97.
Giorgione et al., "Increased Membrane Affinity of the C1 Domain of Protein Kinase Cd Compensates for the Lack of Involvement of Its C2 Domain in Membrane Recruitment," The Journal of Biological Chemistry, 2006, vol. 281(3), pp. 1660-1669.
Haj-Ahmad et al., "Development of a Helper-Independent Human Adenovirus Vector and Its Use in the Transfer of the Herpes Simplex Virus Thymidine Kinase Gene," J. Virology, 1986, vol. 57(1), pp. 267-274.
Held et al. "Live Cell Imaging of GPCR Dependent Second-Messenger Systems Using the CytationTM 3 Cell Imaging Multi-Mode Reader to Image Genetically Encoded Gpcr Reactive Sensors in Real Time." BioTek Application note, 2014, 8 pages [retrieved from: www.biotek.com/assets/tech_resources/Montana%20Molecular_App_Note.pdf].
Hong et al. "Improved molecular toolkit for cAMP studies in live cells," BMC Research Notes, Jul. 2011, vol. 4, 241, 5 pages.
Jensen et al., "Fluorescence changes reveal kinetic steps of muscarinic receptor-mediated modulation of phosphoinositides and Kv7.2/7.3 K+ channels," J. General Physiology, 2009, vol. 133(4), pp. 347-359.
Jiang et al. "Use of a cAMP BRET sensor to characterize a novel regulation of cAMP by the sphingosine 1-phosphate/G13 pathway." The Journal of Biological Chemistry, Apr. 2007, vol. 282, No. 14, 10576-10584.
Kavran et al., "Specificity and Promiscuity in Phosphoinositide Binding by Pleckstrin Homology Domains," J. Biol. Chem., 1998, vol. 273(46), pp. 30497-30508.
Kenakin et al. "Signalling bias in new drug discovery: detection, quantification and therapeutic impact," Nature Reviews Drug Discovery, Mar. 2013, vol. 12, No. 3, pp. 205-216 (Abstract Only).
Kitaguchi et al. "Extracellular calcium influx activates adenylate cyclase 1 and potentiates insulin secretion in MIN6 cells," Biochemical Journal, Mar. 2013, vol. 450, No. 2, pp. 365-373.
Klarenbeek et al. "A mTurquoise-Based cAMP Sensor for Both Flim and Ratiometric Read-Out Has Improved Dynamic Range," PloS One, Apr. 2011, vol. 6, No. 4, e19170, 6 pages.
Kost et al. "Baculovirus as versatile vectors for protein expression in insect and mammalian cells," Nature Biotechnology, May 2005, vol. 23, No. 5, 567-575 (Abstract Only).
Kredel et al. "Optimized and Far-Red-Emitting Variants of Fluorescent Protein eqFP611," Cell Chemical Biology, Mar. 2008, vol. 15, No. 3, pp. 224-233.
Kyte et al. "A simple method for displaying the hydropathic character of a protein," Journal of Molecular Biology, May 1982, vol. 157, No. 1, pp. 105-132 (Abstract Only).
Lam et al., "Improving FRET dynamic range with bright green and red fluorescent proteins," Nature Methods, 2012, vol. 9(10), 26 pages.
Le Poul et al., "Adaption of Aequorin Functional Assay to High Throughput Screening," Journal of Biomolecular Screening, 2002, vol. 7(1), pp. 57-65.
Ledford "Bioengineers look beyond patents: Synthetic-biology company pushes open-source models," Nature, Jul. 2013, vol. 499, No. 7456, pp. 16-17.
Liu et al., "Biased signaling pathways in ßB-adrenergic receptor characterized by 19F-NMR," Science, 2012, vol. 335(6072), 12 pages.
Massie et al., "Construction of a Helper-Free Recombinant Adenovirus That Expresses Polyomavirus Large T Antigen," Mol. Cell. Biol., 1986, vol. 6(8), pp. 2872-2883.
Nagai et al., "Circularly permuted green fluorescent proteins engineered to sense Ca.SUP.2.+," Proceedings of the National Academy of Sciences, 2001, vol. 98(6), pp. 3197-3202.
Nakai et al., "A high signal-to-noise Ca.SUP.2.+ probe composed of a single green fluorescent protein," Nature Biotechnology, 2001, vol. 19, pp. 137-141.
Nausch et al., "Differential patterning of cGMP in vascular smooth muscle cells revealed by single GFP-linked biosensors," Proceedings of the National Academy of Sciences, 2008, vol. 105(1), pp. 365-370.
Ni et al., "Signaling Diversity of PKA Achieved Via a Ca2+-cAMP-PKA Oscillatory Circuit," Nature Chemical Biology, 2011, vol. 7(1), 15 pages.
Oancea et al., "Green Fluorescent Protein (GFP)-tagged Cysteine-rich Domains from Protein Kinase C as Fluorescent Indicators for Diacylglycerol Signaling in Living Cells," The Journal of Cell Biology, 1998, vol. 140(3), pp. 485-498.
Okumoto et al., "Quantitative Imaging with Fluorescent Biosensors," Annu. Rev. Plant Biol., 2012, vo. 63, pp. 663-706.
Palmer et al., "Design and application of genetically encoded biosensors," Trends in Biotechnology, 2011, vol. 29(3), 18 pages.
Pletnev et al., "A Crystallographic Study of Bright Far-Red Fluorescent Protein mKate Reveals pH-induced cis-trans Isomerization of the Chromophore," The Journal of Biological Chemistry, 2008, vol. 283(43), pp. 28980-28987.
Ponsioen et al. "Detecting cAMP-induced Epac activation by fluorescence resonance energy transfer: Epac as a novel cAMP indicator," EMBO Reports, Dec. 2004, vol. 5, No. 12, pp. 1176-1180.
Prinz et al. "Novel, isotype-specific sensors for protein kinase a subunit interaction based on bioluminescence resonance energy transfer (BRET)." Cellular Signalling, Oct. 2006, vol. 18, No. 10, pp. 1616-1625 (Abstract Only).
Raehal et al., "Morphine Side Effects in ß-Arrestin 2 Knockout Mice," The Journal of Pharmacology and Experimental Therapeutics, 2005, vol. 314(3), pp. 1195-1201.
Rajagopal et al., "Quantifying Ligand Bias at Seven-Transmembrane Receptors," Molecular Pharmacology, 2011, vol. 80(3), 28 pages.
Rajagopal et al., "Teaching old receptors new tricks: biasing seven-transmembrane receptors," Nature Reviews Drug Discovery, 2010, vol. 9(5), pp. 373-386.
Rehmann et al. "Structure of Epac2 in complex with a cyclic AMP analogue and RAP1B," Nature, Sep. 2008, vol. 455, No. 7209, pp. 124-127 (Abstract Only).
Rehmann et al. "Structure of the cyclic-AMP-responsive exchange factor Epac2 in its auto-inhibited state," Nature, Feb. 2006, vol. 439, No. 7076, pp. 625-628 (Abstract Only).
Salonikidis et al. "An Ion-insensitive cAMP Biosensor for Long Term Quantitative Ratiometric Fluorescence Resonance Energy Transfer (FRET) Measurements under Variable Physiological Conditions," Journal of Biological Chemistry, Jul. 2011, vol. 286, No. 26, pp. 23419-23431.
Schroeder et al., "FLIPR: A New Instrument for Accurate, High Throughput Optical Screening," Journal of Biomolecular Screening, 1996, vol. 1(2), pp. 75-80.
Shaner et al. "A guide to choosing fluorescent proteins," Nature Methods, Dec. 2005, vol. 2, No. 12, pp. 905-909.
Shaner et al. "Improving the photostability of bright monomeric orange and red fluorescent proteins," Nature Methods, Jun. 2008, vol. 5, No. 6, pp. 545-551 (Abstract Only).

(56) References Cited

OTHER PUBLICATIONS

Shaner et al. "A bright monomeric green fluorescent protein derived from Branchiostoma lanceolatum," Nature Methods, May 2013, vol. 10, No. 5, pp. 407-409 (Abstract Only).
Shaw et al., "Preferential transformation of human neuronal cells by human adenoviruses and the origin of HEK 293 cells," The FASEB Journal, 2002, vol. 16, pp. 869-871.
Shcherbo et al. "Practical and reliable FRET/FLIM pair of fluorescent proteins," BMC Biotechnology, Mar. 2009, vol. 9, 24, 6 pages.
Shui et al., "Circular Permutation of Red Fluorescent Proteins," PLoS One, 2011, vol. 6(5), e20505, 9 pages.
Subach et al. "Conversion of Red Fluorescent Protein into a Bright Blue Probe," Chemistry & Biology, Oct. 2008, vol. 15, No. 10, pp. 1116-1124.
Szymczak et al., "Correction of multi-gene deficiency in vivo using a single 'self-cleaving' 2A peptide-based retroviral vector," Nature Biotechnology, 2004, vol. 22(5), pp. 589-594.
Tewson et al., "Simultaneous Detection of Ca.SUP.2.+ and Diacylglycerol Signaling in Living Cells," PLoS One, 2012, vol. 7(8), e42791, 6 pages.
Topell et al. "Circularly permuted variants of the green fluorescent protein," FEBS Letters, Aug. 1999, vol. 457, No. 2, pp. 283-289.
Tsutsui et al. "Improving membrane voltage measurements using FRET with new fluorescent proteins," Nature Methods, Aug. 2008, vol. 5, No. 8,683-685 (Abstract Only).
Van Der Wal et al., "Monitoring Agonist-induced Phospholipase C Activation in Live Cells by Fluorescence Resonance Energy Transfer," The Journal of Biological Chemistry, 2001, vol. 276(18), pp. 15337-15344.
White et al., "Characterization of a Ca.SUP.2.+ Response to Both UTP and ATP at Human P2Y11 Receptors: Evidence for Agonist-Specific Signaling," Molecular Pharmacology, 2003, vol. 63(6), pp. 1356-1363.
Willoughby et al. "Live-cell imaging of cAMP dynamics," Nature Methods, Jan. 2008, vol. 5, No. 1, 29-36 (Abstract Only).
Woehler et al. "Signal/Noise Analysis of FRET-Based Sensors," Biophysical Journal, Oct. 2010, vol. 99, No. 7, pp. 2344-2354.
Xu et al. "A bioluminescence resonance energy transfer (BRET system: application to interacting circadian clock proteins," Proc. Natl. Acad. Sci. U.S.A., Jan. 1999, vol. 96, No. 1, pp. 151-156.
Zaccolo et al. "A genetically encoded, fluorescent indicator for cyclic AMP in living cells," Nature Cell Biology, Jan. 2000, vol. 2, No. 1, pp. 25-29 (Abstract Only).
Zaccolo et al. "Discrete microdomains with high concentration of cAMP in stimulated rat neonatal cardiac myocytes," Science, Mar. 2002, vol. 295, No. 5560, pp. 1711-1715 (Abstract Only).
Zhang et al. "Generation and identification of recombinant adenovirus by liposome-mediated transfection and PCR analysis," Biotechniques, Nov. 1993, vol. 15, No. 5, pp. 868-872 (Abstract Only).
Zhang et al., "A Sample Statistical Parameter for Use in Evaluation and Validation of High Throughput Screening Assays," Journal of Biomolecular Screening, 1999, vol. 4(2), pp. 67-73.
Zhang et al. "Genetically encoded reporters of protein kinase a activity reveal impact of substrate tethering," Proceedings of the National Academy of Sciences, Dec. 2001, vol. 98, No. 26, pp. 14997-15002.
Zhao et al., "An Expanded Palette of Genetically Encoded Ca.SUP. 2.+ Indicators," Science, 2011, vol. 333(6051), pp. 9 pages.
International Search Report and Written Opinion for International (PCT) Patent Application No. PCT/US14/63916, dated Apr. 15, 2015 14 pages.
International Preliminary Report on Patentability for International (PCT) Patent Application No. PCT/US2014/63916, dated May 19, 2016 10 pages.
Burns et al., "Protein Kinase C Contains Two Phorbol Ester Binding Domains," J. Biol. Chem., 1991, vol. 266(27), pp. 18330-18337.
Dries et al., "A Single Residue in the C1 Domain Sensitizes Novel Protein Kinase C Isoforms to Cellular Diacylglycerol Production," J. Biol. Chem., 2007, vol. 282(2), pp. 826-830.
Hurley et al., "Taxonomy and function of C1 protein kinase C homology domains," Protein Sci., 1997, vol. 6, pp. 477-480.
Nikolaev et al. "Novel Single Chain cAMP Sensors for Receptor-induced Signal Propagation," The Journal of Biological Chemistry, Sep. 2004, vol. 279, No. 36, pp. 37215-37218.
Extended Search Report for European Patent Application No. 14858784.3, dated Jun. 22, 2017 10 pages.
Official Action for European Patent Application No. 14858784.3, dated May 2, 2018 6 pages.
Official Action for European Patent Application No. 14858784.3, dated Mar. 29, 2019 5 pages.
Official Action for Canada Patent Application No. 2,929,392, dated Sep. 17, 2020 5 pages.
Extended Search Report for European Patent Application No. 20175471.0, dated Sep. 30, 2020 11 pages.
Alford, S. C., Ding, Y., Simmen, T., and Campbell, R. E. (2012b). Dimerization-Dependent Green and Yellow Fluorescent Proteins. ACS Synth. Biol. Dec. 2012, vol. 1, No. 12, pp. 569-575.
Almholt, K., Tullin, S., Skyggebjerg, O., and Scudder, K. (2004). Changes in intracellular cAMP reported by a Redistribution.RTM. assay using a cAMP-dependent protein kinase—green fluorescent protein chimera. Cellular Signalling, Aug. 2004, 16(8), 907-920.
Binkowski, B. F., Butler, B. L., Stecha, P. F., Eggers, C. T., Otto, P., Zimmerman, K., Vidugiris, G., Wood, M. G., Encell, L. P., Fan, F., et al. (2011). A Luminescent Biosensor with Increased Dynamic Range for Intracellular cAMP. ACS Chem. Biol. Nov. 2011, vol. 6, No. 11, pp. 1193-1197.
Kenakin, T., and Christopoulos, A. (2013). Signalling bias in new drug discovery: detection, quantification and therapeutic impact. Nat Rev Drug Discov, Mar. 2013, vol. 12, No. 3, pp. 205-216.
Kost, T. A., Condreay, J. P., and Jarvis, D. L. (2005). Baculovirus as versatile vectors for protein expression in insect and mammalian cells. Nature Biotechnology, May 2005, vol. 23, No. 5, 567-575.
Kyte, J., and Doolittle, R. F. (1982). A simple method for displaying the hydropathic character of a protein. Journal of Molecular Biology, May 1982, vol. 157, No. 1, pp. 105-132.
Nikolaev, V. O., B, M., and Imoto, K. (2001). A high signal-to-noise Ca(2+) probe composed of a single green fluorescent protein. Nature Biotechnology 19(2), 137-141, Feb. 19, 2001.
Prinz, A., Diskar, M., Erlbruch, A., and Herberg, F. W. (2006). Novel, isotype-specific sensors for protein kinase A subunit interaction based on bioluminescence resonance energy transfer (BRET). Cell. Signal. vol. 18, No. 10, pp. 1616-1625.
Rehmann, H., Arias-Palomo, E., Hadders, M. A., and Schwede, F. (2008). Structure of Epac2 in complex with a cyclic AMP analogue and RAP1B. Nature, Sep. 2008, vol. 455, No. 7209, pp. 124-127.
Rehmann, H., Das, J., Knipscheer, P., and Wittinghofer, A. (2006). Structure of the cyclic-AMP-responsive exchange factor Epac2 in its auto-inhibited state. Nature, Feb. 2006, vol. 439, No. 7076, pp. 625-628.
Selvaratnam et al., PLoS One, 7(11): e48707 (Nov. 2012).
Shaner, N.C., Lin, M. Z., Mckeown, M. R., Steinbach, P. A., Hazelwood, K. L., Davidson, M. W., and Tsien, R. Y. (2008). Improving the photostability of bright monomeric orange and red fluorescent proteins. Nature Methods, vol. 5, No. 6, pp. 545-551.
Shaner, N.C., Lambert, G. G., Chammas, A., Ni, Y., Cranfill, P. J., Baird, M. A., Sell, B. R., Allen, J. R., Day, R. N., Israelsson, M., et al. (2013). A bright monomeric green fluorescent protein derived from Branchiostoma lanceolatum. Nat Meth 10 (5), 407-409.
Tsalkova et al., JBC 284(35): 23644-23651 (Aug. 28, 2009).
Tsutsui, H., Karasawa, S., Okamura, Y., and Miyawaki, A. (2008). Improving membrane voltage measurements using FRET with new fluorescent proteins. Nature Methods 5(8), 683-685.
Willoughby, D., and Cooper, D. (2007). Live-cell imaging of cAMP dynamics. Nature Methods 5(1), 29-36.
Zaccolo, M., De Giorgi, F., Cho, C. Y., Feng, L., Knapp, T., Negulescu, P. A., Taylor, S. S., Tsien, R. Y., and Pozzan, T. (2000). A genetically encoded, fluorescent indicator for cyclic AMP in living cells. Nat. Cell Biol. 2(1), 25-29.
Zaccolo, M., and Pozzan, T. (2002). Discrete microdomains with high concentration of cAMP in stimulated rat neonatal cardiac myocytes. Science, 296(5560): 1711-1715.

(56) References Cited

OTHER PUBLICATIONS

Zhang, J., Ma, Y., Taylor, S. S., and Tsien, R. Y. Genetically encoded reporters of protein kinase A activity reveal impact of substrate tethering. Proceedings of the National Academy of Sciences, Dec. 2001, vol. 98, No. 26, pp. 14997-15002.

GENETICALLY ENCODED FLUORESCENT SENSORS FOR DETECTING LIGAND BIAS AND INTRACELLULAR SIGNALING THROUGH cAMP PATHWAYS

CROSS-REFERENCE TO RELATED APPLICATIONS

This application is a divisional of U.S. patent application Ser. No. 15/033,147, filed Apr. 29, 2016, which is a § 371 National Phase of International Patent Application No. PCT/US2014/063916, filed Nov. 4, 2014, which claims the benefit of priority to U.S. Provisional Patent Application No. 61/899,611, filed Nov. 4, 2013, each of which is incorporated herein by reference.

GOVERNMENT SUPPORT

This invention was made with government support under NSF SBIR Phase I proposal 1248138. The government has certain rights under this invention.

REFERENCE TO SEQUENCE LISTING

This application contains a Sequence Listing submitted as an electronic text file named "6666-3-PCT_Sequence Listing_ST25.txt", having a size in bytes of 520 KB, and created on Nov. 4, 2014. The information contained in this electronic file is hereby incorporated by reference in its entirety pursuant to 37 CFR § 1.52(e)(5).

FIELD OF THE INVENTION

The field of the present invention is design and construction of fluorescent biological sensors for detection and measurement of intracellular analytes.

BACKGROUND OF THE INVENTION

For over a decade, several attempts have been made to create genetically encoded, fluorescent biosensors that can detect changes in cAMP and report these changes through alterations in fluorescence. Despite strenuous efforts, involving many different design strategies, over the course of more than fifteen years, these earlier attempts at cAMP sensors have not produced signals that are robust and/or reproducible enough for live cell assay on standard, automated fluorescence plate readers. Automated detection of cAMP is of considerable importance because cAMP is an essential signaling component of many drug targets, most notably, G-protein coupled receptors. As background to this invention, a summary of the various design strategies that are known in the art (FRET, Redistribution, BRET and Fluorescent Protein Complementation) are described in the following sections.

Fluorescence Resonance Energy Transfer (FRET)

Zaccolo and colleagues (Zaccolo, M., De Giorgi, F., Cho, C. Y., Feng, L., Knapp, T., Negulescu, P. A., Taylor, S. S., Tsien, R. Y., and Pozzan, T. (2000)). A genetically encoded, fluorescent indicator for cyclic AMP in living cells. Nat. Cell Biol. 2, 25 As baTnitially described a cAMP biosensor in which changes in the distance and orientation between the regulatory and catalytic subunits of Protein Kinase A (PKA) could be detected through changes in the fluorescence energy transfer (FRET) between a donor and acceptor fluorescent protein. When cAMP rises in the cell, the regulatory subunit changes conformation and dissociates from the catalytic subunit. This dissociation increases the distance between the donor and acceptor pair of fluorescent proteins and lowers the fluorescence energy transfer efficiency, which can be detected as a change in the ratio of donor and acceptor emission. The initial sensor was created using a blue and green pair of fluorescent proteins, but other proteins with more favorable characteristics have been used since then including cyan and yellow (Zaccolo & Pozzan, 2002: Zhang et al., 2001).

Similar FRET-based biosensors, where donor and acceptor fluorescent proteins were fused to the regulatory and catalytic subunits of an Epac protein were reported simultaneously by three different groups over a decade ago (Reviewed in Willoughby and Cooper, 2007). Epac, unlike PKA, is a single protein composed of a large regulatory subunit tethered by a hinge region to the catalytic subunit. Donor or acceptor fluorescent proteins fused to the N terminus of Epac are effectively joined to the regulatory subunit, while fluorescent proteins fused to the C-terminus of Epac arc connected to the catalytic subunit. When cAMP binds to the regulatory subunit, a conformational change occurs and the regulatory subunit swings away from the catalytic subunit, thereby freeing it to interact with its substrates. This dissociation of the two subunits produces a modest change in FRET. These FRET-based sensors were initially produced using the cyan and yellow fluorescent proteins (DiPilato et.al. 2004, Ponsioen et al., 2004 & Nikolaev, et.al. 2004), but a variety of other suitable pairs have been used in similar designs including GFP and mCherry (Hong et al., 2011), eCFP and mTurquoise (Klarenbeek et al., 2011) cerulean and citrine (Salonikidis et al., 2011).

While FRET based biosensors have the advantage of ratio metric measurements in living cells, there are disadvantages as well. The donor and acceptor fluorescent proteins use much of the visible spectrum, so they are difficult to combine with other sensors for multiplex measurements, thereby limiting the sensoratio metric measurements in living cells, there are disadvantages as well. The donor and acceptor fluorescent proteins use much of the visible spectrum, so they are difficult to combine with other signal to noise ratios (Woehler et al., 2010) that are only detectable with sophisticated research microscopes in limited applications.

Redistribution

The dissociation of the activated PKA subunits causes a redistribution of the catalytic subunit as it diffuses through the cell. This movement can be detected in an imaging microscope if a fluorescent protein is fused to the catalytic subunit. Activation of the PKA causes the fluorescence to move from small aggregates to a much more diffuse cytosolic labeling (Almholt, 2004). This assay requires sophisticated image analysis and instrumentation for detection and is incompatible with high throughput live cell assay. This method is also described in (patent publication number CA2286293 C).

BRET

Bioluminescence is similar to FRET in that it involves energy transfer from an enzyme and an acceptor fluorescent protein, a process that is sensitive to the distance between the two components (Xu et al., 1999). Accordingly, PKA based sensors have been created by replacing a donor fluorescent protein with a Renilla luciferase (Prinz et al., 2006; Binkowski et al., 2011; see also WO2009142735 A3). A similar strategy was used to create a BRET based Epac sensor in which the energy transfer occurs between the Renilla Luciferase and a YFP (Jiang et al., 2007).

Protein Complementation.

Protein complementation refers to the reconstitution of fluorescence by bringing together fragments of a fluorescent protein (Gosh et al., 2000; Magliery et al., 2005; Cabantous, 2005; Kerppola, 2006, Chu et al., 2009) or pairs of fluorescent proteins whose fluorescent properties depend upon a very specific dimerization (Alford, S. C., Abdelfattah, A. S., Ding, Y., and Campbell, R. E. (2012a). A Fluorogenic Red Fluorescent Protein Heterodimer. Chem. Biol. 19, 353ementation refers to the reconstitution of fluorescence by bringing together fragments of a fluorescent protein (Gosh et al., 2000; Magliery et al., 2005; Cabantous, 2005; Kerppola, 2006, Chu et al., 2009) or pairs of fluorescent proependent fluorescent proteins can replace FRET or BRET pairs of fluorescent proteins to create analogous sensors. In the case of complementing fragments, two portions of the yellow fluorescent protein were fused to either end of a cAMP binding domain taken from the regulatory region of Epac (Kitaguchi et.al., 2013). In this sensor, cAMP binding causes a conformational change that disrupts the interactions of the complementing fragments, producing a decrease in fluorescence. In the case of dimerization dependent fluorescent proteins, the two different fluorescent proteins replace the FRET pairs typically used in PKA sensors to produce a sensor in which the dimerization dependent fluorescence decreases when the regulatory and catalytic subunits dissociate (Held et al., 2014).

A Different cAMP Sensor Design is Robust with Unprecedented Signal to Noise.

To date, the strategies for creating cAMP biosensors have involved placing fluorescent proteins, fluorescent protein fragments, and luciferases at the ends of cAMP binding proteins and subunits. Changes in the conformations of the cAMP binding proteins generate fluorescent signals as subunits dissociate from one another. The present invention describes how a more robust sensor can be created by inserting a single, circularly permuted fluorescent protein into the hinge region of Epac, a cAMP-regulated enzyme. The Epac hinge region connects the cAMP-binding, regulatory region with the catalytic region. Without wishing to be bound by theory, the large relative movements of the two regions can produce a change in the environmentally sensitive, circularly permuted fluorescent protein positioned in or near the interconnecting hinge Rehmann et al., 2006; 2008). In contrast to the prior art described above, the distance between the N- and C-termini of the Epac protein is irrelevant to producing the signal. Similarly, a single fluorescent protein inserted into a synthetic hinge between the catalytic region of Epac and its substrate, RAP1B (Rehmann et al., 2008), produces a fluorescent signal that is dependent upon movements of these regions. The large relative movements of the two subunits or proteins produce robust changes in the fluorescent protein which are either increases or decreases in fluorescence intensity.

SUMMARY OF THE INVENTION

The present disclosure provides cAMP sensor proteins comprising a first polypeptide linked to a single fluorescent protein. Within these cAMP sensor proteins, the first polypeptide comprises a cAMP-binding domain and the single fluorescent protein consists of an uninterrupted amino acid sequence. The binding of cAMP to the cAMP-binding site of these cAMP sensor proteins alters the level of fluorescence from the fluorescent protein.

In certain embodiments, the fluorescent protein comprises at least a portion of a protein selected from GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and synthetic non-Aequorea fluorescent proteins, which may include green fluorescent proteins.

In certain embodiments, the fluorescent protein comprises an amino acid sequence at least about 70%, or at least about 75%, or at least about 80%, or at least about 85%, or at least about 90%, or at least about 95% identical, or at least about 96% identical, or at least about 97% identical, or at least about 98% identical, or at least about 99% identical to a protein selected from GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein.

In certain embodiments, the first polypeptide comprises at least 100 contiguous amino acids from a sequence selected from SEQ ID NO:35, SEQ TD NO:74, SEQ TD NO:75 and SEQ ID NO:76. In related embodiments, the first polypeptide comprises an amino acid sequence at least 90% identical to a sequence selected from the group consisting of SEQ ID NO:35, SEQ ID NO:74, SEQ ID NO:75 and SEQ ID NO:76.

In certain embodiments, the cAMP sensor protein includes a linker between the first polypeptide and the fluorescent protein, or portion thereof.

In certain embodiments, the cAMP sensor protein comprises an amino acid sequence at least 90% identical to at least one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ TD NO:10, SEQ ID NO:11, SEQ ID NO:12, SEQ TD NO:13, SEQ TD NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33.

In certain embodiments, the cAMP sensor protein includes a second polypeptide, wherein the second polypeptide is linked to the fluorescent protein, or portion thereof, such that the fluorescent protein is flanked by the first and second polypeptides. In specific embodiments, the amino acid sequence of the first polypeptide and the amino acid sequence of the second polypeptide are from different proteins. In other embodiments, the amino acid sequence of the first polypeptide and the amino acid sequence of the second polypeptide are from the same protein. In specific embodiments, the first and/or second polypeptide comprises an amino acid sequence from a protein selected from the group consisting of Epac1, Epac2, protein kinase A and RAP1b. In specific embodiments, the first and/or second polypeptide comprises an amino acid sequence at least 90% identical to a sequence selected from the group consisting of SEQ ID NO:35, SEQ ID NO:74, SEQ ID NO:75 and SEQ TD NO:76. In related embodiments, the first and second polypeptides are capable of interacting.

In certain embodiments, the sensor includes a first linker sequence between the fluorescent protein, or portion thereof, and the first or second polypeptide. In related embodiments, the sensor includes a first linker sequence between the first polypeptide and the fluorescent protein, or portion thereof, and a second linker sequence between the second polypeptide and the fluorescent protein, or portion thereof.

In certain embodiments, the fluorescent protein is circularly permuted.

In certain embodiments, the cAMP sensor protein comprises at least one amino acid sequence that is at least 70%, at least 80%, at least 85%, at least 90%, at least 95%, at least 97% or at least 99% identical to a sequence selected from SEQ ID NO:1, SEQ ID NO:2, SEQ ID NO:3, and SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33.

Another aspect of the disclosure provides nucleic acid sequences encoding these sensor proteins. Certain embodiments include a nucleic acid sequence encoding a cAMP sensor protein which includes a first polypeptide linked to a single fluorescent protein, wherein the encoded first polypeptide comprises a cAMP-binding domain and the encoded single fluorescent protein consists of an uninterrupted amino acid sequence and wherein binding of cAMP to the cAMP-binding site of the encoded protein alters a level of fluorescence from the fluorescent protein.

In certain embodiments, a cAMP sensor protein of the present invention is encoded by a nucleic acid molecule comprising a nucleic acid sequence at least 70%, at least 80%, at least 85%, at least 90%, at least 95%, at least 97% or at least 99% identical to a sequence selected from the group consisting of SEQ TD NO:41, SEQ TD NO:42, SEQ TD NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73. In related embodiments, a cAMP sensor protein of the present invention is encoded by a nucleic acid molecule comprising a nucleic acid sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73.

In related embodiments, the nucleic acid sequences encode a cAMP sensor protein in which a second polypeptide is linked to the fluorescent protein, or portion thereof, such that the fluorescent protein is flanked by the first and second polypeptides.

One aspect of the present invention is a method to detect changes in the intracellular level of cAMP, comprising expressing a cAMP sensor protein of the present invention in a cell, and detecting changes in the level of fluorescence from the sensor. In a related embodiment, the cell is treated with a compound (e.g., drug) to determine the effect of the compound on cAMP levels.

DETAILED DESCRIPTION OF THE INVENTION

Figure 1:
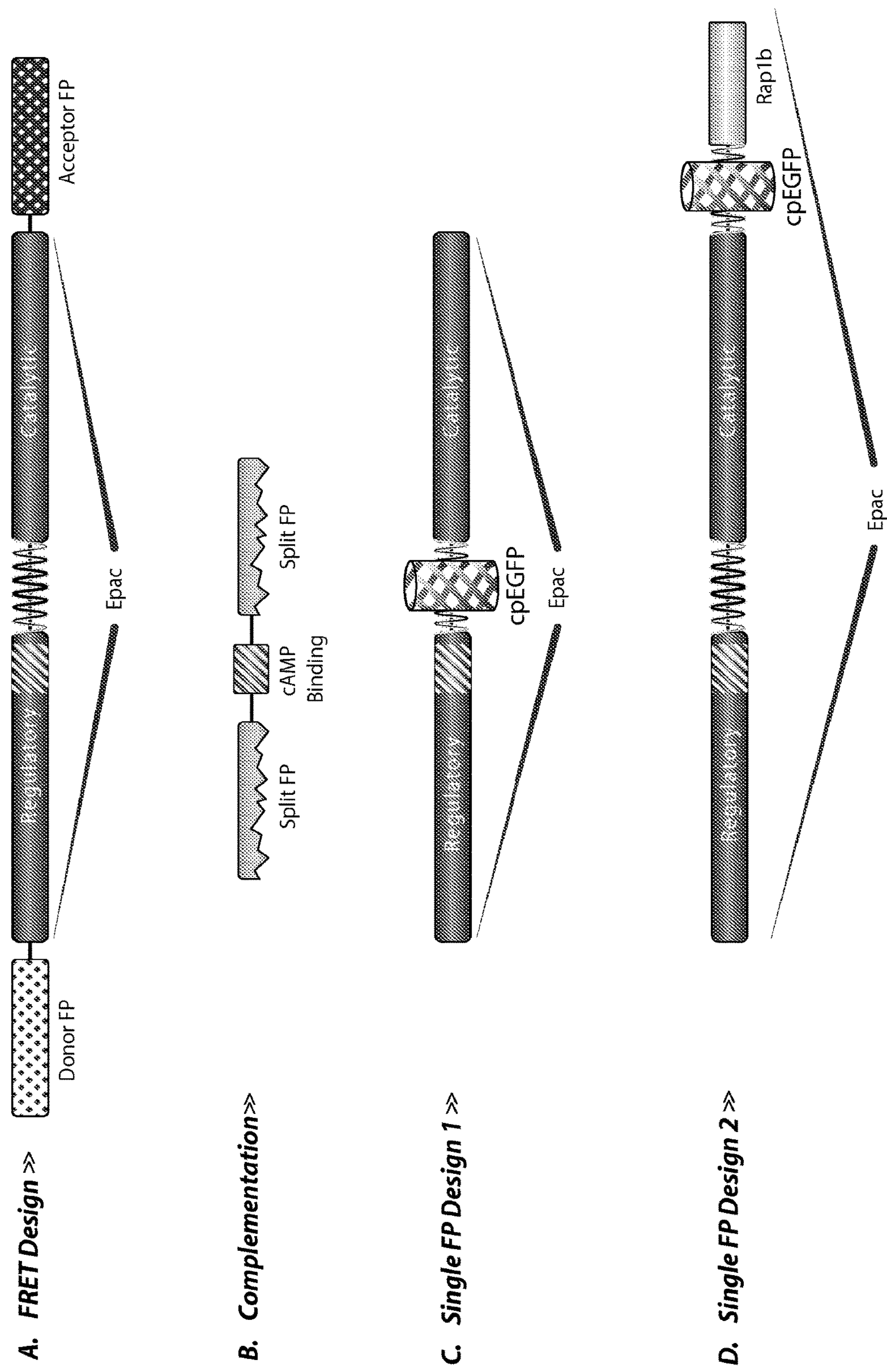
FIG. 1 Various designs for genetically-encoded cAMP sensors. (A) Forster Resonance Energy Transfer (FRET) design; (B) Complementation design; (C) Single FP design 1 of present invention (fluorescent protein flanked by sequences from same protein); (D) Single FP design 2 of present invention (fluorescent protein flanked by sequences from different protein).
Figure 2:
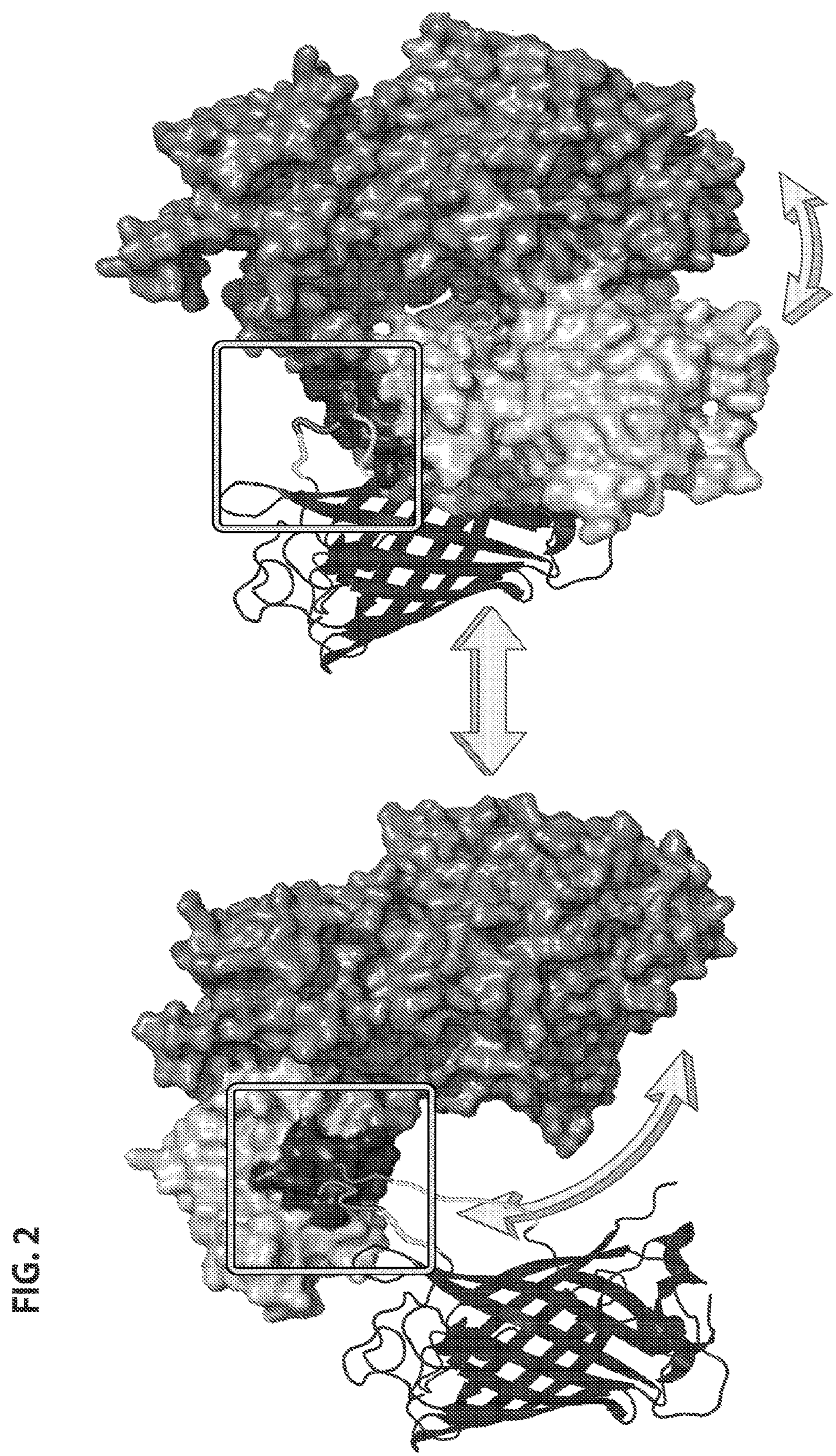
FIG. 2 Space filling model showing the approximate structure of an embodiment of the invention in both the cAMP unbound (left) and bound (right) states.

The present invention is directed to novel fluorescent sensors for the detection of cyclic adenosine monophosphate (cAMP), a second messenger of cell signaling. Described herein is the design and construction of novel, protein-based sensors that specifically detect cAMP, provide robust fluorescence signals in live cells, and can be used in live cell assays on standard fluorescent plate readers or live cell imaging systems. Combined with other sensors, such as a diacylglycerol (DAG) or a phosphatidylinositol 4,5-bisphosphate (PIP2) sensor made from a fluorescent protein with different excitation and emission spectra, such multiplex assays can detect whether the G protein pathways Gq, Gs, and Gi are activated individually or simultaneously.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms “a,” “an,” and “the” include plural referents unless the context clearly dictates otherwise. For example, a nucleic acid molecule refers to one or more nucleic acid molecules. As such, the terms “a”, “an”, “one or more” and “at least one” can be used interchangeably. Similarly the terms “comprising”, “including” and “having” can be used interchangeably. It is further noted that the claims may be drafted to exclude any optional element. As such, this statement is intended to serve as antecedent basis for use of such exclusive terminology as “solely,” “only”, “single” and the like in connection with the recitation of claim elements, or use of a “negative” limitation.

A novel cAMP sensor protein of the present invention can generally be produced by linking a protein comprising a cAMP-binding domain to a single fluorescent protein in such a way that the level of fluorescence emitted by the single fluorescent protein is dependent on the level of cAMP in the environment. Such proteins can be referred to as cAMP sensor proteins or simply as cAMP sensors. Thus, one embodiment of the present invention is a cAMP sensor protein comprising a first polypeptide linked to a single fluorescent protein, wherein the first polypeptide comprises a cAMP-binding domain, wherein the single fluorescent protein consists of an uninterrupted amino acid sequence, and wherein the fluorescence of the cAMP sensor changes upon binding cAMP.

As used herein, reference to a protein (or polypeptide) includes full-length proteins, fusion proteins, or any fragment, domain, conformational epitope, or homolog of such proteins. For example, an Epac protein refers o a full-length Epac protein as well as fragments, domains, conformational epitopes or homologs thereof. Any proteins or polypeptides can be used to construct cAMP sensors of the present invention as long as they have the characteristics and activities disclosed herein.

According to the present disclosure, any polypeptide can be used as the first polypeptide as long as that polypeptide is capable of comprising a cAMP-binding domain and as long as binding of cAMP to the resulting sensor protein construct causes a change in fluorescence of the cAMP sensor. First polypeptides used to construct sensors of the present invention comprise an amino acid sequence from a protein that may or may not naturally comprise a cAMP-binding domain. A protein that naturally comprises a cAMP-binding domain refers to a protein that has a cAMP-binding domain, as isolated from nature (i.e., not engineered by the hand of man). Thus, in one embodiment, the first polypeptide comprises an amino acid sequence from a protein that naturally comprises a cAMP-binding domain. Examples of such proteins are known to those skilled in the art and include, but are not limited to, Epac1, Epac2 and protein kinase A (PKA). AAS used herein, PKA (protein kinase A) refers to the cAMP-binding subunit of PKA (i.e., the regulatory subunit) Thus, in one embodiment the first polypeptide comprises an amino acid sequence from a protein selected from the group consisting of Epac1, Epac2 and protein kinase A (PKA). In one embodiment, the first polypeptide comprises at least 50 contiguous amino acids, at least 100 contiguous amino acids, at least 150 contiguous amino acids, at least 200 contiguous amino acids, or at least 250 contiguous amino acids from a PKA protein. In one embodiment, the first polypeptide comprises at least 50 contiguous amino acids, at least 100 contiguous amino acids, at least 150 contiguous amino acids, at least 200 contiguous amino acids, or at least 250 contiguous amino acids from SEQ ID NO:75. In one embodiment, the first polypeptide comprises at least 200 contiguous amino acids, at least 300 contiguous amino acids, at least 400 contiguous amino acids, at least 500 contiguous amino acids or at least 600 contiguous amino acids from an Epac1 or Epac2 protein. In one embodiment, the first polypeptide comprises at least 200 contiguous amino acids, at least 300 contiguous amino acids, at least 400 contiguous amino acids, at least 500 contiguous amino acids or at least 600 contiguous amino acids from SEQ ID NO:74 or SEQ ID NO:35. In one embodiment the first polypeptide comprises the amino acid sequence of a protein selected from the group consisting of Epac1, Epac2 and protein kinase A (PKA). In one embodiment the first polypeptide comprises an amino acid sequence selected from the group consisting of SEQ ID NO:75, SEQ ID NO:74 and SEQ ID NO:35.

Alternatively, the first polypeptide can comprise an amino acid sequence from a protein that does not naturally contain a cAMP-binding domain, as long as a cAMP-binding domain can be inserted into the first polypeptide and binding of cAMP to the cAMP sensor protein results in a change in fluorescene.

Before proceeding further, it should be appreciated that while exemplary amino acid and nucleic acid sequences useful for constructing cAMP sensors of the present invention are disclosed herein, variants (or homologs) of such sequences may also be used, as long as the variant sequences can function for its intended purpose (e.g., binding cAMP, fluorescing, etc.). As used herein, a variant (or homolog) refers to a protein, or nucleic acid molecule, the sequence of which is similar, but not identical, to a reference sequence (e.g., natural protein, wild type protein, etc.), wherein the activity of the variant protein (or the protein encoded by the variant nucleic acid molecule) is not significantly altered. These variations in sequence can be naturally occurring variations or they can be engineered through the use of genetic engineering technique know to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant sequence functions for its intended purpose. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

With specific regard to proteins, any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:

1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, conservative substitutions can involve the exchange of a member of one of these classes for a member from the same class. In contrast, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within nges, the hydropathic index of amino acids may be considered. Each amino acid has been assi It is also understood in the art that the substitution of like amino acids can be made effectively on the basis of hydrophilicity, particularly where the biologically functionally equivalent protein or peptide thereby created is intended for use in immunological invention. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valinc (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of a protein, or to increase or decrease the activity (e.g., cAMP-binding, fluorescence, etc.), solubility, flexibility or stability of a protein. Exemplary amino acid substitutions are shown in the following table:

Amino Acid Substitutions

| Original Amino Acid | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30% or at least 40%. With regard to the present invention, such an activity may be measured, for example, as the ability of a protein to elicit antibodies against the reference (i.e., non-mutated) protein, by measuring the ability of the protein to bind cAMP, or by measuring the fluorescence of the protein. Methods of making such measurements are known to those skilled in the art.

In addition to amino acid changes, substitutions and deletions, variants (or homologs) of proteins of the present invention include minor modifications to the finished protein, such as, for example, methylation, glycosylation, phosphorylation, acetylation, myristoylation, prenylation, palmitation, amidation.

In certain embodiments, the first polypeptide comprises a variant of a cAMP-binding protein. In one embodiment, the first polypeptide comprises an amino acid sequence at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of a protein selected from the group consisting of Epac1, Epac2 and protein kinase A (PKA). In one embodiment, the first polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from SEQ ID NO:35, SEQ ID NO:74 and SEQ ID NO:75.

As used herein, a cAMP-binding domain refers to a region of a protein that selectively binds to cAMP. cAMP-binding domains of the present invention include full length isoforms, or truncated or mutated versions of it that possess cAMP binding activity. It is well appreciated by those skilled in the art that such binding sites are part of the tertiary structure of a protein and are formed as a result of protein folding. A cAMP-binding domain of the present invention may be formed from a contiguous series of amino acids in a folded protein or it may be formed from amino acid residues that are not contiguous in the linear protein. Any cAMP-binding domain may be used to construct a cAMP sensor protein of the present invention, as long as the resulting protein sensor construct is capable of binding cAMP and such binding causes a change in fluorescence of the cAMP sensor. Without wishing to be bound by theory, it is believed that binding of cAMP to a cAMP sensor protein of the present invention, particularly at the cAMP-binding domain, leads to conformation changes in, at least, the first polypeptide, and such conformational changes alter the chromophore environment of the linked single, fluorescent protein, resulting in a change in fluorescence of the cAMP sensor protein. cAMP-binding domains of the present invention may have mutations to increase their affinity and/or specificity for cAMP. In one embodiment, the cAMP-binding domain comprises an amino acid sequence at least 80%, at least 85%, at least 90%, at least 95%, or at least 95% identical to SEQ ID NO:36 or SEQ ID NO:37, wherein the cAMP-binding domain is capable of binding cAMP. In one embodiment, the cAMP-binding domain comprises SEQ ID NO:36 or SEQ ID NO:37.

As used herein, and with regard to cAMP, selective binding refers to preferential binding of cAMP to a cAMP-binding domain or protein. Preferential binding refers to the fact that a cAMP-binding domain or protein will bind cAMP with an binding affinity greater than its binding affinity for an unrelated molecule (e.g., diacylglycerol, inisitol phosphate, calcium, etc).

As used herein, a fluorescent protein refers to a protein that emits light. Preferred fluorescent proteins are those that, upon absorption of light or other electromagnetic radiation, emit light of a same or different wavelength. Any fluorescent protein can be used to construct a cAMP sensor of the present invention, as long as upon binding of cAMP to the cAMP sensor, the level of fluorescence change. Examples of fluorescent proteins useful for producing cAMP sensor proteins of the present invention include, but are not limited to, green fluorescent protein (GFP), and its variants such as red fluorescent protein, yellow fluorescent protein, enhanced green fluorescent protein (eGFP), enhanced yellow fluorescent protein (eYFP), Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire. Such fluorescent proteins are discussed in Shaner et.al., (2005), and are expressly incorporated herein. Additional examples of fluorescent proteins include mKOK, mUKG (Tsutsui et al., 2008), Clover, Ruby (Lam et al., 2012), mKate (Pletnev et al., 2008), tagRFP, tagGFP (Shcherbo et al., 2009), mNEON green (Shaner et.al 2013), and a variety of synthetic non-Aequorea fluorescent proteins (DNA 2.0, Menlo Park, CA and Ledford, (2013). Thus, in one embodiment, a fluorescent protein of the present invention comprises at least a portion of a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, a fluorescent protein of the present invention comprises at 50 contiguous amino acids, at least 100 contiguous amino acids, at least 150 contiguous amino acids, or at least 200 contiguous amino acids from a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, a fluorescent protein of the present invention comprises at 50 contiguous amino acids, at least 100 contiguous amino acids, at least 150 contiguous amino acids, or at least 200 contiguous amino acids from a sequence selected from the group consisting of SEQ ID NO:38 and SEQ ID NO:77.

Fluorescent proteins useful for producing cAMP sensor proteins of the present invention can also be variants of the fluorescent proteins disclosed herein. Thus, in one embodiment, the single fluorescent protein comprises is a variant of a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, a fluorescent protein of the present invention comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical to a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, a fluorescent protein of the present invention comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical to a sequence selected from the group consisting of SEQ ID NO:38 and SEQ ID NO:77. In one embodiment, a fluorescent protein of the present invention comprises an amino acid sequence from a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, a fluorescent protein of the present invention comprises an amino acid sequence selected from the group consisting of SEQ ID NO:38 and SEQ ID NO:77. It will be appreciated by those skilled in the art that truncated or variant forms of the fluorescent protein will include the amion acids necessary to form the chromophore.

It is understood by those skilled in the art that proteins can be circularly permuted. In a circularly permuted protein, the order of amino acids, or stretches of amino acids (e.g., domains), is changed compared to the order in the original protein. Further, it has been shown that circular permutation of a protein can alter the properties of a protein (for example, the activity or stability of a proteins). For example, when analyte sensing domains are fused to the original N- and C-termini of the fluorescent protein, movement of the termini may, but does not usually, produce changes in fluorescence. However, when the original N- and C-termini are fused, either with or without a short linker, and new N- and C-termini are introduced in the middle of one of the beta sheets of the barrel, a circularly permuted fluorescent protein is produced with new properties. Analyte sensing domains fused to these new termini can produce very large changes in fluorescence. Without wishing to be bound by theory, it is believed that the new N- and C-termini of the circularly permuted fluorescent protein, which are close to the chromophore, enable fusion partners to create a difference in the chromophore environment, thereby producing a change in fluorescence. Thus, for instance in the $Ca^{2+}$ sensor GCaMP3 (described in United States Patent Application 20120034691), the $Ca^{2+}$ binding domains are fused to the N- and C-termini adjacent to the chromophore of the circularly permuted green fluorescent protein. In one conformation, where $Ca^{2+}$ is at low concentrations and the binding domains are not interacting, there is an opening in the side of the beta barrel of the fluorescent protein and the chromophore is solvent accessible. When the $Ca^{2+}$ binding domains bind to one another in response to activation by $Ca^{2+}$, the hole is closed, and the new environment of the chromophore causes it to become fluorescent. Thus, in one embodiment, the single fluorescent protein is circularly permuted. In preferred embodiments, the N and the C termini of the protein are placed adjacent to the chromophore. For example, in one embodiment, the cAMP sensor protein comprises a circularly permuted green fluorescent protein described in Zhao and colleagues (2011), which is incorporated herein in its entirety. In one embodiment, the fluorescent protein is EGFP which has been circularly permuted around amino acids 149-144 [SEQ ID NO:38]. A number of fluorescent proteins are known in the art and may be circularly permuted to be used in the construction of the sensor of the present invention (Baird et al., 1999; Nagai et al., 2004; Nakai at al., 2001; Shui et al., 2011; Carlson et al., 2010; Topell et al., 1999).

In cAMP sensor proteins of the present invention, the first polypeptide is linked to a single fluorescent protein. As used herein, reference to a single fluorescent protein refers to the fact that the fluorescent protein portion of the sensor (i.e., the portion responsible for emitting light) consists of an uninterrupted amino acid sequence. In other words, when constructing cAMP sensor proteins of the present invention, the amino acid sequence of the fluorescent protein portion is a single, contiguous amino acid sequence and is not broken into two or more sequences located in separate regions of the overall cAMP sensor protein. For illustration purposes, the complementation design sensor shown in FIG. 1 represents a sensor construct in which the fluorescent protein has been split into two separate sequences, one of which is attached to one end of a cAMP binding domain, the other of which is attached to the opposite end of a cAMP binding domain. According to the present invention, such a construct does not contain a single fluorescent protein. In embodiments of the present invention, the single fluorescent protein is attached to one end or the other (e.g., either the N-terminal end or the C-terminal end) of the first polypeptide. It will be appreciated by those skilled in the art that in certain fluorescent proteins, the bonds of the amino acids that form the chromophore are broken following final folding of the protein. While such breaking of these bonds results in separation of the sequence of the fluorescent protein, the sequences remain close to one another and are not located in separate regions of the overall sensor protein. Thus, such photoconvertible fluorescent proteins can be used for constructing cAMP sensor proteins of the present invention.

As has been stated, binding of cAMP to the first polypeptide, and in particular to the cAMP-binding domain, causes an alteration in the level of fluorescence from the single fluorescent protein. Without wishing to be bound by theory, it is believed that the binding of cAMP leads to conformational changes in the first polypeptide, which changes the chromophore environment of the single fluorescent protein, thereby altering the level of fluorescence produced by the single fluorescent protein. As used herein an alteration in the level of fluorescence refers to an increase or decrease in the level of fluorescencey produced by the single fluorescent protein. Such alterations will be proportional to the level of cAMP that binds the sensor protein, which corresponds to the level of cAMP in the surrounding environment. In certain embodiments, binding of cAMP to the cAMP sensor protein will cause a change in the level of fluorescence of at least 5%, at least 6%, at least 7%, at least 8%, at least 9%, at least 10%, at least 15%, at least 20% or at least 30%. Methods of measuring changes in fluorescence are known to those skilled in the art.

As stated above, in cAMP sensor proteins of the present invention, the first polypeptide is linked to a single fluorescent protein. In one embodiment, the first polypeptide and the single fluorescent protein are directly linked. As used herein, direct linkage means that amino acids of the first polypeptide are covalently joined to amino acids of the single fluorescent protein. That is, there arc no unrelated amino acid sequences between (covalently joining) an amino acid of the first polypeptide and an amino acid of the singe fluorescent protein. For example, if the first polypeptide consists of the amino acid sequence encoding a protein comprising a cAMP-binding domain, such as Epac2, covalently linkage of an amino acid (e.g., the N-terminal or C-terminal amino acid) with an amino acid of the single fluorescent protein represents direct joining of these two molecules.

Alternatively, the first polypeptide and the single fluorescent protein can be linked by a linker sequence. A linker sequence is a contiguous series of amino acid residues which may or may not be related to either the first polypeptide or the single fluorescent protein. Typically, linker sequences are short sequences, consisting of between 1 and about 10 amino acids and thus, while linker sequences may be related to either the first polypeptide or other single fluorescent protein, linker sequences do not comprise the activity (e.g., cAMP binding or fluorescence) of either. Preferred linker sequences are those that are unrelated to the sequence of either the first polypeptide or the single fluorescent protein. Linker sequences are used to join the N terminal, or the C-terminal, end of the single fluorescent protein with the N-terminal, or the C-terminal, end of the first polypeptide. It should be appreciated that in embodiments in which the single fluorescent protein is circularly permuted, the N- and C-terminal ends of the circularly permuted protein may not be the same as the N and C-terminal ends found in the native fluorescent protein from which the circularly permuted protein was derived. Linkers containing amino acids with side chains that give the linker ridged structure can be used to couple conformational changes in the cAMP binding domain to changes in the structure of the fluorescent protein barrel. Moreover, without being bound by theory, it is believed that, linkers with bulky amino acids that can form a surface/structure capable of occluding the hole in the side of the barrel produced by circular permutation are best capable of producing large changes in fluorescence by protecting the chromophore environment in one configuration and in another configuration producing a large hole in the side of the protein barrel that renders the chromophore less fluorescent. Examples of linkers useful for producing cAMP sensor proteins of the present invention include, but are not limited to, amino acid sequences such as LE, AI, PV, SH, TR, FN, LV, ENNHLS, LVSH, and FNNP.

Heretofore has been described a cAMP sensor protein, comprising a cAMP-binding domain, covalently joined at one end, either directly or indirectly, to a single fluorescent protein. Such cAMP sensor proteins can also comprise additional amino acid sequences. Thus, in one embodiment, the cAMP sensor protein comprises a second polypeptide, wherein the second polypeptide is linked to the single fluorescent protein such that the single fluorescent protein is flanked by the first and second polypeptide. In such an embodiment, each end of the single fluorescent protein (SFP) is covalently joined to a different polypeptide; either the first polypeptide (P1) or the second polypeptide (P2). The possible variations of such a construct can be illustrated as follows: P1-SFP-P2 and P2-SFP-P1. From such illustration, one skilled in the art will understand that in such a construct, the single fluorescent protein resides between the first and second polypeptides. It should further be appreciated that the N-terminal end of the single fluorescent protein can be joined to either the N- or C-terminal end of a polypeptide (first or second). Likewise, the C-terminal end of the single fluorescent protein can be joined to the N- or C-terminal end of the other polypeptide (first or second). Thus it can be seen that many variations are possible, with regard to orientation of the amino and carboxyl ends of the first polypeptide, the single fluorescent protein and the second polypeptide. All such variations are encompassed by the present invention, so long as the variant has the activities described herein. In one embodiment, the N-terminal amino acid of the single fluorescent protein is linked to the carboxyl end of the first polypeptide. In one embodiment, the N-terminal amino acid of the single fluorescent protein is linked to the amino end of the first polypeptide. In one embodiment, the N-terminal amino acid of the single fluorescent protein is linked to the carboxyl end of the second polypeptide. In one embodiment, the N-terminal amino acid of the single fluorescent protein is linked to the amino end of the first polypeptide.

Any polypeptide can be used as the second polypeptide, as long as the resulting cAMP sensor protein functions for the intended purpose described herein; that is, as long as the resulting construct binds cAMP and such binding causes a change in fluorescence of the cAMP sensor. The second polypeptide may or may not comprise an amino acid sequence derived from the same protein from which the amino acid sequence of the first polypeptide was derived. For example, if the first polypeptide comprises an amino acid sequences derived from EPAC1, the second polypeptide can, but need not, comprise an amino acid sequence from EPAC1. Thus, in one embodiment, the second polypeptide and the first polypeptide comprise amino acid sequence from the same protein. Alternatively, in one embodiment, the second polypeptide and the first polypeptide comprise amino acid sequence from unrelated (i.e., different) proteins. According to the present invention, two proteins arc unrelated if their sequences differ by at least 35%, or if their structural relatedness differs by more than 50%. Methods of determining the relatedness of two proteins are known in the art.

In one embodiment, the second polypeptide comprises an amino acid sequence from a protein selected from the group consisting of Epac1, Epac2, protein kinase A (PKA) and RAP1B. In one embodiment, the second polypeptide comprises at least 50 contiguous amino acids, at least 100 contiguous amino acids, or at least 150 contiguous amino acids from a RAP1B protein. In one embodiment, the second polypeptide comprises at least 50 contiguous amino acids, at least 100 contiguous amino acids, or at least 150 contiguous amino acids from SEQ ID NO:76. In one embodiment, the second polypeptide comprises at least 50 contiguous amino acids, at least 100 contiguous amino acids, at least 150 contiguous amino acids, at least 200 contiguous amino acids, or at least 250 contiguous amino acids from a PKA protein. In one embodiment, the second polypeptide comprises at least 50 contiguous amino acids, at least 100 contiguous amino acids, at least 150 contiguous amino acids, at least 200 contiguous amino acids, or at least 250 contiguous amino acids from SEQ ID NO:75. In one embodiment, the second polypeptide comprises at least 200 contiguous amino acids, at least 300 contiguous amino acids, at least 400 contiguous amino acids, at least 500 contiguous amino acids or at least 600 contiguous amino acids from an Epac1 or Epac2 protein. In one embodiment, the second polypeptide comprises at least 200 contiguous amino acids, at least 300 contiguous amino acids, at least 400 contiguous amino acids, at least 500 contiguous amino acids or at least 600 contiguous amino acids from SEQ ID NO:74 or SEQ ID NO:35.

In one embodiment, the second polypeptide comprises a variant of a protein disclosed herein. In one embodiment, the second polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 70% and 99%, in whole integer increments), to the amino acid sequence of a protein selected from the group consisting of Epac1, Epac2, protein kinase A (PKA) and RAP1B. In one embodiment, the second polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from SEQ ID NO:35, SEQ ID NO:74, SEQ ID NO:75 and SEQ ID NO:76. In one embodiment, the second polypeptide comprises a sequence selected from the group consisting of SEQ ID NO:35, SEQ ID NO:74, SEQ ID NO:75 and SEQ ID NO:76.

As has been described for the linkage between the first polypeptide and the single fluorescent protein, the second polypeptide and the single fluorescent protein can be directly linked, or they can be linked by a linker sequence. In one embodiment, the second polypeptide and the single fluorescent protein are directly linked. In one embodiment, the second polypeptide and the single fluorescent protein can be linked by a linker sequence.

Because the first and second polypeptides can comprise amino acid sequences from the same protein, it should be appreciated that while the sequences comprised by the first and second polypeptides can come from the same portion of the same protein, they can also come from different portions (e.g., domains) from the same protein. Thus, the astute person skilled in the art will understand that a cAMP sensor protein can be constructed by dividing a cAMP-binding protein into two portions, one of which contains the cAMP-binding domain, and linking one portion to one end of a single fluorescent protein and the other portion to the other end of the single fluorescent protein. In essence, the single fluorescent portion is inserted into the cAMP-binding protein. It will be appreciated that such insertion can be anywhere within the amino acid sequence of the cAMP-binding protein, as long as the resulting construct can bind cAMP and such binding causes a change in fluorescence of the single fluorescent protein. Thus, in one embodiment, the amino acid sequences comprised by the first and second polypeptides are from different regions of the same protein. In one embodiment, the single fluorescent protein is inserted into a cAMP-binding domain. In certain embodiments, the single fluorescent protein is inserted into the cAMP-binding protein such that the portion of the cAMP binding protein upstream of the insertion site is coupled to the N-terminus of the single fluorescent protein and the portion of the cAMP binding protein downstream of the insertion site is coupled to the C-terminus of the FP. In certain embodiments, the single fluorescent protein is inserted into the cAMP-binding protein such that the portion of the cAMP binding protein upstream of the insertion site is coupled to the C-terminus of the single fluorescent protein and the portion of the cAMP binding protein downstream of the insertion site is coupled to the C-terminus of the FP.

To further illustrate such a construct, it is known that the EPAC1 protein contains a regulatory domain and a catalytic domain. In such case, if the amino acid sequences comprised by the first and second polypeptides arc both from EPAC1, one polypeptide (the first or second) can comprise the regulatory domain while the other polypeptide (either the first or second) can comprise the catalytic domain. In one embodiment, the first and second polypeptides are capable of interacting. For example, the first and second polypeptide may bind to from a complex. In certain embodiments, such binding is non-covalent binding due to, for example, hydrogen, ionic, hydrophobic or Vander Waal interactions. In certain embodiments, one polypeptide comprises enzymatic activity and the other polypeptide is a substrate for the enzyme.

Insertion of single fluorescent protein into the sequence of a cAMP-binding protein can be done by such that the ends of the single fluorescent protein arc linked to two amino acids that are normally adjoining in the cAMP-binding protein. For example, in a construct in which the single fluorescent protein is inserted between amino acids 100 and 101 of EPAC1, one end of the single fluorescent protein will be covalently linked to amino acid 100, while the other end of the single fluorescent protein will be covalently joined to amino acid 101. In such a construct, no amino acids are removed from the cAMP-binding protein. Thus, in certain embodiments the insertion region comprises the native amino acid sequence of the cAMP binding protein.

It is known in the art that some proteins contain regions between domains referred to as hinge regions. Such hinge regions allow movement of the domains relative to one another. Because it is believed that changes in fluorescence of sensors of the present invention results from changes in the environment of the chromophore due to relative movement of sequences flanking the fluorescent protein, such hinge regions can be used as sites of insertion of the fluorescent protein. Thus, in one embodiment, the fluorescent protein is inserted into the hinge region of a cAMP-binding protein. In one embodiment, the fluorescent protein is inserted into a sequence comprising SEQ ID NO:40.

In certain embodiments, insertion of the single fluorescent protein can comprise additions, deletions or alterations (e.g., substitutions) of amino acids that make the sequence deviate from the native sequence. For example, in various embodiments, the insertion region may comprise deletions of at least 1, 2, 3, 4, 5, 6, 7, 8, 9, 10, 11, 12, 13, 14, 15, 16, 17, 18, 19, or 20 amino acids to the native sequence. In various embodiments, the insertion region may comprise deletions of at least 1, 2, 3, 4, 5, 6, 7, 8, 9, 10, 11, 12, 13, 14, 15, 16, 17, 18, 19, 20, 21, or 22 amino acids from the native sequence. In some embodiments the insertion region may comprise one or more substitutions of the amino acids of the native sequence. In some embodiments, the insertion site may be after the last amino acid of a truncated cAMP binding protein. In this embodiment, the cAMP binding protein is coupled to the N-terminus of the single fluorescent protein. In some embodiments, the insertion site may be before the first amino acid of the cAMP binding protein such that the cAMP binding protein is coupled to the C-terminus of the single fluorescent protein.

Exemplary embodiments of the present are listed below in Table 1.

TABLE 1

Sequences of exemplary cAMP sensor proteins and related molecules

| Description | Name of Molecule | Description |
|---|---|---|
| SEQID 1 | EcpG10G2-RasGEF-T2 | Best Upward Sensor amino acid, protein translation of SEQ ID NO: 41 |
| SEQID 2 | Library2-1 G12 | amino acid, protein translation of SEQ ID NO: 42 |
| SEQID 3 | Lib2-1 G12 RasGEF-T2 | amino acid, protein translation of SEQ ID NO: 43 |
| SEQID 4 | EcpG10 G2 | amino acid, protein translation of SEQ ID NO: 44 |
| SEQID 5 | Lib2-2 E7 | amino acid, protein translation of SEQ ID NO: 45 |
| SEQID 6 | Lib6-2 Cl T2 | Best Downward amino acid, protein translation of SEQ ID NO: 46 |
| SEQID 7 | Lib5-1 D2 | amino acid, protein translation of SEQ ID NO: 47 |
| SEQID 8 | Lib5-1 G12 | amino acid, protein translation of SEQ ID NO: 48 |
| SEQID 9 | Lib2-1 B12 | amino acid, protein translation of SEQ ID NO: 49 |
| SEQID 10 | Lib 1 C2 | amino acid, protein translation of SEQ ID NO: 50 |
| SEQID 11 | EcpGl2 | amino acid, protein translation of SEQ ID NO: 51 |
| SEQID 12 | Lib2-2 F9 | amino acid, protein translation of SEQ ID NO: 52 |
| SEQID 13 | Lib2-2 G4 | amino acid, protein translation of SEQ ID NO: 53 |
| SEQID 14 | Lib2-1 C2 | amino acid, protein translation of SEQ ID NO: 54 |
| SEQID 15 | Lib5-1 E7 | amino acid, protein translation of SEQ ID NO: 55 |
| SEQID 16 | Library6-2 Cl | amino acid, protein translation of SEQ ID NO: 56 |
| SEQID 17 | EcpG15 | amino acid, protein translation of SEQ ID NO: 57 |
| SEQID 18 | Lib2-2 D1 | amino acid, protein translation of SEQ ID NO: 58 |
| SEQID 19 | Lib2-2 All | amino acid, protein translation of SEQ ID NO: 59 |

TABLE 1-continued

Sequences of exemplary cAMP sensor proteins and related molecules

| Description | Name of Molecule | Description |
|---|---|---|
| SEQID 20 | Lib2-2 A5 | amino acid, protein translation of SEQ ID NO: 60 |
| SEQID 21 | Lib2-1 D1 | amino acid, protein translation of SEQ ID NO: 61 |
| SEQID 22 | Lib 1 G2 | amino acid, protein translation of SEQ ID NO: 62 |
| SEQID 23 | Libl A6 | amino acid, protein translation of SEQ ID NO: 63 |
| SEQID 24 | Lib6-2 Fl | amino acid, protein translation of SEQ ID NO: 64 |
| SEQID 25 | EcpG10 | amino acid, protein translation of SEQ ID NO: 65 |
| SEQID 26 | EcpG10 G2N-G1C | amino acid, protein translation of SEQ ID NO: 66 |
| SEQID 27 | EPAC2-GFP-RAP1B | amino acid, protein translation of SEQ ID NO: 67 |
| SEQID 28 | EcpG13 | amino acid, protein translation of SEQ ID NO: 68 |
| SEQID 29 | EcpG23 | amino acid, protein translation of SEQ ID NO: 69 |
| SEQID 30 | EcpG9 | amino acid, protein translation of SEQ ID NO: 70 |
| SEQID 31 | EcpG22 | amino acid, protein translation of SEQ ID NO: 71 |
| SEQID 32 | EcpG18 | amino acid, protein translation of SEQ ID NO: 72 |
| SEQID 33 | EcpG24 | amino acid, protein translation of SEQ ID NO: 73 |
| SEQID 34 | Hinge | amino acid, protein translation of SEQ ID NO: 40 |
| SEQID 35 | Human EPAC2 from Genbank-translation | amino acid, protein translation of SEQ ID NO: 39 |
| SEQID 36 | cAMP binding domain A | amino acid, protein translation of SEQ ID NO: |
| SEQID 37 | cAMP binding domain B | amino acid, protein translation of SEQ ID NO: |
| SEQID 38 | cpEGFP | amino acid, protein translation of SEQ ID NO: |
| SEQID 39 | Human EPAC2 from Genbank | Nucleotide of SEQ ID NO: 35 |
| SEQID 40 | Hinge | Nucleotide of SEQ ID NO: 34 |
| SEQID 41 | EcpG10G2-RasGEF-T2 | Nucleotide of SEQ ID NO: 1 |
| SEQID 42 | Library2-1 G12 | Nucleotide of SEQ ID NO: 2 |
| SEQID 43 | Lib2-1 G12 RasGEF-T2 | Nucleotide of SEQ ID NO: 3 |
| SEQID 44 | EcpG1O G2 | Nucleotide of SEQ ID NO: 4 |
| SEQID 45 | Lib2-2 E7 | nucleotide of SEQ ID NO: 5 |
| SEQID 46 | Lib6-2 Cl T2 | nucleotide of SEQ ID NO: 6 |
| SEQID 47 | Lib5-1 D2 | nucleotide of SEQ ID NO: 7 |
| SEQID 48 | Lib5-1 G12 | nucleotide of SEQ ID NO: 8 |
| SEQID 49 | Lib2-1 B12 | nucleotide of SEQ ID NO: 9 |
| SEQID 50 | Lib 1 C2 | nucleotide of SEQ ID NO: 10 |
| SEQID 51 | EcpG12 | nucleotide of SEQ ID NO: 11 |
| SEQID 52 | Lib2-2 F9 | nucleotide of SEQ ID NO: 12 |
| SEQID 53 | Lib2-2 G4 | nucleotide of SEQ ID NO: 13 |
| SEQID 54 | Lib2-1 C2 | nucleotide of SEQ ID NO: 14 |
| SEQID 55 | Lib5-1 E7 | nucleotide of SEQ ID NO: 15 |
| SEQID 56 | Library6-2 Cl | nucleotide of SEQ ID NO: 16 |
| SEQID 57 | EcpGl5 | nucleotide of SEQ ID NO: 17 |
| SEQID 58 | Lib2-2 Dl | nucleotide of SEQ ID NO: 18 |
| SEQID 59 | Lib2-2 All | nucleotide of SEQ ID NO: 19 |
| SEQID 60 | Lib2-2 A5 | nucleotide of SEQ ID NO: 20 |
| SEQID 61 | Lib2-1 Dl | nucleotide of SEQ ID NO: 21 |
| SEQID 62 | Lib 1 G2 | nucleotide of SEQ ID NO: 22 |
| SEQID 63 | Lib 1 A6 | nucleotide of SEQ ID NO: 23 |
| SEQID 64 | Lib6-2 Fl | nucleotide of SEQ ID NO: 24 |
| SEQID 65 | EcpG10 | nucleotide of SEQ ID NO: 25 |
| SEQID 66 | EcpG10 G2N-G1C | nucleotide of SEQ ID NO: 26 |
| SEQID 67 | EPAC2-GFP-RAP1B | nucleotide of SEQ ID NO: 27 |
| SEQID 68 | EcpG13 | nucleotide of SEQ ID NO: 28 |
| SEQID 69 | EcpG23 | nucleotide of SEQ ID NO: 29 |
| SEQID 70 | EcpG9 | nucleotide of SEQ ID NO: 30 |
| SEQID 71 | EcpG22 | nucleotide of SEQ ID NO: 31 |
| SEQID 72 | EcpG18 | nucleotide of SEQ ID NO: 32 |
| SEQID 73 | EcpG24 | nucleotide of SEQ ID NO: 33 |
| SEQID74 | GenBank NP__001092002.1 (Epac1) | Amino acid sequence of Epac1 |
| SEQID 75 | GenBank NP__002725.1 (PKA) | Amino acid sequence of PKA |
| SEQID 76 | GenBank AAH95467.1 (Rap1B) | Amino acid sequence of Rap1B |
| SEQID 77 | EGFP | Enhanced fluorescent green protein |

In one embodiment, a cAMP sensor protein comprises an amino acid sequence at least 70%, at least 80%, at least 85%, at least 90%, at least 95%, at least 97% or at least 99% identical to a sequence in Table 1. In one embodiment, a cAMP sensor protein comprises a sequence in Table 1. In one embodiment, a cAMP sensor protein comprises an amino acid sequence at least 70%, at least 80%, at least 85%, at least 90%, at least 95%, at least 97% or at least 99% identical to a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33. In one embodiment, a cAMP sensor protein comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33.

In one embodiment, a cAMP sensor protein of the present invention is encoded by a nucleic acid molecule comprising a nucleic acid sequence at least 70%, at least 80%, at least 85%, at least 90%, at least 95%, at least 97% or at least 99% identical to a sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73. In one embodiment, a cAMP sensor protein of the present invention is encoded by a nucleic acid molecule comprising a nucleic acid sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ TD NO:69, SEQ ID NO:70, SEQ ID NO:71, SEQ ID NO:72 and SEQ TD NO:73.

cAMP sensor proteins of the present invention are encoded by recombinant nucleic acid molecules of the present invention. In accordance with the present invention, a recombinant nucleic acid molecule is one that has been created by the hand of man. As such, recombinant nucleic acid molecules of the present invention can be a combination of molecules obtained from a natural source, and molecules obtained through synthesis (e.g., cloning of genes or fragments thereof).

A recombinant nucleic acid molecule of the present invention can be produced using a number of methods known to those skilled in the art (see, for example, Sambrook et al., *Molecular Cloning: A Laboratory Manual, Third Edition,* 2001, which is incorporated herein by reference in its entirety). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule variants can be selected from a mixture of modified nucleic acids by screening for the function of the protein encoded by the nucleic acid (e.g., the ability to bind cAMP, the ability to fluoresce, etc.). Such screening methods have been described herein and are routinely performed by those skilled in the art.

One embodiment of the present invention is a nucleic acid molecule encoding a cAMP sensor protein of the present invention. One embodiment of the present invention is a nucleic acid molecule encoding a cAMP sensor protein comprising a first polypeptide linked to a single fluorescent protein, wherein the first polypeptide comprises a cAMP-binding domain, wherein the single fluorescent protein consists of an uninterrupted amino acid sequence, and wherein the fluorescence of the cAMP sensor changes upon binding cAMP. In one embodiment, the nucleic acid molecule encodes a cAMP sensor in which the first polypeptide comprises an amino acid sequence from a protein selected from the group consisting of Epac1, Epac2 and protein kinase A (PKA). In one embodiment, the nucleic acid molecule encodes a cAMP sensor in which the first polypeptide comprises at least 50 contiguous amino acids, at least 100 contiguous amino acids, at least 150 contiguous amino acids, at least 200 contiguous amino acids, or at least 250 contiguous amino acids from a PKA protein. In one embodiment, the nucleic acid molecule encodes a cAMP sensor in which the first polypeptide comprises at least 50 contiguous amino acids, at least 100 contiguous amino acids, at least 150 contiguous amino acids, at least 200 contiguous amino acids, or at least 250 contiguous amino acids from SEQ ID NO:75. In one embodiment, the nucleic acid molecule encodes a cAMP sensor in which the first polypeptide comprises at least 200 contiguous amino acids, at least 300 contiguous amino acids, at least 400 contiguous amino acids, at least 500 contiguous amino acids or at least 600 contiguous amino acids from an Epac1 or Epac2 protein. In one embodiment, the nucleic acid molecule encodes a cAMP sensor in which the first polypeptide comprises at least 200 contiguous amino acids, at least 300 contiguous amino acids, at least 400 contiguous amino acids, at least 500 contiguous amino acids or at least 600 contiguous amino acids from SEQ ID NO:74 or SEQ ID NO:35. In one embodiment, the nucleic acid molecule encodes a cAMP sensor in which the first polypeptide comprises the amino acid sequence of a protein selected from the group consisting of Epac1, Epac2 and protein kinase A (PKA). In one embodiment, the nucleic acid molecule encodes a cAMP sensor in which first polypeptide comprises an amino acid sequence selected from the group consisting of SEQ ID NO:35, SEQ ID NO:74 and SEQ ID NO:75.

One embodiment of the present invention is a nucleic acid molecule encoding a cAMP sensor protein comprising a first polypeptide linked to a single fluorescent protein, wherein the first polypeptide is capable of comprising a cAMP-binding domain, wherein the single fluorescent protein consists of an uninterrupted amino acid sequence, and wherein the fluorescence of the cAMP sensor changes upon binding cAMP. In one embodiment, the nucleic acid molecule encoded a cAMP sensor in which the first polypeptide comprises a sequence from a protein that does not naturally contain a cAMP-binding site. In one embodiment, the nucleic acid molecule encodes a cAMP sensor in which the first polypeptide comprises at least 50 contiguous amino acids, at least 100 contiguous amino acids, or at least 150 contiguous amino acids from a RAP1B protein. In one embodiment, the nucleic acid molecule encodes a cAMP sensor in which the first polypeptide comprises at least 50 contiguous amino acids, at least 100 contiguous amino acids, or at least 150 contiguous amino acids from SEQ ID NO:76.

In one embodiment, a nucleic acid molecule encodes a cAMP sensor protein comprising variant sequences. Thus, in one embodiment, the nucleic acid molecule encodes a cAMP sensor in which the first polypeptide comprises a variant of a cAMP-binding protein. In one embodiment, the nucleic acid molecule encodes a cAMP sensor in which the first polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of a protein selected from the group consisting of Epac1, Epac2, protein kinase A (PKA) and RAP1B. In one embodiment, the nucleic acid molecule encodes a cAMP sensor in which the first polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from SEQ ID NO:35, ID NO:74, SEQ ID NO:75 and SEQ ID NO:76.

One embodiment of the present invention is a nucleic acid molecule encoding a cAMP sensor of the present in invention in which the fluorescent protein comprises at least a portion of a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, the nucleic acid molecule encodes a cAMP sensor in which the fluorescent protein comprises at least 50 contiguous amino acids, at least 100 contiguous amino acids, at least 150 contiguous amino acids, or at least 200 contiguous amino acids from a protein selected from the group consisting of GFP, eGFP, cYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, the nucleic acid molecule encodes a cAMP sensor in which the fluorescent protein comprises the amino acid sequence of a protein selected from group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, the nucleic acid molecule encodes a cAMP sensor in which the fluorescent protein comprises at least 50 contiguous amino acids, at least 100 contiguous amino acids, at least 150 contiguous amino acids, or at least 200 contiguous amino acids from the group consisting of SEQ ID NO:38 and SEQ ID NO:77. In one embodiment, the nucleic acid molecule encodes a cAMP sensor in which the fluorescent protein comprises a sequence selected from the group consisting of SEQ ID NO:38 and SEQ ID NO:77.

One embodiment of the present invention is a nucleic acid molecule encoding a cAMP sensor protein of the present in invention in which the fluorescent protein comprises a variant of a fluorescent protein disclosed herein. In one embodiment, the nucleic acid molecule encodes a cAMP sensor in which the fluorescent protein comprises a variant of a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, the nucleic acid molecule encodes a cAMP sensor in which the fluorescent protein comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical to a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, the nucleic acid molecule encodes a cAMP sensor in which the fluorescent protein comprises a fluorescent protein comprising an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical to a sequence selected from the group consisting of SEQ ID NO:38 and SEQ ID NO:77.

In one embodiment, the nucleic acid molecule encodes a cAMP sensor in which the fluorescent protein comprises an amino acid sequence from a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-Aequorea fluorescent protein. In one embodiment, the nucleic acid molecule encodes a cAMP sensor in which the fluorescent protein comprises an amino acid sequence selected from the group consisting of SEQ ID NO:38 and SEQ ID NO:77.

In one embodiment, the nucleic acid molecule encodes a cAMP sensor in which the fluorescent protein is circularly permuted. In preferred embodiments, the nucleic acid molecule encodes a cAMP sensor in which the fluorescent protein comprises N and the C termini of the protein placed adjacent to the chromophore. In one embodiment, the nucleic acid molecule encodes a cAMP sensor in which the s fluorescent protein is EGFP which has been circularly permuted around amino acids 149-144 [SEQ ID NO:39].

One embodiment of the present invention is a nucleic acid molecule encoding a cAMP sensor protein of the present invention comprising a second polypeptide, wherein the second polypeptide is linked to the single fluorescent protein such that the single fluorescent protein is flanked by the first and second polypeptide. In one embodiment, the nucleic acid molecule encodes a cAMP sensor in which the second polypeptide comprises an amino acid sequence from a protein selected from the group consisting of Epac1, Epac2, protein kinase A (PKA) and RAP1B. In one embodiment, the nucleic acid molecule encodes a cAMP sensor in which the second polypeptide comprises at least 50 contiguous amino acids, at least 100 contiguous amino acids, or at least 150 contiguous amino acids from a RAP1B protein. In one embodiment, the nucleic acid molecule encodes a cAMP sensor in which the second polypeptide comprises at least 50 contiguous amino acids, at least 100 contiguous amino acids, or at least 150 contiguous amino acids from SEQ ID NO:76. In one embodiment, the nucleic acid molecule encodes a cAMP sensor in which the second polypeptide comprises at least 50 contiguous amino acids, at least 100 contiguous amino acids, at least 150 contiguous amino acids, at least 200 contiguous amino acids, or at least 250 contiguous amino acids from a PKA protein. In one embodiment, the nucleic acid molecule encodes a cAMP sensor in which the second polypeptide comprises at least 50 contiguous amino acids, at least 100 contiguous amino acids, at least 150 contiguous amino acids, at least 200 contiguous amino acids, or at least 250 contiguous amino acids from SEQ ID NO:75. In one embodiment, the nucleic acid molecule encodes a cAMP sensor in which the second polypeptide comprises at least 200 contiguous amino acids, at least 300 contiguous amino acids, at least 400 contiguous amino acids, at least 500 contiguous amino acids or at least 600 contiguous amino acids from an Epac1 or Epac2 protein. In one embodiment, the nucleic acid molecule encodes a cAMP sensor in which the second polypeptide comprises at least 200 contiguous amino acids, at least 300 contiguous amino acids, at least 400 contiguous amino acids, at least 500 contiguous amino acids or at least 600 contiguous amino acids from SEQ ID NO:74 or SEQ ID NO:35.

In one embodiment, the nucleic acid molecule encodes a cAMP sensor in which the second polypeptide comprises a variant of a protein disclosed herein. In one embodiment, the nucleic acid molecule encodes a cAMP sensor in which the second polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 70% and 99%, in whole integer increments), to the amino acid sequence of a protein selected from the group consisting of Epac1, Epac2, protein kinase A (PKA) and RAP1B. In one embodiment, the nucleic acid molecule encodes a cAMP sensor in which the second polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from SEQ ID NO:35, SEQ ID NO:74, SEQ ID NO:75 and SEQ ID NO:76.

In one embodiment, a nucleic acid molecule of the present invention encodes a cAMP sensor protein comprising an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ TD NO:30, SEQ ID NO:31, SEQ ID NO:32 and SEQ ID NO:33. In one embodiment, a nucleic acid molecule of the present invention encodes a cAMP sensor protein comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ TD NO:30, SEQ TD NO:31, SEQ TD NO:32 and SEQ TD NO:33. In one embodiment, a nucleic acid molecule of the present invention comprises a nucleic acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ TD NO:52, SEQ ID NO:53, SEQ TD NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73. In one embodiment, a nucleic acid molecule of the present invention comprises a nucleic acid sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ TD NO:58, SEQ ID NO:59, SEQ TD NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73.

Also provided herein are vectors comprising the sensor-encoding nucleic acid sequences. Examples of suitable vectors include, but are not limited to, plasmids, artificial chromosomes, such as BACs, YACs, or PACs, and viral vectors. As used herein, vectors are agents that transport the disclosed nucleic acids into a cell without degradation and, optionally, include a promoter yielding expression of the nucleic acid molecule in the cells into which it is delivered.

Examples of viral vectors useful for practicing the present invention include, but are not limited to, Adenovirus, Adeno-associated virus, herpes virus, Vaccinia virus, Polio virus, Sindbis, and other RNA viruses, including these viruses with the HIV backbone. Any viral families which share the properties of these viruses which make them suitable for use as vectors are suitable. Retroviral vectors, in general are described by Coffin et al., 1997, which is incorporated by reference herein for the vectors and methods of making them. The construction of replication-defective adenoviruses has been described. (Berkner et al. 1987; Massie et al., 1986; Haj-Ahmad et al., 1986; Davidson et al., 1987; Zhang et al., 1993). Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors. Bacculovirus has also been demonstrated as a particularly useful vector for drug discovery applications (Kost ct.al 2005)

Non-viral based vectors, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/ Life Technologies (Carlsbad, Calif.).

Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. .beta.-actin promoter or EF1.alpha. promoter, or from hybrid or chimeric promoters (e.g., CMV promoter fused to the .beta.-actin promoter). Promoters from the host cell or related species are also useful herein. Enhancer generally refers to a sequence of DNA that functions at no fixed distance from the transcription start site and can be either 5' or 3' to the transcription unit. Enhancers usually function to increase transcription from nearby promoters. Enhancers can also contain response elements that mediate the regulation of transcription. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type arc the CMV promoter, the SV40 promoter, the beta.-actin promoter, the EF1.alpha. promoter, and the retroviral long terminal repeat (LTR).

Cells comprising the sensors of the present invention, the sensor-encoding nucleic acid sequences or vectors comprising the sensor-encoding nucleic acid sequence are provided. The cell can be, for example, a eukaryotic or prokaryotic cell. Suitable cells include, but are not limited to cells of E. coli, Pseudomonas, Bacillus, Streptomyces; fungi cells such as yeasts (Saccharomyces, and methylotrophic yeast such as Pichia, Candida, Hansenula, and Torulopsis); and animal cells, such as CHO, R1.1, B-W and LM cells, African Green Monkey kidney cells (for example, COS 1, COS 7, BSC1, BSC40, and BMT10), insect cells (for example, Sf9), human cells and plant cells. Suitable human cells include, for example, HeLa cells or human embryonic kidney (HEK) cells. Cells can be induced pluripotent stem cells (iPSC). Cells that can be used herein are commercially available from, for example, the American Type Culture Collection (ATCC), P.O. Box 1549, Manassas, Va. 20108. See also F. Ausubel et al., Current Protocols in Molecular Biology, John Wiley & Sons, New York, N.Y., (1998). Optionally, the sensor-encoding nucleic acid sequence may be located in the genome of the cell.

Methods of culturing the provided cells are known in the art and the method of transformation and choice of expression vector will depend on the host system selected. Transformation and transfection methods are described, e.g., in Ausubel et al. (1998), and, as described above, expression vectors may be chosen from examples known in the art. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Cells may be stable cell lines or transiently expressing the sensor. Such methods are well known in the art and readily adaptable for use with the compositions and methods described herein.

One embodiment of the present invention is a method of detecting cAMP levels comprising expressing a cAMP sensor protein of the present invention in a cell, and detecting the level of fluorescence from the sensor. In one embodiment, the cAMP sensor protein is expressed in the cell by inserting a nucleic acid molecule encoding the cAMP sensor into the cell. In one embodiment, changes in the level of cAMP are detected by detecting changes in the level of fluorescence from the cAMP sensor protein.

One embodiment of the present invention is a method of identifying a compound that affects cAMP levels in a cell, the method comprising expressing a cAMP sensor protein in a cell and detecting changes in the level of fluorescence from the cAMP sensor protein. In one embodiment, the cell is treated with a test compound and changes in fluorescence form the cAMP sensor protein measured.

As used herein, unless otherwise specified, reference to a percent (%) identity refers to an evaluation of homology which is performed using: (1) a BLAST Basic BLAST homology search using blastp for amino acid searches and blastn for nucleic acid searches with standard default parameters, wherein the query sequence is filtered for low complexity regions by default (described in Altschul et al., 1997); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, Methods of Enzymology, Vol. 194, Guthrie et al., eds., Cold Spring Harbor Laboratory Press (1990); Biology and activities of yeasts, Skinner, et al., eds., Academic Press (1980); Methods in yeast genetics: a laboratory course manual, Rose et al., Cold Spring Harbor Laboratory Press (1990); The Yeast Saccharomyces: Cell Cycle and Cell Biology, Pringle et al., eds., Cold Spring Harbor Laboratory Press (1997); The Yeast Saccharomyces: Gene Expression, Jones et al., eds., Cold Spring Harbor Laboratory Press (1993); The Yeast Saccharomyces: Genome Dynamics, Protein Synthesis, and Energetics, Broach et al., eds., Cold Spring Harbor Laboratory Press (1992); Molecular Cloning: A Laboratory Manual, second edition (Sambrook et al., 1989) and Molecular Cloning: A Laboratory Manual, third edition (Sambrook and Russel, 2001), (jointly referred to herein as "Sambrook" ambrooktice of the present invention will employ, unless otherwise indiCell Biology, Pringle et al., eds., Cold Spring Harbor Laboratory Press (1997); The Yeast Saccharomyces: Gene Expressioane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, NY (jointly referred to herein as "Harlow and Lane"), Beaucage et al. eds., Current Protocols in Nucleic Acid Chemistry John Wiley & Sons, Inc., New York, 2000); Casarett and Doull's Toxicology The Basic Science of Poisons, C. Klaassen, ed., 6th edition (2001), and Vaccines, S. Plotkin and W. Orenstein, eds., 3rd edition (1999).

EXAMPLES

Example 1. Design, Construction and Testing of the cAMP Sensor

A. An enhanced fluorescent green protein (EFGP) was circularly permuted using the methods described in Sambrook, Joseph, Edward F. Fritsch, and Tom Maniatis. Molecular cloning. Vol. 2. New York: Cold spring harbor laboratory press, 1989; and Baird et al., 1999. The sequence of the resulting circularly permuted green fluorescent protein (cpEGFP) is represented by SEQ ID NO:39. The sequence LE was then added to the N-terminal end of the cpEGFP and the sequence TR was added to the C-terminal end of the cpEGFP. The cpEGFP, obtaining the linker sequences, was then inserted at various locations within the sequence of an Epac2 protein (SEQ ID NO:36), resulting in 28 unique prototype sensors. Nucleic acid molecules encoding each construct were cloned into a modified CMV expression plasmid based on pcDNA3 (Life Technologies (Grand Island, NY))

To test the functionality of these 28 prototype sensors, each construct was co-expressed with the beta adrenergic receptor, which couples to the Gs signaling pathway when activated by isoproteronol, in HEK 293 cells, and the fluorescence measured as described below. Briefly, 96-well glass-bottom plates were coated with Poly-D-Lysinc (Fisher Scientific, Pittsburg, PA) and HEK 293 were seeded and cultured in EMEM (ATCC, Manassas, VA) supplemented with 10% fetal bovine serum and Penicillin-Streptomycin at 37hen activated by isoproteronol, in HEK 293 cells, and the fluorescence tract DNA and 30 ng of beta adrenergic receptor per well, using Lipofectamine 2000 Transfection Reagent (Life Technologies, Grand Island, NY) according to the manufacturer's protocol, and incubated for 24-48 hours at 37° C. in 5% CO2.

Prior to screening transfected cells for fluorescence, he EMEM culture medium was removed and 1×DPBS added to each well. A Zeiss Axiovert S100TV inverted microscope equipped with computer controlled excitation/emission filter wheels, shutters, and a Qimaging Retiga Exi CCD camera (Surrey, BC Canada) was used to image cells at 25e A) supplemented with 10% fetal bovine serum and Penicillin-Streptomycin at 37 hn filters were used to resolve the green fluorescence from the cAMP sensors. Cells were analyzed for increases or decreases in fluorescence intensity upon addition of isoproternol, DMSO, forskolin and IBMX. To analyze the image stacks, background fluorescence was defined as a region of the image that contained no cells. The average value of this region was subtracted frame by frame from the measurements of the mean pixel values of the fluorescent cells. Fluorescence intensity data was plotted and analyzed with IGOR (Wavemetrics, Oswego, OR).

For transient expression and screening in an automated fluorescence plate reader, HEK 293T cells were cultured in Corning Co-Star Polystyrene 96-well plates coated with Poly-D-Lysine. HEK293T cells were plated at 35,000 cells/well in 100 μl growth medium per well without antibiotics so that the cells would be 90-95% confluent at the time of transfection (approximately 24 hours later). For each transfection (i.e. one well in a 96-well plate), 160 ng of plasmid DNA (120 ng sensor+40 ng receptor) was diluted in 25 HEK 293T cells were cultured in Corning Co-Star Polystyrene 96-well plates coated with Poly-D-Lysine. HEK293T cells were plated at 35,000 cells/well in 100 screening in an automated and then the mixture was replaced with fresh medium. Prior to scanning a plate on the Biotek Synergy Mx, EMEM culture medium was replaced with 250 μl of 1× DPBS per well. Plates were read at 25° C., using monochromators set to 488/20 nm excitation and 530/20 nm emission to resolve the green fluorescence from the cAMP sensor.

The results of these analyses are shown below in Table 2.

TABLE 2

Relative fluorescence response of various cAMP sensors to isoproternol

| Clone Name | dF/F | Fluorescent Protein insertion site |
|---|---|---|
| EcpG1 | no response | D449 |
| EcpG2 | no response | K450 |
| EcpG3 | no response | E451 |
| EcpG4 | no response | D452 |
| EcpG5 | no response | F453 |
| EcpG6 | no response | N454 |
| EcpG7 | no response | R455 |
| EcpG8 | no response | I456 |
| EcpG9 | 13 | L457 |
| EcpG10 | −30 | R458 |
| EcpG11 | no response | D459 |
| EcpG12 | −36 | V460 |
| EcpG13 | −22 | E461 |
| EcpG14 | no response | A462 |
| EcpG15 | 34 | N463 |
| EcpG16 | no response | E478 |
| EcpG18 | 12 | A486 |
| EcpG19 | no response | G490 |
| EcpG20 | no response | P494 |
| EcpG21 | no response | L648 |
| EcpG22 | −14% | V341 |
| EcpG23 | −16 | L518 |
| EcpG24 | −11 | A520 |
| EcpG25 | no response | Q557 |
| EcpG26 | no response | L592 |
| EcpG27 | no response | I616 |
| EcpG28 | no response | L619 |

As shown above in Table 2, of the 28 prototype sensors tested, nine produced detectable changes in fluorescence in response to drug application. Three of these produced greater than 30% change in fluorescence: EcpG10, EcpG12, and EcpG15. Some sensors increased fluorescence in response to drug and some sensors decreased fluorescence in response to drug. The three prototype sensors with the largest signal maintained their fluorescence and change in fluorescence when the N-terminus of Epac was truncated, removing all the amino acids upstream of P324.

B. Two variants of cpEGFP were created by using linkers other than LE and TR. In one variant, the sequence LVSH was added to the N-terminal end of the cpEGFP and the sequence FNNP added to the C-terminal end. In the second variant, the sequence SH was added to the N-terminal end and the sequence FN added to the C-terminal end. These two cpEGFP variants were inserted into three positions within Epac2, which were identified in part A as yielding the greatest change in fluorescence. These insertions resulted in six new sensors, which were tested as described in part A. The best of these produced a 60% change in fluorescence in response to drug.

C. Additional sensor variants were produced by mixing the N and C terminal portions of the variants described in part B. Briefly, the N-terminal half and C-terminal halves of each of the variant sensor constructs was amplified by using primers hybridizing to the middle of the cpEGFP and the ends of the sensor constructs. The different N-terminal halves were combined systematically with the C-terminal halves using In-Fusion cloning, resulting in six new sensors Some of these sensors, as well as some of the original 28 prototype sensors were used as templates to create more PCR products of the N-terminal and C-terminal halves of the sensors. All of these halves were put into an In-Fusion reaction to c create a library of randomly assembled sensors. This resulted in three new libraries (libraries 1-3), from which a total of 138 sensors were screened as described in part A. Two additional libraries (libraries 4 and 5) were created by applying the above-described shuffling method to the original templates as well as the best sensors from the first two libraries. Forty-three of these sensors were screened and several gave large changes in fluorescence, up to a 61% increase or 53% decrease.

D. Additional sensor variants were produced using a random mutagenesis technique. Briefly, purified PCR product amplified from cpEGFP, without linkers, were used as the template for a PCR reaction using degenerate primers. The degenerate primers added two amino acids to each end of cpEGFP. Since the primers were degenerate at those positions, the resulting population of PCR products contained differing amino acid combinations at each end of the cpEGFP. These PCR products were then inserted into position 10 of the Epac2 protein, resulting in another library of cAMP sensors, seven of which were screened. The best of these, Lib6-2 Cl, produced a 30% change in fluorescence.

E. Additional cAMP sensors were created in which the first and second polypeptides were obtained from different (i.e., unrelated) proteins. Briefly, one end of cpEGFP was joined to Epac2 while the other end was joined to Rap1B. This design tethers a single circularly permuted green fluorescent protein between Epac2 and the small GTPase Rap1B (Rehmann et.al. 2008), such that the cAMP-dependent interaction between these two proteins produces a change in fluorescence. The general structure of such a sensor is illustrated in FIG. 1D. The best of these sensors had a 25% increase in fluorescence in response to drug.

Table 3 below lists the 34 best performing sensors identified from the studies described above n paragraphs 1A-1E:

TABLE 3

Relative Change in fluorescence in Response to Isoproternol

| Clone Name | Relative Change in Fluorescence | Sequence of Clone |
|---|---|---|
| EcpG10 G2-RasGEF-T2 | 110% | SEQ ID NO: 1 |
| Library 2-1 G12 | 73% | SEQ ID NO: 2 |
| Lib2-1 G12-RasGEF-T2 | 74% | SEQ ID NO: 3 |
| Library 4-2 B1 | 61% | SEQ ID NO: 4 |
| EcpG10 G2 | 60% | SEQ ID NO: 5 |
| Library 2-2 E7 | −53% | SEQ ID NO: 6 |
| Lib6-2 C1-T2 | −40% | SEQ ID NO: 7 |
| Library 5-1 D2 | 39% | SEQ ID NO: 8 |
| Library 5-1 G12 | −39% | SEQ ID NO: 9 |
| Library 2-1 B12 | −37% | SEQ ID NO: 10 |
| Library 1 C2 | 36% | SEQ ID NO: 11 |
| EcpG12 | −36% | SEQ ID NO: 12 |
| Library 2-2 F9 | −36% | SEQ ID NO: 13 |
| Library 2-2 G4 | −36% | SEQ ID NO: 14 |
| Library 2-1 C2 | 35% | SEQ ID NO: 15 |
| Library 5-1 E7 | −34% | SEQ ID NO: 16 |
| Library 6-2 C1 | −34% | SEQ ID NO: 17 |
| EcpG15 | 34% | SEQ ID NO: 18 |
| Library 2-2 D1 | −33% | SEQ ID NO: 19 |
| Library 2-2 A11 | 33% | SEQ ID NO: 20 |
| Library 2-2 A5 | −33% | SEQ ID NO: 21 |
| Library 2-1 D1 | 33% | SEQ ID NO: 22 |
| Library 1 G2 | 33% | SEQ ID NO: 23 |
| Library 1 A6 | −33% | SEQ ID NO: 24 |
| Library 6-2 F1 | 30% | SEQ ID NO: 25 |
| EcpG10 | −30% | SEQ ID NO: 26 |
| EcpG10 G2N-G1C | −28% | SEQ ID NO: 27 |
| EPAC2gfpRAP1B | 26% | SEQ ID NO: 28 |
| EcpG13 | −22% | SEQ ID NO: 29 |
| EcpG23 | −16% | SEQ ID NO: 30 |
| EcpG9 | 13% | SEQ ID NO: 31 |
| EcpG22 | −14% | SEQ ID NO: 32 |
| EcpG18 | 12% | SEQ ID NO: 33 |
| EcpG24 | −11% | SEQ ID NO: 34 |

Figure 3:
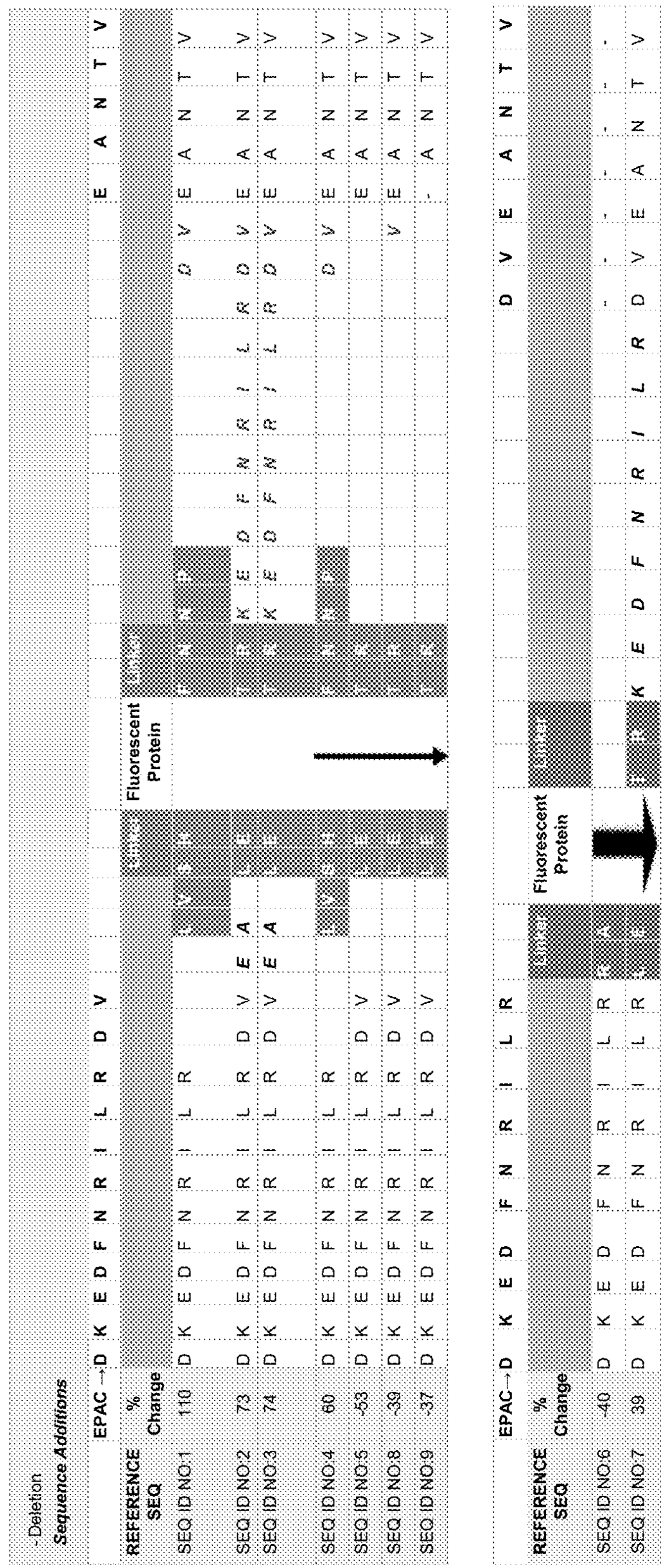
FIG. 3 Amino acid sequences surrounding the site of single FP insertion in nine embodiments. Column labeled ming cAMP sensorsding theaverage change in fluorescence relative to the baseline fluorescence observed prior to stimulation of the cells with drug.
Figure 4:
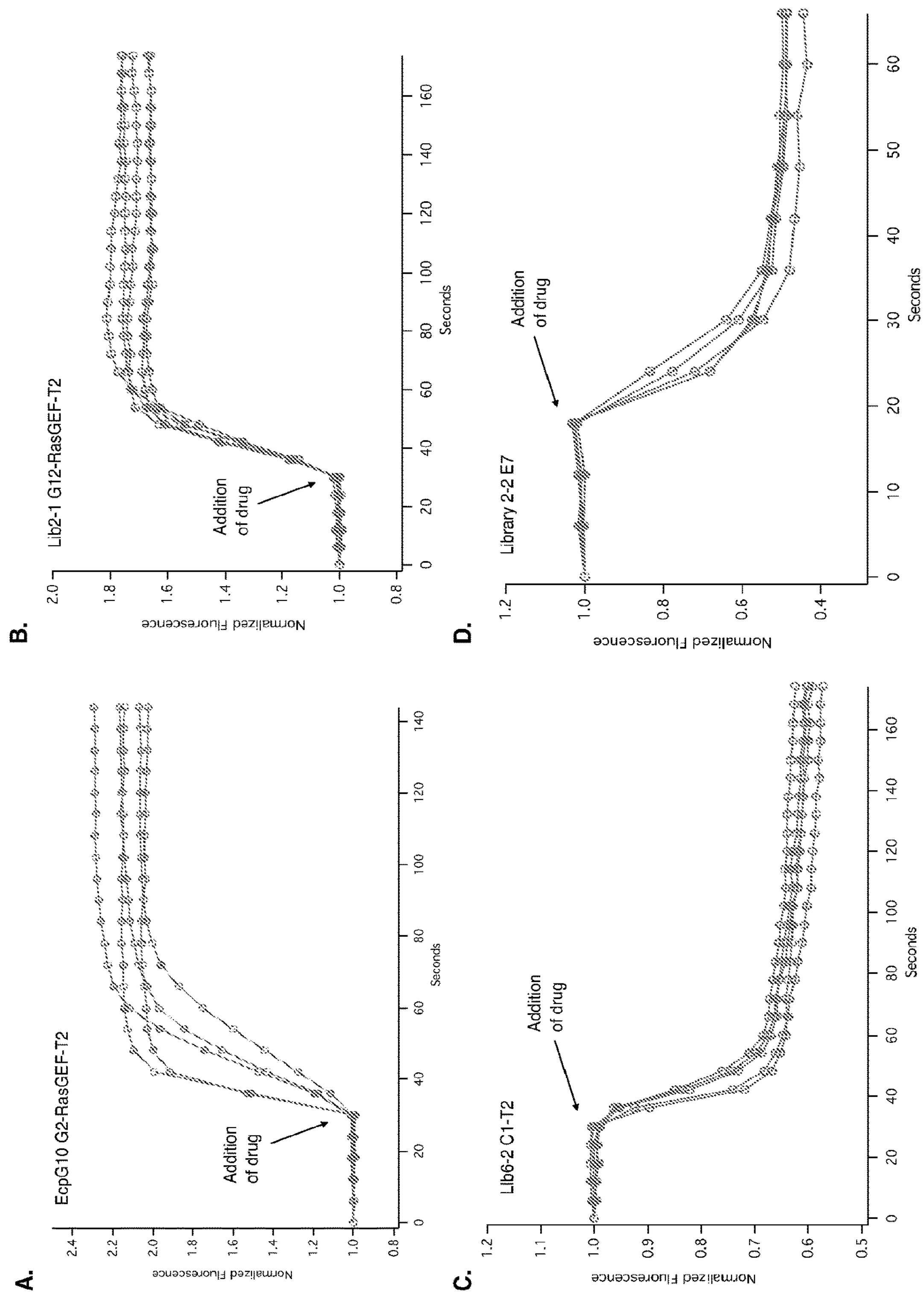
FIG. 4 Normalized response of four embodiments [(A) EcpG10 G2-RasGEF-T2 (SEQID_1); (B) Lib2-1 G12 RasGEF-T2 (SEQID 3); (C) Lib6-2 C1 T2 (SEQID 6); (D) Lib2-2 E7 (SEQID_5)] to 50 um isoproterenol. Cells transfected with an expression vector encoding each cAMP sensor protein constructed according to the disclosed methods, and then stimulated with isoproterenol, a specific ligand for the beta adrenergic GPCR. Receptor activation leads to increased cAMP production detected as a fluorescence change.
Figure 5:
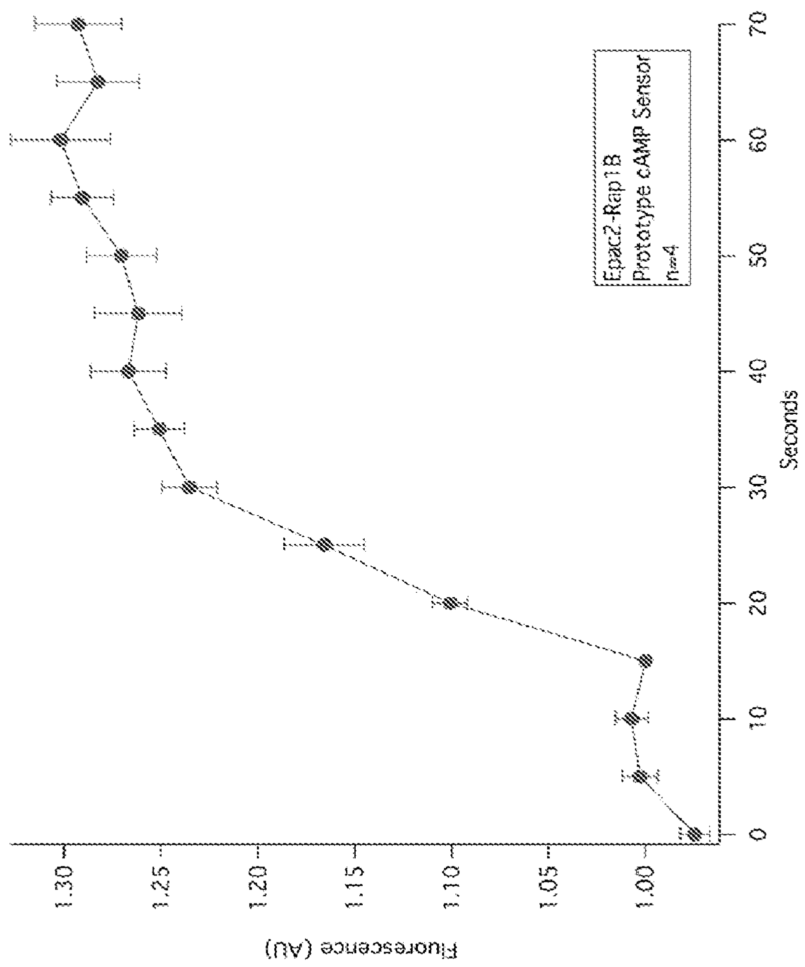
FIG. 5 Average response for a green cAMP Epac2-Rap1B sensor designed to detect pathway activation by way of the interaction between Epac2 and Rap 1B. Response shown follows stimulation with 50 um isoproterenol, a specific ligand for the beta adrenergic GPCR.

F. Nine sensors identified in the studies described above were analyzed to determine the amino acid sequence of the site of insertion. The amino acid sequences around the insertion site in each sensor are listed in FIG. 3.

Example 2. Multiplexing of a cAMP Sensor Protein

The ability of cAMP sensor proteins of the present invention to be multiplexed with other fluorescence based sensors was tested. Briefly, cells were co-transfected with expression vector expressing a cAMP sensor protein of the present invention comprising a green fluorescent protein, and a DAG biosensor comprising a red fluorescent protein. The cells were cultured, treated with isoptroterenol and the resulting fluorescence measured as described in Example 1A. The results of this study are show in FIG. 6.

Figure 6:
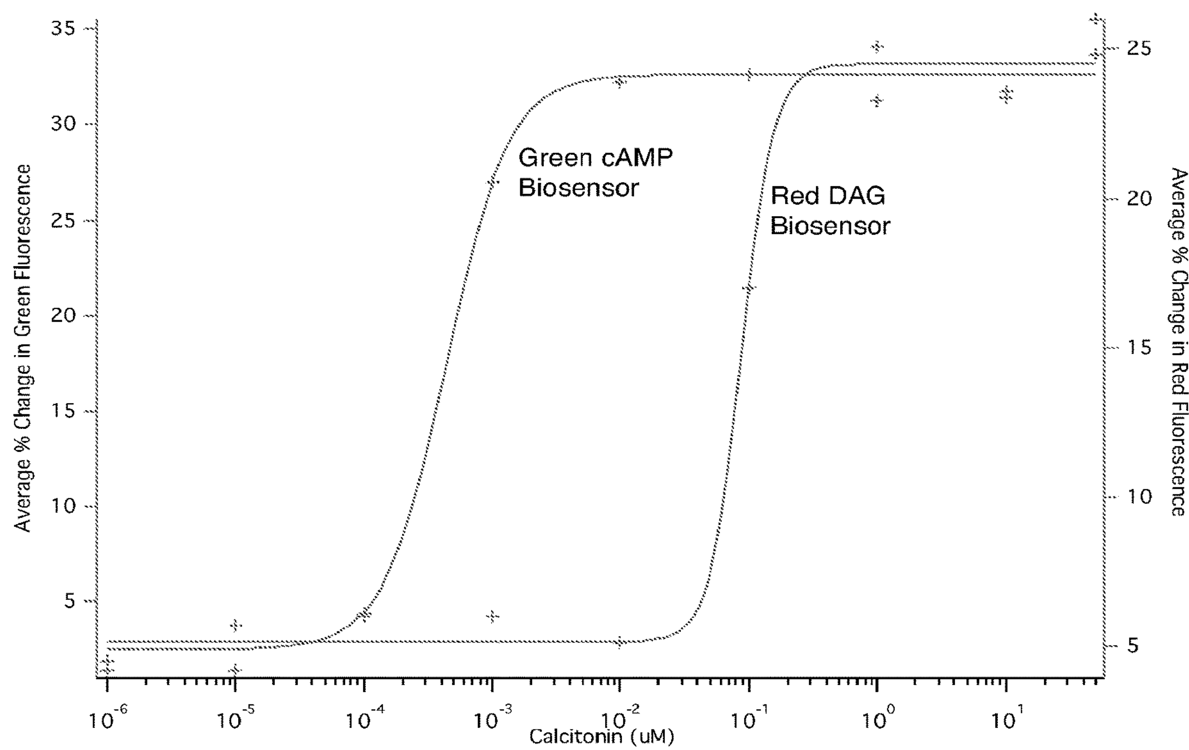
FIG. 6 Multiplexing of a cAMP biosensor based on a single fluorescent protein with a second biosensor of a different color. The G-protein coupled calcitonin receptor was stimulated with different amounts of calcitonin (shown on the X axis) to produce response curves for a red cAMP and a green DAG sensor. The Y axis on the right indicates cAMP response. The Y axis on the left indicates DAG response.

FIG. 6 illustrates how a pair of different colored sensors can be combined to detect the concentration dependent coupling of a receptor to one or more than one pathway. In this case the green cAMP sensor shows that low concentrations of calcitonin can stimulate just one G-protein pathway, while higher concentrations of the agonist produce changes in both cAMP sensor green fluorescence and DAG sensor red fluorescence in the same cells, indicating that two different G-protein pathways have been activated. The results demonstrate that cAMP sensor proteins of the present invention can be multiplexed with sensors comprised of fluorescent proteins with different spectral properties. Multiplexing enables the detection of multiple second messengers and can be used to detect pathway selectivity and agonist (ligand) bias.

Example 3. Multiplexing Using a PIP Sensor

Additional multiplexing studies were done using a red PIP2 sensor to indicate signaling of the Gq pathway. The studies were conducted as described in Example 2. The results of these studies are show in FIG. 7.

Figure 7:
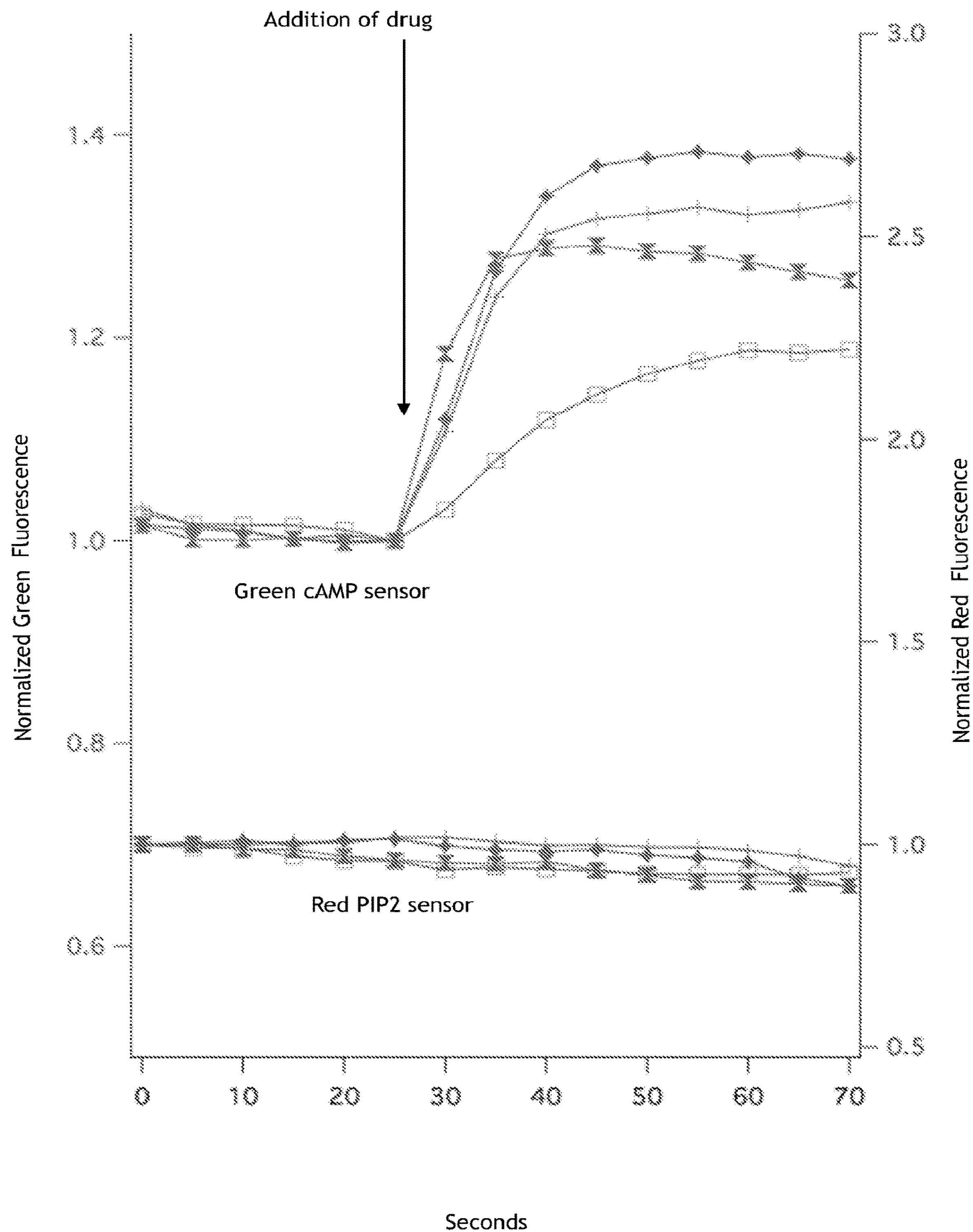
FIG. 7 Multiplexing a red PIP2 sensor (Gq signaling indicator) with the green cAMP sensor indicates a receptor and ligand that signal exclusively via the Gs pathway. The left hand Y axis is the cAMP green fluorescence normalized to the resting state of the cells before stimulation, the right hand axis is of the red fluorescence of the PIP2 sensor.

FIG. 7 illustrates that co-expression of two different colored sensors can be used to determine whether just one pathway is activated. The change in green fluorescence of the cAMP sensor indicates that stimulation of the Beta adrenergic receptor in these cells only produces a change in the activity of adenyl cyclase, presumably through Gs, and it does not signal through the Gq and phospholipase C pathway which can be seen in the red fluorescence.

Example 4. Use of the cAMP Sensor Protein in a Multiplate Assay

The ability of a cAMP sensor potein to be used in a multiplate, drug screening assay was tested. The resutls are shown in FIG. 8.

Figure 8:
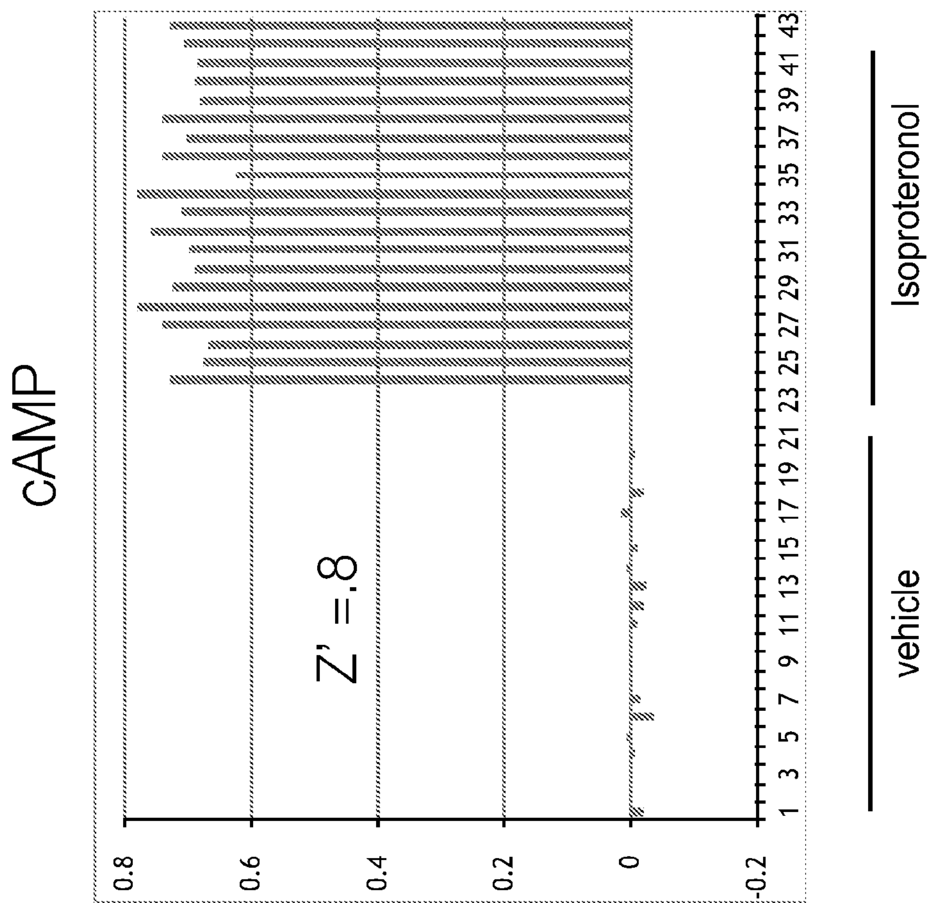
FIG. 8 Live cells expressing one of the fluorescent protein sensors for cAMP described in this invention. Change in fluorescence measured on a standard fluorescence plate reader (Biotek Synergy), five minutes after activating beta adrenergic receptors with 50 uM isoproteronol compared with PBS (vehicle).

FIG. 8 shows the response of one embodiment of the invention that decreases fluorescence in response to an increase in cAMP concentration, following activation of the Gs-coupled beta adrenergic receptor by isoproterenol. This data demonstrates that the cAMP sensor protein produces a consistent, reproducible signal (Z'>0.82) on a standard fluorescence plate reader. Thus, cAMP sensor proteins described herein are robust enough for automated drug screening using a fluorescent plate reader.

REFERENCES

Alford, S. C., Abdelfattah, A. S., Ding, Y., and Campbell, R. E. (2012a). A Fluorogenic Red Fluorescent Protein Heterodimer. Chem. Biol. 19, 353-360.

Alford, S. C., Ding, Y., Simmen, T., and Campbell, R. E. (2012b). Dimerization-Dependent Green and Yellow Fluorescent Proteins. ACS Synth. Biol. 1, 569iment Almholt, K., Tullin, S., Skyggebjerg, O., and Scudder, K. (2004). Changes in intracellular cAMP reported by a Redistribution® assay using a cAMP-dependent protein kinase-green fluorescent protein chimera. Cellular Signalling 16, 907-920.

Altschul, S. F., Madden, T. L., Scherg, O., and Scudder, K. (2004). Changes in intracellular cAMP r (1997). Gapped BLAST and PSI-BLAST: a new generation of protein database search programs. Nucleic Acids Research 25, 3389ST: a Akerboom, J., Chen, T.-W., Wardill, T. J., Tian, L., Marvin, J. S., Mutlu, S., Calderellular cAMP r (1997). Gapped BLAST and PSI-BX.R., et al. (2012). Optimization of a GCaMP Calcium Indicator for Neural Activity Imaging. J. Neurosci. 32, 13819 Calciu Akerboom, J., Rivera, J. D. V., Guilbe, M. M. R., Malay Marvin, J. S., Mutlu, S., Calderellular cAMP r (1997). Gapped BLAST and PSI-BX.R., Schreiter, E. R. (2009). Crystal Structures of the GCaMP Calcium Sensor Reveal the Mechanism of Fluorescence Signal Change and Aid Rational Design. Journal of Biological Chemistry 284, 6455GCaMP Ausubel, F. et al., Current Protocols in Molecular Biology, John Wiley & Sons, New York, N.Y., (1998).

Baird, G. S., Zacharias, D. A., and Tsien, R. Y. (1999). Circular permutation and receptor insertion within green fluorescent proteins. Proceedings of the National Academy of Sciences 96, 11241Calcium Berkner, K. L., Schaffhausen, B. S., Roberts, T. M., and Sharp, P. A. (1987). Abundant expression of polyomavirus middle T antigen and dihydrofolate reductase in an adenovirus recombinant. J. Virol. 61, 1213 of po Binkowski, B. F., Butler, B. L., Stecha, P. F., Eggers, C. T., Otto, P., Zimmerman, K., Vidugiris, G., Wood, M. G., Encell, L. P., Fan, F., et al. (2011). A Luminescent Bioscnsor with Increased Dynamic Range for Intracellular cAMP. ACS Chem. Biol. 6, 1193od, M.

Carlson, H. J., Cotton, D. W., and Campbell, R. E. (2010). Circularly permuted monomeric red fluorescent proteins with new termini in the β-sheet. Protein Science 19, 1490eric r Coffin, J. M., Hughes, S. H., Varmus, H. E., Coffin, J. M., Hughes, S. H., and Varmus, H. E. (1997). The Interactions of Retroviruses and their Hosts (Cold Spring Harbor (NY): Cold Spring Harbor Laboratory Press).

Chou, P. Y., and Fasman, G. D. (1978). Prediction of the secondary structure of proteins from their amino acid sequence. Adv. Enzymol. Relat. Areas Mol. Biol. 47, 45 (NY)

Davidson, D., and Hassell, J. A. (1987). Overproduction of polyomavirus middle T antigen in mammalian cells through the use of an adenovirus vector. J. Virol. 61, 1226olyoma Haj-Ahmad, Y., and Graham, F. L. (1986). Development of a helper-independent human adenovirus vector and its use in the transfer of the herpes simplex virus thymidine kinase gene. J. Virol. 57, 267elper Held, P., Banks, P., Tewson, P., Quinn, A. M., Hughes, T. (2014) Live Cell Imaging of GPCR Dependent Second-Messenger Systems Using the Cytation™ 3 Cell Imaging Multi-Mode Reader to Image Genetically Encoded GPCR Reactive Sensors in Real Time. BioTek Application note. http://www.biotek.com/assets/tech_resources/Montana%20Molecular_App_Note.pdf Hong, K., Spitzer, N. C., and Nicol, X. (2011). Improved molecular toolkit for cAMP studies in live cells. BMC Res Notes 4, 241.

Jiang, L. I., Collins, J., Davis, R., Lin, K.-M., DeCamp, D., Roach, T., Hsueh, R., Rebres, R. A., Ross, E. M., Taussig, R., et al. (2007). Use of a cAMP BRET sensor to characterize a novel regulation of cAMP by the sphingosine 1-phosphate/G13 pathway. J. Biol. Chem. 282, 10576., Ross Kenakin, T., and Christopoulos, A. (2013). Signalling bias in new drug discovery: detection, quantification and therapeutic impact. Nat Rev Drug Discov 12, 205sor t Kitaguchi, T., Oya, M., Wada, Y., Tsuboi, T., and Miyawaki, A. (2013). Extracellular calcium influx activates adenylate cyclase 1 and potentiates insulin secretion in MIN6 cells. Biochem. J. 450, 365f cAM Klarenbeck, J. B., Goedhart, J., Hink, M. A., Gadclla, T. W. J., and Jalink, K. (2011). A mTurquoise-Based cAMP Sensor for Both FLIM and Ratiometric Read-Out Has Improved Dynamic Range. PloS One 6, e19170.

Kost, T. A., Condreay, J. P., and Jarvis, D. L. (2005). Baculovirus as versatile vectors for protein expression in insect and mammalian cells. Nature Biotechnology 23, 567ors f Kredel, S., Nienhaus, K., Oswald, F., Wolff, M., Ivanchenko, S., Cymer, F., Jeromin, A., Michel, F. J., Spindler, K.-D., Heilker, R., et al. (2008). Optimized and Far-Red-Emitting Variants of Fluorescent Protein eqFP611. Chem. Biol. 15, 224-233.

Kyte, J., and Doolittle, R. F. (1982). A simple method for displaying the hydropathic character of a protein. Journal of Molecular Biology 157, 105. Opt Lam, A. J., St-Pierre, F., Gong, Y., Marshall, J. D., Cranfill, P. J., Baird, M. A., McKeown, M. R., Wiedenmann, J., Davidson, M. W., Schnitzer, M. J., et al. (2012). Improving FRET dynamic range with bright green and red fluorescent proteins. Nature Methods 9, 1005range Ledford, H. (2013). Bioengineers look beyond patents Nature 499, 16-17.

Massie, B., Gluzman, Y., and Hassell, J. A. (1986). Construction of a helper-free recombinant adenovirus that expresses polyomavirus large T antigen. Molecular and Cellular Biology 6, 2872c with Nagai, T., Sawano, A., Park, E. S., and Miyawaki, A. (2001). Circularly permuted green fluorescent proteins engineered to sense Ca2. Proceedings of the National Academy of Sciences 98, 3197 with Nakai, J., Ohkura, M., and Imoto, K. (2001). A high signal-to-noise Ca(2+) probe composed of a single green fluorescent protein. Nature Biotechnology 19, 137137or Nikolacv, V. O., B, M., and Imoto, K. (2001). A high signal-to-noise Ca(2+) probe composed of a single green fluorescent protein. Nature Biotechnology 19, 137-141.ademy of Sciences 97218.

Ormolaev, V. O., B, M., and Imoto, K. (2001). A high signal-to-noise Ca(2+) probe composed of a single green fluorescent protein. Nature Biotechnology 19, 137137re Biotechnology 19, 13

Pletnev, S., Shcherbo, D., Chudakov, D. M., Pletneva, N., Merzlyak, E. M., Wlodawer, A., Dauter, Z., and Pletnev, V. (2008). A crystallographic study of bright far-red fluorescent protein mKate reveals pH-induced cis-trans isomerization of the chromophore. J. Biol. Chem. 283, 28980merizat Ponsioen, B., Zhao, J., Riedl, J., Zwartkruis, F., van der Krogt, G., Zaccolo, M., Moolenaar, W. H., Bos, J. L., and Jalink, K. (2004). Detecting cAMP-induced Epac activation by fluorescence resonance energy transfer: Epac as a novel cAMP indicator. EMBO Rep. 5, 1176-1180.

Prinz, A., Diskar, M., Erlbruch, A., and Herberg, F. W. (2006). Novel, isotype-specific sensors for protein kinase A subunit interaction based on bioluminescence resonance energy transfer (BRET). Cell. Signal. 18, 1616pac as Rehmann, H., Arias-Palomo, E., Hadders, M. A., and Schwede, F. (2008). Structure of Epac2 in complex with a cyclic AMP analogue and RAP1B. Nature.

Rehmann, H., Das, J., Knipscheer, P., and Wittinghofer, A. (2006). Structure of the cyclic-AMP-responsive exchange factor Epac2 in its auto-inhibited state. Nature.

Salonikidis, P. S., Niebert, M., Ullrich, T., Bao, G., Zeug, A., and Richter, D. W. (2011). An Ion-insensitive cAMP Biosensor for Long Term Quantitative Ratiometric Fluorescence Resonance Energy Transfer (FRET) Measurements under Variable Physiological Conditions. Journal of Biological Chemistry 286, 23419Term Qu Shcherbo, D., Souslova, E. A., Goedhart, J., Chepurnykh, T. V., Gaintzeva, A., Shemiakina, I. I., Gadella, T. W., Lukyanov, S., and Chudakov, D. M. (2009). Practical and reliable FRET/FLIM pair of fluorescent proteins. BMC Biotechnology 9, 24.

Shaner, N. C., Steinbach, P. A., and Tsien, R. Y. (2005). A guide to choosing fluorescent proteins. Nature Methods 2, 905, S., Shaner, N. C., Lin, M. Z., McKeown, M. R., Steinbach, P. A., Hazelwood, K. L., Davidson, M. W., and Tsien, R. Y. (2008). Improving the photostability of bright monomeric orange and red fluorescent proteins. Nature Methods 5, 545bilit Shaner, N. C., Lambert, G. G., Chammas, A., Ni, Y., Cranfill, P. J., Baird, M. A., Sell, B. R., Allen, J. R., Day, R. N., Israelsson, M., et al. (2013). A bright monomeric green fluorescent protein derived from Branchiostoma lanceolatum. Nat Meth 10, 407-409.

Shui, B., Wang, Q., Lee, F., Byrnes, L. J., Chudakov, D. M., Lukyanov, S. A., Sondermann, H., and Kotlikoff, M. I. (2011). Circular Permutation of Red Fluorescent Proteins. PloS One 6, e20505.

Subach, O. M., Gundorov, I. S., Yoshimura, M., Subach, F. V., Zhang, J., Gr., Sondermann, H., and Kotlikoff, M. I. (2011). Circular Permutation of ReConversion of Red Fluorescent Protein into a Bright Blue Probe. Chem. Biol. 15, 1116of ReC Tcwson, P., Westcnberg, M., Zhao, Y., Campbell, R. E., Quinn, A. M., and Hughes, T. E. (2012). Simultaneous Detection of Ca2+ and Diacylglycerol Signaling in Living Cells. PloS One 7, e42791.

Topell, S., Hennecke, J., and Glockshuber, R. (1999). Circularly permuted variants of the green fluorescent protein. FEBS Lett. 457, 283cerol Tsutsui, H., Karasawa, S., Okamura, Y., and Miyawaki, A. (2008). Improving membrane voltage measurements using FRET with new fluorescent proteins. Nature Methods 5, 683-685.

Willoughby, D., and Cooper, D. (2007). Live-cell imaging of cAMP dynamics. Nature Methods 5, 29-36.

Woehler, A., Wlodarczyk, J., and Neher, E. (2010). Signal/Noise Analysis of FRET-Based Sensors. Biophysical Journal 99, 2344ET-Bas Xu, Y., Piston, D. W., and Johnson, C. H. (1999). A bioluminescence resonance energy transfer (BRET) system: application to interacting circadian clock proteins. Proc. Natl. Acad. Sci. U.S.a. 96, 151Blue Zaccolo, M., De Giorgi, F., Cho, C. Y., Feng, L., Knapp, T., Negulescu, P. A., Taylor, S. S., Tsien, R. Y., and Pozzan, T. (2000). A genetically encoded, fluorescent indicator for cyclic AMP in living cells. Nat. Cell Biol. 2, 251116

Zaccolo, M., and Pozzan, T. (2002). Discrete microdomains with high concentration of cAMP in stimulated rat neonatal cardiac myocytes. Science.

Zhao, Y., Araki, S., Wu, J., Teramoto, T., Chang, Y. F., Nakano, M., Abdelfattah, A. S., Fujiwara, M., Ishihara, T., Nagai, T., et al. (2011). An Expanded Palette of Genetically Encoded Ca2+ Indicators. Science 333, 1888e of G Zhang, W. W., Fang, X., Branch, C. D., Mazur, W., French, B. A., and Roth, J. A. (1993). Generation and identification of recombinant adenovirus by liposome-mediated transfection and PCR analysis.

Zhang, J., Ma, Y., Taylor, S. S., and Tsien, R. Y. Genetically encoded reporters of protein kinase A activity reveal impact of substrate tethering. Proceedings of the National Academy of Sciences 98, 14997ience 3

What is claimed:

1. A cyclic adenosine monophosphate (cAMP) sensor protein comprising a first polypeptide linked to a single circularly permuted fluorescent protein, wherein the first polypeptide comprises at least 100 contiguous amino acids from the amino acid sequence of SEQ ID NO:35, and wherein binding of cAMP to the first polypeptide alters the level of fluorescence from the single circularly permuted fluorescent protein.

2. The cAMP sensor protein of claim 1, wherein the single circularly permuted fluorescent protein comprises an amino acid sequence having a circular permutation of an amino acid sequence that is at least 95% identical to a protein selected from the group consisting of GFP, eGFP, eYFP, Emerald, mApple, mPlum, mCherry, tdTomato, mStrawberry, J-Red, DsRed-monomer, mOrange, MKO, mCitrine, Venus, YPet, CyPet, mCFPm, Cerluean, T-Sapphire, mKOK, mUKG, Clover, mKate, tagRFP, tagGFP, mNEON green, and a synthetic non-Aequorea fluorescent protein.

3. The cAMP sensor protein of claim 1, further comprising a linker between the first polypeptide and the fluorescent protein.

4. The cAMP sensor protein of claim 1, wherein the protein comprises an amino acid sequence at least 90% identical to an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33.

5. The cAMP sensor protein of claim 1 further comprising a second polypeptide, wherein the second polypeptide is linked to the fluorescent protein, such that the fluorescent protein is flanked by the first and second polypeptides.

6. The sensor of claim 5, further comprising a first linker sequence between the fluorescent protein and the first or second polypeptide.

7. The sensor of claim 5, further comprising a first linker sequence between the first polypeptide and the fluorescent protein, and a second linker sequence between the second polypeptide and the fluorescent protein.

8. A cyclic adenosine monophosphate (cAMP) sensor protein comprising a first polypeptide linked to a single circularly permuted fluorescent protein, wherein the first polypeptide comprises an amino acid sequence at least 90% identical to the amino acid sequence of SEQ ID NO:35, and wherein binding of cAMP to the CAMP-binding-site first polypeptide alters the level of fluorescence from the single circularly permuted fluorescent protein.

9. The cAMP sensor protein of claim 8, wherein the single circularly permuted fluorescent protein comprises an amino acid sequence having a circular permutation of an amino acid sequence that is at least 95% identical to a protein selected from the group consisting of GFP, cGFP, eYFP, Emerald, mApple, mPlum, mCherry, tdTomato, mStrawberry, J-Red, DsRed-monomer, mOrange, MKO, mCitrine, Venus, YPet, CyPet, mCFPm, Cerluean, T-Sapphire, mKOK, mUKG, Clover, mKate, tagRFP, tagGFP, mNEON green, and a synthetic non-Aequorea fluorescent protein.

10. The cAMP sensor protein of claim 8, further comprising a linker between the first polypeptide and the fluorescent protein.

11. The cAMP sensor protein of claim 8 further comprising a second polypeptide, wherein the second polypeptide is linked to the fluorescent protein, such that the fluorescent protein is flanked by the first and second polypeptides.

12. The cAMP sensor of claim 11, further comprising a first linker sequence between the fluorescent protein and the first or second polypeptide.

13. The cAMP sensor of claim 11, further comprising a first linker sequence between the first polypeptide and the fluorescent protein, and a second linker sequence between the second polypeptide and the fluorescent protein.

14. The cAMP sensor of claim 11, wherein the first polypeptide comprises an amino acid sequence at least 90% identical to the amino acid sequence of SEQ ID NO:36 or 37.

15. The cAMP sensor of claim 11, wherein the first polypeptide comprises at least 100 contiguous amino acids from the amino acid sequence of SEQ ID NO:36 or 37.

16. The CAMP sensor of claim 1, wherein the first polypeptide comprises an amino acid sequence at least 90% identical to the amino acid sequence of SEQ ID NO:36 or 37.

17. The cAMP sensor of claim 1, wherein the first polypeptide comprises at least 100 contiguous amino acids from the amino acid sequence of SEQ ID NO:36 or 37.

* * * * *

SEQUENCE LISTING

```
<160> NUMBER OF SEQ ID NOS: 77

<210> SEQ ID NO 1
<211> LENGTH: 739
<212> TYPE: PRT
```

<213> ORGANISM: Artificial Sequence
<220> FEATURE:
<223> OTHER INFORMATION: Synthetic

<400> SEQUENCE: 1

Met Gly Ser Asn Asn Asp Arg Ile Pro Asp Lys Glu Asn Thr Pro Leu
1 5 10 15

Ile Glu Pro His Val Pro Leu Arg Pro Ala Asn Thr Ile Thr Lys Val
20 25 30

Pro Ser Glu Lys Ile Leu Arg Ala Gly Lys Ile Leu Arg Asn Ala Ile
35 40 45

Leu Ser Arg Ala Pro His Met Ile Arg Asp Arg Lys Tyr His Leu Lys
50 55 60

Thr Tyr Arg Gln Cys Cys Val Gly Thr Glu Leu Val Asp Trp Met Met
65 70 75 80

Gln Gln Thr Pro Cys Val His Ser Arg Thr Gln Ala Val Gly Met Trp
85 90 95

Gln Val Leu Leu Glu Asp Gly Val Leu Asn His Val Asp Gln Glu His
100 105 110

His Phe Gln Asp Lys Tyr Leu Phe Tyr Arg Phe Leu Asp Asp Glu His
115 120 125

Glu Asp Ala Pro Leu Pro Thr Glu Glu Glu Lys Lys Glu Cys Asp Glu
130 135 140

Glu Leu Gln Asp Thr Met Leu Leu Leu Ser Gln Met Gly Pro Asp Ala
145 150 155 160

His Met Arg Met Ile Leu Arg Lys Pro Pro Gly Gln Arg Thr Val Asp
165 170 175

Asp Leu Glu Ile Ile Tyr Glu Glu Leu Leu His Ile Lys Ala Leu Ser
180 185 190

His Leu Ser Thr Thr Val Lys Arg Glu Leu Ala Gly Val Leu Ile Phe
195 200 205

Glu Ser His Ala Lys Gly Gly Thr Val Leu Phe Asn Gln Gly Glu Glu
210 215 220

Gly Thr Ser Trp Tyr Ile Ile Leu Lys Gly Ser Val Asn Val Val Ile
225 230 235 240

Tyr Gly Lys Gly Val Val Cys Thr Leu His Glu Gly Asp Asp Phe Gly
245 250 255

Lys Leu Ala Leu Val Asn Asp Ala Pro Arg Ala Ala Ser Ile Val Leu
260 265 270

Arg Glu Asp Asn Cys His Phe Leu Arg Val Asp Lys Glu Asp Phe Asn
275 280 285

Arg Ile Leu Arg Leu Val Ser His Asn Val Tyr Ile Lys Ala Asp Lys
290 295 300

Gln Lys Asn Gly Ile Lys Ala Asn Phe Lys Ile Arg His Asn Ile Glu
305 310 315 320

Asp Gly Gly Val Gln Leu Ala Tyr His Tyr Gln Gln Asn Thr Pro Ile
325 330 335

Gly Asp Gly Pro Val Leu Leu Pro Asp Asn His Tyr Leu Ser Val Gln
340 345 350

Ser Ile Leu Ser Lys Asp Pro Asn Glu Lys Arg Asp His Met Val Leu
355 360 365

Leu Glu Phe Val Thr Ala Ala Gly Ile Thr Leu Gly Met Asp Glu Leu
370 375 380

Tyr Lys Gly Gly Thr Gly Gly Ser Met Val Ser Lys Gly Glu Glu Leu

```
385                 390                 395                 400

Phe Thr Gly Val Val Pro Ile Gln Val Glu Leu Asp Gly Asp Val Asn
                405                 410                 415

Gly His Lys Phe Ser Val Ser Gly Glu Gly Glu Gly Asp Ala Thr Tyr
            420                 425                 430

Gly Lys Leu Thr Leu Lys Phe Ile Cys Thr Thr Gly Lys Leu Pro Val
        435                 440                 445

Pro Trp Pro Thr Leu Val Thr Thr Leu Thr Tyr Gly Val Gln Cys Phe
    450                 455                 460

Ser Arg Tyr Pro Asp His Met Lys Gln His Asp Phe Phe Lys Ser Ala
465                 470                 475                 480

Met Pro Glu Gly Tyr Ile Gln Glu Arg Thr Ile Phe Phe Lys Asp Asp
                485                 490                 495

Gly Asn Tyr Lys Thr Arg Ala Glu Val Lys Phe Glu Gly Asp Thr Leu
            500                 505                 510

Val Asn Arg Ile Glu Leu Lys Gly Ile Asp Phe Lys Glu Asp Gly Asn
        515                 520                 525

Ile Leu Gly His Lys Leu Glu Tyr Asn Phe Asn Asn Pro Asp Val Glu
    530                 535                 540

Ala Asn Thr Val Arg Leu Lys Glu His Asp Gln Asp Val Leu Val Leu
545                 550                 555                 560

Glu Lys Val Pro Ala Gly Asn Arg Ala Ser Asn Gln Gly Asn Ser Gln
                565                 570                 575

Pro Gln Gln Lys Tyr Thr Val Met Ser Gly Thr Pro Glu Lys Ile Leu
            580                 585                 590

Glu His Phe Leu Glu Thr Ile Arg Leu Glu Ala Thr Leu Asn Glu Ala
        595                 600                 605

Thr Asp Ser Val Leu Asn Asp Phe Ile Met Met His Cys Val Phe Met
    610                 615                 620

Pro Asn Thr Gln Leu Cys Pro Ala Leu Val Ala His Tyr His Ala Gln
625                 630                 635                 640

Pro Ser Gln Gly Thr Glu Gln Glu Lys Met Asp Tyr Ala Leu Asn Asn
                645                 650                 655

Lys Arg Arg Val Ile Arg Leu Val Leu Gln Trp Ala Ala Met Tyr Gly
            660                 665                 670

Asp Leu Leu Gln Glu Asp Asp Val Ser Met Ala Phe Leu Glu Glu Phe
        675                 680                 685

Tyr Val Ser Val Ser Asp Asp Ala Arg Met Ile Ala Ala Leu Lys Glu
    690                 695                 700

Gln Leu Pro Glu Leu Glu Lys Ile Val Lys Gln Ile Ser Glu Asp Ala
705                 710                 715                 720

Lys Ala Pro Gln Lys Lys His Lys Val Leu Leu Gln Gln Phe Asn Thr
                725                 730                 735

Gly Asp Glu


<210> SEQ ID NO 2
<211> LENGTH: 1269
<212> TYPE: PRT
<213> ORGANISM: Artificial Sequence
<220> FEATURE:
<223> OTHER INFORMATION: Synthetic

<400> SEQUENCE: 2

Met Val Ala Ala His Ala Ala His Ser Ser Ser Ala Glu Trp Ile
1               5                   10                  15
```

```
Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430
```

-continued

```
Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Glu Ala Leu Glu
    450                 455                 460

Asn Val Tyr Ile Lys Ala Asp Lys Gln Lys Asn Gly Ile Lys Ala Asn
465                 470                 475                 480

Phe Lys Ile Arg His Asn Ile Glu Asp Gly Gly Val Gln Leu Ala Tyr
                485                 490                 495

His Tyr Gln Gln Asn Thr Pro Ile Gly Asp Gly Pro Val Leu Leu Pro
            500                 505                 510

Asp Asn His Tyr Leu Ser Val Gln Ser Ile Leu Ser Lys Asp Pro Asn
        515                 520                 525

Glu Lys Arg Asp His Met Val Leu Leu Glu Phe Val Thr Ala Ala Gly
    530                 535                 540

Ile Thr Leu Gly Met Asp Glu Leu Tyr Lys Gly Gly Thr Gly Gly Ser
545                 550                 555                 560

Met Val Ser Lys Gly Glu Glu Leu Phe Thr Gly Val Val Pro Ile Gln
                565                 570                 575

Val Glu Leu Asp Gly Asp Val Asn Gly His Lys Phe Ser Val Ser Gly
            580                 585                 590

Glu Gly Glu Gly Asp Ala Thr Tyr Gly Lys Leu Thr Leu Lys Phe Ile
        595                 600                 605

Cys Thr Thr Gly Lys Leu Pro Val Pro Trp Pro Thr Leu Val Thr Thr
    610                 615                 620

Leu Thr Tyr Gly Val Gln Cys Phe Ser Arg Tyr Pro Asp His Met Lys
625                 630                 635                 640

Gln His Asp Phe Phe Lys Ser Ala Met Pro Glu Gly Tyr Ile Gln Glu
                645                 650                 655

Arg Thr Ile Phe Phe Lys Asp Asp Gly Asn Tyr Lys Thr Arg Ala Glu
            660                 665                 670

Val Lys Phe Glu Gly Asp Thr Leu Val Asn Arg Ile Glu Leu Lys Gly
        675                 680                 685

Ile Asp Phe Lys Glu Asp Gly Asn Ile Leu Gly His Lys Leu Glu Tyr
    690                 695                 700

Asn Thr Arg Lys Glu Asp Phe Asn Arg Ile Leu Arg Asp Val Glu Ala
705                 710                 715                 720

Asn Thr Val Arg Leu Lys Glu His Asp Gln Asp Val Leu Val Leu Glu
                725                 730                 735

Lys Val Pro Ala Gly Asn Arg Ala Ser Asn Gln Gly Asn Ser Gln Pro
            740                 745                 750

Gln Gln Lys Tyr Thr Val Met Ser Gly Thr Pro Glu Lys Ile Leu Glu
        755                 760                 765

His Phe Leu Glu Thr Ile Arg Leu Glu Ala Thr Leu Asn Glu Ala Thr
    770                 775                 780

Asp Ser Val Leu Asn Asp Phe Ile Met Met His Cys Val Phe Met Pro
785                 790                 795                 800

Asn Thr Gln Leu Cys Pro Ala Leu Val Ala His Tyr His Ala Gln Pro
                805                 810                 815

Ser Gln Gly Thr Glu Gln Glu Lys Met Asp Tyr Ala Leu Asn Asn Lys
            820                 825                 830

Arg Arg Val Ile Arg Leu Val Leu Gln Trp Ala Ala Met Tyr Gly Asp
        835                 840                 845

Leu Leu Gln Glu Asp Asp Val Ser Met Ala Phe Leu Glu Glu Phe Tyr
```

```
    850                 855                 860

Val Ser Val Ser Asp Asp Ala Arg Met Ile Ala Ala Leu Lys Glu Gln
865                 870                 875                 880

Leu Pro Glu Leu Glu Lys Ile Val Lys Gln Ile Ser Glu Asp Ala Lys
                885                 890                 895

Ala Pro Gln Lys Lys His Lys Val Leu Leu Gln Gln Phe Asn Thr Gly
            900                 905                 910

Asp Glu Arg Ala Gln Lys Arg Gln Pro Ile Arg Gly Ser Asp Glu Val
        915                 920                 925

Leu Phe Lys Val Tyr Cys Met Asp Pro Thr Tyr Thr Thr Ile Arg Val
    930                 935                 940

Pro Val Ala Thr Ser Val Lys Glu Val Ile Ser Ala Val Ala Asp Lys
945                 950                 955                 960

Leu Gly Ser Gly Glu Gly Leu Ile Ile Val Lys Met Ser Ser Gly Gly
                965                 970                 975

Glu Lys Val Val Leu Lys Pro Asn Asp Val Ser Val Phe Met Thr Leu
            980                 985                 990

Thr Ile Asn Gly Arg Leu Phe Ala  Cys Pro Arg Glu Gln  Phe Asp Ser
        995                 1000                1005

Leu Thr  Pro Leu Pro Glu Gln  Glu Gly Pro Thr Val  Gly Thr Val
    1010                1015                1020

Gly Thr  Phe Glu Leu Met Ser  Ser Lys Asp Leu Ala  Tyr Gln Met
    1025                1030                1035

Thr Ile  Tyr Asp Trp Glu Leu  Phe Asn Cys Val His  Glu Leu Glu
    1040                1045                1050

Leu Ile  Tyr His Thr Phe Gly  Arg His Asn Phe Lys  Lys Thr Thr
    1055                1060                1065

Ala Asn  Leu Asp Leu Phe Leu  Arg Arg Phe Asn Glu  Ile Gln Phe
    1070                1075                1080

Trp Val  Val Thr Glu Ile Cys  Leu Cys Ser Gln Leu  Ser Lys Arg
    1085                1090                1095

Val Gln  Leu Leu Lys Lys Phe  Ile Lys Ile Ala Ala  His Cys Lys
    1100                1105                1110

Glu Tyr  Lys Asn Leu Asn Ser  Phe Phe Ala Ile Val  Met Gly Leu
    1115                1120                1125

Ser Asn  Val Ala Val Ser Arg  Leu Ala Leu Thr Trp  Glu Lys Leu
    1130                1135                1140

Pro Ser  Lys Phe Lys Lys Phe  Tyr Ala Glu Phe Glu  Ser Leu Met
    1145                1150                1155

Asp Pro  Ser Arg Asn His Arg  Ala Tyr Arg Leu Thr  Val Ala Lys
    1160                1165                1170

Leu Glu  Pro Pro Leu Ile Pro  Phe Met Pro Leu Leu  Ile Lys Asp
    1175                1180                1185

Met Thr  Phe Thr His Glu Gly  Asn Lys Thr Phe Ile  Asp Asn Leu
    1190                1195                1200

Val Asn  Phe Glu Lys Met Arg  Met Ile Ala Asn Thr  Ala Arg Thr
    1205                1210                1215

Val Arg  Tyr Tyr Arg Ser Gln  Pro Phe Asn Pro Asp  Ala Ala Gln
    1220                1225                1230

Ala Asn  Lys Asn His Gln Asp  Val Arg Ser Tyr Val  Arg Gln Leu
    1235                1240                1245

Asn Val  Ile Asp Asn Gln Arg  Thr Leu Ser Gln Met  Ser His Arg
    1250                1255                1260
```

Leu Glu Pro Arg Arg Pro
1265

<210> SEQ ID NO 3
<211> LENGTH: 748
<212> TYPE: PRT
<213> ORGANISM: Artificial Sequence
<220> FEATURE:
<223> OTHER INFORMATION: Synthetic

<400> SEQUENCE: 3

```
Met Gly Ser Asn Asn Asp Arg Ile Pro Asp Lys Glu Asn Thr Pro Leu
1               5                   10                  15

Ile Glu Pro His Val Pro Leu Arg Pro Ala Asn Thr Ile Thr Lys Val
            20                  25                  30

Pro Ser Glu Lys Ile Leu Arg Ala Gly Lys Ile Leu Arg Asn Ala Ile
        35                  40                  45

Leu Ser Arg Ala Pro His Met Ile Arg Asp Arg Lys Tyr His Leu Lys
    50                  55                  60

Thr Tyr Arg Gln Cys Cys Val Gly Thr Glu Leu Val Asp Trp Met Met
65                  70                  75                  80

Gln Gln Thr Pro Cys Val His Ser Arg Thr Gln Ala Val Gly Met Trp
                85                  90                  95

Gln Val Leu Leu Glu Asp Gly Val Leu Asn His Val Asp Gln Glu His
            100                 105                 110

His Phe Gln Asp Lys Tyr Leu Phe Tyr Arg Phe Leu Asp Asp Glu His
        115                 120                 125

Glu Asp Ala Pro Leu Pro Thr Glu Glu Glu Lys Lys Glu Cys Asp Glu
    130                 135                 140

Glu Leu Gln Asp Thr Met Leu Leu Leu Ser Gln Met Gly Pro Asp Ala
145                 150                 155                 160

His Met Arg Met Ile Leu Arg Lys Pro Pro Gly Gln Arg Thr Val Asp
                165                 170                 175

Asp Leu Glu Ile Ile Tyr Glu Glu Leu Leu His Ile Lys Ala Leu Ser
            180                 185                 190

His Leu Ser Thr Thr Val Lys Arg Glu Leu Ala Gly Val Leu Ile Phe
        195                 200                 205

Glu Ser His Ala Lys Gly Gly Thr Val Leu Phe Asn Gln Gly Glu Glu
    210                 215                 220

Gly Thr Ser Trp Tyr Ile Ile Leu Lys Gly Ser Val Asn Val Val Ile
225                 230                 235                 240

Tyr Gly Lys Gly Val Val Cys Thr Leu His Glu Gly Asp Asp Phe Gly
                245                 250                 255

Lys Leu Ala Leu Val Asn Asp Ala Pro Arg Ala Ala Ser Ile Val Leu
            260                 265                 270

Arg Glu Asp Asn Cys His Phe Leu Arg Val Asp Lys Glu Asp Phe Asn
        275                 280                 285

Arg Ile Leu Arg Asp Val Glu Ala Leu Glu Asn Val Tyr Ile Lys Ala
    290                 295                 300

Asp Lys Gln Lys Asn Gly Ile Lys Ala Asn Phe Lys Ile Arg His Asn
305                 310                 315                 320

Ile Glu Asp Gly Gly Val Gln Leu Ala Tyr His Tyr Gln Gln Asn Thr
                325                 330                 335

Pro Ile Gly Asp Gly Pro Val Leu Leu Pro Asp Asn His Tyr Leu Ser
            340                 345                 350
```

```
Val Gln Ser Ile Leu Ser Lys Asp Pro Asn Glu Lys Arg Asp His Met
        355                 360                 365

Val Leu Leu Glu Phe Val Thr Ala Ala Gly Ile Thr Leu Gly Met Asp
    370                 375                 380

Glu Leu Tyr Lys Gly Gly Thr Gly Gly Ser Met Val Ser Lys Gly Glu
385                 390                 395                 400

Glu Leu Phe Thr Gly Val Val Pro Ile Gln Val Glu Leu Asp Gly Asp
                405                 410                 415

Val Asn Gly His Lys Phe Ser Val Ser Gly Glu Gly Glu Gly Asp Ala
            420                 425                 430

Thr Tyr Gly Lys Leu Thr Leu Lys Phe Ile Cys Thr Thr Gly Lys Leu
        435                 440                 445

Pro Val Pro Trp Pro Thr Leu Val Thr Thr Leu Thr Tyr Gly Val Gln
    450                 455                 460

Cys Phe Ser Arg Tyr Pro Asp His Met Lys Gln His Asp Phe Phe Lys
465                 470                 475                 480

Ser Ala Met Pro Glu Gly Tyr Ile Gln Glu Arg Thr Ile Phe Phe Lys
                485                 490                 495

Asp Asp Gly Asn Tyr Lys Thr Arg Ala Glu Val Lys Phe Glu Gly Asp
            500                 505                 510

Thr Leu Val Asn Arg Ile Glu Leu Lys Gly Ile Asp Phe Lys Glu Asp
        515                 520                 525

Gly Asn Ile Leu Gly His Lys Leu Glu Tyr Asn Thr Arg Lys Glu Asp
    530                 535                 540

Phe Asn Arg Ile Leu Arg Asp Val Glu Ala Asn Thr Val Arg Leu Lys
545                 550                 555                 560

Glu His Asp Gln Asp Val Leu Val Leu Glu Lys Val Pro Ala Gly Asn
                565                 570                 575

Arg Ala Ser Asn Gln Gly Asn Ser Gln Pro Gln Gln Lys Tyr Thr Val
            580                 585                 590

Met Ser Gly Thr Pro Glu Lys Ile Leu Glu His Phe Leu Glu Thr Ile
        595                 600                 605

Arg Leu Glu Ala Thr Leu Asn Glu Ala Thr Asp Ser Val Leu Asn Asp
    610                 615                 620

Phe Ile Met Met His Cys Val Phe Met Pro Asn Thr Gln Leu Cys Pro
625                 630                 635                 640

Ala Leu Val Ala His Tyr His Ala Gln Pro Ser Gln Gly Thr Glu Gln
                645                 650                 655

Glu Lys Met Asp Tyr Ala Leu Asn Asn Lys Arg Arg Val Ile Arg Leu
            660                 665                 670

Val Leu Gln Trp Ala Ala Met Tyr Gly Asp Leu Leu Gln Glu Asp Asp
        675                 680                 685

Val Ser Met Ala Phe Leu Glu Glu Phe Tyr Val Ser Val Ser Asp Asp
    690                 695                 700

Ala Arg Met Ile Ala Ala Leu Lys Glu Gln Leu Pro Glu Leu Glu Lys
705                 710                 715                 720

Ile Val Lys Gln Ile Ser Glu Asp Ala Lys Ala Pro Gln Lys Lys His
                725                 730                 735

Lys Val Leu Leu Gln Gln Phe Asn Thr Gly Asp Glu
            740                 745
```

<210> SEQ ID NO 4
<211> LENGTH: 1260

```
<212> TYPE: PRT
<213> ORGANISM: Artificial Sequence
<220> FEATURE:
<223> OTHER INFORMATION: Synthetic

<400> SEQUENCE: 4

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380
```

```
Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Val Ser His Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Phe
    690                 695                 700

Asn Asn Pro Asp Val Glu Ala Asn Thr Val Arg Leu Lys Glu His Asp
705                 710                 715                 720

Gln Asp Val Leu Val Leu Glu Lys Val Pro Ala Gly Asn Arg Ala Ser
                725                 730                 735

Asn Gln Gly Asn Ser Gln Pro Gln Gln Lys Tyr Thr Val Met Ser Gly
            740                 745                 750

Thr Pro Glu Lys Ile Leu Glu His Phe Leu Glu Thr Ile Arg Leu Glu
        755                 760                 765

Ala Thr Leu Asn Glu Ala Thr Asp Ser Val Leu Asn Asp Phe Ile Met
    770                 775                 780

Met His Cys Val Phe Met Pro Asn Thr Gln Leu Cys Pro Ala Leu Val
785                 790                 795                 800

Ala His Tyr His Ala Gln Pro Ser Gln Gly Thr Glu Gln Glu Lys Met
```

```
                805                 810                 815

Asp Tyr Ala Leu Asn Asn Lys Arg Arg Val Ile Arg Leu Val Leu Gln
            820                 825                 830

Trp Ala Ala Met Tyr Gly Asp Leu Leu Gln Glu Asp Asp Val Ser Met
        835                 840                 845

Ala Phe Leu Glu Glu Phe Tyr Val Ser Val Ser Asp Asp Ala Arg Met
    850                 855                 860

Ile Ala Ala Leu Lys Glu Gln Leu Pro Glu Leu Glu Lys Ile Val Lys
865                 870                 875                 880

Gln Ile Ser Glu Asp Ala Lys Ala Pro Gln Lys Lys His Lys Val Leu
                885                 890                 895

Leu Gln Gln Phe Asn Thr Gly Asp Glu Arg Ala Gln Lys Arg Gln Pro
            900                 905                 910

Ile Arg Gly Ser Asp Glu Val Leu Phe Lys Val Tyr Cys Met Asp Pro
        915                 920                 925

Thr Tyr Thr Thr Ile Arg Val Pro Val Ala Thr Ser Val Lys Glu Val
    930                 935                 940

Ile Ser Ala Val Ala Asp Lys Leu Gly Ser Gly Glu Gly Leu Ile Ile
945                 950                 955                 960

Val Lys Met Ser Ser Gly Gly Glu Lys Val Val Leu Lys Pro Asn Asp
                965                 970                 975

Val Ser Val Phe Met Thr Leu Thr Ile Asn Gly Arg Leu Phe Ala Cys
            980                 985                 990

Pro Arg Glu Gln Phe Asp Ser Leu  Thr Pro Leu Pro Glu  Gln Glu Gly
        995                 1000                1005

Pro Thr  Val Gly Thr Val Gly  Thr Phe Glu Leu Met  Ser Ser Lys
    1010                1015                1020

Asp Leu  Ala Tyr Gln Met Thr  Ile Tyr Asp Trp Glu  Leu Phe Asn
    1025                1030                1035

Cys Val  His Glu Leu Glu Leu  Ile Tyr His Thr Phe  Gly Arg His
    1040                1045                1050

Asn Phe  Lys Lys Thr Thr Ala  Asn Leu Asp Leu Phe  Leu Arg Arg
    1055                1060                1065

Phe Asn  Glu Ile Gln Phe Trp  Val Val Thr Glu Ile  Cys Leu Cys
    1070                1075                1080

Ser Gln  Leu Ser Lys Arg Val  Gln Leu Leu Lys Lys  Phe Ile Lys
    1085                1090                1095

Ile Ala  Ala His Cys Lys Glu  Tyr Lys Asn Leu Asn  Ser Phe Phe
    1100                1105                1110

Ala Ile  Val Met Gly Leu Ser  Asn Val Ala Val Ser  Arg Leu Ala
    1115                1120                1125

Leu Thr  Trp Glu Lys Leu Pro  Ser Lys Phe Lys Lys  Phe Tyr Ala
    1130                1135                1140

Glu Phe  Glu Ser Leu Met Asp  Pro Ser Arg Asn His  Arg Ala Tyr
    1145                1150                1155

Arg Leu  Thr Val Ala Lys Leu  Glu Pro Pro Leu Ile  Pro Phe Met
    1160                1165                1170

Pro Leu  Leu Ile Lys Asp Met  Thr Phe Thr His Glu  Gly Asn Lys
    1175                1180                1185

Thr Phe  Ile Asp Asn Leu Val  Asn Phe Glu Lys Met  Arg Met Ile
    1190                1195                1200

Ala Asn  Thr Ala Arg Thr Val  Arg Tyr Tyr Arg Ser  Gln Pro Phe
    1205                1210                1215
```

```
Asn Pro  Asp Ala Ala Gln Ala  Asn Lys Asn His Gln  Asp Val Arg
    1220                 1225                 1230

Ser Tyr  Val Arg Gln Leu Asn  Val Ile Asp Asn Gln  Arg Thr Leu
    1235                 1240                 1245

Ser Gln  Met Ser His Arg Leu  Glu Pro Arg Arg Pro
    1250                 1255                 1260


<210> SEQ ID NO 5
<211> LENGTH: 1256
<212> TYPE: PRT
<213> ORGANISM: Artificial Sequence
<220> FEATURE:
<223> OTHER INFORMATION: Synthetic

<400> SEQUENCE: 5

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320
```

```
Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Leu Glu Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Thr
    690                 695                 700

Arg Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735
```

```
Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050

Thr Thr  Ala Asn Leu Asp Leu  Phe Leu Arg Arg Phe  Asn Glu Ile
    1055                1060                1065

Gln Phe  Trp Val Val Thr Glu  Ile Cys Leu Cys Ser  Gln Leu Ser
    1070                1075                1080

Lys Arg  Val Gln Leu Leu Lys  Lys Phe Ile Lys Ile  Ala Ala His
    1085                1090                1095

Cys Lys  Glu Tyr Lys Asn Leu  Asn Ser Phe Phe Ala  Ile Val Met
    1100                1105                1110

Gly Leu  Ser Asn Val Ala Val  Ser Arg Leu Ala Leu  Thr Trp Glu
    1115                1120                1125

Lys Leu  Pro Ser Lys Phe Lys  Lys Phe Tyr Ala Glu  Phe Glu Ser
    1130                1135                1140

Leu Met  Asp Pro Ser Arg Asn  His Arg Ala Tyr Arg  Leu Thr Val
```

```
    1145                1150                1155

Ala Lys  Leu Glu Pro Pro Leu  Ile Pro Phe Met Pro  Leu Leu Ile
    1160                1165                1170

Lys Asp  Met Thr Phe Thr His  Glu Gly Asn Lys Thr  Phe Ile Asp
    1175                1180                1185

Asn Leu  Val Asn Phe Glu Lys  Met Arg Met Ile Ala  Asn Thr Ala
    1190                1195                1200

Arg Thr  Val Arg Tyr Tyr Arg  Ser Gln Pro Phe Asn  Pro Asp Ala
    1205                1210                1215

Ala Gln  Ala Asn Lys Asn His  Gln Asp Val Arg Ser  Tyr Val Arg
    1220                1225                1230

Gln Leu  Asn Val Ile Asp Asn  Gln Arg Thr Leu Ser  Gln Met Ser
    1235                1240                1245

His Arg  Leu Glu Pro Arg Arg  Pro
    1250                1255


<210> SEQ ID NO 6
<211> LENGTH: 535
<212> TYPE: PRT
<213> ORGANISM: Artificial Sequence
<220> FEATURE:
<223> OTHER INFORMATION: Synthetic

<400> SEQUENCE: 6

Met Gly Ser Asn Asn Asp Arg Ile Pro Asp Lys Glu Asn Thr Pro Leu
1               5                   10                  15

Ile Glu Pro His Val Pro Leu Arg Pro Ala Asn Thr Ile Thr Lys Val
            20                  25                  30

Pro Ser Glu Lys Ile Leu Arg Ala Gly Lys Ile Leu Arg Asn Ala Ile
        35                  40                  45

Leu Ser Arg Ala Pro His Met Ile Arg Asp Arg Lys Tyr His Leu Lys
    50                  55                  60

Thr Tyr Arg Gln Cys Cys Val Gly Thr Glu Leu Val Asp Trp Met Met
65                  70                  75                  80

Gln Gln Thr Pro Cys Val His Ser Arg Thr Gln Ala Val Gly Met Trp
                85                  90                  95

Gln Val Leu Leu Glu Asp Gly Val Leu Asn His Val Asp Gln Glu His
            100                 105                 110

His Phe Gln Asp Lys Tyr Leu Phe Tyr Arg Phe Leu Asp Asp Glu His
        115                 120                 125

Glu Asp Ala Pro Leu Pro Thr Glu Glu Glu Lys Lys Glu Cys Asp Glu
    130                 135                 140

Glu Leu Gln Asp Thr Met Leu Leu Leu Ser Gln Met Gly Pro Asp Ala
145                 150                 155                 160

His Met Arg Met Ile Leu Arg Lys Pro Pro Gly Gln Arg Thr Val Asp
                165                 170                 175

Asp Leu Glu Ile Ile Tyr Glu Glu Leu Leu His Ile Lys Ala Leu Ser
            180                 185                 190

His Leu Ser Thr Thr Val Lys Arg Glu Leu Ala Gly Val Leu Ile Phe
        195                 200                 205

Glu Ser His Ala Lys Gly Gly Thr Val Leu Phe Asn Gln Gly Glu Glu
    210                 215                 220

Gly Thr Ser Trp Tyr Ile Ile Leu Lys Gly Ser Val Asn Val Val Ile
225                 230                 235                 240

Tyr Gly Lys Gly Val Val Cys Thr Leu His Glu Gly Asp Asp Phe Gly
```

```
                245                 250                 255

Lys Leu Ala Leu Val Asn Asp Ala Pro Arg Ala Ala Ser Ile Val Leu
            260                 265                 270

Arg Glu Asp Asn Cys His Phe Leu Arg Val Asp Lys Glu Asp Phe Asn
        275                 280                 285

Arg Ile Leu Arg Arg Ala Asn Val Tyr Ile Lys Ala Asp Lys Gln Lys
    290                 295                 300

Asn Gly Ile Lys Ala Asn Phe Lys Ile Arg His Asn Ile Glu Asp Gly
305                 310                 315                 320

Gly Val Gln Leu Ala Tyr His Tyr Gln Gln Asn Thr Pro Ile Gly Asp
                325                 330                 335

Gly Pro Val Leu Leu Pro Asp Asn His Tyr Leu Ser Val Gln Ser Ile
            340                 345                 350

Leu Ser Lys Asp Pro Asn Glu Lys Arg Asp His Met Val Leu Leu Glu
        355                 360                 365

Phe Val Thr Ala Ala Gly Ile Thr Leu Gly Met Asp Glu Leu Tyr Lys
    370                 375                 380

Gly Gly Thr Gly Gly Ser Met Val Ser Lys Gly Glu Glu Leu Phe Thr
385                 390                 395                 400

Gly Val Val Pro Ile Gln Val Glu Leu Asp Gly Asp Val Asn Gly His
                405                 410                 415

Lys Phe Ser Val Ser Gly Glu Gly Glu Gly Asp Ala Thr Tyr Gly Lys
            420                 425                 430

Leu Thr Leu Lys Phe Ile Cys Thr Thr Gly Lys Leu Pro Val Pro Trp
        435                 440                 445

Pro Thr Leu Val Thr Thr Leu Thr Tyr Gly Val Gln Cys Phe Ser Arg
    450                 455                 460

Tyr Pro Asp His Met Lys Gln His Asp Phe Phe Lys Ser Ala Met Pro
465                 470                 475                 480

Glu Gly Tyr Ile Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
        515                 520                 525

Gly His Lys Leu Glu Tyr Asn
    530                 535


<210> SEQ ID NO 7
<211> LENGTH: 1265
<212> TYPE: PRT
<213> ORGANISM: Artificial Sequence
<220> FEATURE:
<223> OTHER INFORMATION: Synthetic

<400> SEQUENCE: 7

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
```

```
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495
```

```
Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Lys
    690                 695                 700

Glu Asp Phe Asn Arg Ile Leu Arg Asp Val Glu Ala Asn Thr Val Arg
705                 710                 715                 720

Leu Lys Glu His Asp Gln Asp Val Leu Val Leu Glu Lys Val Pro Ala
                725                 730                 735

Gly Asn Arg Ala Ser Asn Gln Gly Asn Ser Gln Pro Gln Gln Lys Tyr
            740                 745                 750

Thr Val Met Ser Gly Thr Pro Glu Lys Ile Leu Glu His Phe Leu Glu
        755                 760                 765

Thr Ile Arg Leu Glu Ala Thr Leu Asn Glu Ala Thr Asp Ser Val Leu
    770                 775                 780

Asn Asp Phe Ile Met Met His Cys Val Phe Met Pro Asn Thr Gln Leu
785                 790                 795                 800

Cys Pro Ala Leu Val Ala His Tyr His Ala Gln Pro Ser Gln Gly Thr
                805                 810                 815

Glu Gln Glu Lys Met Asp Tyr Ala Leu Asn Asn Lys Arg Arg Val Ile
            820                 825                 830

Arg Leu Val Leu Gln Trp Ala Ala Met Tyr Gly Asp Leu Leu Gln Glu
        835                 840                 845

Asp Asp Val Ser Met Ala Phe Leu Glu Glu Phe Tyr Val Ser Val Ser
    850                 855                 860

Asp Asp Ala Arg Met Ile Ala Ala Leu Lys Glu Gln Leu Pro Glu Leu
865                 870                 875                 880

Glu Lys Ile Val Lys Gln Ile Ser Glu Asp Ala Lys Ala Pro Gln Lys
                885                 890                 895

Lys His Lys Val Leu Leu Gln Gln Phe Asn Thr Gly Asp Glu Arg Ala
            900                 905                 910
```

```
Gln Lys Arg Gln Pro Ile Arg Gly Ser Asp Glu Val Leu Phe Lys Val
        915                 920                 925

Tyr Cys Met Asp Pro Thr Tyr Thr Thr Ile Arg Val Pro Val Ala Thr
    930                 935                 940

Ser Val Lys Glu Val Ile Ser Ala Val Ala Asp Lys Leu Gly Ser Gly
945                 950                 955                 960

Glu Gly Leu Ile Ile Val Lys Met Ser Ser Gly Gly Glu Lys Val Val
                965                 970                 975

Leu Lys Pro Asn Asp Val Ser Val Phe Met Thr Leu Thr Ile Asn Gly
            980                 985                 990

Arg Leu Phe Ala Cys Pro Arg Glu  Gln Phe Asp Ser Leu  Thr Pro Leu
        995                 1000                1005

Pro Glu  Gln Glu Gly Pro Thr  Val Gly Thr Val Gly  Thr Phe Glu
    1010                1015                1020

Leu Met  Ser Ser Lys Asp Leu  Ala Tyr Gln Met Thr  Ile Tyr Asp
    1025                1030                1035

Trp Glu  Leu Phe Asn Cys Val  His Glu Leu Glu Leu  Ile Tyr His
    1040                1045                1050

Thr Phe  Gly Arg His Asn Phe  Lys Lys Thr Thr Ala  Asn Leu Asp
    1055                1060                1065

Leu Phe  Leu Arg Arg Phe Asn  Glu Ile Gln Phe Trp  Val Val Thr
    1070                1075                1080

Glu Ile  Cys Leu Cys Ser Gln  Leu Ser Lys Arg Val  Gln Leu Leu
    1085                1090                1095

Lys Lys  Phe Ile Lys Ile Ala  Ala His Cys Lys Glu  Tyr Lys Asn
    1100                1105                1110

Leu Asn  Ser Phe Phe Ala Ile  Val Met Gly Leu Ser  Asn Val Ala
    1115                1120                1125

Val Ser  Arg Leu Ala Leu Thr  Trp Glu Lys Leu Pro  Ser Lys Phe
    1130                1135                1140

Lys Lys  Phe Tyr Ala Glu Phe  Glu Ser Leu Met Asp  Pro Ser Arg
    1145                1150                1155

Asn His  Arg Ala Tyr Arg Leu  Thr Val Ala Lys Leu  Glu Pro Pro
    1160                1165                1170

Leu Ile  Pro Phe Met Pro Leu  Leu Ile Lys Asp Met  Thr Phe Thr
    1175                1180                1185

His Glu  Gly Asn Lys Thr Phe  Ile Asp Asn Leu Val  Asn Phe Glu
    1190                1195                1200

Lys Met  Arg Met Ile Ala Asn  Thr Ala Arg Thr Val  Arg Tyr Tyr
    1205                1210                1215

Arg Ser  Gln Pro Phe Asn Pro  Asp Ala Ala Gln Ala  Asn Lys Asn
    1220                1225                1230

His Gln  Asp Val Arg Ser Tyr  Val Arg Gln Leu Asn  Val Ile Asp
    1235                1240                1245

Asn Gln  Arg Thr Leu Ser Gln  Met Ser His Arg Leu  Glu Pro Arg
    1250                1255                1260

Arg Pro
    1265
```

<210> SEQ ID NO 8
<211> LENGTH: 1257
<212> TYPE: PRT
<213> ORGANISM: Artificial Sequence
<220> FEATURE:
<223> OTHER INFORMATION: Synthetic

<400> SEQUENCE: 8

```
Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
```

```
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Leu Glu Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Val Ser Ser Gly Gly Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Thr
    690                 695                 700

Arg Val Glu Ala Asn Thr Val Arg Leu Lys Glu His Asp Gln Asp Val
705                 710                 715                 720

Leu Val Leu Glu Lys Val Pro Ala Gly Asn Arg Ala Ser Asn Gln Gly
                725                 730                 735

Asn Ser Gln Pro Gln Gln Lys Tyr Thr Val Met Ser Gly Thr Pro Glu
            740                 745                 750

Lys Ile Leu Glu His Phe Leu Glu Thr Ile Arg Leu Glu Ala Thr Leu
        755                 760                 765

Asn Glu Ala Thr Asp Ser Val Leu Asn Asp Phe Ile Met Met His Cys
    770                 775                 780

Val Phe Met Pro Asn Thr Gln Leu Cys Pro Ala Leu Val Ala His Tyr
785                 790                 795                 800

His Ala Gln Pro Ser Gln Gly Thr Glu Gln Glu Lys Met Asp Tyr Ala
                805                 810                 815

Leu Asn Asn Lys Arg Arg Val Ile Arg Leu Val Leu Gln Trp Ala Ala
            820                 825                 830
```

```
Met Tyr Gly Asp Leu Leu Gln Glu Asp Asp Val Ser Met Ala Phe Leu
        835                 840                 845

Glu Glu Phe Tyr Val Ser Val Ser Asp Asp Ala Arg Met Ile Ala Ala
    850                 855                 860

Leu Lys Glu Gln Leu Pro Glu Leu Glu Lys Ile Val Lys Gln Ile Ser
865                 870                 875                 880

Glu Asp Ala Lys Ala Pro Gln Lys Lys His Lys Val Leu Leu Gln Gln
                885                 890                 895

Phe Asn Thr Gly Asp Glu Arg Ala Gln Lys Arg Gln Pro Ile Arg Gly
            900                 905                 910

Ser Asp Glu Val Leu Phe Lys Val Tyr Cys Met Asp Pro Thr Tyr Thr
        915                 920                 925

Thr Ile Arg Val Pro Val Ala Thr Ser Val Lys Glu Val Ile Ser Ala
    930                 935                 940

Val Ala Asp Lys Leu Gly Ser Gly Glu Gly Leu Ile Ile Val Lys Met
945                 950                 955                 960

Ser Ser Gly Gly Glu Lys Val Val Leu Lys Pro Asn Asp Val Ser Val
                965                 970                 975

Phe Met Thr Leu Thr Ile Asn Gly Arg Leu Phe Ala Cys Pro Arg Glu
            980                 985                 990

Gln Phe Asp Ser Leu Thr Pro Leu  Pro Glu Gln Glu Gly  Pro Thr Val
        995                 1000                1005

Gly Thr  Val Gly Thr Phe Glu  Leu Met Ser Ser Lys  Asp Leu Ala
    1010                1015                1020

Tyr Gln  Met Thr Ile Tyr Asp  Trp Glu Leu Phe Asn  Cys Val His
    1025                1030                1035

Glu Leu  Glu Leu Ile Tyr His  Thr Phe Gly Arg His  Asn Phe Lys
    1040                1045                1050

Lys Thr  Thr Ala Asn Leu Asp  Leu Phe Leu Arg Arg  Phe Asn Glu
    1055                1060                1065

Ile Gln  Phe Trp Val Val Thr  Glu Ile Cys Leu Cys  Ser Gln Leu
    1070                1075                1080

Ser Lys  Arg Val Gln Leu Leu  Lys Lys Phe Ile Lys  Ile Ala Ala
    1085                1090                1095

His Cys  Lys Glu Tyr Lys Asn  Leu Asn Ser Phe Phe  Ala Ile Val
    1100                1105                1110

Met Gly  Leu Ser Asn Val Ala  Val Ser Arg Leu Ala  Leu Thr Trp
    1115                1120                1125

Glu Lys  Leu Pro Ser Lys Phe  Lys Lys Phe Tyr Ala  Glu Phe Glu
    1130                1135                1140

Ser Leu  Met Asp Pro Ser Arg  Asn His Arg Ala Tyr  Arg Leu Thr
    1145                1150                1155

Val Ala  Lys Leu Glu Pro Pro  Leu Ile Pro Phe Met  Pro Leu Leu
    1160                1165                1170

Ile Lys  Asp Met Thr Phe Thr  His Glu Gly Asn Lys  Thr Phe Ile
    1175                1180                1185

Asp Asn  Leu Val Asn Phe Glu  Lys Met Arg Met Ile  Ala Asn Thr
    1190                1195                1200

Ala Arg  Thr Val Arg Tyr Tyr  Arg Ser Gln Pro Phe  Asn Pro Asp
    1205                1210                1215

Ala Ala  Gln Ala Asn Lys Asn  His Gln Asp Val Arg  Ser Tyr Val
    1220                1225                1230
```

```
Arg Gln  Leu Asn Val Ile Asp  Asn Gln Arg Thr Leu  Ser Gln Met
    1235                1240                1245

Ser His  Arg Leu Glu Pro Arg  Arg Pro
    1250                1255


<210> SEQ ID NO 9
<211> LENGTH: 1255
<212> TYPE: PRT
<213> ORGANISM: Artificial Sequence
<220> FEATURE:
<223> OTHER INFORMATION: Synthetic

<400> SEQUENCE: 9

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335
```

-continued

```
Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Leu Glu Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Thr
    690                 695                 700

Arg Ala Asn Thr Val Arg Leu Lys Glu His Asp Gln Asp Val Leu Val
705                 710                 715                 720

Leu Glu Lys Val Pro Ala Gly Asn Arg Ala Ser Asn Gln Gly Asn Ser
                725                 730                 735

Gln Pro Gln Gln Lys Tyr Thr Val Met Ser Gly Thr Pro Glu Lys Ile
            740                 745                 750

Leu Glu His Phe Leu Glu Thr Ile Arg Leu Glu Ala Thr Leu Asn Glu
```

```
        755                 760                 765

Ala Thr Asp Ser Val Leu Asn Asp Phe Ile Met Met His Cys Val Phe
    770                 775                 780

Met Pro Asn Thr Gln Leu Cys Pro Ala Leu Val Ala His Tyr His Ala
785                 790                 795                 800

Gln Pro Ser Gln Gly Thr Glu Gln Glu Lys Met Asp Tyr Ala Leu Asn
                805                 810                 815

Asn Lys Arg Arg Val Ile Arg Leu Val Leu Gln Trp Ala Ala Met Tyr
            820                 825                 830

Gly Asp Leu Leu Gln Glu Asp Asp Val Ser Met Ala Phe Leu Glu Glu
        835                 840                 845

Phe Tyr Val Ser Val Ser Asp Asp Ala Arg Met Ile Ala Ala Leu Lys
    850                 855                 860

Glu Gln Leu Pro Glu Leu Glu Lys Ile Val Lys Gln Ile Ser Glu Asp
865                 870                 875                 880

Ala Lys Ala Pro Gln Lys Lys His Lys Val Leu Leu Gln Gln Phe Asn
                885                 890                 895

Thr Gly Asp Glu Arg Ala Gln Lys Arg Gln Pro Ile Arg Gly Ser Asp
            900                 905                 910

Glu Val Leu Phe Lys Val Tyr Cys Met Asp Pro Thr Tyr Thr Thr Ile
        915                 920                 925

Arg Val Pro Val Ala Thr Ser Val Lys Glu Val Ile Ser Ala Val Ala
    930                 935                 940

Asp Lys Leu Gly Ser Gly Glu Gly Leu Ile Ile Val Lys Met Ser Ser
945                 950                 955                 960

Gly Gly Glu Lys Val Val Leu Lys Pro Asn Asp Val Ser Val Phe Met
                965                 970                 975

Thr Leu Thr Ile Asn Gly Arg Leu Phe Ala Cys Pro Arg Glu Gln Phe
            980                 985                 990

Asp Ser Leu Thr Pro Leu Pro Glu  Gln Glu Gly Pro Thr  Val Gly Thr
        995                 1000                1005

Val Gly  Thr Phe Glu Leu Met  Ser Ser Lys Asp Leu  Ala Tyr Gln
    1010                1015                1020

Met Thr  Ile Tyr Asp Trp Glu  Leu Phe Asn Cys Val  His Glu Leu
    1025                1030                1035

Glu Leu  Ile Tyr His Thr Phe  Gly Arg His Asn Phe  Lys Lys Thr
    1040                1045                1050

Thr Ala  Asn Leu Asp Leu Phe  Leu Arg Arg Phe Asn  Glu Ile Gln
    1055                1060                1065

Phe Trp  Val Val Thr Glu Ile  Cys Leu Cys Ser Gln  Leu Ser Lys
    1070                1075                1080

Arg Val  Gln Leu Leu Lys Lys  Phe Ile Lys Ile Ala  Ala His Cys
    1085                1090                1095

Lys Glu  Tyr Lys Asn Leu Asn  Ser Phe Phe Ala Ile  Val Met Gly
    1100                1105                1110

Leu Ser  Asn Val Ala Val Ser  Arg Leu Ala Leu Thr  Trp Glu Lys
    1115                1120                1125

Leu Pro  Ser Lys Phe Lys Lys  Phe Tyr Ala Glu Phe  Glu Ser Leu
    1130                1135                1140

Met Asp  Pro Ser Arg Asn His  Arg Ala Tyr Arg Leu  Thr Val Ala
    1145                1150                1155

Lys Leu  Glu Pro Pro Leu Ile  Pro Phe Met Pro Leu  Leu Ile Lys
    1160                1165                1170
```

```
Asp Met  Thr Phe Thr His Glu  Gly Asn Lys Thr Phe  Ile Asp Asn
    1175                 1180                 1185

Leu Val  Asn Phe Glu Lys Met  Arg Met Ile Ala Asn  Thr Ala Arg
    1190                 1195                 1200

Thr Val  Arg Tyr Tyr Arg Ser  Gln Pro Phe Asn Pro  Asp Ala Ala
    1205                 1210                 1215

Gln Ala  Asn Lys Asn His Gln  Asp Val Arg Ser Tyr  Val Arg Gln
    1220                 1225                 1230

Leu Asn  Val Ile Asp Asn Gln  Arg Thr Leu Ser Gln  Met Ser His
    1235                 1240                 1245

Arg Leu  Glu Pro Arg Arg Pro
    1250                 1255


<210> SEQ ID NO 10
<211> LENGTH: 1260
<212> TYPE: PRT
<213> ORGANISM: Artificial Sequence
<220> FEATURE:
<223> OTHER INFORMATION: Synthetic

<400> SEQUENCE: 10

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270
```

```
His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685
```

```
Glu Asp Gly Asn Ile Leu Gly His Lys Leu Glu Tyr Asn Thr Arg Arg
    690                 695                 700

Ile Leu Arg Asp Val Glu Ala Asn Thr Val Arg Leu Lys Glu His Asp
705                 710                 715                 720

Gln Asp Val Leu Val Leu Glu Lys Val Pro Ala Gly Asn Arg Ala Ser
                725                 730                 735

Asn Gln Gly Asn Ser Gln Pro Gln Gln Lys Tyr Thr Val Met Ser Gly
            740                 745                 750

Thr Pro Glu Lys Ile Leu Glu His Phe Leu Glu Thr Ile Arg Leu Glu
        755                 760                 765

Ala Thr Leu Asn Glu Ala Thr Asp Ser Val Leu Asn Asp Phe Ile Met
    770                 775                 780

Met His Cys Val Phe Met Pro Asn Thr Gln Leu Cys Pro Ala Leu Val
785                 790                 795                 800

Ala His Tyr His Ala Gln Pro Ser Gln Gly Thr Glu Gln Glu Lys Met
                805                 810                 815

Asp Tyr Ala Leu Asn Asn Lys Arg Arg Val Ile Arg Leu Val Leu Gln
            820                 825                 830

Trp Ala Ala Met Tyr Gly Asp Leu Leu Gln Glu Asp Asp Val Ser Met
        835                 840                 845

Ala Phe Leu Glu Glu Phe Tyr Val Ser Val Ser Asp Asp Ala Arg Met
    850                 855                 860

Ile Ala Ala Leu Lys Glu Gln Leu Pro Glu Leu Glu Lys Ile Val Lys
865                 870                 875                 880

Gln Ile Ser Glu Asp Ala Lys Ala Pro Gln Lys Lys His Lys Val Leu
                885                 890                 895

Leu Gln Gln Phe Asn Thr Gly Asp Glu Arg Ala Gln Lys Arg Gln Pro
            900                 905                 910

Ile Arg Gly Ser Asp Glu Val Leu Phe Lys Val Tyr Cys Met Asp Pro
        915                 920                 925

Thr Tyr Thr Thr Ile Arg Val Pro Val Ala Thr Ser Val Lys Glu Val
    930                 935                 940

Ile Ser Ala Val Ala Asp Lys Leu Gly Ser Gly Glu Gly Leu Ile Ile
945                 950                 955                 960

Val Lys Met Ser Ser Gly Gly Glu Lys Val Val Leu Lys Pro Asn Asp
                965                 970                 975

Val Ser Val Phe Met Thr Leu Thr Ile Asn Gly Arg Leu Phe Ala Cys
            980                 985                 990

Pro Arg Glu Gln Phe Asp Ser Leu  Thr Pro Leu Pro Glu  Gln Glu Gly
        995                 1000                1005

Pro Thr  Val Gly Thr Val Gly  Thr Phe Glu Leu Met  Ser Ser Lys
    1010                1015                1020

Asp Leu  Ala Tyr Gln Met Thr  Ile Tyr Asp Trp Glu  Leu Phe Asn
    1025                1030                1035

Cys Val  His Glu Leu Glu Leu  Ile Tyr His Thr Phe  Gly Arg His
    1040                1045                1050

Asn Phe  Lys Lys Thr Thr Ala  Asn Leu Asp Leu Phe  Leu Arg Arg
    1055                1060                1065

Phe Asn  Glu Ile Gln Phe Trp  Val Val Thr Glu Ile  Cys Leu Cys
    1070                1075                1080

Ser Gln  Leu Ser Lys Arg Val  Gln Leu Leu Lys Lys  Phe Ile Lys
    1085                1090                1095

Ile Ala  Ala His Cys Lys Glu  Tyr Lys Asn Leu Asn  Ser Phe Phe
```

```
    1100                1105                1110

Ala Ile  Val Met Gly Leu Ser  Asn Val Ala Val Ser  Arg Leu Ala
    1115                1120                1125

Leu Thr  Trp Glu Lys Leu Pro  Ser Lys Phe Lys Lys  Phe Tyr Ala
    1130                1135                1140

Glu Phe  Glu Ser Leu Met Asp  Pro Ser Arg Asn His  Arg Ala Tyr
    1145                1150                1155

Arg Leu  Thr Val Ala Lys Leu  Glu Pro Pro Leu Ile  Pro Phe Met
    1160                1165                1170

Pro Leu  Leu Ile Lys Asp Met  Thr Phe Thr His Glu  Gly Asn Lys
    1175                1180                1185

Thr Phe  Ile Asp Asn Leu Val  Asn Phe Glu Lys Met  Arg Met Ile
    1190                1195                1200

Ala Asn  Thr Ala Arg Thr Val  Arg Tyr Tyr Arg Ser  Gln Pro Phe
    1205                1210                1215

Asn Pro  Asp Ala Ala Gln Ala  Asn Lys Asn His Gln  Asp Val Arg
    1220                1225                1230

Ser Tyr  Val Arg Gln Leu Asn  Val Ile Asp Asn Gln  Arg Thr Leu
    1235                1240                1245

Ser Gln  Met Ser His Arg Leu  Glu Pro Arg Arg Pro
    1250                1255                1260


<210> SEQ ID NO 11
<211> LENGTH: 1256
<212> TYPE: PRT
<213> ORGANISM: Artificial Sequence
<220> FEATURE:
<223> OTHER INFORMATION: Synthetic

<400> SEQUENCE: 11

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
```

```
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Leu Glu Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620
```

```
Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Thr
    690                 695                 700

Arg Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035
```

```
Leu Glu  Leu Ile Tyr His Thr  Phe Gly Arg His Asn  Phe Lys Lys
    1040                 1045                 1050

Thr Thr  Ala Asn Leu Asp Leu  Phe Leu Arg Arg Phe  Asn Glu Ile
    1055                 1060                 1065

Gln Phe  Trp Val Val Thr Glu  Ile Cys Leu Cys Ser  Gln Leu Ser
    1070                 1075                 1080

Lys Arg  Val Gln Leu Leu Lys  Lys Phe Ile Lys Ile  Ala Ala His
    1085                 1090                 1095

Cys Lys  Glu Tyr Lys Asn Leu  Asn Ser Phe Phe Ala  Ile Val Met
    1100                 1105                 1110

Gly Leu  Ser Asn Val Ala Val  Ser Arg Leu Ala Leu  Thr Trp Glu
    1115                 1120                 1125

Lys Leu  Pro Ser Lys Phe Lys  Lys Phe Tyr Ala Glu  Phe Glu Ser
    1130                 1135                 1140

Leu Met  Asp Pro Ser Arg Asn  His Arg Ala Tyr Arg  Leu Thr Val
    1145                 1150                 1155

Ala Lys  Leu Glu Pro Pro Leu  Ile Pro Phe Met Pro  Leu Leu Ile
    1160                 1165                 1170

Lys Asp  Met Thr Phe Thr His  Glu Gly Asn Lys Thr  Phe Ile Asp
    1175                 1180                 1185

Asn Leu  Val Asn Phe Glu Lys  Met Arg Met Ile Ala  Asn Thr Ala
    1190                 1195                 1200

Arg Thr  Val Arg Tyr Tyr Arg  Ser Gln Pro Phe Asn  Pro Asp Ala
    1205                 1210                 1215

Ala Gln  Ala Asn Lys Asn His  Gln Asp Val Arg Ser  Tyr Val Arg
    1220                 1225                 1230

Gln Leu  Asn Val Ile Asp Asn  Gln Arg Thr Leu Ser  Gln Met Ser
    1235                 1240                 1245

His Arg  Leu Glu Pro Arg Arg  Pro
    1250                 1255


<210> SEQ ID NO 12
<211> LENGTH: 1263
<212> TYPE: PRT
<213> ORGANISM: Artificial Sequence
<220> FEATURE:
<223> OTHER INFORMATION: Synthetic

<400> SEQUENCE: 12

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125
```

```
Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Leu Glu Asn Val Tyr
    450                 455                 460

Ile Lys Ala Asp Lys Gln Lys Asn Gly Ile Lys Ala Asn Phe Lys Ile
465                 470                 475                 480

Arg His Asn Ile Glu Asp Gly Gly Val Gln Leu Ala Tyr His Tyr Gln
                485                 490                 495

Gln Asn Thr Pro Ile Gly Asp Gly Pro Val Leu Leu Pro Asp Asn His
            500                 505                 510

Tyr Leu Ser Val Gln Ser Ile Leu Ser Lys Asp Pro Asn Glu Lys Arg
        515                 520                 525

Asp His Met Val Leu Leu Glu Phe Val Thr Ala Ala Gly Ile Thr Leu
    530                 535                 540

Gly Met Asp Glu Leu Tyr Lys Gly Gly Thr Gly Gly Ser Met Val Ser
```

```
545                 550                 555                 560

Lys Gly Glu Glu Leu Phe Thr Gly Val Val Pro Ile Gln Val Glu Leu
                565                 570                 575

Asp Gly Asp Val Asn Gly His Lys Phe Ser Val Ser Gly Glu Gly Glu
            580                 585                 590

Gly Asp Ala Thr Tyr Gly Lys Leu Thr Leu Lys Phe Ile Cys Thr Thr
        595                 600                 605

Gly Lys Leu Pro Val Pro Trp Pro Thr Leu Val Thr Thr Leu Thr Tyr
    610                 615                 620

Gly Val Gln Cys Phe Ser Arg Tyr Pro Asp His Met Lys Gln His Asp
625                 630                 635                 640

Phe Phe Lys Ser Ala Met Pro Glu Gly Tyr Ile Gln Glu Arg Thr Ile
                645                 650                 655

Phe Phe Lys Asp Asp Gly Asn Tyr Lys Thr Arg Ala Glu Val Lys Phe
            660                 665                 670

Glu Gly Asp Thr Leu Val Asn Arg Ile Glu Leu Lys Gly Ile Asp Phe
        675                 680                 685

Lys Glu Asp Gly Asn Ile Leu Gly His Lys Leu Glu Tyr Asn Thr Arg
    690                 695                 700

Phe Asn Arg Ile Leu Arg Asp Val Glu Ala Asn Thr Val Arg Leu Lys
705                 710                 715                 720

Glu His Asp Gln Asp Val Leu Val Leu Glu Lys Val Pro Ala Gly Asn
                725                 730                 735

Arg Ala Ser Asn Gln Gly Asn Ser Gln Pro Gln Gln Lys Tyr Thr Val
            740                 745                 750

Met Ser Gly Thr Pro Glu Lys Ile Leu Glu His Phe Leu Glu Thr Ile
        755                 760                 765

Arg Leu Glu Ala Thr Leu Asn Glu Ala Thr Asp Ser Val Leu Asn Asp
    770                 775                 780

Phe Ile Met Met His Cys Val Phe Met Pro Asn Thr Gln Leu Cys Pro
785                 790                 795                 800

Ala Leu Val Ala His Tyr His Ala Gln Pro Ser Gln Gly Thr Glu Gln
                805                 810                 815

Glu Lys Met Asp Tyr Ala Leu Asn Asn Lys Arg Arg Val Ile Arg Leu
            820                 825                 830

Val Leu Gln Trp Ala Ala Met Tyr Gly Asp Leu Leu Gln Glu Asp Asp
        835                 840                 845

Val Ser Met Ala Phe Leu Glu Glu Phe Tyr Val Ser Val Ser Asp Asp
    850                 855                 860

Ala Arg Met Ile Ala Ala Leu Lys Glu Gln Leu Pro Glu Leu Glu Lys
865                 870                 875                 880

Ile Val Lys Gln Ile Ser Glu Asp Ala Lys Ala Pro Gln Lys Lys His
                885                 890                 895

Lys Val Leu Leu Gln Gln Phe Asn Thr Gly Asp Glu Arg Ala Gln Lys
            900                 905                 910

Arg Gln Pro Ile Arg Gly Ser Asp Glu Val Leu Phe Lys Val Tyr Cys
        915                 920                 925

Met Asp Pro Thr Tyr Thr Thr Ile Arg Val Pro Val Ala Thr Ser Val
    930                 935                 940

Lys Glu Val Ile Ser Ala Val Ala Asp Lys Leu Gly Ser Gly Glu Gly
945                 950                 955                 960

Leu Ile Ile Val Lys Met Ser Ser Gly Gly Glu Lys Val Val Leu Lys
                965                 970                 975
```

```
Pro Asn Asp Val Ser Val Phe Met Thr Leu Thr Ile Asn Gly Arg Leu
            980                 985                 990

Phe Ala Cys Pro Arg Glu Gln Phe  Asp Ser Leu Thr Pro  Leu Pro Glu
        995                 1000                1005

Gln Glu  Gly Pro Thr Val Gly  Thr Val Gly Thr Phe  Glu Leu Met
    1010                 1015                 1020

Ser Ser  Lys Asp Leu Ala Tyr  Gln Met Thr Ile Tyr  Asp Trp Glu
    1025                 1030                 1035

Leu Phe  Asn Cys Val His Glu  Leu Glu Leu Ile Tyr  His Thr Phe
    1040                 1045                 1050

Gly Arg  His Asn Phe Lys Lys  Thr Thr Ala Asn Leu  Asp Leu Phe
    1055                 1060                 1065

Leu Arg  Arg Phe Asn Glu Ile  Gln Phe Trp Val Val  Thr Glu Ile
    1070                 1075                 1080

Cys Leu  Cys Ser Gln Leu Ser  Lys Arg Val Gln Leu  Leu Lys Lys
    1085                 1090                 1095

Phe Ile  Lys Ile Ala Ala His  Cys Lys Glu Tyr Lys  Asn Leu Asn
    1100                 1105                 1110

Ser Phe  Phe Ala Ile Val Met  Gly Leu Ser Asn Val  Ala Val Ser
    1115                 1120                 1125

Arg Leu  Ala Leu Thr Trp Glu  Lys Leu Pro Ser Lys  Phe Lys Lys
    1130                 1135                 1140

Phe Tyr  Ala Glu Phe Glu Ser  Leu Met Asp Pro Ser  Arg Asn His
    1145                 1150                 1155

Arg Ala  Tyr Arg Leu Thr Val  Ala Lys Leu Glu Pro  Pro Leu Ile
    1160                 1165                 1170

Pro Phe  Met Pro Leu Leu Ile  Lys Asp Met Thr Phe  Thr His Glu
    1175                 1180                 1185

Gly Asn  Lys Thr Phe Ile Asp  Asn Leu Val Asn Phe  Glu Lys Met
    1190                 1195                 1200

Arg Met  Ile Ala Asn Thr Ala  Arg Thr Val Arg Tyr  Tyr Arg Ser
    1205                 1210                 1215

Gln Pro  Phe Asn Pro Asp Ala  Ala Gln Ala Asn Lys  Asn His Gln
    1220                 1225                 1230

Asp Val  Arg Ser Tyr Val Arg  Gln Leu Asn Val Ile  Asp Asn Gln
    1235                 1240                 1245

Arg Thr  Leu Ser Gln Met Ser  His Arg Leu Glu Pro  Arg Arg Pro
    1250                 1255                 1260
```

<210> SEQ ID NO 13
<211> LENGTH: 1255
<212> TYPE: PRT
<213> ORGANISM: Artificial Sequence
<220> FEATURE:
<223> OTHER INFORMATION: Synthetic

<400> SEQUENCE: 13

```
Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60
```

```
Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Leu Glu Asn Val
    450                 455                 460

Tyr Ile Lys Ala Asp Lys Gln Lys Asn Gly Ile Lys Ala Asn Phe Lys
465                 470                 475                 480
```

-continued

```
Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Arg Gly Val Val Pro Ile Gln Val
                565                 570                 575

Glu Leu Asp Gly Asp Val Asn Gly His Lys Phe Ser Val Ser Gly Glu
            580                 585                 590

Gly Glu Gly Asp Ala Thr Tyr Gly Lys Leu Thr Leu Lys Phe Ile Cys
        595                 600                 605

Thr Thr Gly Lys Leu Pro Val Pro Trp Pro Thr Leu Val Thr Thr Leu
    610                 615                 620

Thr Tyr Gly Val Gln Cys Phe Ser Arg Tyr Pro Asp His Met Lys Gln
625                 630                 635                 640

His Asp Phe Phe Lys Ser Ala Met Pro Glu Gly Tyr Ile Gln Glu Arg
                645                 650                 655

Thr Ile Phe Phe Lys Asp Asp Gly Asn Tyr Lys Thr Arg Ala Glu Val
            660                 665                 670

Lys Phe Glu Gly Asp Thr Leu Val Asn Arg Ile Glu Leu Lys Gly Ile
        675                 680                 685

Asp Phe Lys Glu Asp Gly Asn Ile Leu Gly His Lys Leu Glu Tyr Asn
    690                 695                 700

Thr Arg Asn Thr Val Arg Leu Lys Glu His Asp Gln Asp Val Leu Val
705                 710                 715                 720

Leu Glu Lys Val Pro Ala Gly Asn Arg Ala Ser Asn Gln Gly Asn Ser
                725                 730                 735

Gln Pro Gln Gln Lys Tyr Thr Val Met Ser Gly Thr Pro Glu Lys Ile
            740                 745                 750

Leu Glu His Phe Leu Glu Thr Ile Arg Leu Glu Ala Thr Leu Asn Glu
        755                 760                 765

Ala Thr Asp Ser Val Leu Asn Asp Phe Ile Met Met His Cys Val Phe
    770                 775                 780

Met Pro Asn Thr Gln Leu Cys Pro Ala Leu Val Ala His Tyr His Ala
785                 790                 795                 800

Gln Pro Ser Gln Gly Thr Glu Gln Glu Lys Met Asp Tyr Ala Leu Asn
                805                 810                 815

Asn Lys Arg Arg Val Ile Arg Leu Val Leu Gln Trp Ala Ala Met Tyr
            820                 825                 830

Gly Asp Leu Leu Gln Glu Asp Asp Val Ser Met Ala Phe Leu Glu Glu
        835                 840                 845

Phe Tyr Val Ser Val Ser Asp Asp Ala Arg Met Ile Ala Ala Leu Lys
    850                 855                 860

Glu Gln Leu Pro Glu Leu Glu Lys Ile Val Lys Gln Ile Ser Glu Asp
865                 870                 875                 880

Ala Lys Ala Pro Gln Lys Lys His Lys Val Leu Leu Gln Gln Phe Asn
                885                 890                 895

Thr Gly Asp Glu Arg Ala Gln Lys Arg Gln Pro Ile Arg Gly Ser Asp
```

```
            900                 905                 910

Glu Val Leu Phe Lys Val Tyr Cys Met Asp Pro Thr Tyr Thr Thr Ile
        915                 920                 925

Arg Val Pro Val Ala Thr Ser Val Lys Glu Val Ile Ser Ala Val Ala
    930                 935                 940

Asp Lys Leu Gly Ser Gly Glu Gly Leu Ile Ile Val Lys Met Ser Ser
945                 950                 955                 960

Gly Gly Glu Lys Val Val Leu Lys Pro Asn Asp Val Ser Val Phe Met
                965                 970                 975

Thr Leu Thr Ile Asn Gly Arg Leu Phe Ala Cys Pro Arg Glu Gln Phe
            980                 985                 990

Asp Ser Leu Thr Pro Leu Pro Glu  Gln Glu Gly Pro Thr  Val Gly Thr
        995                 1000                1005

Val Gly  Thr Phe Glu Leu Met  Ser Ser Lys Asp Leu  Ala Tyr Gln
    1010                 1015                 1020

Met Thr  Ile Tyr Asp Trp Glu  Leu Phe Asn Cys Val  His Glu Leu
    1025                 1030                 1035

Glu Leu  Ile Tyr His Thr Phe  Gly Arg His Asn Phe  Lys Lys Thr
    1040                 1045                 1050

Thr Ala  Asn Leu Asp Leu Phe  Leu Arg Arg Phe Asn  Glu Ile Gln
    1055                 1060                 1065

Phe Trp  Val Val Thr Glu Ile  Cys Leu Cys Ser Gln  Leu Ser Lys
    1070                 1075                 1080

Arg Val  Gln Leu Leu Lys Lys  Phe Ile Lys Ile Ala  Ala His Cys
    1085                 1090                 1095

Lys Glu  Tyr Lys Asn Leu Asn  Ser Phe Phe Ala Ile  Val Met Gly
    1100                 1105                 1110

Leu Ser  Asn Val Ala Val Ser  Arg Leu Ala Leu Thr  Trp Glu Lys
    1115                 1120                 1125

Leu Pro  Ser Lys Phe Lys Lys  Phe Tyr Ala Glu Phe  Glu Ser Leu
    1130                 1135                 1140

Met Asp  Pro Ser Arg Asn His  Arg Ala Tyr Arg Leu  Thr Val Ala
    1145                 1150                 1155

Lys Leu  Glu Pro Pro Leu Ile  Pro Phe Met Pro Leu  Leu Ile Lys
    1160                 1165                 1170

Asp Met  Thr Phe Thr His Glu  Gly Asn Lys Thr Phe  Ile Asp Asn
    1175                 1180                 1185

Leu Val  Asn Phe Glu Lys Met  Arg Met Ile Ala Asn  Thr Ala Arg
    1190                 1195                 1200

Thr Val  Arg Tyr Tyr Arg Ser  Gln Pro Phe Asn Pro  Asp Ala Ala
    1205                 1210                 1215

Gln Ala  Asn Lys Asn His Gln  Asp Val Arg Ser Tyr  Val Arg Gln
    1220                 1225                 1230

Leu Asn  Val Ile Asp Asn Gln  Arg Thr Leu Ser Gln  Met Ser His
    1235                 1240                 1245

Arg Leu  Glu Pro Arg Arg Pro
    1250                 1255
```

<210> SEQ ID NO 14
<211> LENGTH: 1255
<212> TYPE: PRT
<213> ORGANISM: Artificial Sequence
<220> FEATURE:
<223> OTHER INFORMATION: Synthetic

<400> SEQUENCE: 14

```
Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415
```

-continued

```
Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Phe Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Val
    690                 695                 700

Glu Ala Asn Thr Val Arg Leu Lys Glu His Asp Gln Asp Val Leu Val
705                 710                 715                 720

Leu Glu Lys Val Pro Ala Gly Asn Arg Ala Ser Asn Gln Gly Asn Ser
                725                 730                 735

Gln Pro Gln Gln Lys Tyr Thr Val Met Ser Gly Thr Pro Glu Lys Ile
            740                 745                 750

Leu Glu His Phe Leu Glu Thr Ile Arg Leu Glu Ala Thr Leu Asn Glu
        755                 760                 765

Ala Thr Asp Ser Val Leu Asn Asp Phe Ile Met Met His Cys Val Phe
    770                 775                 780

Met Pro Asn Thr Gln Leu Cys Pro Ala Leu Val Ala His Tyr His Ala
785                 790                 795                 800

Gln Pro Ser Gln Gly Thr Glu Gln Glu Lys Met Asp Tyr Ala Leu Asn
                805                 810                 815

Asn Lys Arg Arg Val Ile Arg Leu Val Leu Gln Trp Ala Ala Met Tyr
            820                 825                 830
```

```
Gly Asp Leu Leu Gln Glu Asp Asp Val Ser Met Ala Phe Leu Glu Glu
        835                 840                 845

Phe Tyr Val Ser Val Ser Asp Asp Ala Arg Met Ile Ala Ala Leu Lys
    850                 855                 860

Glu Gln Leu Pro Glu Leu Glu Lys Ile Val Lys Gln Ile Ser Glu Asp
865                 870                 875                 880

Ala Lys Ala Pro Gln Lys Lys His Lys Val Leu Leu Gln Gln Phe Asn
                885                 890                 895

Thr Gly Asp Glu Arg Ala Gln Lys Arg Gln Pro Ile Arg Gly Ser Asp
            900                 905                 910

Glu Val Leu Phe Lys Val Tyr Cys Met Asp Pro Thr Tyr Thr Thr Ile
        915                 920                 925

Arg Val Pro Val Ala Thr Ser Val Lys Glu Val Ile Ser Ala Val Ala
    930                 935                 940

Asp Lys Leu Gly Ser Gly Glu Gly Leu Ile Ile Val Lys Met Ser Ser
945                 950                 955                 960

Gly Gly Glu Lys Val Val Leu Lys Pro Asn Asp Val Ser Val Phe Met
                965                 970                 975

Thr Leu Thr Ile Asn Gly Arg Leu Phe Ala Cys Pro Arg Glu Gln Phe
            980                 985                 990

Asp Ser Leu Thr Pro Leu Pro Glu  Gln Glu Gly Pro Thr  Val Gly Thr
        995                 1000                1005

Val Gly  Thr Phe Glu Leu Met  Ser Ser Lys Asp Leu  Ala Tyr Gln
    1010                1015                1020

Met Thr  Ile Tyr Asp Trp Glu  Leu Phe Asn Cys Val  His Glu Leu
    1025                1030                1035

Glu Leu  Ile Tyr His Thr Phe  Gly Arg His Asn Phe  Lys Lys Thr
    1040                1045                1050

Thr Ala  Asn Leu Asp Leu Phe  Leu Arg Arg Phe Asn  Glu Ile Gln
    1055                1060                1065

Phe Trp  Val Val Thr Glu Ile  Cys Leu Cys Ser Gln  Leu Ser Lys
    1070                1075                1080

Arg Val  Gln Leu Leu Lys Lys  Phe Ile Lys Ile Ala  Ala His Cys
    1085                1090                1095

Lys Glu  Tyr Lys Asn Leu Asn  Ser Phe Phe Ala Ile  Val Met Gly
    1100                1105                1110

Leu Ser  Asn Val Ala Val Ser  Arg Leu Ala Leu Thr  Trp Glu Lys
    1115                1120                1125

Leu Pro  Ser Lys Phe Lys Lys  Phe Tyr Ala Glu Phe  Glu Ser Leu
    1130                1135                1140

Met Asp  Pro Ser Arg Asn His  Arg Ala Tyr Arg Leu  Thr Val Ala
    1145                1150                1155

Lys Leu  Glu Pro Pro Leu Ile  Pro Phe Met Pro Leu  Leu Ile Lys
    1160                1165                1170

Asp Met  Thr Phe Thr His Glu  Gly Asn Lys Thr Phe  Ile Asp Asn
    1175                1180                1185

Leu Val  Asn Phe Glu Lys Met  Arg Met Ile Ala Asn  Thr Ala Arg
    1190                1195                1200

Thr Val  Arg Tyr Tyr Arg Ser  Gln Pro Phe Asn Pro  Asp Ala Ala
    1205                1210                1215

Gln Ala  Asn Lys Asn His Gln  Asp Val Arg Ser Tyr  Val Arg Gln
    1220                1225                1230

Leu Asn  Val Ile Asp Asn Gln  Arg Thr Leu Ser Gln  Met Ser His
```

```
    1235                1240                1245

Arg Leu  Glu Pro Arg Arg Pro
    1250                1255


<210> SEQ ID NO 15
<211> LENGTH: 1261
<212> TYPE: PRT
<213> ORGANISM: Artificial Sequence
<220> FEATURE:
<223> OTHER INFORMATION: Synthetic

<400> SEQUENCE: 15

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
```

```
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Leu Glu Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Pro Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Thr
    690                 695                 700

Arg Ile Leu Arg Asp Val Glu Ala Asn Thr Val Arg Leu Lys Glu His
705                 710                 715                 720

Asp Gln Asp Val Leu Val Leu Glu Lys Val Pro Ala Gly Asn Arg Ala
                725                 730                 735

Ser Asn Gln Gly Asn Ser Gln Pro Gln Gln Lys Tyr Thr Val Met Ser
            740                 745                 750

Gly Thr Pro Glu Lys Ile Leu Glu His Phe Leu Glu Thr Ile Arg Leu
        755                 760                 765
```

```
Glu Ala Thr Leu Asn Glu Ala Thr Asp Ser Val Leu Asn Asp Phe Ile
    770                 775                 780

Met Met His Cys Val Phe Met Pro Asn Thr Gln Leu Cys Pro Ala Leu
785                 790                 795                 800

Val Ala His Tyr His Ala Gln Pro Ser Gln Gly Thr Glu Gln Glu Lys
                805                 810                 815

Met Asp Tyr Ala Leu Asn Asn Lys Arg Arg Val Ile Arg Leu Val Leu
            820                 825                 830

Gln Trp Ala Ala Met Tyr Gly Asp Leu Leu Gln Glu Asp Asp Val Ser
        835                 840                 845

Met Ala Phe Leu Glu Glu Phe Tyr Val Ser Val Ser Asp Asp Ala Arg
    850                 855                 860

Met Ile Ala Ala Leu Lys Glu Gln Leu Pro Glu Leu Glu Lys Ile Val
865                 870                 875                 880

Lys Gln Ile Ser Glu Asp Ala Lys Ala Pro Gln Lys Lys His Lys Val
                885                 890                 895

Leu Leu Gln Gln Phe Asn Thr Gly Asp Glu Arg Ala Gln Lys Arg Gln
            900                 905                 910

Pro Ile Arg Gly Ser Asp Glu Val Leu Phe Lys Val Tyr Cys Met Asp
        915                 920                 925

Pro Thr Tyr Thr Thr Ile Arg Val Pro Val Ala Thr Ser Val Lys Glu
    930                 935                 940

Val Ile Ser Ala Val Ala Asp Lys Leu Gly Ser Gly Glu Gly Leu Ile
945                 950                 955                 960

Ile Val Lys Met Ser Ser Gly Gly Glu Lys Val Val Leu Lys Pro Asn
                965                 970                 975

Asp Val Ser Val Phe Met Thr Leu Thr Ile Asn Gly Arg Leu Phe Ala
            980                 985                 990

Cys Pro Arg Glu Gln Phe Asp Ser  Leu Thr Pro Leu Pro  Glu Gln Glu
        995                 1000                1005

Gly Pro  Thr Val Gly Thr Val  Gly Thr Phe Glu Leu  Met Ser Ser
    1010                1015                1020

Lys Asp  Leu Ala Tyr Gln Met  Thr Ile Tyr Asp Trp  Glu Leu Phe
    1025                1030                1035

Asn Cys  Val His Glu Leu Glu  Leu Ile Tyr His Thr  Phe Gly Arg
    1040                1045                1050

His Asn  Phe Lys Lys Thr Thr  Ala Asn Leu Asp Leu  Phe Leu Arg
    1055                1060                1065

Arg Phe  Asn Glu Ile Gln Phe  Trp Val Val Thr Glu  Ile Cys Leu
    1070                1075                1080

Cys Ser  Gln Leu Ser Lys Arg  Val Gln Leu Leu Lys  Lys Phe Ile
    1085                1090                1095

Lys Ile  Ala Ala His Cys Lys  Glu Tyr Lys Asn Leu  Asn Ser Phe
    1100                1105                1110

Phe Ala  Ile Val Met Gly Leu  Ser Asn Val Ala Val  Ser Arg Leu
    1115                1120                1125

Ala Leu  Thr Trp Glu Lys Leu  Pro Ser Lys Phe Lys  Lys Phe Tyr
    1130                1135                1140

Ala Glu  Phe Glu Ser Leu Met  Asp Pro Ser Arg Asn  His Arg Ala
    1145                1150                1155

Tyr Arg  Leu Thr Val Ala Lys  Leu Glu Pro Pro Leu  Ile Pro Phe
    1160                1165                1170
```

```
Met Pro  Leu Leu Ile Lys Asp  Met Thr Phe Thr His  Glu Gly Asn
    1175                 1180                 1185

Lys Thr  Phe Ile Asp Asn Leu  Val Asn Phe Glu Lys  Met Arg Met
    1190                 1195                 1200

Ile Ala  Asn Thr Ala Arg Thr  Val Arg Tyr Tyr Arg  Ser Gln Pro
    1205                 1210                 1215

Phe Asn  Pro Asp Ala Ala Gln  Ala Asn Lys Asn His  Gln Asp Val
    1220                 1225                 1230

Arg Ser  Tyr Val Arg Gln Leu  Asn Val Ile Asp Asn  Gln Arg Thr
    1235                 1240                 1245

Leu Ser  Gln Met Ser His Arg  Leu Glu Pro Arg Arg  Pro
    1250                 1255                 1260


<210> SEQ ID NO 16
<211> LENGTH: 700
<212> TYPE: PRT
<213> ORGANISM: Artificial Sequence
<220> FEATURE:
<223> OTHER INFORMATION: Synthetic

<400> SEQUENCE: 16

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270
```

```
His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Arg Ala Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr
```

```
    690                 695                 700


<210> SEQ ID NO 17
<211> LENGTH: 1256
<212> TYPE: PRT
<213> ORGANISM: Artificial Sequence
<220> FEATURE:
<223> OTHER INFORMATION: Synthetic

<400> SEQUENCE: 17

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
```

```
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Glu Ala Asn Leu
    450                 455                 460

Glu Asn Val Tyr Ile Lys Ala Asp Lys Gln Lys Asn Gly Ile Lys Ala
465                 470                 475                 480

Asn Phe Lys Ile Arg His Asn Ile Glu Asp Gly Gly Val Gln Leu Ala
                485                 490                 495

Tyr His Tyr Gln Gln Asn Thr Pro Ile Gly Asp Gly Pro Val Leu Leu
            500                 505                 510

Pro Asp Asn His Tyr Leu Ser Val Gln Ser Ile Leu Ser Lys Asp Pro
        515                 520                 525

Asn Glu Lys Arg Asp His Met Val Leu Leu Glu Phe Val Thr Ala Ala
    530                 535                 540

Gly Ile Thr Leu Gly Met Asp Glu Leu Tyr Lys Gly Gly Thr Gly Gly
545                 550                 555                 560

Ser Met Val Ser Lys Gly Glu Glu Leu Phe Thr Gly Val Val Pro Ile
                565                 570                 575

Gln Val Glu Leu Asp Gly Asp Val Asn Gly His Lys Phe Ser Val Ser
            580                 585                 590

Gly Glu Gly Glu Gly Asp Ala Thr Tyr Gly Lys Leu Thr Leu Lys Phe
        595                 600                 605

Ile Cys Thr Thr Gly Lys Leu Pro Val Pro Trp Pro Thr Leu Val Thr
    610                 615                 620

Thr Leu Thr Tyr Gly Val Gln Cys Phe Ser Arg Tyr Pro Asp His Met
625                 630                 635                 640

Lys Gln His Asp Phe Phe Lys Ser Ala Met Pro Glu Gly Tyr Ile Gln
                645                 650                 655

Glu Arg Thr Ile Phe Phe Lys Asp Asp Gly Asn Tyr Lys Thr Arg Ala
            660                 665                 670

Glu Val Lys Phe Glu Gly Asp Thr Leu Val Asn Arg Ile Glu Leu Lys
        675                 680                 685

Gly Ile Asp Phe Lys Glu Asp Gly Asn Ile Leu Gly His Lys Leu Glu
    690                 695                 700

Tyr Asn Thr Arg Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780
```

```
Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050

Thr Thr  Ala Asn Leu Asp Leu  Phe Leu Arg Arg Phe  Asn Glu Ile
    1055                1060                1065

Gln Phe  Trp Val Val Thr Glu  Ile Cys Leu Cys Ser  Gln Leu Ser
    1070                1075                1080

Lys Arg  Val Gln Leu Leu Lys  Lys Phe Ile Lys Ile  Ala Ala His
    1085                1090                1095

Cys Lys  Glu Tyr Lys Asn Leu  Asn Ser Phe Phe Ala  Ile Val Met
    1100                1105                1110

Gly Leu  Ser Asn Val Ala Val  Ser Arg Leu Ala Leu  Thr Trp Glu
    1115                1120                1125

Lys Leu  Pro Ser Lys Phe Lys  Lys Phe Tyr Ala Glu  Phe Glu Ser
    1130                1135                1140

Leu Met  Asp Pro Ser Arg Asn  His Arg Ala Tyr Arg  Leu Thr Val
    1145                1150                1155

Ala Lys  Leu Glu Pro Pro Leu  Ile Pro Phe Met Pro  Leu Leu Ile
    1160                1165                1170

Lys Asp  Met Thr Phe Thr His  Glu Gly Asn Lys Thr  Phe Ile Asp
    1175                1180                1185
```

```
Asn Leu  Val Asn Phe Glu Lys  Met Arg Met Ile Ala  Asn Thr Ala
    1190                 1195                 1200

Arg Thr  Val Arg Tyr Tyr Arg  Ser Gln Pro Phe Asn  Pro Asp Ala
    1205                 1210                 1215

Ala Gln  Ala Asn Lys Asn His  Gln Asp Val Arg Ser  Tyr Val Arg
    1220                 1225                 1230

Gln Leu  Asn Val Ile Asp Asn  Gln Arg Thr Leu Ser  Gln Met Ser
    1235                 1240                 1245

His Arg  Leu Glu Pro Arg Arg  Pro
    1250                 1255


<210> SEQ ID NO 18
<211> LENGTH: 1255
<212> TYPE: PRT
<213> ORGANISM: Artificial Sequence
<220> FEATURE:
<223> OTHER INFORMATION: Synthetic

<400> SEQUENCE: 18

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285
```

```
Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Val
    690                 695                 700

Glu Ala Asn Thr Val Arg Leu Lys Glu His Asp Gln Asp Val Leu Val
```

```
705                 710                 715                 720

Leu Glu Lys Val Pro Ala Gly Asn Arg Ala Ser Asn Gln Gly Asn Ser
                725                 730                 735

Gln Pro Gln Gln Lys Tyr Thr Val Met Ser Gly Thr Pro Glu Lys Ile
            740                 745                 750

Leu Glu His Phe Leu Glu Thr Ile Arg Leu Glu Ala Thr Leu Asn Glu
        755                 760                 765

Ala Thr Asp Ser Val Leu Asn Asp Phe Ile Met Met His Cys Val Phe
    770                 775                 780

Met Pro Asn Thr Gln Leu Cys Pro Ala Leu Val Ala His Tyr His Ala
785                 790                 795                 800

Gln Pro Ser Gln Gly Thr Glu Gln Glu Lys Met Asp Tyr Ala Leu Asn
                805                 810                 815

Asn Lys Arg Arg Val Ile Arg Leu Val Leu Gln Trp Ala Ala Met Tyr
            820                 825                 830

Gly Asp Leu Leu Gln Glu Asp Asp Val Ser Met Ala Phe Leu Glu Glu
        835                 840                 845

Phe Tyr Val Ser Val Ser Asp Asp Ala Arg Met Ile Ala Ala Leu Lys
    850                 855                 860

Glu Gln Leu Pro Glu Leu Glu Lys Ile Val Lys Gln Ile Ser Glu Asp
865                 870                 875                 880

Ala Lys Ala Pro Gln Lys Lys His Lys Val Leu Leu Gln Gln Phe Asn
                885                 890                 895

Thr Gly Asp Glu Arg Ala Gln Lys Arg Gln Pro Ile Arg Gly Ser Asp
            900                 905                 910

Glu Val Leu Phe Lys Val Tyr Cys Met Asp Pro Thr Tyr Thr Thr Ile
        915                 920                 925

Arg Val Pro Val Ala Thr Ser Val Lys Glu Val Ile Ser Ala Val Ala
    930                 935                 940

Asp Lys Leu Gly Ser Gly Glu Gly Leu Ile Ile Val Lys Met Ser Ser
945                 950                 955                 960

Gly Gly Glu Lys Val Val Leu Lys Pro Asn Asp Val Ser Val Phe Met
                965                 970                 975

Thr Leu Thr Ile Asn Gly Arg Leu Phe Ala Cys Pro Arg Glu Gln Phe
            980                 985                 990

Asp Ser Leu Thr Pro Leu Pro Glu  Gln Glu Gly Pro Thr  Val Gly Thr
        995                 1000                1005

Val Gly  Thr Phe Glu Leu Met  Ser Ser Lys Asp Leu  Ala Tyr Gln
    1010                1015                1020

Met Thr  Ile Tyr Asp Trp Glu  Leu Phe Asn Cys Val  His Glu Leu
    1025                1030                1035

Glu Leu  Ile Tyr His Thr Phe  Gly Arg His Asn Phe  Lys Lys Thr
    1040                1045                1050

Thr Ala  Asn Leu Asp Leu Phe  Leu Arg Arg Phe Asn  Glu Ile Gln
    1055                1060                1065

Phe Trp  Val Val Thr Glu Ile  Cys Leu Cys Ser Gln  Leu Ser Lys
    1070                1075                1080

Arg Val  Gln Leu Leu Lys Lys  Phe Ile Lys Ile Ala  Ala His Cys
    1085                1090                1095

Lys Glu  Tyr Lys Asn Leu Asn  Ser Phe Phe Ala Ile  Val Met Gly
    1100                1105                1110

Leu Ser  Asn Val Ala Val Ser  Arg Leu Ala Leu Thr  Trp Glu Lys
    1115                1120                1125
```

```
Leu Pro  Ser Lys Phe Lys Lys  Phe Tyr Ala Glu Phe  Glu Ser Leu
    1130                 1135                 1140

Met Asp  Pro Ser Arg Asn His  Arg Ala Tyr Arg Leu  Thr Val Ala
    1145                 1150                 1155

Lys Leu  Glu Pro Pro Leu Ile  Pro Phe Met Pro Leu  Leu Ile Lys
    1160                 1165                 1170

Asp Met  Thr Phe Thr His Glu  Gly Asn Lys Thr Phe  Ile Asp Asn
    1175                 1180                 1185

Leu Val  Asn Phe Glu Lys Met  Arg Met Ile Ala Asn  Thr Ala Arg
    1190                 1195                 1200

Thr Val  Arg Tyr Tyr Arg Ser  Gln Pro Phe Asn Pro  Asp Ala Ala
    1205                 1210                 1215

Gln Ala  Asn Lys Asn His Gln  Asp Val Arg Ser Tyr  Val Arg Gln
    1220                 1225                 1230

Leu Asn  Val Ile Asp Asn Gln  Arg Thr Leu Ser Gln  Met Ser His
    1235                 1240                 1245

Arg Leu  Glu Pro Arg Arg Pro
    1250                 1255


<210> SEQ ID NO 19
<211> LENGTH: 1258
<212> TYPE: PRT
<213> ORGANISM: Artificial Sequence
<220> FEATURE:
<223> OTHER INFORMATION: Synthetic

<400> SEQUENCE: 19

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220
```

```
Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640
```

```
Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Ile
    690                 695                 700

Leu Arg Asp Val Glu Ala Asn Thr Val Arg Leu Lys Glu His Asp Gln
705                 710                 715                 720

Asp Val Leu Val Leu Glu Lys Val Pro Ala Gly Asn Arg Ala Ser Asn
                725                 730                 735

Gln Gly Asn Ser Gln Pro Gln Gln Lys Tyr Thr Val Met Ser Gly Thr
            740                 745                 750

Pro Glu Lys Ile Leu Glu His Phe Leu Glu Thr Ile Arg Leu Glu Ala
        755                 760                 765

Thr Leu Asn Glu Ala Thr Asp Ser Val Leu Asn Asp Phe Ile Met Met
    770                 775                 780

His Cys Val Phe Met Pro Asn Thr Gln Leu Cys Pro Ala Leu Val Ala
785                 790                 795                 800

His Tyr His Ala Gln Pro Ser Gln Gly Thr Glu Gln Glu Lys Met Asp
                805                 810                 815

Tyr Ala Leu Asn Asn Lys Arg Arg Val Ile Arg Leu Val Leu Gln Trp
            820                 825                 830

Ala Ala Met Tyr Gly Asp Leu Leu Gln Glu Asp Asp Val Ser Met Ala
        835                 840                 845

Phe Leu Glu Glu Phe Tyr Val Ser Val Ser Asp Asp Ala Arg Met Ile
    850                 855                 860

Ala Ala Leu Lys Glu Gln Leu Pro Glu Leu Glu Lys Ile Val Lys Gln
865                 870                 875                 880

Ile Ser Glu Asp Ala Lys Ala Pro Gln Lys Lys His Lys Val Leu Leu
                885                 890                 895

Gln Gln Phe Asn Thr Gly Asp Glu Arg Ala Gln Lys Arg Gln Pro Ile
            900                 905                 910

Arg Gly Ser Asp Glu Val Leu Phe Lys Val Tyr Cys Met Asp Pro Thr
        915                 920                 925

Tyr Thr Thr Ile Arg Val Pro Val Ala Thr Ser Val Lys Glu Val Ile
    930                 935                 940

Ser Ala Val Ala Asp Lys Leu Gly Ser Gly Glu Gly Leu Ile Ile Val
945                 950                 955                 960

Lys Met Ser Ser Gly Gly Glu Lys Val Val Leu Lys Pro Asn Asp Val
                965                 970                 975

Ser Val Phe Met Thr Leu Thr Ile Asn Gly Arg Leu Phe Ala Cys Pro
            980                 985                 990

Arg Glu Gln Phe Asp Ser Leu Thr  Pro Leu Pro Glu Gln  Glu Gly Pro
        995                 1000                1005

Thr Val  Gly Thr Val Gly Thr  Phe Glu Leu Met Ser  Ser Lys Asp
    1010                1015                1020

Leu Ala  Tyr Gln Met Thr Ile  Tyr Asp Trp Glu Leu  Phe Asn Cys
    1025                1030                1035

Val His  Glu Leu Glu Leu Ile  Tyr His Thr Phe Gly  Arg His Asn
    1040                1045                1050

Phe Lys  Lys Thr Thr Ala Asn  Leu Asp Leu Phe Leu  Arg Arg Phe
```

```
    1055                1060                1065

Asn Glu  Ile Gln Phe Trp Val  Val Thr Glu Ile Cys  Leu Cys Ser
    1070                1075                1080

Gln Leu  Ser Lys Arg Val Gln  Leu Leu Lys Lys Phe  Ile Lys Ile
    1085                1090                1095

Ala Ala  His Cys Lys Glu Tyr  Lys Asn Leu Asn Ser  Phe Phe Ala
    1100                1105                1110

Ile Val  Met Gly Leu Ser Asn  Val Ala Val Ser Arg  Leu Ala Leu
    1115                1120                1125

Thr Trp  Glu Lys Leu Pro Ser  Lys Phe Lys Lys Phe  Tyr Ala Glu
    1130                1135                1140

Phe Glu  Ser Leu Met Asp Pro  Ser Arg Asn His Arg  Ala Tyr Arg
    1145                1150                1155

Leu Thr  Val Ala Lys Leu Glu  Pro Pro Leu Ile Pro  Phe Met Pro
    1160                1165                1170

Leu Leu  Ile Lys Asp Met Thr  Phe Thr His Glu Gly  Asn Lys Thr
    1175                1180                1185

Phe Ile  Asp Asn Leu Val Asn  Phe Glu Lys Met Arg  Met Ile Ala
    1190                1195                1200

Asn Thr  Ala Arg Thr Val Arg  Tyr Tyr Arg Ser Gln  Pro Phe Asn
    1205                1210                1215

Pro Asp  Ala Ala Gln Ala Asn  Lys Asn His Gln Asp  Val Arg Ser
    1220                1225                1230

Tyr Val  Arg Gln Leu Asn Val  Ile Asp Asn Gln Arg  Thr Leu Ser
    1235                1240                1245

Gln Met  Ser His Arg Leu Glu  Pro Arg Arg
    1250                1255


<210> SEQ ID NO 20
<211> LENGTH: 1252
<212> TYPE: PRT
<213> ORGANISM: Artificial Sequence
<220> FEATURE:
<223> OTHER INFORMATION: Synthetic

<400> SEQUENCE: 20

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
```

```
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575
```

```
Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Asn
    690                 695                 700

Thr Val Arg Leu Lys Glu His Asp Gln Asp Val Leu Val Leu Glu Lys
705                 710                 715                 720

Val Pro Ala Gly Asn Arg Ala Ser Asn Gln Gly Asn Ser Gln Pro Gln
                725                 730                 735

Gln Lys Tyr Thr Val Met Ser Gly Thr Pro Glu Lys Ile Leu Glu His
            740                 745                 750

Phe Leu Glu Thr Ile Arg Leu Glu Ala Thr Leu Asn Glu Ala Thr Asp
        755                 760                 765

Ser Val Leu Asn Asp Phe Ile Met Met His Cys Val Phe Met Pro Asn
    770                 775                 780

Thr Gln Leu Cys Pro Ala Leu Val Ala His Tyr His Ala Gln Pro Ser
785                 790                 795                 800

Gln Gly Thr Glu Gln Glu Lys Met Asp Tyr Ala Leu Asn Asn Lys Arg
                805                 810                 815

Arg Val Ile Arg Leu Val Leu Gln Trp Ala Ala Met Tyr Gly Asp Leu
            820                 825                 830

Leu Gln Glu Asp Asp Val Ser Met Ala Phe Leu Glu Glu Phe Tyr Val
        835                 840                 845

Ser Val Ser Asp Asp Ala Arg Met Ile Ala Ala Leu Lys Glu Gln Leu
    850                 855                 860

Pro Glu Leu Glu Lys Ile Val Lys Gln Ile Ser Glu Asp Ala Lys Ala
865                 870                 875                 880

Pro Gln Lys Lys His Lys Val Leu Leu Gln Gln Phe Asn Thr Gly Asp
                885                 890                 895

Glu Arg Ala Gln Lys Arg Gln Pro Ile Arg Gly Ser Asp Glu Val Leu
            900                 905                 910

Phe Lys Val Tyr Cys Met Asp Pro Thr Tyr Thr Thr Ile Arg Val Pro
        915                 920                 925

Val Ala Thr Ser Val Lys Glu Val Ile Ser Ala Val Ala Asp Lys Leu
    930                 935                 940

Gly Ser Gly Glu Gly Leu Ile Ile Val Lys Met Ser Ser Gly Gly Glu
945                 950                 955                 960

Lys Val Val Leu Lys Pro Asn Asp Val Ser Val Phe Met Thr Leu Thr
                965                 970                 975

Ile Asn Gly Arg Leu Phe Ala Cys Pro Arg Glu Gln Phe Asp Ser Leu
            980                 985                 990
```

```
Thr Pro Leu Pro Glu Gln Glu Gly  Pro Thr Val Gly Thr  Val Gly Thr
        995                 1000                 1005

Phe Glu  Leu Met Ser Ser Lys  Asp Leu Ala Tyr Gln  Met Thr Ile
    1010                 1015                 1020

Tyr Asp  Trp Glu Leu Phe Asn  Cys Val His Glu Leu  Glu Leu Ile
    1025                 1030                 1035

Tyr His  Thr Phe Gly Arg His  Asn Phe Lys Lys Thr  Thr Ala Asn
    1040                 1045                 1050

Leu Asp  Leu Phe Leu Arg Arg  Phe Asn Glu Ile Gln  Phe Trp Val
    1055                 1060                 1065

Val Thr  Glu Ile Cys Leu Cys  Ser Gln Leu Ser Lys  Arg Val Gln
    1070                 1075                 1080

Leu Leu  Lys Lys Phe Ile Lys  Ile Ala Ala His Cys  Lys Glu Tyr
    1085                 1090                 1095

Lys Asn  Leu Asn Ser Phe Phe  Ala Ile Val Met Gly  Leu Ser Asn
    1100                 1105                 1110

Val Ala  Val Ser Arg Leu Ala  Leu Thr Trp Glu Lys  Leu Pro Ser
    1115                 1120                 1125

Lys Phe  Lys Lys Phe Tyr Ala  Glu Phe Glu Ser Leu  Met Asp Pro
    1130                 1135                 1140

Ser Arg  Asn His Arg Ala Tyr  Arg Leu Thr Val Ala  Lys Leu Glu
    1145                 1150                 1155

Pro Pro  Leu Ile Pro Phe Met  Pro Leu Leu Ile Lys  Asp Met Thr
    1160                 1165                 1170

Phe Thr  His Glu Gly Asn Lys  Thr Phe Ile Asp Asn  Leu Val Asn
    1175                 1180                 1185

Phe Glu  Lys Met Arg Met Ile  Ala Asn Thr Ala Arg  Thr Val Arg
    1190                 1195                 1200

Tyr Tyr  Arg Ser Gln Pro Phe  Asn Pro Asp Ala Ala  Gln Ala Asn
    1205                 1210                 1215

Lys Asn  His Gln Asp Val Arg  Ser Tyr Val Arg Gln  Leu Asn Val
    1220                 1225                 1230

Ile Asp  Asn Gln Arg Thr Leu  Ser Gln Met Ser His  Arg Leu Glu
    1235                 1240                 1245

Pro Arg  Arg Pro
    1250


<210> SEQ ID NO 21
<211> LENGTH: 1260
<212> TYPE: PRT
<213> ORGANISM: Artificial Sequence
<220> FEATURE:
<223> OTHER INFORMATION: Synthetic

<400> SEQUENCE: 21

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80
```

-continued

```
Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
```

```
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Asn
    690                 695                 700

Arg Ile Leu Arg Asp Val Glu Ala Asn Thr Val Arg Leu Lys Glu His
705                 710                 715                 720

Asp Gln Asp Val Leu Val Leu Glu Lys Val Pro Ala Gly Asn Arg Ala
                725                 730                 735

Ser Asn Gln Gly Asn Ser Gln Pro Gln Gln Lys Tyr Thr Val Met Ser
            740                 745                 750

Gly Thr Pro Glu Lys Ile Leu Glu His Phe Leu Glu Thr Ile Arg Leu
        755                 760                 765

Glu Ala Thr Leu Asn Glu Ala Thr Asp Ser Val Leu Asn Asp Phe Ile
    770                 775                 780

Met Met His Cys Val Phe Met Pro Asn Thr Gln Leu Cys Pro Ala Leu
785                 790                 795                 800

Val Ala His Tyr His Ala Gln Pro Ser Gln Gly Thr Glu Gln Glu Lys
                805                 810                 815

Met Asp Tyr Ala Leu Asn Asn Lys Arg Arg Val Ile Arg Leu Val Leu
            820                 825                 830

Gln Trp Ala Ala Met Tyr Gly Asp Leu Leu Gln Glu Asp Asp Val Ser
        835                 840                 845

Met Ala Phe Leu Glu Glu Phe Tyr Val Ser Val Ser Asp Asp Ala Arg
    850                 855                 860

Met Ile Ala Ala Leu Lys Glu Gln Leu Pro Glu Leu Glu Lys Ile Val
865                 870                 875                 880

Lys Gln Ile Ser Glu Asp Ala Lys Ala Pro Gln Lys Lys His Lys Val
                885                 890                 895

Leu Leu Gln Gln Phe Asn Thr Gly Asp Glu Arg Ala Gln Lys Arg Gln
            900                 905                 910

Pro Ile Arg Gly Ser Asp Glu Val Leu Phe Lys Val Tyr Cys Met Asp
        915                 920                 925
```

```
Pro Thr Tyr Thr Thr Ile Arg Val Pro Val Ala Thr Ser Val Lys Glu
    930                 935                 940

Val Ile Ser Ala Val Ala Asp Lys Leu Gly Ser Gly Glu Gly Leu Ile
945                 950                 955                 960

Ile Val Lys Met Ser Ser Gly Gly Glu Lys Val Val Leu Lys Pro Asn
                965                 970                 975

Asp Val Ser Val Phe Met Thr Leu Thr Ile Asn Gly Arg Leu Phe Ala
            980                 985                 990

Cys Pro Arg Glu Gln Phe Asp Ser  Leu Thr Pro Leu Pro  Glu Gln Glu
        995                 1000                1005

Gly Pro  Thr Val Gly Thr Val  Gly Thr Phe Glu Leu  Met Ser Ser
    1010                 1015                1020

Lys Asp  Leu Ala Tyr Gln Met  Thr Ile Tyr Asp Trp  Glu Leu Phe
    1025                 1030                1035

Asn Cys  Val His Glu Leu Glu  Leu Ile Tyr His Thr  Phe Gly Arg
    1040                 1045                1050

His Asn  Phe Lys Lys Thr Thr  Ala Asn Leu Asp Leu  Phe Leu Arg
    1055                 1060                1065

Arg Phe  Asn Glu Ile Gln Phe  Trp Val Val Thr Glu  Ile Cys Leu
    1070                 1075                1080

Cys Ser  Gln Leu Ser Lys Arg  Val Gln Leu Leu Lys  Lys Phe Ile
    1085                 1090                1095

Lys Ile  Ala Ala His Cys Lys  Glu Tyr Lys Asn Leu  Asn Ser Phe
    1100                 1105                1110

Phe Ala  Ile Val Met Gly Leu  Ser Asn Val Ala Val  Ser Arg Leu
    1115                 1120                1125

Ala Leu  Thr Trp Glu Lys Leu  Pro Ser Lys Phe Lys  Lys Phe Tyr
    1130                 1135                1140

Ala Glu  Phe Glu Ser Leu Met  Asp Pro Ser Arg Asn  His Arg Ala
    1145                 1150                1155

Tyr Arg  Leu Thr Val Ala Lys  Leu Glu Pro Pro Leu  Ile Pro Phe
    1160                 1165                1170

Met Pro  Leu Leu Ile Lys Asp  Met Thr Phe Thr His  Glu Gly Asn
    1175                 1180                1185

Lys Thr  Phe Ile Asp Asn Leu  Val Asn Phe Glu Lys  Met Arg Met
    1190                 1195                1200

Ile Ala  Asn Thr Ala Arg Thr  Val Arg Tyr Tyr Arg  Ser Gln Pro
    1205                 1210                1215

Phe Asn  Pro Asp Ala Ala Gln  Ala Asn Lys Asn His  Gln Asp Val
    1220                 1225                1230

Arg Ser  Tyr Val Arg Gln Leu  Asn Val Ile Asp Asn  Gln Arg Thr
    1235                 1240                1245

Leu Ser  Gln Met Ser His Arg  Leu Glu Pro Arg Arg
    1250                 1255                1260


<210> SEQ ID NO 22
<211> LENGTH: 1270
<212> TYPE: PRT
<213> ORGANISM: Artificial Sequence
<220> FEATURE:
<223> OTHER INFORMATION: Synthetic

<400> SEQUENCE: 22

Met Val Ala Ala His Ala Ala His Ser Ser Ser Ser Ala Glu Trp Ile
1               5                   10                  15
```

```
Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430
```

```
Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Glu Ala Asn Leu
    450                 455                 460

Glu Asn Val Tyr Ile Lys Ala Asp Lys Gln Lys Asn Gly Ile Lys Ala
465                 470                 475                 480

Asn Phe Lys Ile Arg His Asn Ile Glu Asp Gly Gly Val Gln Leu Ala
                485                 490                 495

Tyr His Tyr Gln Gln Asn Thr Pro Ile Gly Asp Gly Pro Val Leu Leu
            500                 505                 510

Pro Asp Asn His Tyr Leu Ser Val Gln Ser Ile Leu Ser Lys Asp Pro
        515                 520                 525

Asn Glu Lys Arg Asp His Met Val Leu Leu Glu Phe Val Thr Ala Ala
    530                 535                 540

Gly Ile Thr Leu Gly Met Asp Glu Leu Tyr Lys Gly Gly Thr Gly Gly
545                 550                 555                 560

Ser Met Val Ser Lys Gly Glu Glu Leu Phe Thr Gly Val Val Pro Ile
                565                 570                 575

Gln Val Glu Leu Asp Gly Asp Val Asn Gly His Lys Phe Ser Val Ser
            580                 585                 590

Gly Glu Gly Glu Gly Asp Ala Thr Tyr Gly Lys Leu Thr Leu Lys Phe
        595                 600                 605

Ile Cys Thr Thr Gly Lys Leu Pro Val Pro Trp Pro Thr Leu Val Thr
    610                 615                 620

Thr Leu Thr Tyr Gly Val Gln Cys Phe Ser Arg Tyr Pro Asp His Met
625                 630                 635                 640

Lys Gln His Asp Phe Phe Lys Ser Ala Met Pro Glu Gly Tyr Ile Gln
                645                 650                 655

Glu Arg Thr Ile Phe Phe Lys Asp Asp Gly Asn Tyr Lys Thr Arg Ala
            660                 665                 670

Glu Val Lys Phe Glu Gly Asp Thr Leu Val Asn Arg Ile Glu Leu Lys
        675                 680                 685

Gly Ile Asp Phe Lys Glu Asp Gly Asn Ile Leu Gly His Lys Leu Glu
    690                 695                 700

Tyr Asn Thr Arg Lys Glu Asp Phe Asn Arg Ile Leu Arg Asp Val Glu
705                 710                 715                 720

Ala Asn Thr Val Arg Leu Lys Glu His Asp Gln Asp Val Leu Val Leu
                725                 730                 735

Glu Lys Val Pro Ala Gly Asn Arg Ala Ser Asn Gln Gly Asn Ser Gln
            740                 745                 750

Pro Gln Gln Lys Tyr Thr Val Met Ser Gly Thr Pro Glu Lys Ile Leu
        755                 760                 765

Glu His Phe Leu Glu Thr Ile Arg Leu Glu Ala Thr Leu Asn Glu Ala
    770                 775                 780

Thr Asp Ser Val Leu Asn Asp Phe Ile Met Met His Cys Val Phe Met
785                 790                 795                 800

Pro Asn Thr Gln Leu Cys Pro Ala Leu Val Ala His Tyr His Ala Gln
                805                 810                 815

Pro Ser Gln Gly Thr Glu Gln Glu Lys Met Asp Tyr Ala Leu Asn Asn
            820                 825                 830

Lys Arg Arg Val Ile Arg Leu Val Leu Gln Trp Ala Ala Met Tyr Gly
        835                 840                 845

Asp Leu Leu Gln Glu Asp Asp Val Ser Met Ala Phe Leu Glu Glu Phe
```

```
    850                 855                 860

Tyr Val Ser Val Ser Asp Asp Ala Arg Met Ile Ala Ala Leu Lys Glu
865                 870                 875                 880

Gln Leu Pro Glu Leu Glu Lys Ile Val Lys Gln Ile Ser Glu Asp Ala
                885                 890                 895

Lys Ala Pro Gln Lys Lys His Lys Val Leu Leu Gln Gln Phe Asn Thr
            900                 905                 910

Gly Asp Glu Arg Ala Gln Lys Arg Gln Pro Ile Arg Gly Ser Asp Glu
        915                 920                 925

Val Leu Phe Lys Val Tyr Cys Met Asp Pro Thr Tyr Thr Thr Ile Arg
    930                 935                 940

Val Pro Val Ala Thr Ser Val Lys Glu Val Ile Ser Ala Val Ala Asp
945                 950                 955                 960

Lys Leu Gly Ser Gly Glu Gly Leu Ile Ile Val Lys Met Ser Ser Gly
                965                 970                 975

Gly Glu Lys Val Val Leu Lys Pro Asn Asp Val Ser Val Phe Met Thr
            980                 985                 990

Leu Thr Ile Asn Gly Arg Leu Phe  Ala Cys Pro Arg Glu  Gln Phe Asp
        995                 1000                1005

Ser Leu  Thr Pro Leu Pro Glu  Gln Glu Gly Pro Thr  Val Gly Thr
    1010                 1015                1020

Val Gly  Thr Phe Glu Leu Met  Ser Ser Lys Asp Leu  Ala Tyr Gln
    1025                 1030                1035

Met Thr  Ile Tyr Asp Trp Glu  Leu Phe Asn Cys Val  His Glu Leu
    1040                 1045                1050

Glu Leu  Ile Tyr His Thr Phe  Gly Arg His Asn Phe  Lys Lys Thr
    1055                 1060                1065

Thr Ala  Asn Leu Asp Leu Phe  Leu Arg Arg Phe Asn  Glu Ile Gln
    1070                 1075                1080

Phe Trp  Val Val Thr Glu Ile  Cys Leu Cys Ser Gln  Leu Ser Lys
    1085                 1090                1095

Arg Val  Gln Leu Leu Lys Lys  Phe Ile Lys Ile Ala  Ala His Cys
    1100                 1105                1110

Lys Glu  Tyr Lys Asn Leu Asn  Ser Phe Phe Ala Ile  Val Met Gly
    1115                 1120                1125

Leu Ser  Asn Val Ala Val Ser  Arg Leu Ala Leu Thr  Trp Glu Lys
    1130                 1135                1140

Leu Pro  Ser Lys Phe Lys Lys  Phe Tyr Ala Glu Phe  Glu Ser Leu
    1145                 1150                1155

Met Asp  Pro Ser Arg Asn His  Arg Ala Tyr Arg Leu  Thr Val Ala
    1160                 1165                1170

Lys Leu  Glu Pro Pro Leu Ile  Pro Phe Met Pro Leu  Leu Ile Lys
    1175                 1180                1185

Asp Met  Thr Phe Thr His Glu  Gly Asn Lys Thr Phe  Ile Asp Asn
    1190                 1195                1200

Leu Val  Asn Phe Glu Lys Met  Arg Met Ile Ala Asn  Thr Ala Arg
    1205                 1210                1215

Thr Val  Arg Tyr Tyr Arg Ser  Gln Pro Phe Asn Pro  Asp Ala Ala
    1220                 1225                1230

Gln Ala  Asn Lys Asn His Gln  Asp Val Arg Ser Tyr  Val Arg Gln
    1235                 1240                1245

Leu Asn  Val Ile Asp Asn Gln  Arg Thr Leu Ser Gln  Met Ser His
    1250                 1255                1260
```

```
Arg Leu  Glu Pro Arg Arg Pro
    1265                1270


<210> SEQ ID NO 23
<211> LENGTH: 1253
<212> TYPE: PRT
<213> ORGANISM: Artificial Sequence
<220> FEATURE:
<223> OTHER INFORMATION: Synthetic

<400> SEQUENCE: 23

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350
```

```
His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Leu Glu Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Thr
    690                 695                 700

Arg Thr Val Arg Leu Lys Glu His Asp Gln Asp Val Leu Val Leu Glu
705                 710                 715                 720

Lys Val Pro Ala Gly Asn Arg Ala Ser Asn Gln Gly Asn Ser Gln Pro
                725                 730                 735

Gln Gln Lys Tyr Thr Val Met Ser Gly Thr Pro Glu Lys Ile Leu Glu
            740                 745                 750

His Phe Leu Glu Thr Ile Arg Leu Glu Ala Thr Leu Asn Glu Ala Thr
        755                 760                 765
```

```
Asp Ser Val Leu Asn Asp Phe Ile Met Met His Cys Val Phe Met Pro
    770                 775                 780

Asn Thr Gln Leu Cys Pro Ala Leu Val Ala His Tyr His Ala Gln Pro
785                 790                 795                 800

Ser Gln Gly Thr Glu Gln Glu Lys Met Asp Tyr Ala Leu Asn Asn Lys
                805                 810                 815

Arg Arg Val Ile Arg Leu Val Leu Gln Trp Ala Ala Met Tyr Gly Asp
            820                 825                 830

Leu Leu Gln Glu Asp Asp Val Ser Met Ala Phe Leu Glu Glu Phe Tyr
        835                 840                 845

Val Ser Val Ser Asp Asp Ala Arg Met Ile Ala Ala Leu Lys Glu Gln
    850                 855                 860

Leu Pro Glu Leu Glu Lys Ile Val Lys Gln Ile Ser Glu Asp Ala Lys
865                 870                 875                 880

Ala Pro Gln Lys Lys His Lys Val Leu Leu Gln Gln Phe Asn Thr Gly
                885                 890                 895

Asp Glu Arg Ala Gln Lys Arg Gln Pro Ile Arg Gly Ser Asp Glu Val
            900                 905                 910

Leu Phe Lys Val Tyr Cys Met Asp Pro Thr Tyr Thr Thr Ile Arg Val
        915                 920                 925

Pro Val Ala Thr Ser Val Lys Glu Val Ile Ser Ala Val Ala Asp Lys
    930                 935                 940

Leu Gly Ser Gly Glu Gly Leu Ile Ile Val Lys Met Ser Ser Gly Gly
945                 950                 955                 960

Glu Lys Val Val Leu Lys Pro Asn Asp Val Ser Val Phe Met Thr Leu
                965                 970                 975

Thr Ile Asn Gly Arg Leu Phe Ala Cys Pro Arg Glu Gln Phe Asp Ser
            980                 985                 990

Leu Thr Pro Leu Pro Glu Gln Glu  Gly Pro Thr Val Gly  Thr Val Gly
        995                 1000                1005

Thr Phe  Glu Leu Met Ser Ser  Lys Asp Leu Ala Tyr  Gln Met Thr
    1010                1015                1020

Ile Tyr  Asp Trp Glu Leu Phe  Asn Cys Val His Glu  Leu Glu Leu
    1025                1030                1035

Ile Tyr  His Thr Phe Gly Arg  His Asn Phe Lys Lys  Thr Thr Ala
    1040                1045                1050

Asn Leu  Asp Leu Phe Leu Arg  Arg Phe Asn Glu Ile  Gln Phe Trp
    1055                1060                1065

Val Val  Thr Glu Ile Cys Leu  Cys Ser Gln Leu Ser  Lys Arg Val
    1070                1075                1080

Gln Leu  Leu Lys Lys Phe Ile  Lys Ile Ala Ala His  Cys Lys Glu
    1085                1090                1095

Tyr Lys  Asn Leu Asn Ser Phe  Phe Ala Ile Val Met  Gly Leu Ser
    1100                1105                1110

Asn Val  Ala Val Ser Arg Leu  Ala Leu Thr Trp Glu  Lys Leu Pro
    1115                1120                1125

Ser Lys  Phe Lys Lys Phe Tyr  Ala Glu Phe Glu Ser  Leu Met Asp
    1130                1135                1140

Pro Ser  Arg Asn His Arg Ala  Tyr Arg Leu Thr Val  Ala Lys Leu
    1145                1150                1155

Glu Pro  Pro Leu Ile Pro Phe  Met Pro Leu Leu Ile  Lys Asp Met
    1160                1165                1170

Thr Phe  Thr His Glu Gly Asn  Lys Thr Phe Ile Asp  Asn Leu Val
```

```
    1175                1180                1185

Asn Phe  Glu Lys Met Arg Met  Ile Ala Asn Thr Ala  Arg Thr Val
    1190                1195                1200

Arg Tyr  Tyr Arg Ser Gln Pro  Phe Asn Pro Asp Ala  Ala Gln Ala
    1205                1210                1215

Asn Lys  Asn His Gln Asp Val  Arg Ser Tyr Val Arg  Gln Leu Asn
    1220                1225                1230

Val Ile  Asp Asn Gln Arg Thr  Leu Ser Gln Met Ser  His Arg Leu
    1235                1240                1245

Glu Pro  Arg Arg Pro
    1250


<210> SEQ ID NO 24
<211> LENGTH: 1256
<212> TYPE: PRT
<213> ORGANISM: Artificial Sequence
<220> FEATURE:
<223> OTHER INFORMATION: Synthetic

<400> SEQUENCE: 24

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
```

```
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Met Ser Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Val Ser Asp
    690                 695                 700
```

```
Val Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050

Thr Thr  Ala Asn Leu Asp Leu  Phe Leu Arg Arg Phe  Asn Glu Ile
    1055                1060                1065

Gln Phe  Trp Val Val Thr Glu  Ile Cys Leu Cys Ser  Gln Leu Ser
    1070                1075                1080

Lys Arg  Val Gln Leu Leu Lys  Lys Phe Ile Lys Ile  Ala Ala His
    1085                1090                1095

Cys Lys  Glu Tyr Lys Asn Leu  Asn Ser Phe Phe Ala  Ile Val Met
    1100                1105                1110
```

```
Gly Leu  Ser Asn Val Ala Val  Ser Arg Leu Ala Leu  Thr Trp Glu
    1115                 1120                 1125

Lys Leu  Pro Ser Lys Phe Lys  Lys Phe Tyr Ala Glu  Phe Glu Ser
    1130                 1135                 1140

Leu Met  Asp Pro Ser Arg Asn  His Arg Ala Tyr Arg  Leu Thr Val
    1145                 1150                 1155

Ala Lys  Leu Glu Pro Pro Leu  Ile Pro Phe Met Pro  Leu Leu Ile
    1160                 1165                 1170

Lys Asp  Met Thr Phe Thr His  Glu Gly Asn Lys Thr  Phe Ile Asp
    1175                 1180                 1185

Asn Leu  Val Asn Phe Glu Lys  Met Arg Met Ile Ala  Asn Thr Ala
    1190                 1195                 1200

Arg Thr  Val Arg Tyr Tyr Arg  Ser Gln Pro Phe Asn  Pro Asp Ala
    1205                 1210                 1215

Ala Gln  Ala Asn Lys Asn His  Gln Asp Val Arg Ser  Tyr Val Arg
    1220                 1225                 1230

Gln Leu  Asn Val Ile Asp Asn  Gln Arg Thr Leu Ser  Gln Met Ser
    1235                 1240                 1245

His Arg  Leu Glu Pro Arg Arg  Pro
    1250                 1255


<210> SEQ ID NO 25
<211> LENGTH: 1256
<212> TYPE: PRT
<213> ORGANISM: Artificial Sequence
<220> FEATURE:
<223> OTHER INFORMATION: Synthetic

<400> SEQUENCE: 25

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205
```

```
Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
```

-continued

```
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Asp
    690                 695                 700

Val Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050
```

```
Thr Thr  Ala Asn Leu Asp Leu  Phe Leu Arg Arg Phe  Asn Glu Ile
    1055                 1060                 1065

Gln Phe  Trp Val Val Thr Glu  Ile Cys Leu Cys Ser  Gln Leu Ser
    1070                 1075                 1080

Lys Arg  Val Gln Leu Leu Lys  Lys Phe Ile Lys Ile  Ala Ala His
    1085                 1090                 1095

Cys Lys  Glu Tyr Lys Asn Leu  Asn Ser Phe Phe Ala  Ile Val Met
    1100                 1105                 1110

Gly Leu  Ser Asn Val Ala Val  Ser Arg Leu Ala Leu  Thr Trp Glu
    1115                 1120                 1125

Lys Leu  Pro Ser Lys Phe Lys  Lys Phe Tyr Ala Glu  Phe Glu Ser
    1130                 1135                 1140

Leu Met  Asp Pro Ser Arg Asn  His Arg Ala Tyr Arg  Leu Thr Val
    1145                 1150                 1155

Ala Lys  Leu Glu Pro Pro Leu  Ile Pro Phe Met Pro  Leu Leu Ile
    1160                 1165                 1170

Lys Asp  Met Thr Phe Thr His  Glu Gly Asn Lys Thr  Phe Ile Asp
    1175                 1180                 1185

Asn Leu  Val Asn Phe Glu Lys  Met Arg Met Ile Ala  Asn Thr Ala
    1190                 1195                 1200

Arg Thr  Val Arg Tyr Tyr Arg  Ser Gln Pro Phe Asn  Pro Asp Ala
    1205                 1210                 1215

Ala Gln  Ala Asn Lys Asn His  Gln Asp Val Arg Ser  Tyr Val Arg
    1220                 1225                 1230

Gln Leu  Asn Val Ile Asp Asn  Gln Arg Thr Leu Ser  Gln Met Ser
    1235                 1240                 1245

His Arg  Leu Glu Pro Arg Arg  Pro
    1250                 1255
```

<210> SEQ ID NO 26
<211> LENGTH: 1258
<212> TYPE: PRT
<213> ORGANISM: Artificial Sequence
<220> FEATURE:
<223> OTHER INFORMATION: Synthetic

<400> SEQUENCE: 26

```
Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140
```

```
Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Val Ser His Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560
```

```
Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Phe
    690                 695                 700

Asn Asp Val Glu Ala Asn Thr Val Arg Leu Lys Glu His Asp Gln Asp
705                 710                 715                 720

Val Leu Val Leu Glu Lys Val Pro Ala Gly Asn Arg Ala Ser Asn Gln
                725                 730                 735

Gly Asn Ser Gln Pro Gln Gln Lys Tyr Thr Val Met Ser Gly Thr Pro
            740                 745                 750

Glu Lys Ile Leu Glu His Phe Leu Glu Thr Ile Arg Leu Glu Ala Thr
        755                 760                 765

Leu Asn Glu Ala Thr Asp Ser Val Leu Asn Asp Phe Ile Met Met His
    770                 775                 780

Cys Val Phe Met Pro Asn Thr Gln Leu Cys Pro Ala Leu Val Ala His
785                 790                 795                 800

Tyr His Ala Gln Pro Ser Gln Gly Thr Glu Gln Glu Lys Met Asp Tyr
                805                 810                 815

Ala Leu Asn Asn Lys Arg Arg Val Ile Arg Leu Val Leu Gln Trp Ala
            820                 825                 830

Ala Met Tyr Gly Asp Leu Leu Gln Glu Asp Asp Val Ser Met Ala Phe
        835                 840                 845

Leu Glu Glu Phe Tyr Val Ser Val Ser Asp Asp Ala Arg Met Ile Ala
    850                 855                 860

Ala Leu Lys Glu Gln Leu Pro Glu Leu Glu Lys Ile Val Lys Gln Ile
865                 870                 875                 880

Ser Glu Asp Ala Lys Ala Pro Gln Lys Lys His Lys Val Leu Leu Gln
                885                 890                 895

Gln Phe Asn Thr Gly Asp Glu Arg Ala Gln Lys Arg Gln Pro Ile Arg
            900                 905                 910

Gly Ser Asp Glu Val Leu Phe Lys Val Tyr Cys Met Asp Pro Thr Tyr
        915                 920                 925

Thr Thr Ile Arg Val Pro Val Ala Thr Ser Val Lys Glu Val Ile Ser
    930                 935                 940

Ala Val Ala Asp Lys Leu Gly Ser Gly Glu Gly Leu Ile Ile Val Lys
945                 950                 955                 960

Met Ser Ser Gly Gly Glu Lys Val Val Leu Lys Pro Asn Asp Val Ser
                965                 970                 975

Val Phe Met Thr Leu Thr Ile Asn Gly Arg Leu Phe Ala Cys Pro Arg
```

```
            980                 985                 990

Glu Gln Phe Asp Ser Leu Thr Pro  Leu Pro Glu Gln Glu  Gly Pro Thr
        995                 1000                1005

Val Gly  Thr Val Gly Thr Phe  Glu Leu Met Ser Ser  Lys Asp Leu
    1010                1015                1020

Ala Tyr  Gln Met Thr Ile Tyr  Asp Trp Glu Leu Phe  Asn Cys Val
    1025                1030                1035

His Glu  Leu Glu Leu Ile Tyr  His Thr Phe Gly Arg  His Asn Phe
    1040                1045                1050

Lys Lys  Thr Thr Ala Asn Leu  Asp Leu Phe Leu Arg  Arg Phe Asn
    1055                1060                1065

Glu Ile  Gln Phe Trp Val Val  Thr Glu Ile Cys Leu  Cys Ser Gln
    1070                1075                1080

Leu Ser  Lys Arg Val Gln Leu  Leu Lys Lys Phe Ile  Lys Ile Ala
    1085                1090                1095

Ala His  Cys Lys Glu Tyr Lys  Asn Leu Asn Ser Phe  Phe Ala Ile
    1100                1105                1110

Val Met  Gly Leu Ser Asn Val  Ala Val Ser Arg Leu  Ala Leu Thr
    1115                1120                1125

Trp Glu  Lys Leu Pro Ser Lys  Phe Lys Lys Phe Tyr  Ala Glu Phe
    1130                1135                1140

Glu Ser  Leu Met Asp Pro Ser  Arg Asn His Arg Ala  Tyr Arg Leu
    1145                1150                1155

Thr Val  Ala Lys Leu Glu Pro  Pro Leu Ile Pro Phe  Met Pro Leu
    1160                1165                1170

Leu Ile  Lys Asp Met Thr Phe  Thr His Glu Gly Asn  Lys Thr Phe
    1175                1180                1185

Ile Asp  Asn Leu Val Asn Phe  Glu Lys Met Arg Met  Ile Ala Asn
    1190                1195                1200

Thr Ala  Arg Thr Val Arg Tyr  Tyr Arg Ser Gln Pro  Phe Asn Pro
    1205                1210                1215

Asp Ala  Ala Gln Ala Asn Lys  Asn His Gln Asp Val  Arg Ser Tyr
    1220                1225                1230

Val Arg  Gln Leu Asn Val Ile  Asp Asn Gln Arg Thr  Leu Ser Gln
    1235                1240                1245

Met Ser  His Arg Leu Glu Pro  Arg Arg Pro
    1250                1255


<210> SEQ ID NO 27
<211> LENGTH: 1439
<212> TYPE: PRT
<213> ORGANISM: Artificial Sequence
<220> FEATURE:
<223> OTHER INFORMATION: Synthetic

<400> SEQUENCE: 27

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
```

-continued

```
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Glu Ala Asn Thr
    450                 455                 460

Val Arg Leu Lys Glu His Asp Gln Asp Val Leu Val Leu Glu Lys Val
465                 470                 475                 480

Pro Ala Gly Asn Arg Ala Ser Asn Gln Gly Asn Ser Gln Pro Gln Gln
                485                 490                 495
```

```
Lys Tyr Thr Val Met Ser Gly Thr Pro Glu Lys Ile Leu Glu His Phe
            500                 505                 510

Leu Glu Thr Ile Arg Leu Glu Ala Thr Leu Asn Glu Ala Thr Asp Ser
        515                 520                 525

Val Leu Asn Asp Phe Ile Met Met His Cys Val Phe Met Pro Asn Thr
    530                 535                 540

Gln Leu Cys Pro Ala Leu Val Ala His Tyr His Ala Gln Pro Ser Gln
545                 550                 555                 560

Gly Thr Glu Gln Glu Lys Met Asp Tyr Ala Leu Asn Asn Lys Arg Arg
                565                 570                 575

Val Ile Arg Leu Val Leu Gln Trp Ala Ala Met Tyr Gly Asp Leu Leu
            580                 585                 590

Gln Glu Asp Asp Val Ser Met Ala Phe Leu Glu Glu Phe Tyr Val Ser
        595                 600                 605

Val Ser Asp Asp Ala Arg Met Ile Ala Ala Leu Lys Glu Gln Leu Pro
    610                 615                 620

Glu Leu Glu Lys Ile Val Lys Gln Ile Ser Glu Asp Ala Lys Ala Pro
625                 630                 635                 640

Gln Lys Lys His Lys Val Leu Leu Gln Gln Phe Asn Thr Gly Asp Glu
                645                 650                 655

Arg Ala Gln Lys Arg Gln Pro Ile Arg Gly Ser Asp Glu Val Leu Phe
            660                 665                 670

Lys Val Tyr Cys Met Asp Pro Thr Tyr Thr Thr Ile Arg Val Pro Val
        675                 680                 685

Ala Thr Ser Val Lys Glu Val Ile Ser Ala Val Ala Asp Lys Leu Gly
    690                 695                 700

Ser Gly Glu Gly Leu Ile Ile Val Lys Met Ser Ser Gly Gly Glu Lys
705                 710                 715                 720

Val Val Leu Lys Pro Asn Asp Val Ser Val Phe Met Thr Leu Thr Ile
                725                 730                 735

Asn Gly Arg Leu Phe Ala Cys Pro Arg Glu Gln Phe Asp Ser Leu Thr
            740                 745                 750

Pro Leu Pro Glu Gln Glu Gly Pro Thr Val Gly Thr Val Gly Thr Phe
        755                 760                 765

Glu Leu Met Ser Ser Lys Asp Leu Ala Tyr Gln Met Thr Ile Tyr Asp
    770                 775                 780

Trp Glu Leu Phe Asn Cys Val His Glu Leu Glu Leu Ile Tyr His Thr
785                 790                 795                 800

Phe Gly Arg His Asn Phe Lys Lys Thr Thr Ala Asn Leu Asp Leu Phe
                805                 810                 815

Leu Arg Arg Phe Asn Glu Ile Gln Phe Trp Val Val Thr Glu Ile Cys
            820                 825                 830

Leu Cys Ser Gln Leu Ser Lys Arg Val Gln Leu Leu Lys Lys Phe Ile
        835                 840                 845

Lys Ile Ala Ala His Cys Lys Glu Tyr Lys Asn Leu Asn Ser Phe Phe
    850                 855                 860

Ala Ile Val Met Gly Leu Ser Asn Val Ala Val Ser Arg Leu Ala Leu
865                 870                 875                 880

Thr Trp Glu Lys Leu Pro Ser Lys Phe Lys Lys Phe Tyr Ala Glu Phe
                885                 890                 895

Glu Ser Leu Met Asp Pro Ser Arg Asn His Arg Ala Tyr Arg Leu Thr
            900                 905                 910
```

```
Val Ala Lys Leu Glu Pro Pro Leu Ile Pro Phe Met Pro Leu Leu Ile
        915                 920                 925

Lys Asp Met Thr Phe Thr His Glu Gly Asn Lys Thr Phe Ile Asp Asn
    930                 935                 940

Leu Val Asn Phe Glu Lys Met Arg Met Ile Ala Asn Thr Ala Arg Thr
945                 950                 955                 960

Val Arg Tyr Tyr Arg Ser Gln Pro Phe Asn Pro Asp Ala Ala Gln Ala
                965                 970                 975

Asn Lys Asn His Gln Asp Val Arg Ser Tyr Val Arg Gln Leu Asn Val
            980                 985                 990

Ile Asp Asn Gln Arg Thr Leu Ser  Gln Met Ser His Arg  Leu Glu Pro
        995                 1000                 1005

Arg Arg  Pro Leu Glu Asn Val  Tyr Ile Lys Ala Asp  Lys Gln Lys
    1010                 1015                 1020

Asn Gly  Ile Lys Ala Asn Phe  Lys Ile Arg His Asn  Ile Glu Asp
    1025                 1030                 1035

Gly Gly  Val Gln Leu Ala Tyr  His Tyr Gln Gln Asn  Thr Pro Ile
    1040                 1045                 1050

Gly Asp  Gly Pro Val Leu Leu  Pro Asp Asn His Tyr  Leu Ser Val
    1055                 1060                 1065

Gln Ser  Ile Leu Ser Lys Asp  Pro Asn Glu Lys Arg  Asp His Met
    1070                 1075                 1080

Val Leu  Leu Glu Phe Val Thr  Ala Ala Gly Ile Thr  Leu Gly Met
    1085                 1090                 1095

Asp Glu  Leu Tyr Lys Gly Gly  Thr Gly Gly Ser Met  Val Ser Lys
    1100                 1105                 1110

Gly Glu  Glu Leu Phe Thr Gly  Val Val Pro Ile Gln  Val Glu Leu
    1115                 1120                 1125

Asp Gly  Asp Val Asn Gly His  Lys Phe Ser Val Ser  Gly Glu Gly
    1130                 1135                 1140

Glu Gly  Asp Ala Thr Tyr Gly  Lys Leu Thr Leu Lys  Phe Ile Cys
    1145                 1150                 1155

Thr Thr  Gly Lys Leu Pro Val  Pro Trp Pro Thr Leu  Val Thr Thr
    1160                 1165                 1170

Leu Thr  Tyr Gly Val Gln Cys  Phe Ser Arg Tyr Pro  Asp His Met
    1175                 1180                 1185

Lys Gln  His Asp Phe Phe Lys  Ser Ala Met Pro Glu  Gly Tyr Ile
    1190                 1195                 1200

Gln Glu  Arg Thr Ile Phe Phe  Lys Asp Asp Gly Asn  Tyr Lys Thr
    1205                 1210                 1215

Arg Ala  Glu Val Lys Phe Glu  Gly Asp Thr Leu Val  Asn Arg Ile
    1220                 1225                 1230

Glu Leu  Lys Gly Ile Asp Phe  Lys Glu Asp Gly Asn  Ile Leu Gly
    1235                 1240                 1245

His Lys  Leu Glu Tyr Asn Thr  Arg Arg Glu Tyr Lys  Leu Val Val
    1250                 1255                 1260

Leu Gly  Ser Gly Gly Val Gly  Lys Ser Ala Leu Thr  Val Gln Phe
    1265                 1270                 1275

Val Gln  Gly Ile Phe Val Glu  Lys Tyr Asp Pro Thr  Ile Glu Asp
    1280                 1285                 1290

Ser Tyr  Arg Lys Gln Val Glu  Val Asp Ala Gln Gln  Cys Met Leu
    1295                 1300                 1305

Glu Ile  Leu Asp Thr Ala Gly  Thr Glu Gln Phe Thr  Ala Met Arg
```

```
    1310                1315                1320

Asp Leu  Tyr Met Lys Asn Gly  Gln Gly Phe Ala Leu  Val Tyr Ser
    1325                1330                1335

Ile Thr  Ala Gln Ser Thr Phe  Asn Asp Leu Gln Asp  Leu Arg Glu
    1340                1345                1350

Gln Ile  Leu Arg Val Lys Asp  Thr Asp Asp Val Pro  Met Ile Leu
    1355                1360                1365

Val Gly  Asn Lys Cys Asp Leu  Glu Asp Glu Arg Val  Val Gly Lys
    1370                1375                1380

Glu Gln  Gly Gln Asn Leu Ala  Arg Gln Trp Asn Asn  Cys Ala Phe
    1385                1390                1395

Leu Glu  Ser Ser Ala Lys Ser  Lys Ile Asn Val Asn  Glu Ile Phe
    1400                1405                1410

Tyr Asp  Leu Val Arg Gln Ile  Asn Arg Lys Thr Pro  Val Pro Gly
    1415                1420                1425

Lys Ala  Arg Lys Lys Ser Ser  Cys Gln Leu Leu
    1430                1435


<210> SEQ ID NO 28
<211> LENGTH: 1256
<212> TYPE: PRT
<213> ORGANISM: Artificial Sequence
<220> FEATURE:
<223> OTHER INFORMATION: Synthetic

<400> SEQUENCE: 28

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
```

```
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Glu Leu Glu Asn
    450                 455                 460

Val Tyr Ile Lys Ala Asp Lys Gln Lys Asn Gly Ile Lys Ala Asn Phe
465                 470                 475                 480

Lys Ile Arg His Asn Ile Glu Asp Gly Gly Val Gln Leu Ala Tyr His
                485                 490                 495

Tyr Gln Gln Asn Thr Pro Ile Gly Asp Gly Pro Val Leu Leu Pro Asp
            500                 505                 510

Asn His Tyr Leu Ser Val Gln Ser Ile Leu Ser Lys Asp Pro Asn Glu
        515                 520                 525

Lys Arg Asp His Met Val Leu Leu Glu Phe Val Thr Ala Ala Gly Ile
    530                 535                 540

Thr Leu Gly Met Asp Glu Leu Tyr Lys Gly Gly Thr Gly Gly Ser Met
545                 550                 555                 560

Val Ser Lys Gly Glu Glu Leu Phe Thr Gly Val Val Pro Ile Gln Val
                565                 570                 575

Glu Leu Asp Gly Asp Val Asn Gly His Lys Phe Ser Val Ser Gly Glu
            580                 585                 590

Gly Glu Gly Asp Ala Thr Tyr Gly Lys Leu Thr Leu Lys Phe Ile Cys
        595                 600                 605

Thr Thr Gly Lys Leu Pro Val Pro Trp Pro Thr Leu Val Thr Thr Leu
    610                 615                 620

Thr Tyr Gly Val Gln Cys Phe Ser Arg Tyr Pro Asp His Met Lys Gln
625                 630                 635                 640

His Asp Phe Phe Lys Ser Ala Met Pro Glu Gly Tyr Ile Gln Glu Arg
                645                 650                 655
```

```
Thr Ile Phe Phe Lys Asp Asp Gly Asn Tyr Lys Thr Arg Ala Glu Val
            660                 665                 670

Lys Phe Glu Gly Asp Thr Leu Val Asn Arg Ile Glu Leu Lys Gly Ile
        675                 680                 685

Asp Phe Lys Glu Asp Gly Asn Ile Leu Gly His Lys Leu Glu Tyr Asn
    690                 695                 700

Thr Arg Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050

Thr Thr  Ala Asn Leu Asp Leu  Phe Leu Arg Arg Phe  Asn Glu Ile
    1055                1060                1065
```

```
Gln Phe  Trp Val Val Thr Glu  Ile Cys Leu Cys Ser  Gln Leu Ser
    1070                 1075                 1080

Lys Arg  Val Gln Leu Leu Lys  Lys Phe Ile Lys Ile  Ala Ala His
    1085                 1090                 1095

Cys Lys  Glu Tyr Lys Asn Leu  Asn Ser Phe Phe Ala  Ile Val Met
    1100                 1105                 1110

Gly Leu  Ser Asn Val Ala Val  Ser Arg Leu Ala Leu  Thr Trp Glu
    1115                 1120                 1125

Lys Leu  Pro Ser Lys Phe Lys  Lys Phe Tyr Ala Glu  Phe Glu Ser
    1130                 1135                 1140

Leu Met  Asp Pro Ser Arg Asn  His Arg Ala Tyr Arg  Leu Thr Val
    1145                 1150                 1155

Ala Lys  Leu Glu Pro Pro Leu  Ile Pro Phe Met Pro  Leu Leu Ile
    1160                 1165                 1170

Lys Asp  Met Thr Phe Thr His  Glu Gly Asn Lys Thr  Phe Ile Asp
    1175                 1180                 1185

Asn Leu  Val Asn Phe Glu Lys  Met Arg Met Ile Ala  Asn Thr Ala
    1190                 1195                 1200

Arg Thr  Val Arg Tyr Tyr Arg  Ser Gln Pro Phe Asn  Pro Asp Ala
    1205                 1210                 1215

Ala Gln  Ala Asn Lys Asn His  Gln Asp Val Arg Ser  Tyr Val Arg
    1220                 1225                 1230

Gln Leu  Asn Val Ile Asp Asn  Gln Arg Thr Leu Ser  Gln Met Ser
    1235                 1240                 1245

His Arg  Leu Glu Pro Arg Arg  Pro
    1250                 1255
```

<210> SEQ ID NO 29
<211> LENGTH: 1256
<212> TYPE: PRT
<213> ORGANISM: Artificial Sequence
<220> FEATURE:
<223> OTHER INFORMATION: Synthetic

<400> SEQUENCE: 29

```
Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160
```

-continued

```
Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Glu Ala Asn Thr
    450                 455                 460

Val Arg Leu Lys Glu His Asp Gln Asp Val Leu Val Leu Glu Lys Val
465                 470                 475                 480

Pro Ala Gly Asn Arg Ala Ser Asn Gln Gly Asn Ser Gln Pro Gln Gln
                485                 490                 495

Lys Tyr Thr Val Met Ser Gly Thr Pro Glu Lys Ile Leu Glu His Phe
            500                 505                 510

Leu Glu Thr Ile Arg Leu Leu Glu Asn Val Tyr Ile Lys Ala Asp Lys
        515                 520                 525

Gln Lys Asn Gly Ile Lys Ala Asn Phe Lys Ile Arg His Asn Ile Glu
    530                 535                 540

Asp Gly Gly Val Gln Leu Ala Tyr His Tyr Gln Gln Asn Thr Pro Ile
545                 550                 555                 560

Gly Asp Gly Pro Val Leu Leu Pro Asp Asn His Tyr Leu Ser Val Gln
                565                 570                 575

Ser Ile Leu Ser Lys Asp Pro Asn Glu Lys Arg Asp His Met Val Leu
```

```
            580                 585                 590

Leu Glu Phe Val Thr Ala Ala Gly Ile Thr Leu Gly Met Asp Glu Leu
        595                 600                 605

Tyr Lys Gly Gly Thr Gly Gly Ser Met Val Ser Lys Gly Glu Glu Leu
    610                 615                 620

Phe Thr Gly Val Val Pro Ile Gln Val Glu Leu Asp Gly Asp Val Asn
625                 630                 635                 640

Gly His Lys Phe Ser Val Ser Gly Glu Gly Glu Gly Asp Ala Thr Tyr
                645                 650                 655

Gly Lys Leu Thr Leu Lys Phe Ile Cys Thr Thr Gly Lys Leu Pro Val
            660                 665                 670

Pro Trp Pro Thr Leu Val Thr Thr Leu Thr Tyr Gly Val Gln Cys Phe
        675                 680                 685

Ser Arg Tyr Pro Asp His Met Lys Gln His Asp Phe Phe Lys Ser Ala
    690                 695                 700

Met Pro Glu Gly Tyr Ile Gln Glu Arg Thr Ile Phe Phe Lys Asp Asp
705                 710                 715                 720

Gly Asn Tyr Lys Thr Arg Ala Glu Val Lys Phe Glu Gly Asp Thr Leu
                725                 730                 735

Val Asn Arg Ile Glu Leu Lys Gly Ile Asp Phe Lys Glu Asp Gly Asn
            740                 745                 750

Ile Leu Gly His Lys Leu Glu Tyr Asn Thr Arg Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005
```

```
Thr Val  Gly Thr Phe Glu Leu  Met Ser Ser Lys Asp  Leu Ala Tyr
    1010                 1015                 1020

Gln Met  Thr Ile Tyr Asp Trp  Glu Leu Phe Asn Cys  Val His Glu
    1025                 1030                 1035

Leu Glu  Leu Ile Tyr His Thr  Phe Gly Arg His Asn  Phe Lys Lys
    1040                 1045                 1050

Thr Thr  Ala Asn Leu Asp Leu  Phe Leu Arg Arg Phe  Asn Glu Ile
    1055                 1060                 1065

Gln Phe  Trp Val Val Thr Glu  Ile Cys Leu Cys Ser  Gln Leu Ser
    1070                 1075                 1080

Lys Arg  Val Gln Leu Leu Lys  Lys Phe Ile Lys Ile  Ala Ala His
    1085                 1090                 1095

Cys Lys  Glu Tyr Lys Asn Leu  Asn Ser Phe Phe Ala  Ile Val Met
    1100                 1105                 1110

Gly Leu  Ser Asn Val Ala Val  Ser Arg Leu Ala Leu  Thr Trp Glu
    1115                 1120                 1125

Lys Leu  Pro Ser Lys Phe Lys  Lys Phe Tyr Ala Glu  Phe Glu Ser
    1130                 1135                 1140

Leu Met  Asp Pro Ser Arg Asn  His Arg Ala Tyr Arg  Leu Thr Val
    1145                 1150                 1155

Ala Lys  Leu Glu Pro Pro Leu  Ile Pro Phe Met Pro  Leu Leu Ile
    1160                 1165                 1170

Lys Asp  Met Thr Phe Thr His  Glu Gly Asn Lys Thr  Phe Ile Asp
    1175                 1180                 1185

Asn Leu  Val Asn Phe Glu Lys  Met Arg Met Ile Ala  Asn Thr Ala
    1190                 1195                 1200

Arg Thr  Val Arg Tyr Tyr Arg  Ser Gln Pro Phe Asn  Pro Asp Ala
    1205                 1210                 1215

Ala Gln  Ala Asn Lys Asn His  Gln Asp Val Arg Ser  Tyr Val Arg
    1220                 1225                 1230

Gln Leu  Asn Val Ile Asp Asn  Gln Arg Thr Leu Ser  Gln Met Ser
    1235                 1240                 1245

His Arg  Leu Glu Pro Arg Arg  Pro
    1250                 1255


<210> SEQ ID NO 30
<211> LENGTH: 1256
<212> TYPE: PRT
<213> ORGANISM: Artificial Sequence
<220> FEATURE:
<223> OTHER INFORMATION: Synthetic

<400> SEQUENCE: 30

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95
```

```
Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Leu Glu Asn Val Tyr Ile Lys
    450                 455                 460

Ala Asp Lys Gln Lys Asn Gly Ile Lys Ala Asn Phe Lys Ile Arg His
465                 470                 475                 480

Asn Ile Glu Asp Gly Gly Val Gln Leu Ala Tyr His Tyr Gln Gln Asn
                485                 490                 495

Thr Pro Ile Gly Asp Gly Pro Val Leu Leu Pro Asp Asn His Tyr Leu
            500                 505                 510
```

```
Ser Val Gln Ser Ile Leu Ser Lys Asp Pro Asn Glu Lys Arg Asp His
        515                 520                 525

Met Val Leu Leu Glu Phe Val Thr Ala Ala Gly Ile Thr Leu Gly Met
    530                 535                 540

Asp Glu Leu Tyr Lys Gly Gly Thr Gly Gly Ser Met Val Ser Lys Gly
545                 550                 555                 560

Glu Glu Leu Phe Thr Gly Val Val Pro Ile Gln Val Glu Leu Asp Gly
                565                 570                 575

Asp Val Asn Gly His Lys Phe Ser Val Ser Gly Glu Gly Glu Gly Asp
            580                 585                 590

Ala Thr Tyr Gly Lys Leu Thr Leu Lys Phe Ile Cys Thr Thr Gly Lys
        595                 600                 605

Leu Pro Val Pro Trp Pro Thr Leu Val Thr Thr Leu Thr Tyr Gly Val
    610                 615                 620

Gln Cys Phe Ser Arg Tyr Pro Asp His Met Lys Gln His Asp Phe Phe
625                 630                 635                 640

Lys Ser Ala Met Pro Glu Gly Tyr Ile Gln Glu Arg Thr Ile Phe Phe
                645                 650                 655

Lys Asp Asp Gly Asn Tyr Lys Thr Arg Ala Glu Val Lys Phe Glu Gly
            660                 665                 670

Asp Thr Leu Val Asn Arg Ile Glu Leu Lys Gly Ile Asp Phe Lys Glu
        675                 680                 685

Asp Gly Asn Ile Leu Gly His Lys Leu Glu Tyr Asn Thr Arg Arg Asp
    690                 695                 700

Val Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
```

```
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050

Thr Thr  Ala Asn Leu Asp Leu  Phe Leu Arg Arg Phe  Asn Glu Ile
    1055                1060                1065

Gln Phe  Trp Val Val Thr Glu  Ile Cys Leu Cys Ser  Gln Leu Ser
    1070                1075                1080

Lys Arg  Val Gln Leu Leu Lys  Lys Phe Ile Lys Ile  Ala Ala His
    1085                1090                1095

Cys Lys  Glu Tyr Lys Asn Leu  Asn Ser Phe Phe Ala  Ile Val Met
    1100                1105                1110

Gly Leu  Ser Asn Val Ala Val  Ser Arg Leu Ala Leu  Thr Trp Glu
    1115                1120                1125

Lys Leu  Pro Ser Lys Phe Lys  Lys Phe Tyr Ala Glu  Phe Glu Ser
    1130                1135                1140

Leu Met  Asp Pro Ser Arg Asn  His Arg Ala Tyr Arg  Leu Thr Val
    1145                1150                1155

Ala Lys  Leu Glu Pro Pro Leu  Ile Pro Phe Met Pro  Leu Leu Ile
    1160                1165                1170

Lys Asp  Met Thr Phe Thr His  Glu Gly Asn Lys Thr  Phe Ile Asp
    1175                1180                1185

Asn Leu  Val Asn Phe Glu Lys  Met Arg Met Ile Ala  Asn Thr Ala
    1190                1195                1200

Arg Thr  Val Arg Tyr Tyr Arg  Ser Gln Pro Phe Asn  Pro Asp Ala
    1205                1210                1215

Ala Gln  Ala Asn Lys Asn His  Gln Asp Val Arg Ser  Tyr Val Arg
    1220                1225                1230

Gln Leu  Asn Val Ile Asp Asn  Gln Arg Thr Leu Ser  Gln Met Ser
    1235                1240                1245

His Arg  Leu Glu Pro Arg Arg  Pro
    1250                1255


<210> SEQ ID NO 31
<211> LENGTH: 1256
<212> TYPE: PRT
<213> ORGANISM: Artificial Sequence
<220> FEATURE:
<223> OTHER INFORMATION: Synthetic

<400> SEQUENCE: 31

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
```

```
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Leu Glu Asn Val Tyr Ile Lys Ala Asp Lys Gln
            340                 345                 350

Lys Asn Gly Ile Lys Ala Asn Phe Lys Ile Arg His Asn Ile Glu Asp
        355                 360                 365

Gly Gly Val Gln Leu Ala Tyr His Tyr Gln Gln Asn Thr Pro Ile Gly
    370                 375                 380

Asp Gly Pro Val Leu Leu Pro Asp Asn His Tyr Leu Ser Val Gln Ser
385                 390                 395                 400

Ile Leu Ser Lys Asp Pro Asn Glu Lys Arg Asp His Met Val Leu Leu
                405                 410                 415

Glu Phe Val Thr Ala Ala Gly Ile Thr Leu Gly Met Asp Glu Leu Tyr
            420                 425                 430

Lys Gly Gly Thr Gly Gly Ser Met Val Ser Lys Gly Glu Glu Leu Phe
        435                 440                 445
```

```
Thr Gly Val Val Pro Ile Gln Val Glu Leu Asp Gly Asp Val Asn Gly
    450                 455                 460

His Lys Phe Ser Val Ser Gly Glu Gly Glu Gly Asp Ala Thr Tyr Gly
465                 470                 475                 480

Lys Leu Thr Leu Lys Phe Ile Cys Thr Thr Gly Lys Leu Pro Val Pro
                485                 490                 495

Trp Pro Thr Leu Val Thr Thr Leu Thr Tyr Gly Val Gln Cys Phe Ser
            500                 505                 510

Arg Tyr Pro Asp His Met Lys Gln His Asp Phe Phe Lys Ser Ala Met
        515                 520                 525

Pro Glu Gly Tyr Ile Gln Glu Arg Thr Ile Phe Phe Lys Asp Asp Gly
    530                 535                 540

Asn Tyr Lys Thr Arg Ala Glu Val Lys Phe Glu Gly Asp Thr Leu Val
545                 550                 555                 560

Asn Arg Ile Glu Leu Lys Gly Ile Asp Phe Lys Glu Asp Gly Asn Ile
                565                 570                 575

Leu Gly His Lys Leu Glu Tyr Asn Thr Arg Asp Asp Leu Glu Ile Ile
            580                 585                 590

Tyr Glu Glu Leu Leu His Ile Lys Ala Leu Ser His Leu Ser Thr Thr
        595                 600                 605

Val Lys Arg Glu Leu Ala Gly Val Leu Ile Phe Glu Ser His Ala Lys
    610                 615                 620

Gly Gly Thr Val Leu Phe Asn Gln Gly Glu Glu Gly Thr Ser Trp Tyr
625                 630                 635                 640

Ile Ile Leu Lys Gly Ser Val Asn Val Val Ile Tyr Gly Lys Gly Val
                645                 650                 655

Val Cys Thr Leu His Glu Gly Asp Asp Phe Gly Lys Leu Ala Leu Val
            660                 665                 670

Asn Asp Ala Pro Arg Ala Ala Ser Ile Val Leu Arg Glu Asp Asn Cys
        675                 680                 685

His Phe Leu Arg Val Asp Lys Glu Asp Phe Asn Arg Ile Leu Arg Asp
    690                 695                 700

Val Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860
```

```
Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050

Thr Thr  Ala Asn Leu Asp Leu  Phe Leu Arg Arg Phe  Asn Glu Ile
    1055                1060                1065

Gln Phe  Trp Val Val Thr Glu  Ile Cys Leu Cys Ser  Gln Leu Ser
    1070                1075                1080

Lys Arg  Val Gln Leu Leu Lys  Lys Phe Ile Lys Ile  Ala Ala His
    1085                1090                1095

Cys Lys  Glu Tyr Lys Asn Leu  Asn Ser Phe Phe Ala  Ile Val Met
    1100                1105                1110

Gly Leu  Ser Asn Val Ala Val  Ser Arg Leu Ala Leu  Thr Trp Glu
    1115                1120                1125

Lys Leu  Pro Ser Lys Phe Lys  Lys Phe Tyr Ala Glu  Phe Glu Ser
    1130                1135                1140

Leu Met  Asp Pro Ser Arg Asn  His Arg Ala Tyr Arg  Leu Thr Val
    1145                1150                1155

Ala Lys  Leu Glu Pro Pro Leu  Ile Pro Phe Met Pro  Leu Leu Ile
    1160                1165                1170

Lys Asp  Met Thr Phe Thr His  Glu Gly Asn Lys Thr  Phe Ile Asp
    1175                1180                1185

Asn Leu  Val Asn Phe Glu Lys  Met Arg Met Ile Ala  Asn Thr Ala
    1190                1195                1200

Arg Thr  Val Arg Tyr Tyr Arg  Ser Gln Pro Phe Asn  Pro Asp Ala
    1205                1210                1215

Ala Gln  Ala Asn Lys Asn His  Gln Asp Val Arg Ser  Tyr Val Arg
    1220                1225                1230

Gln Leu  Asn Val Ile Asp Asn  Gln Arg Thr Leu Ser  Gln Met Ser
    1235                1240                1245

His Arg  Leu Glu Pro Arg Arg  Pro
    1250                1255
```

<210> SEQ ID NO 32
<211> LENGTH: 1256
<212> TYPE: PRT
<213> ORGANISM: Artificial Sequence
<220> FEATURE:
<223> OTHER INFORMATION: Synthetic

<400> SEQUENCE: 32

```
Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
```

```
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Glu Ala Asn Thr
    450                 455                 460

Val Arg Leu Lys Glu His Asp Gln Asp Val Leu Val Leu Glu Lys Val
465                 470                 475                 480

Pro Ala Gly Asn Arg Ala Leu Glu Asn Val Tyr Ile Lys Ala Asp Lys
                485                 490                 495

Gln Lys Asn Gly Ile Lys Ala Asn Phe Lys Ile Arg His Asn Ile Glu
            500                 505                 510

Asp Gly Gly Val Gln Leu Ala Tyr His Tyr Gln Gln Asn Thr Pro Ile
        515                 520                 525

Gly Asp Gly Pro Val Leu Leu Pro Asp Asn His Tyr Leu Ser Val Gln
    530                 535                 540

Ser Ile Leu Ser Lys Asp Pro Asn Glu Lys Arg Asp His Met Val Leu
545                 550                 555                 560

Leu Glu Phe Val Thr Ala Ala Gly Ile Thr Leu Gly Met Asp Glu Leu
                565                 570                 575

Tyr Lys Gly Gly Thr Gly Gly Ser Met Val Ser Lys Gly Glu Glu Leu
            580                 585                 590

Phe Thr Gly Val Val Pro Ile Gln Val Glu Leu Asp Gly Asp Val Asn
        595                 600                 605

Gly His Lys Phe Ser Val Ser Gly Glu Gly Glu Gly Asp Ala Thr Tyr
    610                 615                 620

Gly Lys Leu Thr Leu Lys Phe Ile Cys Thr Thr Gly Lys Leu Pro Val
625                 630                 635                 640

Pro Trp Pro Thr Leu Val Thr Thr Leu Thr Tyr Gly Val Gln Cys Phe
                645                 650                 655

Ser Arg Tyr Pro Asp His Met Lys Gln His Asp Phe Phe Lys Ser Ala
            660                 665                 670

Met Pro Glu Gly Tyr Ile Gln Glu Arg Thr Ile Phe Phe Lys Asp Asp
        675                 680                 685

Gly Asn Tyr Lys Thr Arg Ala Glu Val Lys Phe Glu Gly Asp Thr Leu
    690                 695                 700

Val Asn Arg Ile Glu Leu Lys Gly Ile Asp Phe Lys Glu Asp Gly Asn
705                 710                 715                 720

Ile Leu Gly His Lys Leu Glu Tyr Asn Thr Arg Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800
```

```
Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050

Thr Thr  Ala Asn Leu Asp Leu  Phe Leu Arg Arg Phe  Asn Glu Ile
    1055                1060                1065

Gln Phe  Trp Val Val Thr Glu  Ile Cys Leu Cys Ser  Gln Leu Ser
    1070                1075                1080

Lys Arg  Val Gln Leu Leu Lys  Lys Phe Ile Lys Ile  Ala Ala His
    1085                1090                1095

Cys Lys  Glu Tyr Lys Asn Leu  Asn Ser Phe Phe Ala  Ile Val Met
    1100                1105                1110

Gly Leu  Ser Asn Val Ala Val  Ser Arg Leu Ala Leu  Thr Trp Glu
    1115                1120                1125

Lys Leu  Pro Ser Lys Phe Lys  Lys Phe Tyr Ala Glu  Phe Glu Ser
    1130                1135                1140

Leu Met  Asp Pro Ser Arg Asn  His Arg Ala Tyr Arg  Leu Thr Val
    1145                1150                1155

Ala Lys  Leu Glu Pro Pro Leu  Ile Pro Phe Met Pro  Leu Leu Ile
    1160                1165                1170

Lys Asp  Met Thr Phe Thr His  Glu Gly Asn Lys Thr  Phe Ile Asp
    1175                1180                1185

Asn Leu  Val Asn Phe Glu Lys  Met Arg Met Ile Ala  Asn Thr Ala
    1190                1195                1200
```

Arg Thr Val Arg Tyr Tyr Arg Ser Gln Pro Phe Asn Pro Asp Ala
1205 1210 1215

Ala Gln Ala Asn Lys Asn His Gln Asp Val Arg Ser Tyr Val Arg
1220 1225 1230

Gln Leu Asn Val Ile Asp Asn Gln Arg Thr Leu Ser Gln Met Ser
1235 1240 1245

His Arg Leu Glu Pro Arg Arg Pro
1250 1255

<210> SEQ ID NO 33
<211> LENGTH: 1256
<212> TYPE: PRT
<213> ORGANISM: Artificial Sequence
<220> FEATURE:
<223> OTHER INFORMATION: Synthetic

<400> SEQUENCE: 33

Met Val Ala Ala His Ala Ala His Ser Ser Ser Ser Ala Glu Trp Ile
1 5 10 15

Ala Cys Leu Asp Lys Arg Pro Leu Glu Arg Ser Ser Glu Asp Val Asp
20 25 30

Ile Ile Phe Thr Arg Leu Lys Glu Val Lys Ala Phe Glu Lys Phe His
35 40 45

Pro Asn Leu Leu His Gln Ile Cys Leu Cys Gly Tyr Tyr Glu Asn Leu
50 55 60

Glu Lys Gly Ile Thr Leu Phe Arg Gln Gly Asp Ile Gly Thr Asn Trp
65 70 75 80

Tyr Ala Val Leu Ala Gly Ser Leu Asp Val Lys Val Ser Glu Thr Ser
85 90 95

Ser His Gln Asp Ala Val Thr Ile Cys Thr Leu Gly Ile Gly Thr Ala
100 105 110

Phe Gly Glu Ser Ile Leu Asp Asn Thr Pro Arg His Ala Thr Ile Val
115 120 125

Thr Arg Glu Ser Ser Glu Leu Leu Arg Ile Glu Gln Lys Asp Phe Lys
130 135 140

Ala Leu Trp Glu Lys Tyr Arg Gln Tyr Met Ala Gly Leu Leu Ala Pro
145 150 155 160

Pro Tyr Gly Val Met Glu Thr Gly Ser Asn Asn Asp Arg Ile Pro Asp
165 170 175

Lys Glu Asn Thr Pro Leu Ile Glu Pro His Val Pro Leu Arg Pro Ala
180 185 190

Asn Thr Ile Thr Lys Val Pro Ser Glu Lys Ile Leu Arg Ala Gly Lys
195 200 205

Ile Leu Arg Asn Ala Ile Leu Ser Arg Ala Pro His Met Ile Arg Asp
210 215 220

Arg Lys Tyr His Leu Lys Thr Tyr Arg Gln Cys Cys Val Gly Thr Glu
225 230 235 240

Leu Val Asp Trp Met Met Gln Gln Thr Pro Cys Val His Ser Arg Thr
245 250 255

Gln Ala Val Gly Met Trp Gln Val Leu Leu Glu Asp Gly Val Leu Asn
260 265 270

His Val Asp Gln Glu His His Phe Gln Asp Lys Tyr Leu Phe Tyr Arg
275 280 285

Phe Leu Asp Asp Glu His Glu Asp Ala Pro Leu Pro Thr Glu Glu Glu
290 295 300

```
Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Glu Ala Asn Thr
    450                 455                 460

Val Arg Leu Lys Glu His Asp Gln Asp Val Leu Val Leu Glu Lys Val
465                 470                 475                 480

Pro Ala Gly Asn Arg Ala Ser Asn Gln Gly Asn Ser Gln Pro Gln Gln
                485                 490                 495

Lys Tyr Thr Val Met Ser Gly Thr Pro Glu Lys Ile Leu Glu His Phe
            500                 505                 510

Leu Glu Thr Ile Arg Leu Glu Ala Leu Glu Asn Val Tyr Ile Lys Ala
        515                 520                 525

Asp Lys Gln Lys Asn Gly Ile Lys Ala Asn Phe Lys Ile Arg His Asn
    530                 535                 540

Ile Glu Asp Gly Gly Val Gln Leu Ala Tyr His Tyr Gln Gln Asn Thr
545                 550                 555                 560

Pro Ile Gly Asp Gly Pro Val Leu Leu Pro Asp Asn His Tyr Leu Ser
                565                 570                 575

Val Gln Ser Ile Leu Ser Lys Asp Pro Asn Glu Lys Arg Asp His Met
            580                 585                 590

Val Leu Leu Glu Phe Val Thr Ala Ala Gly Ile Thr Leu Gly Met Asp
        595                 600                 605

Glu Leu Tyr Lys Gly Gly Thr Gly Gly Ser Met Val Ser Lys Gly Glu
    610                 615                 620

Glu Leu Phe Thr Gly Val Val Pro Ile Gln Val Glu Leu Asp Gly Asp
625                 630                 635                 640

Val Asn Gly His Lys Phe Ser Val Ser Gly Glu Gly Glu Gly Asp Ala
                645                 650                 655

Thr Tyr Gly Lys Leu Thr Leu Lys Phe Ile Cys Thr Thr Gly Lys Leu
            660                 665                 670

Pro Val Pro Trp Pro Thr Leu Val Thr Thr Leu Thr Tyr Gly Val Gln
        675                 680                 685

Cys Phe Ser Arg Tyr Pro Asp His Met Lys Gln His Asp Phe Phe Lys
    690                 695                 700

Ser Ala Met Pro Glu Gly Tyr Ile Gln Glu Arg Thr Ile Phe Phe Lys
705                 710                 715                 720

Asp Asp Gly Asn Tyr Lys Thr Arg Ala Glu Val Lys Phe Glu Gly Asp
```

```
                725                 730                 735

Thr Leu Val Asn Arg Ile Glu Leu Lys Gly Ile Asp Phe Lys Glu Asp
            740                 745                 750

Gly Asn Ile Leu Gly His Lys Leu Glu Tyr Asn Thr Arg Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
        995                 1000                1005

Thr Val  Gly Thr Phe Glu Leu  Met Ser Ser Lys Asp  Leu Ala Tyr
    1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050

Thr Thr  Ala Asn Leu Asp Leu  Phe Leu Arg Arg Phe  Asn Glu Ile
    1055                1060                1065

Gln Phe  Trp Val Val Thr Glu  Ile Cys Leu Cys Ser  Gln Leu Ser
    1070                1075                1080

Lys Arg  Val Gln Leu Leu Lys  Lys Phe Ile Lys Ile  Ala Ala His
    1085                1090                1095

Cys Lys  Glu Tyr Lys Asn Leu  Asn Ser Phe Phe Ala  Ile Val Met
    1100                1105                1110

Gly Leu  Ser Asn Val Ala Val  Ser Arg Leu Ala Leu  Thr Trp Glu
    1115                1120                1125

Lys Leu  Pro Ser Lys Phe Lys  Lys Phe Tyr Ala Glu  Phe Glu Ser
    1130                1135                1140
```

```
Leu Met Asp Pro Ser Arg Asn His Arg Ala Tyr Arg Leu Thr Val
    1145                1150                1155

Ala Lys Leu Glu Pro Pro Leu Ile Pro Phe Met Pro Leu Leu Ile
    1160                1165                1170

Lys Asp Met Thr Phe Thr His Glu Gly Asn Lys Thr Phe Ile Asp
    1175                1180                1185

Asn Leu Val Asn Phe Glu Lys Met Arg Met Ile Ala Asn Thr Ala
    1190                1195                1200

Arg Thr Val Arg Tyr Tyr Arg Ser Gln Pro Phe Asn Pro Asp Ala
    1205                1210                1215

Ala Gln Ala Asn Lys Asn His Gln Asp Val Arg Ser Tyr Val Arg
    1220                1225                1230

Gln Leu Asn Val Ile Asp Asn Gln Arg Thr Leu Ser Gln Met Ser
    1235                1240                1245

His Arg Leu Glu Pro Arg Arg Pro
    1250                1255


<210> SEQ ID NO 34
<211> LENGTH: 14
<212> TYPE: PRT
<213> ORGANISM: Homo sapiens

<400> SEQUENCE: 34

Lys Glu Asp Phe Asn Arg Ile Leu Arg Asp Val Glu Ala Asn
1               5                   10


<210> SEQ ID NO 35
<211> LENGTH: 1011
<212> TYPE: PRT
<213> ORGANISM: Homo sapiens

<400> SEQUENCE: 35

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190
```

```
Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Glu Ala Asn Thr
    450                 455                 460

Val Arg Leu Lys Glu His Asp Gln Asp Val Leu Val Leu Glu Lys Val
465                 470                 475                 480

Pro Ala Gly Asn Arg Ala Ser Asn Gln Gly Asn Ser Gln Pro Gln Gln
                485                 490                 495

Lys Tyr Thr Val Met Ser Gly Thr Pro Glu Lys Ile Leu Glu His Phe
            500                 505                 510

Leu Glu Thr Ile Arg Leu Glu Ala Thr Leu Asn Glu Ala Thr Asp Ser
        515                 520                 525

Val Leu Asn Asp Phe Ile Met Met His Cys Val Phe Met Pro Asn Thr
    530                 535                 540

Gln Leu Cys Pro Ala Leu Val Ala His Tyr His Ala Gln Pro Ser Gln
545                 550                 555                 560

Gly Thr Glu Gln Glu Lys Met Asp Tyr Ala Leu Asn Asn Lys Arg Arg
                565                 570                 575

Val Ile Arg Leu Val Leu Gln Trp Ala Ala Met Tyr Gly Asp Leu Leu
            580                 585                 590

Gln Glu Asp Asp Val Ser Met Ala Phe Leu Glu Glu Phe Tyr Val Ser
        595                 600                 605
```

```
Val Ser Asp Asp Ala Arg Met Ile Ala Ala Leu Lys Glu Gln Leu Pro
    610                 615                 620

Glu Leu Glu Lys Ile Val Lys Gln Ile Ser Glu Asp Ala Lys Ala Pro
625                 630                 635                 640

Gln Lys Lys His Lys Val Leu Leu Gln Gln Phe Asn Thr Gly Asp Glu
                645                 650                 655

Arg Ala Gln Lys Arg Gln Pro Ile Arg Gly Ser Asp Glu Val Leu Phe
            660                 665                 670

Lys Val Tyr Cys Met Asp Pro Thr Tyr Thr Thr Ile Arg Val Pro Val
        675                 680                 685

Ala Thr Ser Val Lys Glu Val Ile Ser Ala Val Ala Asp Lys Leu Gly
    690                 695                 700

Ser Gly Glu Gly Leu Ile Ile Val Lys Met Ser Ser Gly Gly Glu Lys
705                 710                 715                 720

Val Val Leu Lys Pro Asn Asp Val Ser Val Phe Met Thr Leu Thr Ile
                725                 730                 735

Asn Gly Arg Leu Phe Ala Cys Pro Arg Glu Gln Phe Asp Ser Leu Thr
            740                 745                 750

Pro Leu Pro Glu Gln Glu Gly Pro Thr Val Gly Thr Val Gly Thr Phe
        755                 760                 765

Glu Leu Met Ser Ser Lys Asp Leu Ala Tyr Gln Met Thr Ile Tyr Asp
    770                 775                 780

Trp Glu Leu Phe Asn Cys Val His Glu Leu Glu Leu Ile Tyr His Thr
785                 790                 795                 800

Phe Gly Arg His Asn Phe Lys Lys Thr Thr Ala Asn Leu Asp Leu Phe
                805                 810                 815

Leu Arg Arg Phe Asn Glu Ile Gln Phe Trp Val Val Thr Glu Ile Cys
            820                 825                 830

Leu Cys Ser Gln Leu Ser Lys Arg Val Gln Leu Leu Lys Lys Phe Ile
        835                 840                 845

Lys Ile Ala Ala His Cys Lys Glu Tyr Lys Asn Leu Asn Ser Phe Phe
    850                 855                 860

Ala Ile Val Met Gly Leu Ser Asn Val Ala Val Ser Arg Leu Ala Leu
865                 870                 875                 880

Thr Trp Glu Lys Leu Pro Ser Lys Phe Lys Lys Phe Tyr Ala Glu Phe
                885                 890                 895

Glu Ser Leu Met Asp Pro Ser Arg Asn His Arg Ala Tyr Arg Leu Thr
            900                 905                 910

Val Ala Lys Leu Glu Pro Pro Leu Ile Pro Phe Met Pro Leu Leu Ile
        915                 920                 925

Lys Asp Met Thr Phe Thr His Glu Gly Asn Lys Thr Phe Ile Asp Asn
    930                 935                 940

Leu Val Asn Phe Glu Lys Met Arg Met Ile Ala Asn Thr Ala Arg Thr
945                 950                 955                 960

Val Arg Tyr Tyr Arg Ser Gln Pro Phe Asn Pro Asp Ala Ala Gln Ala
                965                 970                 975

Asn Lys Asn His Gln Asp Val Arg Ser Tyr Val Arg Gln Leu Asn Val
            980                 985                 990

Ile Asp Asn Gln Arg Thr Leu Ser  Gln Met Ser His Arg  Leu Glu Pro
        995                 1000                1005

Arg Arg  Pro
    1010
```

```
<210> SEQ ID NO 36
<211> LENGTH: 124
<212> TYPE: PRT
<213> ORGANISM: Artificial Sequence
<220> FEATURE:
<223> OTHER INFORMATION: Synthetic

<400> SEQUENCE: 36

Ala Phe Glu Lys Phe His Pro Asn Leu Leu His Gln Ile Cys Leu Cys
1               5                   10                  15

Gly Tyr Tyr Glu Asn Leu Glu Lys Gly Ile Thr Leu Phe Arg Gln Gly
            20                  25                  30

Asp Ile Gly Thr Asn Trp Tyr Ala Val Leu Ala Gly Ser Leu Asp Val
        35                  40                  45

Lys Val Ser Glu Thr Ser Ser His Gln Asp Ala Val Thr Ile Cys Thr
    50                  55                  60

Leu Gly Ile Gly Thr Ala Phe Gly Glu Ser Ile Leu Asp Asn Thr Pro
65                  70                  75                  80

Arg His Ala Thr Ile Val Thr Arg Glu Ser Ser Glu Leu Leu Arg Ile
                85                  90                  95

Glu Gln Lys Asp Phe Lys Ala Leu Trp Glu Lys Tyr Arg Gln Tyr Met
            100                 105                 110

Ala Gly Leu Leu Ala Pro Pro Tyr Gly Val Met Glu
        115                 120


<210> SEQ ID NO 37
<211> LENGTH: 121
<212> TYPE: PRT
<213> ORGANISM: Artificial Sequence
<220> FEATURE:
<223> OTHER INFORMATION: Synthetic

<400> SEQUENCE: 37

Ala Leu Ser His Leu Ser Thr Thr Val Lys Arg Glu Leu Ala Gly Val
1               5                   10                  15

Leu Ile Phe Glu Ser His Ala Lys Gly Gly Thr Val Leu Phe Asn Gln
            20                  25                  30

Gly Glu Glu Gly Thr Ser Trp Tyr Ile Ile Leu Lys Gly Ser Val Asn
        35                  40                  45

Val Val Ile Tyr Gly Lys Gly Val Val Cys Thr Leu His Glu Gly Asp
    50                  55                  60

Asp Phe Gly Lys Leu Ala Leu Val Asn Asp Ala Pro Arg Ala Ala Ser
65                  70                  75                  80

Ile Val Leu Arg Glu Asp Asn Cys His Phe Leu Arg Val Asp Lys Glu
                85                  90                  95

Asp Phe Asn Arg Ile Leu Arg Asp Val Glu Ala Asn Thr Val Arg Leu
            100                 105                 110

Lys Glu His Asp Gln Asp Val Leu Val
        115                 120


<210> SEQ ID NO 38
<211> LENGTH: 241
<212> TYPE: PRT
<213> ORGANISM: Artificial Sequence
<220> FEATURE:
<223> OTHER INFORMATION: Synthetic

<400> SEQUENCE: 38

Asn Val Tyr Ile Lys Ala Asp Lys Gln Lys Asn Gly Ile Lys Ala Asn
1               5                   10                  15
```

```
Phe Lys Ile Arg His Asn Ile Glu Asp Gly Gly Val Gln Leu Ala Tyr
            20                  25                  30

His Tyr Gln Gln Asn Thr Pro Ile Gly Asp Gly Pro Val Leu Leu Pro
        35                  40                  45

Asp Asn His Tyr Leu Ser Val Gln Ser Ala Leu Ser Lys Asp Pro Asn
    50                  55                  60

Glu Lys Arg Asp His Met Val Leu Leu Glu Phe Val Thr Ala Ala Gly
65                  70                  75                  80

Ile Thr His Gly Met Asp Glu Leu Tyr Lys Gly Gly Thr Gly Gly Ser
                85                  90                  95

Met Val Ser Lys Gly Glu Glu Leu Phe Thr Gly Val Val Pro Ile Gln
            100                 105                 110

Val Glu Leu Asp Gly Asp Val Asn Gly His Lys Phe Ser Val Ser Gly
        115                 120                 125

Glu Gly Glu Gly Asp Ala Thr Tyr Gly Lys Leu Thr Leu Lys Phe Ile
    130                 135                 140

Cys Thr Thr Gly Lys Leu Pro Val Pro Trp Pro Thr Leu Val Thr Thr
145                 150                 155                 160

Leu Thr Tyr Gly Val Gln Cys Phe Ser Arg Tyr Pro Asp His Met Lys
                165                 170                 175

Gln His Asp Phe Phe Lys Ser Ala Met Pro Glu Gly Tyr Ile Gln Glu
            180                 185                 190

Arg Thr Ile Phe Phe Lys Asp Asp Gly Asn Tyr Lys Thr Arg Ala Glu
        195                 200                 205

Val Lys Phe Glu Gly Asp Thr Leu Val Asn Arg Ile Glu Leu Lys Gly
    210                 215                 220

Ile Asp Phe Lys Glu Asp Gly Asn Ile Leu Gly His Lys Leu Glu Tyr
225                 230                 235                 240

Asn
```

<210> SEQ ID NO 39
<211> LENGTH: 3033
<212> TYPE: DNA
<213> ORGANISM: Homo sapiens

<400> SEQUENCE: 39

```
atggtcgctg cgcacgctgc ccattcttcc tcctctgccg agtggatcgc ctgcctggat      60

aaaagaccac tggagcgatc cagcgaagat gtggatataa tcttcactcg actgaaagaa     120

gttaaagctt ttgagaaatt tcacccaaat ctccttcatc agatttgctt atgtggttat     180

tatgagaatc tggaaaaggg aataacatta tttcgccagg gtgatattgg aacaaactgg     240

tatgctgtcc tggcagggtc tttggatgtt aaagtatctg agaccagcag tcaccaggat     300

gctgtgacca tctgtaccct gggaattggg acggcctttg gagagtccat tctggacaac     360

acaccccgcc atgcaaccat cgttaccagg gagagcagtg aactgctccg catcgagcag     420

aaggacttca aggcactatg ggagaaatat cgacagtata tggcaggact tctggctcct     480

ccttatggtg ttatggaaac gggctctaac aatgacagga ttcctgacaa ggagaacaca     540

cctctcattg aacctcacgt tcctcttcgt cctgctaaca ccattaccaa ggtcccttca     600

gagaagatcc tcagagctgg aaaaatttta cgaaatgcca ttctctctcg agcacctcac     660

atgataagag atagaaaata ccacctaaag acatacagac aatgctgtgt gggaactgaa     720

ctggtggact ggatgatgca gcagacacca tgtgttcact cccggactca agctgttggc     780
```

```
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
gaggcgaata cagtcagact taaagaacat gaccaagatg tcttggtgct ggagaaggtc   1440
ccagcaggga acagagcttc taatcaagga aactcacagc ctcagcaaaa gtatactgtg   1500
atgtcaggaa cacctgaaaa aattttagag cattttctag aaacaatacg ccttgaggca   1560
actttaaatg aagcaacaga ttctgtttta aatgacttta ttatgatgca ctgtgttttt   1620
atgccaaata cccagctttg cccggcactg gtggcccact accacgcaca gccttcacaa   1680
ggtacagaac aggagaaaat ggattatgcc ctcaacaata agaggcgagt catccgcctg   1740
gttctacagt gggctgccat gtatggagac ctcctgcaag aggatgacgt gtctatggcc   1800
ttcctggagg agttttatgt atctgtatca gatgatgccc ggatgattgc tgccctcaag   1860
gagcaactgc cagagttgga gaagattgtc aagcaaatct cagaagatgc aaaggcacca   1920
caaaagaagc acaaggttct tttgcaacag ttcaatacgg gcgatgagag agcccagaag   1980
cgccagccta tccgcggctc tgatgaagtt ctgtttaagg tctattgcat ggacccccacc  2040
tacacaacca ttcgggtgcc agtggccact tcggtgaagg aagtcatcag tgcagttgcc   2100
gacaagctgg gctccgggga gggcctgatc atagtcaaga tgagttccgg aggagaaaag   2160
gtggtgctca aacctaatga tgtttcagta tttatgacgc tcaccattaa tggacgcctg   2220
tttgcttgcc cgcgagagca attcgattca ctgactccct taccagaaca ggaaggccca   2280
actgttggaa cagtgggaac ttttgaactg atgagctcca aagatttagc ataccagatg   2340
acaatttatg attgggaact cttcaactgc gtgcatgagc tggagctaat ctatcacaca   2400
tttggaaggc ataattttaa aaagaccaca gcaaacttgg atttgttcct gaggagattt   2460
aatgaaattc agttttgggt cgtcactgag atctgccttt gttctcagct cagcaagcgt   2520
gttcagctat taaaaaaatt tattaagata gcagcccact gtaaggagta taaaaatctg   2580
aattcctttt ttgccatcgt catgggacta agtaacgttg ctgtgagccg cttggcacta   2640
acgtgggaga aactgccaag caagttcaag aagttctatg cggagtttga aagtttaatg   2700
gacccttcaa ggaaccacag ggcctacagg ctgacagtag ctaagctgga acctcctctc   2760
atccccttca tgcctttgct cattaaagat atgacattta ctcatgaggg gaacaagacg   2820
ttcattgaca atctagtaaa ctttgaaaaa atgcgcatga ttgcaaatac ggccagaaca   2880
gtgagatact acaggagcca acccttcaat cctgatgcag ctcaagctaa taagaaccat   2940
caggatgtcc ggagttatgt acggcaatta aatgtgattg acaaccagag aactttatca   3000
cagatgtcac acagattaga gcctcgtcga cca                                3033
```

<210> SEQ ID NO 40
<211> LENGTH: 42

<212> TYPE: DNA
<213> ORGANISM: Homo sapiens

<400> SEQUENCE: 40
aaggaggatt tcaaccggat cctaagggac gtggaggcga at 42

<210> SEQ ID NO 41
<211> LENGTH: 2217
<212> TYPE: DNA
<213> ORGANISM: Artificial Sequence
<220> FEATURE:
<223> OTHER INFORMATION: Synthetic

<400> SEQUENCE: 41
atgggctcta acaatgacag gattcctgac aaggagaaca cacctctcat tgaacctcac 60
gttcctcttc gtcctgctaa caccattacc aaggtccctt cagagaagat cctcagagct 120 ggaaaaaattt tacgaaatgc cattctctct cgagcacctc acatgataag agatagaaaa 180
taccacctaa agacatacag acaatgctgt gtgggaactg aactggtgga ctggatgatg 240
cagcagacac catgtgttca ctcccggact caagctgttg gcatgtggca agtcctgtta 300
gaagatggtg ttctcaacca cgtggaccag gagcaccatt tccaagacaa atatttattc 360
tatcgatttc tggatgatga gcacgaggat gccccttttgc ctactgagga ggagaagaag 420
gagtgtgatg aggagctcca ggacaccatg ctgctgctgt cacagatggg ccccgacgcc 480
cacatgagga tgatccttcg caaaccacct ggccagagga ctgtggatga cctagagatt 540
atctatgagg agcttcttca tattaaagcc ttatcccatc tttctaccac agtgaaacga 600
gagttagcag gtgttctcat ttttgagtct cacgccaaag gagggactgt gttgtttaac 660
cagggggaag aaggtacctc ctggtacatt attctaaaag gatcagtgaa tgtagtcatt 720
tacggcaagg gtgtggtctg caccctgcat gaaggagatg acttcggcaa gttagcacta 780
gtgaatgatg ccccacgagc tgcctctatc gtcttacgag aagataactg ccatttctta 840
agagtagaca aggaggattt caaccggatc ctaaggctgg tgtcgcacaa cgtctatatc 900
aaggccgaca agcagaagaa cggcatcaag gcgaacttca agatccgcca caacatcgag 960
gacggcggcg tgcagctcgc ctaccactac cagcagaaca cccccatcgg cgacggcccc 1020
gtgctgctgc ccgacaacca ctacctgagc gtgcagtcca tactttcgaa agaccccaac 1080
gagaagcgcg atcacatggt cctgctggag ttcgtgaccg ccgccgggat cactctcggc 1140
atggacgagc tgtacaaggg cggtaccgga gggagcatgg tgagcaaggg cgaggagctg 1200
ttcaccgggg tggtgcccat ccaggtcgag ctggacggcg acgtaaacgg ccacaagttc 1260
agcgtgtccg gcgagggtga gggcgatgcc acctacggca agctgaccct gaagttcatc 1320
tgcaccaccg gcaagctgcc cgtgccctgg cccaccctcg tgaccaccct gacctacggc 1380
gtgcagtgct tcagccgcta ccccgaccac atgaagcagc acgacttctt caagtccgcc 1440
atgcccgaag gctacatcca ggagcgcacc atcttcttca aggacgacgg caactacaag 1500
acccgcgccg aggtgaagtt cgagggcgac accctggtga accgcatcga gctgaagggc 1560
atcgacttca aggaggacgg caacatcctg gggcacaagc tggagtacaa cttcaacaac 1620
cctgacgtgg aggcgaatac agtcagactt aaagaacatg accaagatgt cttggtgctg 1680
gagaaggtcc cagcagggaa cagagcttct aatcaaggaa actcacagcc tcagcaaaag 1740
tatactgtga tgtcaggaac acctgaaaaa attttagagc attttctaga aacaatacgc 1800
cttgaggcaa ctttaaatga agcaacagat tctgttttaa atgactttat tatgatgcac 1860

```
tgtgttttta tgccaaatac ccagctttgc ccggcactgg tggcccacta ccacgcacag   1920

ccttcacaag gtacagaaca ggagaaaatg gattatgccc tcaacaataa gaggcgagtc   1980

atccgcctgg ttctacagtg ggctgccatg tatggagacc tcctgcaaga ggatgacgtg   2040

tctatggcct tcctggagga gttttatgta tctgtatcag atgatgcccg gatgattgct   2100

gccctcaagg agcaactgcc agagttggag aagattgtca agcaaatctc agaagatgca   2160

aaggcaccac aaaagaagca caaggttctt ttgcaacagt tcaatacggg cgatgag      2217
```

<210> SEQ ID NO 42
<211> LENGTH: 3807
<212> TYPE: DNA
<213> ORGANISM: Artificial Sequence
<220> FEATURE:
<223> OTHER INFORMATION: Synthetic

<400> SEQUENCE: 42

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc ccctttgcct    900

actgaggagg agaagaagga gtgtgatgag gagctccagg acaccatgct gctgctgtca    960

cagatgggcc ccgacgccca catgaggatg atccttcgca aaccacctgg ccagaggact   1020

gtggatgacc tagagattat ctatgaggag cttcttcata ttaaagcctt atcccatctt   1080

tctaccacag tgaaacgaga gttagcaggt gttctcattt ttgagtctca cgccaaagga   1140

gggactgtgt tgtttaacca gggggaagaa ggtacctcct ggtacattat tctaaaagga   1200

tcagtgaatg tagtcattta cggcaagggt gtggtctgca ccctgcatga aggagatgac   1260

ttcggcaagt tagcactagt gaatgatgcc ccacgagctg cctctatcgt cttacgagaa   1320

gataactgcc atttcttaag agtagacaag gaggatttca accggatcct aagggacgtg   1380

gaggcgctcg agaacgtcta tatcaaggcc gacaagcaga agaacggcat caaggcgaac   1440

ttcaagatcc gccacaacat cgaggacggc ggcgtgcagc tcgcctacca ctaccagcag   1500

aacaccccca tcggcgacgg ccccgtgctg ctgcccgaca accactacct gagcgtgcag   1560

tccatacttt cgaaagaccc caacgagaag cgcgatcaca tggtcctgct ggagttcgtg   1620

accgccgccg ggatcactct cggcatggac gagctgtaca agggcggtac cggagggagc   1680

atggtgagca agggcgagga gctgttcacc ggggtggtgc ccatccaggt cgagctggac   1740
```

```
ggcgacgtaa acggccacaa gttcagcgtg tccggcgagg gtgagggcga tgccacctac   1800

ggcaagctga ccctgaagtt catctgcacc accggcaagc tgcccgtgcc ctggcccacc   1860

ctcgtgacca ccctgaccta cggcgtgcag tgcttcagcc gctaccccga ccacatgaag   1920

cagcacgact tcttcaagtc cgccatgccc gaaggctaca tccaggagcg caccatcttc   1980

ttcaaggacg acggcaacta caagacccgc gccgaggtga agttcgaggg cgacaccctg   2040

gtgaaccgca tcgagctgaa gggcatcgac ttcaaggagg acggcaacat cctggggcac   2100

aagctggagt acaacacgcg taaggaggat ttcaaccgga tcctaaggga cgtggaggcg   2160

aatacagtca gacttaaaga acatgaccaa gatgtcttgg tgctggagaa ggtcccagca   2220

gggaacagag cttctaatca aggaaactca cagcctcagc aaaagtatac tgtgatgtca   2280

ggaacacctg aaaaaatttt agagcatttt ctagaaacaa tacgccttga ggcaacttta   2340

aatgaagcaa cagattctgt tttaaatgac tttattatga tgcactgtgt ttttatgcca   2400

aatacccagc tttgcccggc actggtggcc cactaccacg cacagccttc acaaggtaca   2460

gaacaggaga aaatggatta tgccctcaac aataagaggc gagtcatccg cctggttcta   2520

cagtgggctg ccatgtatgg agacctcctg caagaggatg acgtgtctat ggccttcctg   2580

gaggagtttt atgtatctgt atcagatgat gcccggatga ttgctgccct caaggagcaa   2640

ctgccagagt tggagaagat tgtcaagcaa atctcagaag atgcaaaggc accacaaaag   2700

aagcacaagg ttcttttgca acagttcaat acgggcgatg agagagccca gaagcgccag   2760

cctatccgcg gctctgatga agttctgttt aaggtctatt gcatggaccc cacctacaca   2820

accattcggg tgccagtggc cacttcggtg aaggaagtca tcagtgcagt tgccgacaag   2880

ctgggctccg ggagggcct gatcatagtc aagatgagtt ccggaggaga aaaggtggtg   2940

ctcaaaccta atgatgtttc agtatttatg acgctcacca ttaatggacg cctgtttgct   3000

tgcccgcgag agcaattcga ttcactgact cccttaccag aacaggaagg cccaactgtt   3060

ggaacagtgg gaacttttga actgatgagc tccaaagatt tagcatacca gatgacaatt   3120

tatgattggg aactcttcaa ctgcgtgcat gagctggagc taatctatca cacatttgga   3180

aggcataatt ttaaaaagac cacagcaaac ttggatttgt tcctgaggag atttaatgaa   3240

attcagtttt gggtcgtcac tgagatctgc ctttgttctc agctcagcaa gcgtgttcag   3300

ctattaaaaa aatttattaa gatagcagcc cactgtaagg agtataaaaa tctgaattcc   3360

ttttttgcca tcgtcatggg actaagtaac gttgctgtga gccgcttggc actaacgtgg   3420

gagaaactgc caagcaagtt caagaagttc tatgcggagt ttgaaagttt aatggaccct   3480

tcaaggaacc acagggccta caggctgaca gtagctaagc tggaacctcc tctcatcccc   3540

ttcatgcctt tgctcattaa agatatgaca tttactcatg aggggaacaa gacgttcatt   3600

gacaatctag taaactttga aaaaatgcgc atgattgcaa atacggccag aacagtgaga   3660

tactacagga gccaaccctt caatcctgat gcagctcaag ctaataagaa ccatcaggat   3720

gtccggagtt atgtacggca attaaatgtg attgacaacc agagaacttt atcacagatg   3780

tcacacagat tagagcctcg tcgacca                                       3807
```

<210> SEQ ID NO 43
<211> LENGTH: 2244
<212> TYPE: DNA
<213> ORGANISM: Artificial Sequence
<220> FEATURE:
<223> OTHER INFORMATION: Synthetic

<400> SEQUENCE: 43

```
atgggctcta acaatgacag gattcctgac aaggagaaca cacctctcat tgaacctcac     60
gttcctcttc gtcctgctaa caccattacc aaggtccctt cagagaagat cctcagagct    120
ggaaaaattt tacgaaatgc cattctctct cgagcacctc acatgataag agatagaaaa    180
taccacctaa agacatacag acaatgctgt gtgggaactg aactggtgga ctggatgatg    240
cagcagacac catgtgttca ctcccggact caagctgttg gcatgtggca agtcctgtta    300
gaagatggtg ttctcaacca cgtggaccag gagcaccatt tccaagacaa atatttattc    360
tatcgatttc tggatgatga gcacgaggat gcccctttgc ctactgagga ggagaagaag    420
gagtgtgatg aggagctcca ggacaccatg ctgctgctgt cacagatggg ccccgacgcc    480
cacatgagga tgatccttcg caaaccacct ggccagagga ctgtggatga cctagagatt    540
atctatgagg agcttcttca tattaaagcc ttatcccatc tttctaccac agtgaaacga    600
gagttagcag gtgttctcat ttttgagtct cacgccaaag gagggactgt gttgtttaac    660
caggggggaag aaggtacctc ctggtacatt attctaaaag gatcagtgaa tgtagtcatt    720
tacggcaagg gtgtggtctg caccctgcat gaaggagatg acttcggcaa gttagcacta    780
gtgaatgatg ccccacgagc tgcctctatc gtcttacgag aagataactg ccatttctta    840
agagtagaca aggaggattt caaccggatc ctaagggacg tggaggcgct cgagaacgtc    900
tatatcaagg ccgacaagca gaagaacggc atcaaggcga acttcaagat ccgccacaac    960
atcgaggacg gcggcgtgca gctcgcctac cactaccagc agaacacccc catcggcgac   1020
ggccccgtgc tgctgcccga caaccactac ctgagcgtgc agtccatact ttcgaaagac   1080
cccaacgaga agcgcgatca catggtcctg ctggagttcg tgaccgccgc cgggatcact   1140
ctcggcatgg acgagctgta caagggcggt accggaggga gcatggtgag caagggcgag   1200
gagctgttca ccggggtggt gcccatccag gtcgagctgg acggcgacgt aaacggccac   1260
aagttcagcg tgtccggcga gggtgagggc gatgccacct acggcaagct gaccctgaag   1320
ttcatctgca ccaccggcaa gctgcccgtg ccctggccca ccctcgtgac caccctgacc   1380
tacggcgtgc agtgcttcag ccgctacccc gaccacatga agcagcacga cttcttcaag   1440
tccgccatgc ccgaaggcta catccaggag cgcaccatct tcttcaagga cgacggcaac   1500
tacaagaccc gcgccgaggt gaagttcgag ggcgacaccc tggtgaaccg catcgagctg   1560
aagggcatcg acttcaagga ggacggcaac atcctggggc acaagctgga gtacaacacg   1620
cgtaaggagg atttcaaccg gatcctaagg gacgtggagg cgaatacagt cagacttaaa   1680
gaacatgacc aagatgtctt ggtgctggag aaggtcccag cagggaacag agcttctaat   1740
caaggaaact cacagcctca gcaaaagtat actgtgatgt caggaacacc tgaaaaaatt   1800
ttagagcatt ttctagaaac aatacgcctt gaggcaactt taaatgaagc aacagattct   1860
gttttaaatg actttattat gatgcactgt gtttttatgc caaataccca gctttgcccg   1920
gcactggtgg cccactacca cgcacagcct tcacaaggta cagaacagga gaaaatggat   1980
tatgccctca acaataagag gcgagtcatc cgcctggttc tacagtgggc tgccatgtat   2040
ggagacctcc tgcaagagga tgacgtgtct atggccttcc tggaggagtt ttatgtatct   2100
gtatcagatg atgcccggat gattgctgcc ctcaaggagc aactgccaga gttggagaag   2160
attgtcaagc aaatctcaga agatgcaaag gcaccacaaa agaagcacaa ggttcttttg   2220
caacagttca atacgggcga tgag                                          2244
```

<210> SEQ ID NO 44
<211> LENGTH: 3780
<212> TYPE: DNA
<213> ORGANISM: Artificial Sequence
<220> FEATURE:
<223> OTHER INFORMATION: Synthetic

<400> SEQUENCE: 44
atggtcgctg cgcacgctgc ccattcttcc tcctctgccg agtggatcgc ctgcctggat 60
aaaagaccac tggagcgatc cagcgaagat gtggatataa tcttcactcg actgaaagaa 120
gttaaagctt ttgagaaatt tcacccaaat ctccttcatc agatttgctt atgtggttat 180
tatgagaatc tggaaaaggg aataacatta tttcgccagg gtgatattgg aacaaactgg 240
tatgctgtcc tggcagggtc tttggatgtt aaagtatctg agaccagcag tcaccaggat 300
gctgtgacca tctgtaccct gggaattggg acggcctttg gagagtccat tctggacaac 360
acaccccgcc atgcaaccat cgttaccagg gagagcagtg aactgctccg catcgagcag 420
aaggacttca aggcactatg ggagaaatat cgacagtata tggcaggact tctggctcct 480
ccttatggtg ttatggaaac gggctctaac aatgacagga ttcctgacaa ggagaacaca 540
cctctcattg aacctcacgt tcctcttcgt cctgctaaca ccattaccaa ggtcccttca 600
gagaagatcc tcagagctgg aaaaatttta cgaaatgcca ttctctctcg agcacctcac 660
atgataagag atagaaaata ccacctaaag acatacagac aatgctgtgt gggaactgaa 720
ctggtggact ggatgatgca gcagacacca tgtgttcact cccggactca agctgttggc 780
atgtggcaag tcctgttaga agatggtgtt ctcaaccacg tggaccagga gcaccatttc 840
caagacaaat atttattcta tcgatttctg gatgatgagc acgaggatgc ccctttgcct 900
actgaggagg agaagaagga gtgtgatgag gagctccagg acaccatgct gctgctgtca 960
cagatgggcc ccgacgccca catgaggatg atccttcgca aaccacctgg ccagaggact 1020
gtggatgacc tagagattat ctatgaggag cttcttcata ttaaagcctt atcccatctt 1080
tctaccacag tgaaacgaga gttagcaggt gttctcattt ttgagtctca cgccaaagga 1140
gggactgtgt tgtttaacca gggggaagaa ggtacctcct ggtacattat tctaaaagga 1200
tcagtgaatg tagtcattta cggcaagggt gtggtctgca ccctgcatga aggagatgac 1260
ttcggcaagt tagcactagt gaatgatgcc ccacgagctg cctctatcgt cttacgagaa 1320
gataactgcc atttcttaag agtagacaag gaggatttca accggatcct aaggctggtg 1380
tcgcacaacg tctatatcaa ggccgacaag cagaagaacg gcatcaaggc gaacttcaag 1440
atccgccaca acatcgagga cggcggcgtg cagctcgcct accactacca gcagaacacc 1500
cccatcggcg acggccccgt gctgctgccc gacaaccact acctgagcgt gcagtccata 1560
ctttcgaaag accccaacga gaagcgcgat cacatggtcc tgctggagtt cgtgaccgcc 1620
gccgggatca ctctcggcat ggacgagctg tacaagggcg gtaccggagg gagcatggtg 1680
agcaagggcg aggagctgtt caccggggtg gtgcccatcc aggtcgagct ggacggcgac 1740
gtaaacggcc acaagttcag cgtgtccggc gagggtgagg gcgatgccac ctacggcaag 1800
ctgaccctga agttcatctg caccaccggc aagctgcccg tgccctggcc caccctcgtg 1860
accaccctga cctacggcgt gcagtgcttc agccgctacc ccgaccacat gaagcagcac 1920
gacttcttca agtccgccat gcccgaaggc tacatccagg agcgcaccat cttcttcaag 1980
gacgacggca actacaagac ccgcgccgag gtgaagttcg agggcgacac cctggtgaac 2040
cgcatcgagc tgaagggcat cgacttcaag gaggacggca acatcctggg gcacaagctg 2100

```
gagtacaact tcaacaaccc tgacgtggag gcgaatacag tcagacttaa agaacatgac   2160
caagatgtct tggtgctgga gaaggtccca gcagggaaca gagcttctaa tcaaggaaac   2220
tcacagcctc agcaaaagta tactgtgatg tcaggaacac ctgaaaaaat tttagagcat   2280
tttctagaaa caatacgcct tgaggcaact ttaaatgaag caacagattc tgttttaaat   2340
gactttatta tgatgcactg tgtttttatg ccaaataccc agctttgccc ggcactggtg   2400
gcccactacc acgcacagcc ttcacaaggt acagaacagg agaaaatgga ttatgccctc   2460
aacaataaga ggcgagtcat ccgcctggtt ctacagtggg ctgccatgta tggagacctc   2520
ctgcaagagg atgacgtgtc tatggccttc ctggaggagt tttatgtatc tgtatcagat   2580
gatgcccgga tgattgctgc cctcaaggag caactgccag agttggagaa gattgtcaag   2640
caaatctcag aagatgcaaa ggcaccacaa aagaagcaca aggttctttt gcaacagttc   2700
aatacgggcg atgagagagc ccagaagcgc cagcctatcc gcggctctga tgaagttctg   2760
tttaaggtct attgcatgga ccccacctac acaaccattc gggtgccagt ggccacttcg   2820
gtgaaggaag tcatcagtgc agttgccgac aagctgggct ccggggaggg cctgatcata   2880
gtcaagatga gttccggagg agaaaaggtg gtgctcaaac ctaatgatgt ttcagtattt   2940
atgacgctca ccattaatgg acgcctgttt gcttgcccgc gagagcaatt cgattcactg   3000
actcccttac cagaacagga aggcccaact gttggaacag tgggaacttt tgaactgatg   3060
agctccaaag atttagcata ccagatgaca atttatgatt gggaactctt caactgcgtg   3120
catgagctgg agctaatcta tcacacattt ggaaggcata attttaaaaa gaccacagca   3180
aacttggatt tgttcctgag gagatttaat gaaattcagt tttgggtcgt cactgagatc   3240
tgcctttgtt ctcagctcag caagcgtgtt cagctattaa aaaaatttat taagatagca   3300
gcccactgta aggagtataa aaatctgaat tcctttttg ccatcgtcat gggactaagt   3360
aacgttgctg tgagccgctt ggcactaacg tgggagaaac tgccaagcaa gttcaagaag   3420
ttctatgcgg agtttgaaag tttaatggac ccttcaagga accacagggc ctacaggctg   3480
acagtagcta agctggaacc tcctctcatc cccttcatgc ctttgctcat taaagatatg   3540
acatttactc atgaggggaa caagacgttc attgacaatc tagtaaactt tgaaaaaatg   3600
cgcatgattg caaatacggc cagaacagtg agatactaca ggagccaacc cttcaatcct   3660
gatgcagctc aagctaataa gaaccatcag gatgtccgga gttatgtacg gcaattaaat   3720
gtgattgaca accagagaac tttatcacag atgtcacaca gattagagcc tcgtcgacca   3780
```

```
<210> SEQ ID NO 45
<211> LENGTH: 3768
<212> TYPE: DNA
<213> ORGANISM: Artificial Sequence
<220> FEATURE:
<223> OTHER INFORMATION: Synthetic

<400> SEQUENCE: 45

atggtcgctg cgcacgctgc ccattcttcc tcctctgccg agtggatcgc ctgcctggat     60
aaaagaccac tggagcgatc cagcgaagat gtggatataa tcttcactcg actgaaagaa    120
gttaaagctt ttgagaaatt tcacccaaat ctccttcatc agatttgctt atgtggttat    180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg gagagtccat tctggacaac    360
acaccccgcc atgcaaccat cgttaccagg gagagcagtg aactgctccg catcgagcag    420
```

```
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
ctcgagaacg tctatatcaa ggccgacaag cagaagaacg gcatcaaggc gaacttcaag   1440
atccgccaca acatcgagga cggcggcgtg cagctcgcct accactacca gcagaacacc   1500
cccatcggcg acggccccgt gctgctgccc gacaaccact acctgagcgt gcagtccata   1560
ctttcgaaag accccaacga gaagcgcgat cacatggtcc tgctggagtt cgtgaccgcc   1620
gccgggatca ctctcggcat ggacgagctg tacaagggcg gtaccggagg gagcatggtg   1680
agcaagggcg aggagctgtt caccggggtg gtgcccatcc aggtcgagct ggacggcgac   1740
gtaaacggcc acaagttcag cgtgtccggc gagggtgagg gcgatgccac ctacggcaag   1800
ctgaccctga agttcatctg caccaccggc aagctgcccg tgccctggcc caccctcgtg   1860
accaccctga cctacggcgt gcagtgcttc agccgctacc ccgaccacat gaagcagcac   1920
gacttcttca agtccgccat gcccgaaggc tacatccagg agcgcaccat cttcttcaag   1980
gacgacggca actacaagac ccgcgccgag gtgaagttcg agggcgacac cctggtgaac   2040
cgcatcgagc tgaagggcat cgacttcaag gaggacggca acatcctggg gcacaagctg   2100
gagtacaaca cgcgtgaggc gaatacagtc agacttaaag aacatgacca agatgtcttg   2160
gtgctggaga aggtcccagc agggaacaga gcttctaatc aaggaaactc acagcctcag   2220
caaaagtata ctgtgatgtc aggaacacct gaaaaaattt tagagcattt tctagaaaca   2280
atacgccttg aggcaacttt aaatgaagca acagattctg ttttaaatga ctttattatg   2340
atgcactgtg tttttatgcc aaatacccag ctttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg gagacctcct gcaagaggat   2520
gacgtgtcta tggccttcct ggaggagttt tatgtatctg tatcagatga tgcccggatg   2580
attgctgccc tcaaggagca actgccagag ttggagaaga ttgtcaagca aatctcagaa   2640
gatgcaaagg caccacaaaa gaagcacaag gttcttttgc aacagttcaa tacgggcgat   2700
gagagagccc agaagcgcca gcctatccgc ggctctgatg aagttctgtt taaggtctat   2760
```

```
tgcatggacc ccacctacac aaccattcgg gtgccagtgg ccacttcggt gaaggaagtc   2820

atcagtgcag ttgccgacaa gctgggctcc ggggagggcc tgatcatagt caagatgagt   2880

tccggaggag aaaaggtggt gctcaaacct aatgatgttt cagtatttat gacgctcacc   2940

attaatggac gcctgtttgc ttgcccgcga gagcaattcg attcactgac tcccttacca   3000

gaacaggaag gcccaactgt tggaacagtg ggaacttttg aactgatgag ctccaaagat   3060

ttagcatacc agatgacaat ttatgattgg gaactcttca actgcgtgca tgagctggag   3120

ctaatctatc acacatttgg aaggcataat tttaaaaaga ccacagcaaa cttggatttg   3180

ttcctgagga gatttaatga aattcagttt tgggtcgtca ctgagatctg cctttgttct   3240

cagctcagca agcgtgttca gctattaaaa aaatttatta agatagcagc ccactgtaag   3300

gagtataaaa atctgaattc ctttttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca                3768
```

<210> SEQ ID NO 46
<211> LENGTH: 1605
<212> TYPE: DNA
<213> ORGANISM: Artificial Sequence
<220> FEATURE:
<223> OTHER INFORMATION: Synthetic

<400> SEQUENCE: 46

```
atgggctcta acaatgacag gattcctgac aaggagaaca cacctctcat tgaacctcac     60

gttcctcttc gtcctgctaa caccattacc aaggtccctt cagagaagat cctcagagct    120

ggaaaaattt tacgaaatgc cattctctct cgagcacctc acatgataag agatagaaaa    180

taccacctaa agacatacag acaatgctgt gtgggaactg aactggtgga ctggatgatg    240

cagcagacac catgtgttca ctcccggact caagctgttg gcatgtggca agtcctgtta    300

gaagatggtg ttctcaacca cgtggaccag gagcaccatt tccaagacaa atatttattc    360

tatcgatttc tggatgatga gcacgaggat gccccttttgc ctactgagga ggagaagaag    420

gagtgtgatg aggagctcca ggacaccatg ctgctgctgt cacagatggg ccccgacgcc    480

cacatgagga tgatccttcg caaaccacct ggccagagga ctgtggatga cctagagatt    540

atctatgagg agcttcttca tattaaagcc ttatcccatc tttctaccac agtgaaacga    600

gagttagcag gtgttctcat ttttgagtct cacgccaaag gagggactgt gttgtttaac    660

caggggggaag aaggtacctc ctggtacatt attctaaaag gatcagtgaa tgtagtcatt    720

tacggcaagg gtgtggtctg caccctgcat gaaggagatg acttcggcaa gttagcacta    780

gtgaatgatg ccccacgagc tgcctctatc gtcttacgag aagataactg ccatttctta    840

agagtagaca aggaggattt caaccggatc ctaaggcgtg cgaacgtcta tatcaaggcc    900

gacaagcaga agaacggcat caaggcgaac ttcaagatcc gccacaacat cgaggacggc    960

ggcgtgcagc tcgcctacca ctaccagcag aacaccccca tcggcgacgg ccccgtgctg   1020

ctgcccgaca accactacct gagcgtgcag tccatacttt cgaaagaccc caacgagaag   1080
```

```
cgcgatcaca tggtcctgct ggagttcgtg accgccgccg ggatcactct cggcatggac   1140

gagctgtaca agggcggtac cggagggagc atggtgagca agggcgagga gctgttcacc   1200

ggggtggtgc ccatccaggt cgagctggac ggcgacgtaa acggccacaa gttcagcgtg   1260

tccggcgagg gtgagggcga tgccacctac ggcaagctga ccctgaagtt catctgcacc   1320

accggcaagc tgcccgtgcc ctggcccacc ctcgtgacca ccctgaccta cggcgtgcag   1380

tgcttcagcc gctaccccga ccacatgaag cagcacgact tcttcaagtc cgccatgccc   1440

gaaggctaca tccaggagcg caccatcttc ttcaaggacg acggcaacta caagacccgc   1500

gccgaggtga agttcgaggg cgacaccctg gtgaaccgca tcgagctgaa gggcatcgac   1560

ttcaaggagg acggcaacat cctggggcac aagctggagt acaac                   1605
```

```
<210> SEQ ID NO 47
<211> LENGTH: 3795
<212> TYPE: DNA
<213> ORGANISM: Artificial Sequence
<220> FEATURE:
<223> OTHER INFORMATION: Synthetic

<400> SEQUENCE: 47

atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc ccctttgcct    900

actgaggagg agaagaagga gtgtgatgag gagctccagg acaccatgct gctgctgtca    960

cagatgggcc ccgacgccca catgaggatg atccttcgca aaccacctgg ccagaggact   1020

gtggatgacc tagagattat ctatgaggag cttcttcata ttaaagcctt atcccatctt   1080

tctaccacag tgaaacgaga gttagcaggt gttctcattt ttgagtctca cgccaaagga   1140

gggactgtgt tgtttaacca gggggaagaa ggtacctcct ggtacattat tctaaaagga   1200

tcagtgaatg tagtcattta cggcaagggt gtggtctgca ccctgcatga aggagatgac   1260

ttcggcaagt tagcactagt gaatgatgcc ccacgagctg cctctatcgt cttacgagaa   1320

gataactgcc atttcttaag agtagacaag gaggatttca accggatcct aaggctcgag   1380

aacgtctata tcaaggccga caagcagaag aacggcatca aggcgaactt caagatccgc   1440

cacaacatcg aggacggcgg cgtgcagctc gcctaccact accagcagaa cacccccatc   1500
```

```
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgta aggaggattt caaccggatc ctaagggacg tggaggcgaa tacagtcaga   2160
cttaaagaac atgaccaaga tgtcttggtg ctggagaagg tcccagcagg gaacagagct   2220
tctaatcaag gaaactcaca gcctcagcaa aagtatactg tgatgtcagg aacacctgaa   2280
aaaattttag agcattttct agaaacaata cgccttgagg caactttaaa tgaagcaaca   2340
gattctgttt taaatgactt tattatgatg cactgtgttt ttatgccaaa tacccagctt   2400
tgcccggcac tggtggccca ctaccacgca cagccttcac aaggtacaga acaggagaaa   2460
atggattatg ccctcaacaa taagaggcga gtcatccgcc tggttctaca gtgggctgcc   2520
atgtatggag acctcctgca agaggatgac gtgtctatgg ccttcctgga ggagttttat   2580
gtatctgtat cagatgatgc ccggatgatt gctgccctca aggagcaact gccagagttg   2640
gagaagattg tcaagcaaat ctcagaagat gcaaaggcac cacaaaagaa gcacaaggtt   2700
cttttgcaac agttcaatac gggcgatgag agagcccaga agcgccagcc tatccgcggc   2760
tctgatgaag ttctgtttaa ggtctattgc atggacccca cctacacaac cattcgggtg   2820
ccagtggcca cttcggtgaa ggaagtcatc agtgcagttg ccgacaagct gggctccggg   2880
gagggcctga tcatagtcaa gatgagttcc ggaggagaaa aggtggtgct caaacctaat   2940
gatgtttcag tatttatgac gctcaccatt aatggacgcc tgtttgcttg cccgcgagag   3000
caattcgatt cactgactcc cttaccagaa caggaaggcc caactgttgg aacagtggga   3060
acttttgaac tgatgagctc caaagattta gcataccaga tgacaattta tgattgggaa   3120
ctcttcaact gcgtgcatga gctggagcta atctatcaca catttggaag gcataatttt   3180
aaaaagacca cagcaaactt ggatttgttc ctgaggagat ttaatgaaat tcagttttgg   3240
gtcgtcactg agatctgcct ttgttctcag ctcagcaagc gtgttcagct attaaaaaaa   3300
tttattaaga tagcagccca ctgtaaggag tataaaaatc tgaattcctt ttttgccatc   3360
gtcatgggac taagtaacgt tgctgtgagc cgcttggcac taacgtggga gaaactgcca   3420
agcaagttca agaagttcta tgcggagttt gaaagtttaa tggacccttc aaggaaccac   3480
agggcctaca ggctgacagt agctaagctg gaacctcctc tcatcccctt catgcctttg   3540
ctcattaaag atatgacatt tactcatgag gggaacaaga cgttcattga caatctagta   3600
aactttgaaa aaatgcgcat gattgcaaat acggccagaa cagtgagata ctacaggagc   3660
caacccttca atcctgatgc agctcaagct aataagaacc atcaggatgt ccggagttat   3720
gtacggcaat taaatgtgat tgacaaccag agaactttat cacagatgtc acacagatta   3780
gagcctcgtc gacca                                                    3795
```

<210> SEQ ID NO 48
<211> LENGTH: 3771
<212> TYPE: DNA
<213> ORGANISM: Artificial Sequence
<220> FEATURE:
<223> OTHER INFORMATION: Synthetic

<400> SEQUENCE: 48
atggtcgctg cgcacgctgc ccattcttcc tcctctgccg agtggatcgc ctgcctggat 60
aaaagaccac tggagcgatc cagcgaagat gtggatataa tcttcactcg actgaaagaa 120
gttaaagctt ttgagaaatt tcacccaaat ctccttcatc agatttgctt atgtggttat 180
tatgagaatc tggaaaaggg aataacatta tttcgccagg gtgatattgg aacaaactgg 240
tatgctgtcc tggcagggtc tttggatgtt aaagtatctg agaccagcag tcaccaggat 300
gctgtgacca tctgtaccct gggaattggg acggcctttg gagagtccat tctggacaac 360
acaccccgcc atgcaaccat cgttaccagg gagagcagtg aactgctccg catcgagcag 420
aaggacttca aggcactatg ggagaaatat cgacagtata tggcaggact tctggctcct 480
ccttatggtg ttatggaaac gggctctaac aatgacagga ttcctgacaa ggagaacaca 540
cctctcattg aacctcacgt tcctcttcgt cctgctaaca ccattaccaa ggtcccttca 600
gagaagatcc tcagagctgg aaaaatttta cgaaatgcca ttctctctcg agcacctcac 660
atgataagag atagaaaata ccacctaaag acatacagac aatgctgtgt gggaactgaa 720
ctggtggact ggatgatgca gcagacacca tgtgttcact cccggactca agctgttggc 780
atgtggcaag tcctgttaga agatggtgtt ctcaaccacg tggaccagga gcaccatttc 840
caagacaaat atttattcta tcgatttctg gatgatgagc acgaggatgc ccctttgcct 900
actgaggagg agaagaagga gtgtgatgag gagctccagg acaccatgct gctgctgtca 960
cagatgggcc ccgacgccca catgaggatg atccttcgca aaccacctgg ccagaggact 1020
gtggatgacc tagagattat ctatgaggag cttcttcata ttaaagcctt atcccatctt 1080
tctaccacag tgaaacgaga gttagcaggt gttctcattt ttgagtctca cgccaaagga 1140
gggactgtgt tgtttaacca gggggaagaa ggtacctcct ggtacattat tctaaaagga 1200
tcagtgaatg tagtcattta cggcaagggt gtggtctgca ccctgcatga aggagatgac 1260
ttcggcaagt tagcactagt gaatgatgcc ccacgagctg cctctatcgt cttacgagaa 1320
gataactgcc atttcttaag agtagacaag gaggatttca accggatcct aagggacgtg 1380
ctcgagaacg tctatatcaa ggccgacaag cagaagaacg gcatcaaggc gaacttcaag 1440
atccgccaca acatcgagga cggcggcgtg cagctcgcct accactacca gcagaacacc 1500
cccatcggcg acggccccgt gctgctgccc gacaaccact acctgagcgt gcagtccata 1560
ctttcgaaag accccaacga gaagcgcgat cacatggtcc tgctggagtt cgtgaccgcc 1620
gccgggatca ctctcggcat ggacgagctg tacaagggcg gtaccggagg gagcatggtg 1680
agcaagggcg aggaggtttc ctccgggggg gtgcccatcc aggtcgagct ggacggcgac 1740
gtaaacggcc acaagttcag cgtgtccggc gagggtgagg gcgatgccac ctacggcaag 1800
ctgaccctga agttcatctg caccaccggc aagctgcccg tgccctggcc caccctcgtg 1860
accaccctga cctacggcgt gcagtgcttc agccgctacc ccgaccacat gaagcagcac 1920
gacttcttca agtccgccat gcccgaaggc tacatccagg agcgcaccat cttcttcaag 1980
gacgacggca actacaagac ccgcgccgag gtgaagttcg agggcgacac cctggtgaac 2040
cgcatcgagc tgaagggcat cgacttcaag gaggacggca acatcctggg gcacaagctg 2100

```
gagtacaaca cgcgtgtgga ggcgaataca gtcagactta aagaacatga ccaagatgtc   2160

ttggtgctgg agaaggtccc agcagggaac agagcttcta atcaaggaaa ctcacagcct   2220

cagcaaaagt atactgtgat gtcaggaaca cctgaaaaaa ttttagagca ttttctagaa   2280

acaatacgcc ttgaggcaac tttaaatgaa gcaacagatt ctgttttaaa tgactttatt   2340

atgatgcact gtgtttttat gccaaatacc cagctttgcc cggcactggt ggcccactac   2400

cacgcacagc cttcacaagg tacagaacag gagaaaatgg attatgccct caacaataag   2460

aggcgagtca tccgcctggt tctacagtgg gctgccatgt atggagacct cctgcaagag   2520

gatgacgtgt ctatggcctt cctggaggag ttttatgtat ctgtatcaga tgatgcccgg   2580

atgattgctg ccctcaagga gcaactgcca gagttggaga agattgtcaa gcaaatctca   2640

gaagatgcaa aggcaccaca aaagaagcac aaggttcttt tgcaacagtt caatacgggc   2700

gatgagagag cccagaagcg ccagcctatc cgcggctctg atgaagttct gtttaaggtc   2760

tattgcatgg accccaccta cacaaccatt cgggtgccag tggccacttc ggtgaaggaa   2820

gtcatcagtg cagttgccga caagctgggc tccggggagg gcctgatcat agtcaagatg   2880

agttccggag gagaaaaggt ggtgctcaaa cctaatgatg tttcagtatt tatgacgctc   2940

accattaatg gacgcctgtt tgcttgcccg cgagagcaat tcgattcact gactccctta   3000

ccagaacagg aaggcccaac tgttggaaca gtgggaactt ttgaactgat gagctccaaa   3060

gatttagcat accagatgac aatttatgat tgggaactct tcaactgcgt gcatgagctg   3120

gagctaatct atcacacatt tggaaggcat aattttaaaa agaccacagc aaacttggat   3180

ttgttcctga ggagatttaa tgaaattcag ttttgggtcg tcactgagat ctgcctttgt   3240

tctcagctca gcaagcgtgt tcagctatta aaaaaattta ttaagatagc agcccactgt   3300

aaggagtata aaaatctgaa ttcctttttt gccatcgtca tgggactaag taacgttgct   3360

gtgagccgct tggcactaac gtgggagaaa ctgccaagca agttcaagaa gttctatgcg   3420

gagtttgaaa gtttaatgga cccttcaagg aaccacaggg cctacaggct gacagtagct   3480

aagctggaac ctcctctcat ccccttcatg cctttgctca ttaaagatat gacatttact   3540

catgagggga acaagacgtt cattgacaat ctagtaaact ttgaaaaaat gcgcatgatt   3600

gcaaatacgg ccagaacagt gagatactac aggagccaac ccttcaatcc tgatgcagct   3660

caagctaata agaaccatca ggatgtccgg agttatgtac ggcaattaaa tgtgattgac   3720

aaccagagaa ctttatcaca gatgtcacac agattagagc ctcgtcgacc a            3771
```

<210> SEQ ID NO 49
<211> LENGTH: 3765
<212> TYPE: DNA
<213> ORGANISM: Artificial Sequence
<220> FEATURE:
<223> OTHER INFORMATION: Synthetic

<400> SEQUENCE: 49

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420
```

```
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
ctcgagaacg tctatatcaa ggccgacaag cagaagaacg gcatcaaggc gaacttcaag   1440
atccgccaca acatcgagga cggcggcgtg cagctcgcct accactacca gcagaacacc   1500
cccatcggcg acggccccgt gctgctgccc gacaaccact acctgagcgt gcagtccata   1560
ctttcgaaag accccaacga gaagcgcgat cacatggtcc tgctggagtt cgtgaccgcc   1620
gccgggatca ctctcggcat ggacgagctg tacaagggcg gtaccggagg gagcatggtg   1680
agcaagggcg aggagctgtt caccggggtg gtgcccatcc aggtcgagct ggacggcgac   1740
gtaaacggcc acaagttcag cgtgtccggc gagggtgagg gcgatgccac ctacggcaag   1800
ctgaccctga agttcatctg caccaccggc aagctgcccg tgccctggcc caccctcgtg   1860
accaccctga cctacggcgt gcagtgcttc agccgctacc ccgaccacat gaagcagcac   1920
gacttcttca agtccgccat gcccgaaggc tacatccagg agcgcaccat cttcttcaag   1980
gacgacggca actacaagac ccgcgccgag gtgaagttcg agggcgacac cctggtgaac   2040
cgcatcgagc tgaagggcat cgacttcaag gaggacggca acatcctggg gcacaagctg   2100
gagtacaaca cgcgtgcgaa tacagtcaga cttaaagaac atgaccaaga tgtcttggtg   2160
ctggagaagg tcccagcagg gaacagagct tctaatcaag gaaactcaca gcctcagcaa   2220
aagtatactg tgatgtcagg aacacctgaa aaaattttag agcattttct agaaacaata   2280
cgccttgagg caactttaaa tgaagcaaca gattctgttt taaatgactt tattatgatg   2340
cactgtgttt ttatgccaaa tacccagctt tgcccggcac tggtggccca ctaccacgca   2400
cagccttcac aaggtacaga acaggagaaa atggattatg ccctcaacaa taagaggcga   2460
gtcatccgcc tggttctaca gtgggctgcc atgtatggag acctcctgca agaggatgac   2520
gtgtctatgg ccttcctgga ggagttttat gtatctgtat cagatgatgc ccggatgatt   2580
gctgccctca aggagcaact gccagagttg gagaagattg tcaagcaaat ctcagaagat   2640
gcaaaggcac cacaaaagaa gcacaaggtt cttttgcaac agttcaatac gggcgatgag   2700
agagcccaga agcgccagcc tatccgcggc tctgatgaag ttctgtttaa ggtctattgc   2760
```

```
atggacccca cctacacaac cattcgggtg ccagtggcca cttcggtgaa ggaagtcatc   2820

agtgcagttg ccgacaagct gggctccggg gagggcctga tcatagtcaa gatgagttcc   2880

ggaggagaaa aggtggtgct caaacctaat gatgtttcag tatttatgac gctcaccatt   2940

aatggacgcc tgtttgcttg cccgcgagag caattcgatt cactgactcc cttaccagaa   3000

caggaaggcc caactgttgg aacagtggga acttttgaac tgatgagctc caaagattta   3060

gcataccaga tgacaattta tgattgggaa ctcttcaact gcgtgcatga gctggagcta   3120

atctatcaca catttggaag gcataatttt aaaaagacca cagcaaactt ggatttgttc   3180

ctgaggagat ttaatgaaat tcagttttgg gtcgtcactg agatctgcct ttgttctcag   3240

ctcagcaagc gtgttcagct attaaaaaaa tttattaaga tagcagccca ctgtaaggag   3300

tataaaaatc tgaattcctt ttttgccatc gtcatgggac taagtaacgt tgctgtgagc   3360

cgcttggcac taacgtggga gaaactgcca agcaagttca agaagttcta tgcggagttt   3420

gaaagtttaa tggacccttc aaggaaccac agggcctaca ggctgacagt agctaagctg   3480

gaacctcctc tcatcccctt catgcctttg ctcattaaag atatgacatt tactcatgag   3540

gggaacaaga cgttcattga caatctagta aactttgaaa aaatgcgcat gattgcaaat   3600

acggccagaa cagtgagata ctacaggagc caacccttca atcctgatgc agctcaagct   3660

aataagaacc atcaggatgt ccggagttat gtacggcaat taaatgtgat tgacaaccag   3720

agaactttat cacagatgtc acacagatta gagcctcgtc gacca                    3765
```

<210> SEQ ID NO 50
<211> LENGTH: 3780
<212> TYPE: DNA
<213> ORGANISM: Artificial Sequence
<220> FEATURE:
<223> OTHER INFORMATION: Synthetic

<400> SEQUENCE: 50

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc ccctttgcct    900

actgaggagg agaagaagga gtgtgatgag gagctccagg acaccatgct gctgctgtca    960

cagatgggcc ccgacgccca catgaggatg atccttcgca aaccacctgg ccagaggact   1020

gtggatgacc tagagattat ctatgaggag cttcttcata ttaaagcctt atcccatctt   1080
```

```
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgtc ggatcctaag ggacgtggag gcgaatacag tcagacttaa agaacatgac   2160
caagatgtct tggtgctgga gaaggtccca gcagggaaca gagcttctaa tcaaggaaac   2220
tcacagcctc agcaaaagta tactgtgatg tcaggaacac ctgaaaaaat tttagagcat   2280
tttctagaaa caatacgcct tgaggcaact ttaaatgaag caacagattc tgttttaaat   2340
gactttatta tgatgcactg tgtttttatg ccaaataccc agctttgccc ggcactggtg   2400
gcccactacc acgcacagcc ttcacaaggt acagaacagg agaaaatgga ttatgccctc   2460
aacaataaga ggcgagtcat ccgcctggtt ctacagtggg ctgccatgta tggagacctc   2520
ctgcaagagg atgacgtgtc tatggccttc ctggaggagt tttatgtatc tgtatcagat   2580
gatgcccgga tgattgctgc cctcaaggag caactgccag agttggagaa gattgtcaag   2640
caaatctcag aagatgcaaa ggcaccacaa aagaagcaca aggttctttt gcaacagttc   2700
aatacgggcg atgagagagc ccagaagcgc cagcctatcc gcggctctga tgaagttctg   2760
tttaaggtct attgcatgga ccccacctac acaaccattc gggtgccagt ggccacttcg   2820
gtgaaggaag tcatcagtgc agttgccgac aagctgggct ccggggaggg cctgatcata   2880
gtcaagatga gttccggagg agaaaaggtg gtgctcaaac ctaatgatgt ttcagtattt   2940
atgacgctca ccattaatgg acgcctgttt gcttgcccgc gagagcaatt cgattcactg   3000
actcccttac cagaacagga aggcccaact gttggaacag tgggaacttt tgaactgatg   3060
agctccaaag atttagcata ccagatgaca atttatgatt gggaactctt caactgcgtg   3120
catgagctgg agctaatcta tcacacattt ggaaggcata attttaaaaa gaccacagca   3180
aacttggatt tgttcctgag gagatttaat gaaattcagt tttgggtcgt cactgagatc   3240
tgcctttgtt ctcagctcag caagcgtgtt cagctattaa aaaaatttat taagatagca   3300
gcccactgta aggagtataa aaatctgaat tcctttttg ccatcgtcat gggactaagt    3360
aacgttgctg tgagccgctt ggcactaacg tgggagaaac tgccaagcaa gttcaagaag   3420
```

```
ttctatgcgg agtttgaaag tttaatggac ccttcaagga accacagggc ctacaggctg   3480

acagtagcta agctggaacc tcctctcatc cccttcatgc ctttgctcat taaagatatg   3540

acatttactc atgaggggaa caagacgttc attgacaatc tagtaaactt tgaaaaaatg   3600

cgcatgattg caaatacggc cagaacagtg agatactaca ggagccaacc cttcaatcct   3660

gatgcagctc aagctaataa gaaccatcag gatgtccgga gttatgtacg gcaattaaat   3720

gtgattgaca accagagaac tttatcacag atgtcacaca gattagagcc tcgtcgacca   3780


<210> SEQ ID NO 51
<211> LENGTH: 3768
<212> TYPE: DNA
<213> ORGANISM: Artificial Sequence
<220> FEATURE:
<223> OTHER INFORMATION: Synthetic

<400> SEQUENCE: 51

atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc cccttttgcct    900

actgaggagg agaagaagga gtgtgatgag gagctccagg acaccatgct gctgctgtca    960

cagatgggcc ccgacgccca catgaggatg atccttcgca aaccacctgg ccagaggact   1020

gtggatgacc tagagattat ctatgaggag cttcttcata ttaaagcctt atcccatctt   1080

tctaccacag tgaaacgaga gttagcaggt gttctcattt ttgagtctca cgccaaagga   1140

gggactgtgt tgtttaacca gggggaagaa ggtacctcct ggtacattat tctaaaagga   1200

tcagtgaatg tagtcattta cggcaagggt gtggtctgca ccctgcatga aggagatgac   1260

ttcggcaagt tagcactagt gaatgatgcc ccacgagctg cctctatcgt cttacgagaa   1320

gataactgcc atttcttaag agtagacaag gaggatttca accggatcct aagggacgtg   1380

ctcgagaacg tctatatcaa ggccgacaag cagaagaacg gcatcaaggc gaacttcaag   1440

atccgccaca acatcgagga cggcggcgtg cagctcgcct accactacca gcagaacacc   1500

cccatcggcg acggccccgt gctgctgccc gacaaccact acctgagcgt gcagtccata   1560

ctttcgaaag accccaacga gaagcgcgat cacatggtcc tgctggagtt cgtgaccgcc   1620

gccgggatca ctctcggcat ggacgagctg tacaagggcg gtaccggagg gagcatggtg   1680

agcaagggcg aggagctgtt caccggggtg gtgcccatcc aggtcgagct ggacggcgac   1740
```

```
gtaaacggcc acaagttcag cgtgtccggc gagggtgagg gcgatgccac ctacggcaag   1800

ctgaccctga agttcatctg caccaccggc aagctgcccg tgccctggcc caccctcgtg   1860

accaccctga cctacggcgt gcagtgcttc agccgctacc ccgaccacat gaagcagcac   1920

gacttcttca agtccgccat gcccgaaggc tacatccagg agcgcaccat cttcttcaag   1980

gacgacggca actacaagac ccgcgccgag gtgaagttcg agggcgacac cctggtgaac   2040

cgcatcgagc tgaagggcat cgacttcaag gaggacggca acatcctggg gcacaagctg   2100

gagtacaaca cgcgtgaggc gaatacagtc agacttaaag aacatgacca agatgtcttg   2160

gtgctggaga aggtcccagc agggaacaga gcttctaatc aaggaaactc acagcctcag   2220

caaaagtata ctgtgatgtc aggaacacct gaaaaaattt tagagcattt tctagaaaca   2280

atacgccttg aggcaacttt aaatgaagca acagattctg ttttaaatga ctttattatg   2340

atgcactgtg tttttatgcc aaatacccag ctttgcccgg cactggtggc ccactaccac   2400

gcacagcctt cacaaggtac agaacaggag aaaatggatt atgccctcaa caataagagg   2460

cgagtcatcc gcctggttct acagtgggct gccatgtatg gagacctcct gcaagaggat   2520

gacgtgtcta tggccttcct ggaggagttt tatgtatctg tatcagatga tgcccggatg   2580

attgctgccc tcaaggagca actgccagag ttggagaaga ttgtcaagca aatctcagaa   2640

gatgcaaagg caccacaaaa gaagcacaag gttcttttgc aacagttcaa tacgggcgat   2700

gagagagccc agaagcgcca gcctatccgc ggctctgatg aagttctgtt taaggtctat   2760

tgcatggacc ccacctacac aaccattcgg gtgccagtgg ccacttcggt gaaggaagtc   2820

atcagtgcag ttgccgacaa gctgggctcc ggggagggcc tgatcatagt caagatgagt   2880

tccggaggag aaaaggtggt gctcaaacct aatgatgttt cagtatttat gacgctcacc   2940

attaatggac gcctgtttgc ttgcccgcga gagcaattcg attcactgac tcccttacca   3000

gaacaggaag gcccaactgt tggaacagtg ggaacttttg aactgatgag ctccaaagat   3060

ttagcatacc agatgacaat ttatgattgg gaactcttca actgcgtgca tgagctggag   3120

ctaatctatc acacatttgg aaggcataat tttaaaaaga ccacagcaaa cttggatttg   3180

ttcctgagga gatttaatga aattcagttt tgggtcgtca ctgagatctg cctttgttct   3240

cagctcagca agcgtgttca gctattaaaa aaatttatta agatagcagc ccactgtaag   3300

gagtataaaa atctgaattc ctttttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca                3768
```

<210> SEQ ID NO 52
<211> LENGTH: 3789
<212> TYPE: DNA
<213> ORGANISM: Artificial Sequence
<220> FEATURE:
<223> OTHER INFORMATION: Synthetic

<400> SEQUENCE: 52

```
atggtcgctg cgcacgctgc ccattcttcc tcctctgccg agtggatcgc ctgcctggat     60
aaaagaccac tggagcgatc cagcgaagat gtggatataa tcttcactcg actgaaagaa    120
gttaaagctt ttgagaaatt tcacccaaat ctccttcatc agatttgctt atgtggttat    180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg gagagtccat tctggacaac    360
acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacctc   1380
gagaacgtct atatcaaggc cgacaagcag aagaacggca tcaaggcgaa cttcaagatc   1440
cgccacaaca tcgaggacgg cggcgtgcag ctcgcctacc actaccagca gaacaccccc   1500
atcggcgacg gccccgtgct gctgcccgac aaccactacc tgagcgtgca gtccatactt   1560
tcgaaagacc ccaacgagaa gcgcgatcac atggtcctgc tggagttcgt gaccgccgcc   1620
gggatcactc tcggcatgga cgagctgtac aagggcggta ccggagggag catggtgagc   1680
aagggcgagg agctgttcac cggggtggtg cccatccagg tcgagctgga cggcgacgta   1740
aacggccaca agttcagcgt gtccggcgag ggtgagggcg atgccaccta cggcaagctg   1800
accctgaagt tcatctgcac caccggcaag ctgcccgtgc cctggcccac cctcgtgacc   1860
accctgacct acggcgtgca gtgcttcagc cgctaccccg accacatgaa gcagcacgac   1920
ttcttcaagt ccgccatgcc cgaaggctac atccaggagc gcaccatctt cttcaaggac   1980
gacggcaact acaagacccg cgccgaggtg aagttcgagg gcgacaccct ggtgaaccgc   2040
atcgagctga agggcatcga cttcaaggag gacggcaaca tcctggggca caagctggag   2100
tacaacacgc gtttcaaccg gatcctaagg gacgtggagg cgaatacagt cagacttaaa   2160
gaacatgacc aagatgtctt ggtgctggag aaggtcccag cagggaacag agcttctaat   2220
caaggaaact cacagcctca gcaaaagtat actgtgatgt caggaacacc tgaaaaaatt   2280
ttagagcatt ttctagaaac aatacgcctt gaggcaactt taaatgaagc aacagattct   2340
gttttaaatg actttattat gatgcactgt gtttttatgc caaataccca gctttgcccg   2400
```

gcactggtgg cccactacca cgcacagcct tcacaaggta cagaacagga gaaaatggat 2460
tatgccctca acaataagag gcgagtcatc cgcctggttc tacagtgggc tgccatgtat 2520
ggagacctcc tgcaagagga tgacgtgtct atggccttcc tggaggagtt ttatgtatct 2580
gtatcagatg atgcccggat gattgctgcc ctcaaggagc aactgccaga gttggagaag 2640
attgtcaagc aaatctcaga agatgcaaag gcaccacaaa agaagcacaa ggttcttttg 2700
caacagttca atacgggcga tgagagagcc cagaagcgcc agcctatccg cggctctgat 2760
gaagttctgt ttaaggtcta ttgcatggac cccacctaca caaccattcg ggtgccagtg 2820
gccacttcgg tgaaggaagt catcagtgca gttgccgaca agctgggctc cggggagggc 2880
ctgatcatag tcaagatgag ttccggagga gaaaaggtgg tgctcaaacc taatgatgtt 2940
tcagtattta tgacgctcac cattaatgga cgcctgtttg cttgcccgcg agagcaattc 3000
gattcactga ctcccttacc agaacaggaa ggcccaactg ttggaacagt gggaactttt 3060
gaactgatga gctccaaaga tttagcatac cagatgacaa tttatgattg ggaactcttc 3120
aactgcgtgc atgagctgga gctaatctat cacacatttg gaaggcataa ttttaaaaag 3180
accacagcaa acttggattt gttcctgagg agatttaatg aaattcagtt ttgggtcgtc 3240
actgagatct gcctttgttc tcagctcagc aagcgtgttc agctattaaa aaaatttatt 3300
aagatagcag cccactgtaa ggagtataaa aatctgaatt cctttttgc catcgtcatg 3360 ggactaagta acgttgctgt gagccgcttg gcactaacgt gggagaaact gccaagcaag 3420
ttcaagaagt tctatgcgga gtttgaaagt ttaatggacc cttcaaggaa ccacagggcc 3480
tacaggctga cagtagctaa gctggaacct cctctcatcc ccttcatgcc tttgctcatt 3540
aaagatatga catttactca tgaggggaac aagacgttca ttgacaatct agtaaacttt 3600
gaaaaaatgc gcatgattgc aaatacggcc agaacagtga gatactacag gagccaaccc 3660
ttcaatcctg atgcagctca agctaataag aaccatcagg atgtccggag ttatgtacgg 3720
caattaaatg tgattgacaa ccagagaact ttatcacaga tgtcacacag attagagcct 3780
cgtcgacca 3789

<210> SEQ ID NO 53
<211> LENGTH: 3764
<212> TYPE: DNA
<213> ORGANISM: Artificial Sequence
<220> FEATURE:
<223> OTHER INFORMATION: Synthetic

<400> SEQUENCE: 53
atggtcgctg cgcacgctgc ccattcttcc tcctctgccg agtggatcgc ctgcctggat 60
aaaagaccac tggagcgatc cagcgaagat gtggatataa tcttcactcg actgaaagaa 120
gttaaagctt ttgagaaatt tcacccaaat ctccttcatc agatttgctt atgtggttat 180
tatgagaatc tggaaaaggg aataacatta tttcgccagg gtgatattgg aacaaactgg 240
tatgctgtcc tggcagggtc tttggatgtt aaagtatctg agaccagcag tcaccaggat 300
gctgtgacca tctgtaccct gggaattggg acggcctttg gagagtccat tctggacaac 360
acaccccgcc atgcaaccat cgttaccagg gagagcagtg aactgctccg catcgagcag 420
aaggacttca aggcactatg ggagaaatat cgacagtata tggcaggact tctggctcct 480
ccttatggtg ttatggaaac gggctctaac aatgacagga ttcctgacaa ggagaacaca 540
cctctcattg aacctcacgt tcctcttcgt cctgctaaca ccattaccaa ggtcccttca 600

```
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
ctcgagaacg tctatatcaa ggccgacaag cagaagaacg gcatcaaggc gaacttcaag   1440
atccgccaca acatcgagga cggcggcgtg cagctcgcct accactacca gcagaacacc   1500
cccatcggcg acggccccgt gctgctgccc gacaaccact acctgagcgt gcagtccata   1560
ctttcgaaag accccaacga gaagcgcgat cacatggtcc tgctggagtt cgtgaccgcc   1620
gccgggatca ctctcggcat ggacgagctg tacaagggcg gtaccggagg gagcatggtg   1680
agcaagggcg aggagctgtt cacccggggg gtggtgccca tccaggtcga gctggacggc   1740
gacgtaaacg gccacaagtt cagcgtgtcc ggcgagggtg agggcgatgc cacctacggc   1800
aagctgaccc tgaagttcat ctgcaccacc ggcaagctgc ccgtgccctg gcccaccctc   1860
gtgaccaccc tgacctacgg cgtgcagtgc ttcagccgct accccgacca catgaagcag   1920
cacgacttct tcaagtccgc catgcccgaa ggctacatcc aggagcgcac catcttcttc   1980
aaggacgacg gcaactacaa gacccgcgcc gaggtgaagt tcgagggcga caccctggtg   2040
aaccgcatcg agctgaaggg catcgacttc aaggaggacg gcaacatcct ggggcacaag   2100
ctggagtaca acacgcgtaa tacagtcaga cttaaagaac atgaccaaga tgtcttggtg   2160
ctggagaagg tcccagcagg gaacagagct tctaatcaag gaaactcaca gcctcagcaa   2220
aagtatactg tgatgtcagg aacacctgaa aaaattttag agcattttct agaaacaata   2280
cgccttgagg caactttaaa tgaagcaaca gattctgttt taaatgactt tattatgatg   2340
cactgtgttt ttatgccaaa tacccagctt tgcccggcac tggtggccca ctaccacgca   2400
cagccttcac aaggtacaga acaggagaaa atggattatg ccctcaacaa taagaggcga   2460
gtcatccgcc tggttctaca gtgggctgcc atgtatggag acctcctgca agaggatgac   2520
gtgtctatgg ccttcctgga ggagttttat gtatctgtat cagatgatgc ccggatgatt   2580
gctgccctca aggagcaact gccagagttg gagaagattg tcaagcaaat ctcagaagat   2640
gcaaaggcac cacaaaagaa gcacaaggtt cttttgcaac agttcaatac gggcgatgag   2700
agagcccaga agcgccagcc tatccgcggc tctgatgaag ttctgtttaa ggtctattgc   2760
atggacccca cctacacaac cattcgggtg ccagtggcca cttcggtgaa ggaagtcatc   2820
agtgcagttg ccgacaagct gggctccggg gagggcctga tcatagtcaa gatgagttcc   2880
ggaggagaaa aggtggtgct caaacctaat gatgtttcag tatttatgac gctcaccatt   2940
aatggacgcc tgtttgcttg cccgcgagag caattcgatt cactgactcc cttaccagaa   3000
```

```
caggaaggcc caactgttgg aacagtggga acttttgaac tgatgagctc caaagattta   3060

gcataccaga tgacaattta tgattgggaa ctcttcaact gcgtgcatga gctggagcta   3120

atctatcaca catttggaag gcataatttt aaaaagacca cagcaaactt ggatttgttc   3180

ctgaggagat ttaatgaaat tcagttttgg gtcgtcactg agatctgcct ttgttctcag   3240

ctcagcaagc gtgttcagct attaaaaaaa tttattaaga tagcagccca ctgtaaggag   3300

tataaaaatc tgaattcctt ttttgccatc gtcatgggac taagtaacgt tgctgtgagc   3360

cgcttggcac taacgtggga gaaactgcca agcaagttca agaagttcta tgcggagttt   3420

gaaagtttaa tggacccttc aaggaaccac agggcctaca ggctgacagt agctaagctg   3480

gaacctcctc tcatcccctt catgcctttg ctcattaaag atatgacatt tactcatgag   3540

gggaacaaga cgttcattga caatctagta aactttgaaa aatgcgcat gattgcaaat    3600

acggccagaa cagtgagata ctacaggagc caacccttca atcctgatgc agctcaagct   3660

aataagaacc atcaggatgt ccggagttat gtacggcaat taaatgtgat tgacaaccag   3720

agaactttat cacagatgtc acacagatta gagcctcgtc gacc                    3764
```

<210> SEQ ID NO 54
<211> LENGTH: 3765
<212> TYPE: DNA
<213> ORGANISM: Artificial Sequence
<220> FEATURE:
<223> OTHER INFORMATION: Synthetic

<400> SEQUENCE: 54

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc ccctttgcct    900

actgaggagg agaagaagga gtgtgatgag gagctccagg acaccatgct gctgctgtca    960

cagatgggcc ccgacgccca catgaggatg atccttcgca aaccacctgg ccagaggact   1020

gtggatgacc tagagattat ctatgaggag cttcttcata ttaaagcctt atcccatctt   1080

tctaccacag tgaaacgaga gttagcaggt gttctcattt ttgagtctca cgccaaagga   1140

gggactgtgt tgtttaacca gggggaagaa ggtacctcct ggtacattat tctaaaagga   1200

tcagtgaatg tagtcattta cggcaagggt gtggtctgca ccctgcatga aggagatgac   1260
```

```
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgttcaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgtg tggaggcgaa tacagtcaga cttaaagaac atgaccaaga tgtcttggtg   2160
ctggagaagg tcccagcagg gaacagagct tctaatcaag gaaactcaca gcctcagcaa   2220
aagtatactg tgatgtcagg aacacctgaa aaaattttag agcattttct agaaacaata   2280
cgccttgagg caactttaaa tgaagcaaca gattctgttt taaatgactt tattatgatg   2340
cactgtgttt ttatgccaaa tacccagctt tgcccggcac tggtggccca ctaccacgca   2400
cagccttcac aaggtacaga acaggagaaa atggattatg ccctcaacaa taagaggcga   2460
gtcatccgcc tggttctaca gtgggctgcc atgtatggag acctcctgca agaggatgac   2520
gtgtctatgg ccttcctgga ggagttttat gtatctgtat cagatgatgc ccggatgatt   2580
gctgccctca aggagcaact gccagagttg gagaagattg tcaagcaaat ctcagaagat   2640
gcaaaggcac cacaaaagaa gcacaaggtt cttttgcaac agttcaatac gggcgatgag   2700
agagcccaga agcgccagcc tatccgcggc tctgatgaag ttctgtttaa ggtctattgc   2760
atggacccca cctacacaac cattcgggtg ccagtggcca cttcggtgaa ggaagtcatc   2820
agtgcagttg ccgacaagct gggctccggg gagggcctga tcatagtcaa gatgagttcc   2880
ggaggagaaa aggtggtgct caaacctaat gatgtttcag tatttatgac gctcaccatt   2940
aatggacgcc tgtttgcttg cccgcgagag caattcgatt cactgactcc cttaccagaa   3000
caggaaggcc caactgttgg aacagtggga acttttgaac tgatgagctc caaagattta   3060
gcataccaga tgacaattta tgattgggaa ctcttcaact gcgtgcatga gctggagcta   3120
atctatcaca catttggaag gcataatttt aaaaagacca cagcaaactt ggatttgttc   3180
ctgaggagat ttaatgaaat tcagttttgg gtcgtcactg agatctgcct ttgttctcag   3240
ctcagcaagc gtgttcagct attaaaaaaa tttattaaga tagcagccca ctgtaaggag   3300
tataaaaatc tgaattcctt ttttgccatc gtcatgggac taagtaacgt tgctgtgagc   3360
cgcttggcac taacgtggga gaaactgcca agcaagttca agaagttcta tgcggagttt   3420
gaaagtttaa tggacccttc aaggaaccac agggcctaca ggctgacagt agctaagctg   3480
gaacctcctc tcatcccctt catgcctttg ctcattaaag atatgacatt tactcatgag   3540
gggaacaaga cgttcattga caatctagta aactttgaaa aaatgcgcat gattgcaaat   3600
acggccagaa cagtgagata ctacaggagc caacccttca atcctgatgc agctcaagct   3660
```

aataagaacc atcaggatgt ccggagttat gtacggcaat taaatgtgat tgacaaccag 3720
agaactttat cacagatgtc acacagatta gagcctcgtc gacca 3765

<210> SEQ ID NO 55
<211> LENGTH: 3783
<212> TYPE: DNA
<213> ORGANISM: Artificial Sequence
<220> FEATURE:
<223> OTHER INFORMATION: Synthetic

<400> SEQUENCE: 55
atggtcgctg cgcacgctgc ccattcttcc tcctctgccg agtggatcgc ctgcctggat 60
aaaagaccac tggagcgatc cagcgaagat gtggatataa tcttcactcg actgaaagaa 120
gttaaagctt ttgagaaatt tcacccaaat ctccttcatc agatttgctt atgtggttat 180
tatgagaatc tggaaaaggg aataacatta tttcgccagg gtgatattgg aacaaactgg 240
tatgctgtcc tggcagggtc tttggatgtt aaagtatctg agaccagcag tcaccaggat 300
gctgtgacca tctgtaccct gggaattggg acggcctttg gagagtccat tctggacaac 360
acaccccgcc atgcaaccat cgttaccagg gagagcagtg aactgctccg catcgagcag 420
aaggacttca aggcactatg ggagaaatat cgacagtata tggcaggact tctggctcct 480
ccttatggtg ttatggaaac gggctctaac aatgacagga ttcctgacaa ggagaacaca 540
cctctcattg aacctcacgt tcctcttcgt cctgctaaca ccattaccaa ggtcccttca 600
gagaagatcc tcagagctgg aaaaatttta cgaaatgcca ttctctctcg agcacctcac 660
atgataagag atagaaaata ccacctaaag acatacagac aatgctgtgt gggaactgaa 720
ctggtggact ggatgatgca gcagacacca tgtgttcact cccggactca agctgttggc 780
atgtggcaag tcctgttaga agatggtgtt ctcaaccacg tggaccagga gcaccatttc 840
caagacaaat atttattcta tcgatttctg gatgatgagc acgaggatgc ccctttgcct 900
actgaggagg agaagaagga gtgtgatgag gagctccagg acaccatgct gctgctgtca 960
cagatgggcc ccgacgccca catgaggatg atccttcgca aaccacctgg ccagaggact 1020
gtggatgacc tagagattat ctatgaggag cttcttcata ttaaagcctt atcccatctt 1080
tctaccacag tgaaacgaga gttagcaggt gttctcattt ttgagtctca cgccaaagga 1140
gggactgtgt tgtttaacca gggggaagaa ggtacctcct ggtacattat tctaaaagga 1200
tcagtgaatg tagtcattta cggcaagggt gtggtctgca ccctgcatga aggagatgac 1260
ttcggcaagt tagcactagt gaatgatgcc ccacgagctg cctctatcgt cttacgagaa 1320
gataactgcc atttcttaag agtagacaag gaggatttca accggatcct aagggacgtg 1380
ctcgagaacg tctatatcaa ggccgacaag cagaagaacg gcatcaaggc gaacttcaag 1440
atccgccaca acatcgagga cggcggcgtg cagctcgcct accactacca gcagaacacc 1500
cccatcggcg acggccccgt gctgctgccc gacaaccact acctgagcgt gcagtccata 1560
ctttcgaaag accccaacga gaagcgcgat cacatggtcc tgctggagtt cgtaaccgcc 1620
cccgggatca ctctcggcat ggacgagctg tacaagggcg gtaccggagg gagcatggtg 1680
agcaagggcg aggagctgtt caccggggtg gtgcccatcc aggtcgagct ggacggcgac 1740
gtaaacggcc acaagttcag cgtgtccggc gagggtgagg gcgatgccac ctacggcaag 1800
ctgaccctga agttcatctg caccaccggc aagctgcccg tgccctggcc caccctcgtg 1860
accaccctga cctacggcgt gcagtgcttc agccgctacc ccgaccacat gaagcagcac 1920

```
gacttcttca agtccgccat gcccgaaggc tacatccagg agcgcaccat cttcttcaag   1980

gacgacggca actacaagac ccgcgccgag gtgaagttcg agggcgacac cctggtgaac   2040

cgcatcgagc tgaagggcat cgacttcaag gaggacggca acatcctggg gcacaagctg   2100

gagtacaaca cgcgtatcct aagggacgtg gaggcgaata cagtcagact taaagaacat   2160

gaccaagatg tcttggtgct ggagaaggtc ccagcaggga acagagcttc taatcaagga   2220

aactcacagc ctcagcaaaa gtatactgtg atgtcaggaa cacctgaaaa aattttagag   2280

cattttctag aaacaatacg ccttgaggca actttaaatg aagcaacaga ttctgtttta   2340

aatgacttta ttatgatgca ctgtgttttt atgccaaata cccagctttg cccggcactg   2400

gtggcccact accacgcaca gccttcacaa ggtacagaac aggagaaaat ggattatgcc   2460

ctcaacaata agaggcgagt catccgcctg gttctacagt gggctgccat gtatggagac   2520

ctcctgcaag aggatgacgt gtctatggcc ttcctggagg agttttatgt atctgtatca   2580

gatgatgccc ggatgattgc tgccctcaag gagcaactgc cagagttgga gaagattgtc   2640

aagcaaatct cagaagatgc aaaggcacca caaaagaagc acaaggttct tttgcaacag   2700

ttcaatacgg gcgatgagag agcccagaag cgccagccta tccgcggctc tgatgaagtt   2760

ctgtttaagg tctattgcat ggaccccacc tacacaacca ttcgggtgcc agtggccact   2820

tcggtgaagg aagtcatcag tgcagttgcc gacaagctgg gctccgggga gggcctgatc   2880

atagtcaaga tgagttccgg aggagaaaag gtggtgctca aacctaatga tgtttcagta   2940

tttatgacgc tcaccattaa tggacgcctg tttgcttgcc cgcgagagca attcgattca   3000

ctgactccct taccagaaca ggaaggccca actgttggaa cagtgggaac ttttgaactg   3060

atgagctcca aagatttagc ataccagatg acaatttatg attgggaact cttcaactgc   3120

gtgcatgagc tggagctaat ctatcacaca tttggaaggc ataattttaa aaagaccaca   3180

gcaaacttgg atttgttcct gaggagattt aatgaaattc agttttgggt cgtcactgag   3240

atctgccttt gttctcagct cagcaagcgt gttcagctat taaaaaaatt tattaagata   3300

gcagcccact gtaaggagta taaaaatctg aattcctttt ttgccatcgt catgggacta   3360

agtaacgttg ctgtgagccg cttggcacta acgtgggaga aactgccaag caagttcaag   3420

aagttctatg cggagtttga aagtttaatg gacccttcaa ggaaccacag ggcctacagg   3480

ctgacagtag ctaagctgga acctcctctc atccccttca tgcctttgct cattaaagat   3540

atgacattta ctcatgaggg gaacaagacg ttcattgaca atctagtaaa ctttgaaaaa   3600

atgcgcatga ttgcaaatac ggccagaaca gtgagatact acaggagcca acccttcaat   3660

cctgatgcag ctcaagctaa taagaaccat caggatgtcc ggagttatgt acggcaatta   3720

aatgtgattg acaaccagag aactttatca cagatgtcac acagattaga gcctcgtcga   3780

cca                                                                 3783
```

```
<210> SEQ ID NO 56
<211> LENGTH: 2103
<212> TYPE: DNA
<213> ORGANISM: Artificial Sequence
<220> FEATURE:
<223> OTHER INFORMATION: Synthetic

<400> SEQUENCE: 56

atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180
```

```
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg gagagtccat tctggacaac    360
acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggcgtgcg   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aac                                                                 2103
```

<210> SEQ ID NO 57
<211> LENGTH: 3768
<212> TYPE: DNA
<213> ORGANISM: Artificial Sequence
<220> FEATURE:
<223> OTHER INFORMATION: Synthetic

<400> SEQUENCE: 57

```
atggtcgctg cgcacgctgc ccattcttcc tcctctgccg agtggatcgc ctgcctggat     60
```

```
aaaagaccac tggagcgatc cagcgaagat gtggatataa tcttcactcg actgaaagaa    120
gttaaagctt ttgagaaatt tcacccaaat ctccttcatc agatttgctt atgtggttat    180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg gagagtccat tctggacaac    360
acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc cccttttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
gaggcgaatc tcgagaacgt ctatatcaag gccgacaagc agaagaacgg catcaaggcg   1440
aacttcaaga tccgccacaa catcgaggac ggcggcgtgc agctcgccta ccactaccag   1500
cagaacaccc ccatcggcga cggccccgtg ctgctgcccg acaaccacta cctgagcgtg   1560
cagtccatac tttcgaaaga ccccaacgag aagcgcgatc acatggtcct gctggagttc   1620
gtgaccgccg ccgggatcac tctcggcatg gacgagctgt acaagggcgg taccggaggg   1680
agcatggtga gcaagggcga ggagctgttc accggggtgg tgcccatcca ggtcgagctg   1740
gacggcgacg taaacggcca caagttcagc gtgtccggcg agggtgaggg cgatgccacc   1800
tacggcaagc tgaccctgaa gttcatctgc accaccggca agctgcccgt gccctggccc   1860
accctcgtga ccaccctgac ctacggcgtg cagtgcttca gccgctaccc cgaccacatg   1920
aagcagcacg acttcttcaa gtccgccatg cccgaaggct acatccagga gcgcaccatc   1980
ttcttcaagg acgacggcaa ctacaagacc cgcgccgagg tgaagttcga gggcgacacc   2040
ctggtgaacc gcatcgagct gaagggcatc gacttcaagg aggacggcaa catcctgggg   2100
cacaagctgg agtacaacac gcgtacagtc agacttaaag aacatgacca agatgtcttg   2160
gtgctggaga aggtcccagc agggaacaga gcttctaatc aaggaaactc acagcctcag   2220
caaaagtata ctgtgatgtc aggaacacct gaaaaaattt tagagcattt tctagaaaca   2280
atacgccttg aggcaacttt aaatgaagca acagattctg ttttaaatga ctttattatg   2340
atgcactgtg tttttatgcc aaatacccag ctttgcccgg cactggtggc ccactaccac   2400
gcacagcctt cacaaggtac agaacaggag aaaatggatt atgccctcaa caataagagg   2460
```

cgagtcatcc gcctggttct acagtgggct gccatgtatg gagacctcct gcaagaggat 2520
gacgtgtcta tggccttcct ggaggagttt tatgtatctg tatcagatga tgcccggatg 2580
attgctgccc tcaaggagca actgccagag ttggagaaga ttgtcaagca aatctcagaa 2640
gatgcaaagg caccacaaaa gaagcacaag gttcttttgc aacagttcaa tacgggcgat 2700
gagagagccc agaagcgcca gcctatccgc ggctctgatg aagttctgtt taaggtctat 2760
tgcatggacc ccacctacac aaccattcgg gtgccagtgg ccacttcggt gaaggaagtc 2820
atcagtgcag ttgccgacaa gctgggctcc ggggagggcc tgatcatagt caagatgagt 2880
tccggaggag aaaaggtggt gctcaaacct aatgatgttt cagtatttat gacgctcacc 2940
attaatggac gcctgtttgc ttgcccgcga gagcaattcg attcactgac tcccttacca 3000
gaacaggaag gcccaactgt tggaacagtg ggaacttttg aactgatgag ctccaaagat 3060
ttagcatacc agatgacaat ttatgattgg gaactcttca actgcgtgca tgagctggag 3120
ctaatctatc acacatttgg aaggcataat tttaaaaaga ccacagcaaa cttggatttg 3180
ttcctgagga gatttaatga aattcagttt tgggtcgtca ctgagatctg cctttgttct 3240
cagctcagca agcgtgttca gctattaaaa aaatttatta agatagcagc ccactgtaag 3300
gagtataaaa atctgaattc ctttttttgcc atcgtcatgg gactaagtaa cgttgctgtg 3360
agccgcttgg cactaacgtg ggagaaactg ccaagcaagt tcaagaagtt ctatgcggag 3420
tttgaaagtt taatggaccc ttcaaggaac cacagggcct acaggctgac agtagctaag 3480
ctggaacctc ctctcatccc cttcatgcct ttgctcatta aagatatgac atttactcat 3540
gaggggaaca agacgttcat tgacaatcta gtaaactttg aaaaaatgcg catgattgca 3600
aatacggcca gaacagtgag atactacagg agccaaccct tcaatcctga tgcagctcaa 3660
gctaataaga accatcagga tgtccggagt tatgtacggc aattaaatgt gattgacaac 3720
cagagaactt tatcacagat gtcacacaga ttagagcctc gtcgacca 3768

<210> SEQ ID NO 58
<211> LENGTH: 3765
<212> TYPE: DNA
<213> ORGANISM: Artificial Sequence
<220> FEATURE:
<223> OTHER INFORMATION: Synthetic

<400> SEQUENCE: 58
atggtcgctg cgcacgctgc ccattcttcc tcctctgccg agtggatcgc ctgcctggat 60
aaaagaccac tggagcgatc cagcgaagat gtggatataa tcttcactcg actgaaagaa 120
gttaaagctt ttgagaaatt tcacccaaat ctccttcatc agatttgctt atgtggttat 180
tatgagaatc tggaaaaggg aataacatta tttcgccagg gtgatattgg aacaaactgg 240
tatgctgtcc tggcagggtc tttggatgtt aaagtatctg agaccagcag tcaccaggat 300
gctgtgacca tctgtaccct gggaattggg acggcctttg gagagtccat tctggacaac 360
acaccccgcc atgcaaccat cgttaccagg gagagcagtg aactgctccg catcgagcag 420
aaggacttca aggcactatg ggagaaatat cgacagtata tggcaggact tctggctcct 480
ccttatggtg ttatggaaac gggctctaac aatgacagga ttcctgacaa ggagaacaca 540
cctctcattg aacctcacgt tcctcttcgt cctgctaaca ccattaccaa ggtcccttca 600
gagaagatcc tcagagctgg aaaaatttta cgaaatgcca ttctctctcg agcacctcac 660
atgataagag atagaaaata ccacctaaag acatacagac aatgctgtgt gggaactgaa 720

```
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgtg tggaggcgaa tacagtcaga cttaaagaac atgaccaaga tgtcttggtg   2160
ctggagaagg tcccagcagg gaacagagct tctaatcaag gaaactcaca gcctcagcaa   2220
aagtatactg tgatgtcagg aacacctgaa aaaattttag agcattttct agaaacaata   2280
cgccttgagg caactttaaa tgaagcaaca gattctgttt taaatgactt tattatgatg   2340
cactgtgttt ttatgccaaa tacccagctt tgcccggcac tggtggccca ctaccacgca   2400
cagccttcac aaggtacaga acaggagaaa atggattatg ccctcaacaa taagaggcga   2460
gtcatccgcc tggttctaca gtgggctgcc atgtatggag acctcctgca agaggatgac   2520
gtgtctatgg ccttcctgga ggagttttat gtatctgtat cagatgatgc ccggatgatt   2580
gctgccctca aggagcaact gccagagttg gagaagattg tcaagcaaat ctcagaagat   2640
gcaaaggcac cacaaaagaa gcacaaggtt cttttgcaac agttcaatac gggcgatgag   2700
agagcccaga agcgccagcc tatccgcggc tctgatgaag ttctgtttaa ggtctattgc   2760
atggacccca cctacacaac cattcgggtg ccagtggcca cttcggtgaa ggaagtcatc   2820
agtgcagttg ccgacaagct gggctccggg gagggcctga tcatagtcaa gatgagttcc   2880
ggaggagaaa aggtggtgct caaacctaat gatgtttcag tatttatgac gctcaccatt   2940
aatggacgcc tgtttgcttg cccgcgagag caattcgatt cactgactcc cttaccagaa   3000
caggaaggcc caactgttgg aacagtggga acttttgaac tgatgagctc caaagattta   3060
gcataccaga tgacaattta tgattgggaa ctcttcaact gcgtgcatga gctggagcta   3120
```

```
atctatcaca catttggaag gcataatttt aaaaagacca cagcaaactt ggatttgttc   3180

ctgaggagat ttaatgaaat tcagttttgg gtcgtcactg agatctgcct ttgttctcag   3240

ctcagcaagc gtgttcagct attaaaaaaa tttattaaga tagcagccca ctgtaaggag   3300

tataaaaatc tgaattcctt ttttgccatc gtcatgggac taagtaacgt tgctgtgagc   3360

cgcttggcac taacgtggga gaaactgcca agcaagttca agaagttcta tgcggagttt   3420

gaaagtttaa tggacccttc aaggaaccac agggcctaca ggctgacagt agctaagctg   3480

gaacctcctc tcatcccctt catgcctttg ctcattaaag atatgacatt tactcatgag   3540

gggaacaaga cgttcattga caatctagta aactttgaaa aaatgcgcat gattgcaaat   3600

acggccagaa cagtgagata ctacaggagc caacccttca atcctgatgc agctcaagct   3660

aataagaacc atcaggatgt ccggagttat gtacggcaat taaatgtgat tgacaaccag   3720

agaactttat cacagatgtc acacagatta gagcctcgtc gacca                   3765
```

<210> SEQ ID NO 59
<211> LENGTH: 3776
<212> TYPE: DNA
<213> ORGANISM: Artificial Sequence
<220> FEATURE:
<223> OTHER INFORMATION: Synthetic

<400> SEQUENCE: 59

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc ccctttgcct    900

actgaggagg agaagaagga gtgtgatgag gagctccagg acaccatgct gctgctgtca    960

cagatgggcc ccgacgccca catgaggatg atccttcgca aaccacctgg ccagaggact   1020

gtggatgacc tagagattat ctatgaggag cttcttcata ttaaagcctt atcccatctt   1080

tctaccacag tgaaacgaga gttagcaggt gttctcattt ttgagtctca cgccaaagga   1140

gggactgtgt tgtttaacca gggggaagaa ggtacctcct ggtacattat tctaaaagga   1200

tcagtgaatg tagtcattta cggcaagggt gtggtctgca ccctgcatga aggagatgac   1260

ttcggcaagt tagcactagt gaatgatgcc ccacgagctg cctctatcgt cttacgagaa   1320

gataactgcc atttcttaag agtagacaag gaggatttca accggatcct aaggctcgag   1380
```

```
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgta tcctaaggga cgtggaggcg aatacagtca gacttaaaga acatgaccaa   2160
gatgtcttgg tgctggagaa ggtcccagca gggaacagag cttctaatca aggaaactca   2220
cagcctcagc aaaagtatac tgtgatgtca ggaacacctg aaaaaatttt agagcatttt   2280
ctagaaacaa tacgccttga ggcaacttta aatgaagcaa cagattctgt tttaaatgac   2340
tttattatga tgcactgtgt ttttatgcca aatacccagc tttgcccggc actggtggcc   2400
cactaccacg cacagccttc acaaggtaca gaacaggaga aaatggatta tgccctcaac   2460
aataagaggc gagtcatccg cctggttcta cagtgggctg ccatgtatgg agacctcctg   2520
caagaggatg acgtgtctat ggccttcctg gaggagtttt atgtatctgt atcagatgat   2580
gcccggatga ttgctgccct caaggagcaa ctgccagagt tggagaagat tgtcaagcaa   2640
atctcagaag atgcaaaggc accacaaaag aagcacaagg ttcttttgca acagttcaat   2700
acgggcgatg agagagccca gaagcgccag cctatccgcg gctctgatga agttctgttt   2760
aaggtctatt gcatggaccc cacctacaca accattcggg tgccagtggc cacttcggtg   2820
aaggaagtca tcagtgcagt tgccgacaag ctgggctccg gggagggcct gatcatagtc   2880
aagatgagtt ccggaggaga aaaggtggtg ctcaaaccta atgatgtttc agtatttatg   2940
acgctcacca ttaatggacg cctgtttgct tgcccgcgag agcaattcga ttcactgact   3000
cccttaccag aacaggaagg cccaactgtt ggaacagtgg gaacttttga actgatgagc   3060
tccaaagatt tagcatacca gatgacaatt tatgattggg aactcttcaa ctgcgtgcat   3120
gagctggagc taatctatca cacatttgga aggcataatt ttaaaaagac cacagcaaac   3180
ttggatttgt tcctgaggag atttaatgaa attcagtttt gggtcgtcac tgagatctgc   3240
ctttgttctc agctcagcaa gcgtgttcag ctattaaaaa aatttattaa gatagcagcc   3300
cactgtaagg agtataaaaa tctgaattcc ttttttgcca tcgtcatggg actaagtaac   3360
gttgctgtga gccgcttggc actaacgtgg gagaaactgc caagcaagtt caagaagttc   3420
tatgcggagt ttgaaagttt aatggaccct tcaaggaacc acagggccta caggctgaca   3480
gtagctaagc tggaacctcc tctcatcccc ttcatgcctt tgctcattaa agatatgaca   3540
tttactcatg aggggaacaa gacgttcatt gacaatctag taaactttga aaaaatgcgc   3600
atgattgcaa atacggccag aacagtgaga tactacagga gccaaccctt caatcctgat   3660
gcagctcaag ctaataagaa ccatcaggat gtccggagtt atgtacggca attaaatgtg   3720
attgacaacc agagaacttt atcacagatg tcacacagat tagagcctcg tcgacc       3776
```

<210> SEQ ID NO 60
<211> LENGTH: 3756
<212> TYPE: DNA
<213> ORGANISM: Artificial Sequence
<220> FEATURE:
<223> OTHER INFORMATION: Synthetic

<400> SEQUENCE: 60
atggtcgctg cgcacgctgc ccattcttcc tcctctgccg agtggatcgc ctgcctggat 60
aaaagaccac tggagcgatc cagcgaagat gtggatataa tcttcactcg actgaaagaa 120
gttaaagctt ttgagaaatt tcacccaaat ctccttcatc agatttgctt atgtggttat 180
tatgagaatc tggaaaaggg aataacatta tttcgccagg gtgatattgg aacaaactgg 240
tatgctgtcc tggcagggtc tttggatgtt aaagtatctg agaccagcag tcaccaggat 300
gctgtgacca tctgtaccct gggaattggg acggcctttg gagagtccat tctggacaac 360
acaccccgcc atgcaaccat cgttaccagg gagagcagtg aactgctccg catcgagcag 420
aaggacttca aggcactatg ggagaaatat cgacagtata tggcaggact tctggctcct 480
ccttatggtg ttatggaaac gggctctaac aatgacagga ttcctgacaa ggagaacaca 540
cctctcattg aacctcacgt tcctcttcgt cctgctaaca ccattaccaa ggtcccttca 600
gagaagatcc tcagagctgg aaaaatttta cgaaatgcca ttctctctcg agcacctcac 660
atgataagag atagaaaata ccacctaaag acatacagac aatgctgtgt gggaactgaa 720
ctggtggact ggatgatgca gcagacacca tgtgttcact cccggactca agctgttggc 780
atgtggcaag tcctgttaga agatggtgtt ctcaaccacg tggaccagga gcaccatttc 840
caagacaaat atttattcta tcgatttctg gatgatgagc acgaggatgc ccctttgcct 900
actgaggagg agaagaagga gtgtgatgag gagctccagg acaccatgct gctgctgtca 960
cagatgggcc ccgacgccca catgaggatg atccttcgca aaccacctgg ccagaggact 1020
gtggatgacc tagagattat ctatgaggag cttcttcata ttaaagcctt atcccatctt 1080
tctaccacag tgaaacgaga gttagcaggt gttctcattt ttgagtctca cgccaaagga 1140
gggactgtgt tgtttaacca gggggaagaa ggtacctcct ggtacattat tctaaaagga 1200
tcagtgaatg tagtcattta cggcaagggt gtggtctgca ccctgcatga aggagatgac 1260
ttcggcaagt tagcactagt gaatgatgcc ccacgagctg cctctatcgt cttacgagaa 1320
gataactgcc atttcttaag agtagacaag gaggatttca accggatcct aaggctcgag 1380
aacgtctata tcaaggccga caagcagaag aacggcatca aggcgaactt caagatccgc 1440
cacaacatcg aggacggcgg cgtgcagctc gcctaccact accagcagaa cacccccatc 1500
ggcgacggcc ccgtgctgct gcccgacaac cactacctga gcgtgcagtc catactttcg 1560
aaagacccca acgagaagcg cgatcacatg gtcctgctgg agttcgtgac cgccgccggg 1620
atcactctcg gcatggacga gctgtacaag ggcggtaccg gagggagcat ggtgagcaag 1680
ggcgaggagc tgttcaccgg ggtggtgccc atccaggtcg agctggacgg cgacgtaaac 1740
ggccacaagt tcagcgtgtc cggcgagggt gagggcgatg ccacctacgg caagctgacc 1800
ctgaagttca tctgcaccac cggcaagctg cccgtgccct ggcccaccct cgtgaccacc 1860
ctgacctacg gcgtgcagtg cttcagccgc taccccgacc acatgaagca gcacgacttc 1920
ttcaagtccg ccatgcccga aggctacatc caggagcgca ccatcttctt caaggacgac 1980
ggcaactaca agacccgcgc cgaggtgaag ttcgagggcg acaccctggt gaaccgcatc 2040

```
gagctgaagg gcatcgactt caaggaggac ggcaacatcc tggggcacaa gctggagtac   2100

aacacgcgta atacagtcag acttaaagaa catgaccaag atgtcttggt gctggagaag   2160

gtcccagcag ggaacagagc ttctaatcaa ggaaactcac agcctcagca aaagtatact   2220

gtgatgtcag gaacacctga aaaaatttta gagcattttc tagaaacaat acgccttgag   2280

gcaactttaa atgaagcaac agattctgtt ttaaatgact ttattatgat gcactgtgtt   2340

tttatgccaa atacccagct ttgcccggca ctggtggccc actaccacgc acagccttca   2400

caaggtacag aacaggagaa aatggattat gccctcaaca ataagaggcg agtcatccgc   2460

ctggttctac agtgggctgc catgtatgga gacctcctgc aagaggatga cgtgtctatg   2520

gccttcctgg aggagtttta tgtatctgta tcagatgatg cccggatgat tgctgccctc   2580

aaggagcaac tgccagagtt ggagaagatt gtcaagcaaa tctcagaaga tgcaaaggca   2640

ccacaaaaga agcacaaggt tcttttgcaa cagttcaata cgggcgatga gagagcccag   2700

aagcgccagc ctatccgcgg ctctgatgaa gttctgttta aggtctattg catggacccc   2760

acctacacaa ccattcgggt gccagtggcc acttcggtga aggaagtcat cagtgcagtt   2820

gccgacaagc tgggctccgg ggagggcctg atcatagtca agatgagttc cggaggagaa   2880

aaggtggtgc tcaaacctaa tgatgtttca gtatttatga cgctcaccat taatggacgc   2940

ctgtttgctt gcccgcgaga gcaattcgat tcactgactc ccttaccaga acaggaaggc   3000

ccaactgttg gaacagtggg aacttttgaa ctgatgagct ccaaagattt agcataccag   3060

atgacaattt atgattggga actcttcaac tgcgtgcatg agctggagct aatctatcac   3120

acatttggaa ggcataattt taaaaagacc acagcaaact tggatttgtt cctgaggaga   3180

tttaatgaaa ttcagttttg ggtcgtcact gagatctgcc tttgttctca gctcagcaag   3240

cgtgttcagc tattaaaaaa atttattaag atagcagccc actgtaagga gtataaaaat   3300

ctgaattcct tttttgccat cgtcatggga ctaagtaacg ttgctgtgag ccgcttggca   3360

ctaacgtggg agaaactgcc aagcaagttc aagaagttct atgcggagtt tgaaagttta   3420

atggaccctt caaggaacca cagggcctac aggctgacag tagctaagct ggaacctcct   3480

ctcatcccct tcatgccttt gctcattaaa gatatgacat ttactcatga ggggaacaag   3540

acgttcattg acaatctagt aaactttgaa aaaatgcgca tgattgcaaa tacggccaga   3600

acagtgagat actacaggag ccaacccttc aatcctgatg cagctcaagc taataagaac   3660

catcaggatg tccggagtta tgtacggcaa ttaaatgtga ttgacaacca gagaacttta   3720

tcacagatgt cacacagatt agagcctcgt cgacca                             3756
```

<210> SEQ ID NO 61
<211> LENGTH: 3783
<212> TYPE: DNA
<213> ORGANISM: Artificial Sequence
<220> FEATURE:
<223> OTHER INFORMATION: Synthetic

<400> SEQUENCE: 61

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360
```

```
acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc cccttttgcct   900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgta accggatcct aagggacgtg gaggcgaata cagtcagact taaagaacat   2160
gaccaagatg tcttggtgct ggagaaggtc ccagcaggga acagagcttc taatcaagga   2220
aactcacagc ctcagcaaaa gtatactgtg atgtcaggaa cacctgaaaa aattttagag   2280
cattttctag aaacaatacg ccttgaggca actttaaatg aagcaacaga ttctgtttta   2340
aatgacttta ttatgatgca ctgtgttttt atgccaaata cccagctttg cccggcactg   2400
gtggcccact accacgcaca gccttcacaa ggtacagaac aggagaaaat ggattatgcc   2460
ctcaacaata agaggcgagt catccgcctg gttctacagt gggctgccat gtatggagac   2520
ctcctgcaag aggatgacgt gtctatggcc ttcctggagg agttttatgt atctgtatca   2580
gatgatgccc ggatgattgc tgccctcaag gagcaactgc cagagttgga gaagattgtc   2640
aagcaaatct cagaagatgc aaaggcacca caaaagaagc acaaggttct tttgcaacag   2700
```

```
ttcaatacgg gcgatgagag agcccagaag cgccagccta tccgcggctc tgatgaagtt   2760

ctgtttaagg tctattgcat ggaccccacc tacacaacca ttcgggtgcc agtggccact   2820

tcggtgaagg aagtcatcag tgcagttgcc gacaagctgg gctccgggga gggcctgatc   2880

atagtcaaga tgagttccgg aggagaaaag gtggtgctca aacctaatga tgtttcagta   2940

tttatgacgc tcaccattaa tggacgcctg tttgcttgcc cgcgagagca attcgattca   3000

ctgactccct taccagaaca ggaaggccca actgttggaa cagtgggaac ttttgaactg   3060

atgagctcca aagatttagc ataccagatg acaatttatg attgggaact cttcaactgc   3120

gtgcatgagc tggagctaat ctatcacaca tttggaaggc ataattttaa aaagaccaca   3180

gcaaacttgg atttgttcct gaggagattt aatgaaattc agttttgggt cgtcactgag   3240

atctgccttt gttctcagct cagcaagcgt gttcagctat taaaaaaatt tattaagata   3300

gcagcccact gtaaggagta taaaaatctg aattcctttt ttgccatcgt catgggacta   3360

agtaacgttg ctgtgagccg cttggcacta acgtgggaga aactgccaag caagttcaag   3420

aagttctatg cggagtttga aagtttaatg gacccttcaa ggaaccacag ggcctacagg   3480

ctgacagtag ctaagctgga acctcctctc atccccttca tgcctttgct cattaaagat   3540

atgacattta ctcatgaggg gaacaagacg ttcattgaca atctagtaaa ctttgaaaaa   3600

atgcgcatga ttgcaaatac ggccagaaca gtgagatact acaggagcca acccttcaat   3660

cctgatgcag ctcaagctaa taagaaccat caggatgtcc ggagttatgt acggcaatta   3720

aatgtgattg acaaccagag aactttatca cagatgtcac acagattaga gcctcgtcga   3780

cca                                                                 3783
```

<210> SEQ ID NO 62
<211> LENGTH: 3810
<212> TYPE: DNA
<213> ORGANISM: Artificial Sequence
<220> FEATURE:
<223> OTHER INFORMATION: Synthetic

<400> SEQUENCE: 62

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc ccctttgcct    900

actgaggagg agaagaagga gtgtgatgag gagctccagg acaccatgct gctgctgtca    960
```

```
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
gaggcgaatc tcgagaacgt ctatatcaag gccgacaagc agaagaacgg catcaaggcg   1440
aacttcaaga tccgccacaa catcgaggac ggcggcgtgc agctcgccta ccactaccag   1500
cagaacaccc ccatcggcga cggccccgtg ctgctgcccg acaaccacta cctgagcgtg   1560
cagtccatac tttcgaaaga ccccaacgag aagcgcgatc acatggtcct gctggagttc   1620
gtgaccgccg ccgggatcac tctcggcatg gacgagctgt acaagggcgg taccggaggg   1680
agcatggtga gcaagggcga ggagctgttc accggggtgg tgcccatcca ggtcgagctg   1740
gacggcgacg taaacggcca caagttcagc gtgtccggcg agggtgaggg cgatgccacc   1800
tacggcaagc tgaccctgaa gttcatctgc accaccggca agctgcccgt gccctggccc   1860
accctcgtga ccaccctgac ctacggcgtg cagtgcttca gccgctaccc cgaccacatg   1920
aagcagcacg acttcttcaa gtccgccatg cccgaaggct acatccagga gcgcaccatc   1980
ttcttcaagg acgacggcaa ctacaagacc cgcgccgagg tgaagttcga gggcgacacc   2040
ctggtgaacc gcatcgagct gaagggcatc gacttcaagg aggacggcaa catcctgggg   2100
cacaagctgg agtacaacac gcgtaaggag gatttcaacc ggatcctaag ggacgtggag   2160
gcgaatacag tcagacttaa agaacatgac caagatgtct tggtgctgga gaaggtccca   2220
gcagggaaca gagcttctaa tcaaggaaac tcacagcctc agcaaaagta tactgtgatg   2280
tcaggaacac ctgaaaaaat tttagagcat tttctagaaa caatacgcct tgaggcaact   2340
ttaaatgaag caacagattc tgttttaaat gactttatta tgatgcactg tgtttttatg   2400
ccaaataccc agctttgccc ggcactggtg gcccactacc acgcacagcc ttcacaaggt   2460
acagaacagg agaaaatgga ttatgccctc aacaataaga ggcgagtcat ccgcctggtt   2520
ctacagtggg ctgccatgta tggagacctc ctgcaagagg atgacgtgtc tatggccttc   2580
ctggaggagt tttatgtatc tgtatcagat gatgcccgga tgattgctgc cctcaaggag   2640
caactgccag agttggagaa gattgtcaag caaatctcag aagatgcaaa ggcaccacaa   2700
aagaagcaca aggttctttt gcaacagttc aatacgggcg atgagagagc ccagaagcgc   2760
cagcctatcc gcggctctga tgaagttctg tttaaggtct attgcatgga ccccacctac   2820
acaaccattc gggtgccagt ggccacttcg gtgaaggaag tcatcagtgc agttgccgac   2880
aagctgggct ccggggaggg cctgatcata gtcaagatga gttccggagg agaaaaggtg   2940
gtgctcaaac ctaatgatgt ttcagtattt atgacgctca ccattaatgg acgcctgttt   3000
gcttgcccgc gagagcaatt cgattcactg actcccttac cagaacagga aggcccaact   3060
gttggaacag tgggaacttt tgaactgatg agctccaaag atttagcata ccagatgaca   3120
atttatgatt gggaactctt caactgcgtg catgagctgg agctaatcta tcacacattt   3180
ggaaggcata attttaaaaa gaccacagca aacttggatt tgttcctgag gagatttaat   3240
gaaattcagt tttgggtcgt cactgagatc tgcctttgtt ctcagctcag caagcgtgtt   3300
```

```
cagctattaa aaaaatttat taagatagca gcccactgta aggagtataa aaatctgaat   3360
tcctttttg ccatcgtcat gggactaagt aacgttgctg tgagccgctt ggcactaacg   3420
tgggagaaac tgccaagcaa gttcaagaag ttctatgcgg agtttgaaag tttaatggac   3480
ccttcaagga accacagggc ctacaggctg acagtagcta agctggaacc tcctctcatc   3540
cccttcatgc ctttgctcat taaagatatg acatttactc atgaggggaa caagacgttc   3600
attgacaatc tagtaaactt tgaaaaaatg cgcatgattg caaatacggc cagaacagtg   3660
agatactaca ggagccaacc cttcaatcct gatgcagctc aagctaataa gaaccatcag   3720
gatgtccgga gttatgtacg gcaattaaat gtgattgaca accagagaac tttatcacag   3780
atgtcacaca gattagagcc tcgtcgacca                                    3810
```

<210> SEQ ID NO 63
<211> LENGTH: 3759
<212> TYPE: DNA
<213> ORGANISM: Artificial Sequence
<220> FEATURE:
<223> OTHER INFORMATION: Synthetic

<400> SEQUENCE: 63

```
atggtcgctg cgcacgctgc ccattcttcc tcctctgccg agtggatcgc ctgcctggat     60
aaaagaccac tggagcgatc cagcgaagat gtggatataa tcttcactcg actgaaagaa    120
gttaaagctt ttgagaaatt tcacccaaat ctccttcatc agatttgctt atgtggttat    180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg gagagtccat tctggacaac    360
acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc cccttttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
ctcgagaacg tctatatcaa ggccgacaag cagaagaacg gcatcaaggc gaacttcaag   1440
atccgccaca acatcgagga cggcggcgtg cagctcgcct accactacca gcagaacacc   1500
cccatcggcg acggccccgt gctgctgccc gacaaccact acctgagcgt gcagtccata   1560
```

```
ctttcgaaag accccaacga gaagcgcgat cacatggtcc tgctggagtt cgtgaccgcc   1620

gccgggatca ctctcggcat ggacgagctg tacaagggcg gtaccggagg gagcatggtg   1680

agcaagggcg aggagctgtt caccggggtg gtgcccatcc aggtcgagct ggacggcgac   1740

gtaaacggcc acaagttcag cgtgtccggc gagggtgagg gcgatgccac ctacggcaag   1800

ctgaccctga agttcatctg caccaccggc aagctgcccg tgccctggcc caccctcgtg   1860

accaccctga cctacggcgt gcagtgcttc agccgctacc ccgaccacat gaagcagcac   1920

gacttcttca agtccgccat gcccgaaggc tacatccagg agcgcaccat cttcttcaag   1980

gacgacggca actacaagac ccgcgccgag gtgaagttcg agggcgacac cctggtgaac   2040

cgcatcgagc tgaagggcat cgacttcaag gaggacggca acatcctggg gcacaagctg   2100

gagtacaaca cgcgtacagt cagacttaaa gaacatgacc aagatgtctt ggtgctggag   2160

aaggtcccag cagggaacag agcttctaat caaggaaact cacagcctca gcaaaagtat   2220

actgtgatgt caggaacacc tgaaaaaatt ttagagcatt ttctagaaac aatacgcctt   2280

gaggcaactt taaatgaagc aacagattct gttttaaatg actttattat gatgcactgt   2340

gtttttatgc caaataccca gctttgcccg gcactggtgg cccactacca cgcacagcct   2400

tcacaaggta cagaacagga gaaaatggat tatgccctca acaataagag gcgagtcatc   2460

cgcctggttc tacagtgggc tgccatgtat ggagacctcc tgcaagagga tgacgtgtct   2520

atggccttcc tggaggagtt ttatgtatct gtatcagatg atgcccggat gattgctgcc   2580

ctcaaggagc aactgccaga gttggagaag attgtcaagc aaatctcaga agatgcaaag   2640

gcaccacaaa agaagcacaa ggttcttttg caacagttca atacgggcga tgagagagcc   2700

cagaagcgcc agcctatccg cggctctgat gaagttctgt ttaaggtcta ttgcatggac   2760

cccacctaca caaccattcg ggtgccagtg gccacttcgg tgaaggaagt catcagtgca   2820

gttgccgaca agctgggctc cggggagggc ctgatcatag tcaagatgag ttccggagga   2880

gaaaaggtgg tgctcaaacc taatgatgtt tcagtattta tgacgctcac cattaatgga   2940

cgcctgtttg cttgcccgcg agagcaattc gattcactga ctcccttacc agaacaggaa   3000

ggcccaactg ttggaacagt gggaactttt gaactgatga gctccaaaga tttagcatac   3060

cagatgacaa tttatgattg ggaactcttc aactgcgtgc atgagctgga gctaatctat   3120

cacacatttg gaaggcataa ttttaaaaag accacagcaa acttggattt gttcctgagg   3180

agatttaatg aaattcagtt ttgggtcgtc actgagatct gcctttgttc tcagctcagc   3240

aagcgtgttc agctattaaa aaaatttatt aagatagcag cccactgtaa ggagtataaa   3300

aatctgaatt cctttttttgc catcgtcatg ggactaagta acgttgctgt gagccgcttg   3360

gcactaacgt gggagaaact gccaagcaag ttcaagaagt tctatgcgga gtttgaaagt   3420

ttaatggacc cttcaaggaa ccacagggcc tacaggctga cagtagctaa gctggaacct   3480

cctctcatcc ccttcatgcc tttgctcatt aaagatatga catttactca tgaggggaac   3540

aagacgttca ttgacaatct agtaaacttt gaaaaaatgc gcatgattgc aaatacggcc   3600

agaacagtga gatactacag gagccaaccc ttcaatcctg atgcagctca agctaataag   3660

aaccatcagg atgtccggag ttatgtacgg caattaaatg tgattgacaa ccagagaact   3720

ttatcacaga tgtcacacag attagagcct cgtcgacca                          3759
```

<210> SEQ ID NO 64
<211> LENGTH: 3768
<212> TYPE: DNA

<213> ORGANISM: Artificial Sequence
<220> FEATURE:
<223> OTHER INFORMATION: Synthetic

<400> SEQUENCE: 64

```
atggtcgctg cgcacgctgc ccattcttcc tcctctgccg agtggatcgc ctgcctggat     60
aaaagaccac tggagcgatc cagcgaagat gtggatataa tcttcactcg actgaaagaa    120
gttaaagctt ttgagaaatt tcacccaaat ctccttcatc agatttgctt atgtggttat    180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg gagagtccat tctggacaac    360
acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggatgtcg   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacgtatcag acgtggaggc gaatacagtc agacttaaag aacatgacca agatgtcttg   2160
gtgctggaga aggtcccagc agggaacaga gcttctaatc aaggaaactc acagcctcag   2220
```

```
caaaagtata ctgtgatgtc aggaacacct gaaaaaattt tagagcattt tctagaaaca   2280

atacgccttg aggcaacttt aaatgaagca acagattctg ttttaaatga ctttattatg   2340

atgcactgtg tttttatgcc aaatacccag ctttgcccgg cactggtggc ccactaccac   2400

gcacagcctt cacaaggtac agaacaggag aaaatggatt atgccctcaa caataagagg   2460

cgagtcatcc gcctggttct acagtgggct gccatgtatg gagacctcct gcaagaggat   2520

gacgtgtcta tggccttcct ggaggagttt tatgtatctg tatcagatga tgcccggatg   2580

attgctgccc tcaaggagca actgccagag ttggagaaga ttgtcaagca aatctcagaa   2640

gatgcaaagg caccacaaaa gaagcacaag gttcttttgc aacagttcaa tacgggcgat   2700

gagagagccc agaagcgcca gcctatccgc ggctctgatg aagttctgtt taaggtctat   2760

tgcatggacc ccacctacac aaccattcgg gtgccagtgg ccacttcggt gaaggaagtc   2820

atcagtgcag ttgccgacaa gctgggctcc ggggagggcc tgatcatagt caagatgagt   2880

tccggaggag aaaaggtggt gctcaaacct aatgatgttt cagtatttat gacgctcacc   2940

attaatggac gcctgtttgc ttgcccgcga gagcaattcg attcactgac tcccttacca   3000

gaacaggaag gcccaactgt tggaacagtg ggaacttttg aactgatgag ctccaaagat   3060

ttagcatacc agatgacaat ttatgattgg gaactcttca actgcgtgca tgagctggag   3120

ctaatctatc acacatttgg aaggcataat tttaaaaaga ccacagcaaa cttggatttg   3180

ttcctgagga gatttaatga aattcagttt tgggtcgtca ctgagatctg cctttgttct   3240

cagctcagca agcgtgttca gctattaaaa aaatttatta agatagcagc ccactgtaag   3300

gagtataaaa atctgaattc ctttttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca                3768
```

<210> SEQ ID NO 65
<211> LENGTH: 3768
<212> TYPE: DNA
<213> ORGANISM: Artificial Sequence
<220> FEATURE:
<223> OTHER INFORMATION: Synthetic

<400> SEQUENCE: 65

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480
```

```
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgtg acgtggaggc gaatacagtc agacttaaag aacatgacca agatgtcttg   2160
gtgctggaga aggtcccagc agggaacaga gcttctaatc aaggaaactc acagcctcag   2220
caaaagtata ctgtgatgtc aggaacacct gaaaaaattt tagagcattt tctagaaaca   2280
atacgccttg aggcaacttt aaatgaagca acagattctg ttttaaatga ctttattatg   2340
atgcactgtg tttttatgcc aaatacccag ctttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg gagacctcct gcaagaggat   2520
gacgtgtcta tggccttcct ggaggagttt tatgtatctg tatcagatga tgcccggatg   2580
attgctgccc tcaaggagca actgccagag ttggagaaga ttgtcaagca aatctcagaa   2640
gatgcaaagg caccacaaaa gaagcacaag gttcttttgc aacagttcaa tacgggcgat   2700
gagagagccc agaagcgcca gcctatccgc ggctctgatg aagttctgtt taaggtctat   2760
tgcatggacc ccacctacac aaccattcgg gtgccagtgg ccacttcggt gaaggaagtc   2820
atcagtgcag ttgccgacaa gctgggctcc ggggagggcc tgatcatagt caagatgagt   2880
```

```
tccggaggag aaaaggtggt gctcaaacct aatgatgttt cagtatttat gacgctcacc   2940

attaatggac gcctgtttgc ttgcccgcga gagcaattcg attcactgac tcccttacca   3000

gaacaggaag gcccaactgt tggaacagtg ggaacttttg aactgatgag ctccaaagat   3060

ttagcatacc agatgacaat ttatgattgg gaactcttca actgcgtgca tgagctggag   3120

ctaatctatc acacatttgg aaggcataat tttaaaaaga ccacagcaaa cttggatttg   3180

ttcctgagga gatttaatga aattcagttt tgggtcgtca ctgagatctg cctttgttct   3240

cagctcagca agcgtgttca gctattaaaa aaatttatta agatagcagc ccactgtaag   3300

gagtataaaa atctgaattc ctttttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca                3768
```

<210> SEQ ID NO 66
<211> LENGTH: 3774
<212> TYPE: DNA
<213> ORGANISM: Artificial Sequence
<220> FEATURE:
<223> OTHER INFORMATION: Synthetic

<400> SEQUENCE: 66

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc ccctttgcct    900

actgaggagg agaagaagga gtgtgatgag gagctccagg acaccatgct gctgctgtca    960

cagatgggcc ccgacgccca catgaggatg atccttcgca aaccacctgg ccagaggact   1020

gtggatgacc tagagattat ctatgaggag cttcttcata ttaaagcctt atcccatctt   1080

tctaccacag tgaaacgaga gttagcaggt gttctcattt ttgagtctca cgccaaagga   1140
```

-continued

```
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctggtg   1380
tcgcacaacg tctatatcaa ggccgacaag cagaagaacg gcatcaaggc gaacttcaag   1440
atccgccaca acatcgagga cggcggcgtg cagctcgcct accactacca gcagaacacc   1500
cccatcggcg acggccccgt gctgctgccc gacaaccact acctgagcgt gcagtccata   1560
ctttcgaaag accccaacga gaagcgcgat cacatggtcc tgctggagtt cgtgaccgcc   1620
gccgggatca ctctcggcat ggacgagctg tacaagggcg gtaccggagg gagcatggtg   1680
agcaagggcg aggagctgtt caccggggtg gtgcccatcc aggtcgagct ggacggcgac   1740
gtaaacggcc acaagttcag cgtgtccggc gagggtgagg gcgatgccac ctacggcaag   1800
ctgaccctga agttcatctg caccaccggc aagctgcccg tgccctggcc caccctcgtg   1860
accaccctga cctacggcgt gcagtgcttc agccgctacc ccgaccacat gaagcagcac   1920
gacttcttca agtccgccat gcccgaaggc tacatccagg agcgcaccat cttcttcaag   1980
gacgacggca actacaagac ccgcgccgag gtgaagttcg agggcgacac cctggtgaac   2040
cgcatcgagc tgaagggcat cgacttcaag gaggacggca acatcctggg gcacaagctg   2100
gagtacaact tcaacgacgt ggaggcgaat acagtcagac ttaaagaaca tgaccaagat   2160
gtcttggtgc tggagaaggt cccagcaggg aacagagctt ctaatcaagg aaactcacag   2220
cctcagcaaa agtatactgt gatgtcagga acacctgaaa aaattttaga gcattttcta   2280
gaaacaatac gccttgaggc aactttaaat gaagcaacag attctgtttt aaatgacttt   2340
attatgatgc actgtgtttt tatgccaaat acccagcttt gcccggcact ggtggcccac   2400
taccacgcac agccttcaca aggtacagaa caggagaaaa tggattatgc cctcaacaat   2460
aagaggcgag tcatccgcct ggttctacag tgggctgcca tgtatggaga cctcctgcaa   2520
gaggatgacg tgtctatggc cttcctggag gagttttatg tatctgtatc agatgatgcc   2580
cggatgattg ctgccctcaa ggagcaactg ccagagttgg agaagattgt caagcaaatc   2640
tcagaagatg caaaggcacc acaaaagaag cacaaggttc ttttgcaaca gttcaatacg   2700
ggcgatgaga gagcccagaa gcgccagcct atccgcggct ctgatgaagt tctgtttaag   2760
gtctattgca tggaccccac ctacacaacc attcgggtgc cagtggccac ttcggtgaag   2820
gaagtcatca gtgcagttgc cgacaagctg ggctccgggg agggcctgat catagtcaag   2880
atgagttccg gaggagaaaa ggtggtgctc aaacctaatg atgtttcagt atttatgacg   2940
ctcaccatta atggacgcct gtttgcttgc ccgcgagagc aattcgattc actgactccc   3000
ttaccagaac aggaaggccc aactgttgga acagtgggaa cttttgaact gatgagctcc   3060
aaagatttag cataccagat gacaatttat gattgggaac tcttcaactg cgtgcatgag   3120
ctggagctaa tctatcacac atttggaagg cataatttta aaaagaccac agcaaacttg   3180
gatttgttcc tgaggagatt taatgaaatt cagttttggg tcgtcactga gatctgcctt   3240
tgttctcagc tcagcaagcg tgttcagcta ttaaaaaaat ttattaagat agcagcccac   3300
tgtaaggagt ataaaaatct gaattccttt tttgccatcg tcatgggact aagtaacgtt   3360
gctgtgagcc gcttggcact aacgtgggag aaactgccaa gcaagttcaa gaagttctat   3420
gcggagtttg aaagtttaat ggacccttca aggaaccaca gggcctacag gctgacagta   3480
gctaagctgg aacctcctct catcccctta atgcctttgc tcattaaaga tatgacattt   3540
```

actcatgagg ggaacaagac gttcattgac aatctagtaa actttgaaaa aatgcgcatg 3600
attgcaaata cggccagaac agtgagatac tacaggagcc aacccttcaa tcctgatgca 3660
gctcaagcta ataagaacca tcaggatgtc cggagttatg tacggcaatt aaatgtgatt 3720
gacaaccaga gaactttatc acagatgtca cacagattag agcctcgtcg acca 3774

<210> SEQ ID NO 67
<211> LENGTH: 4317
<212> TYPE: DNA
<213> ORGANISM: Artificial Sequence
<220> FEATURE:
<223> OTHER INFORMATION: Synthetic

<400> SEQUENCE: 67
atggtcgctg cgcacgctgc ccattcttcc tcctctgccg agtggatcgc ctgcctggat 60
aaaagaccac tggagcgatc cagcgaagat gtggatataa tcttcactcg actgaaagaa 120
gttaaagctt ttgagaaatt tcacccaaat ctccttcatc agatttgctt atgtggttat 180
tatgagaatc tggaaaaggg aataacatta tttcgccagg gtgatattgg aacaaactgg 240
tatgctgtcc tggcagggtc tttggatgtt aaagtatctg agaccagcag tcaccaggat 300
gctgtgacca tctgtaccct gggaattggg acggcctttg gagagtccat tctggacaac 360
acaccccgcc atgcaaccat cgttaccagg gagagcagtg aactgctccg catcgagcag 420
aaggacttca aggcactatg ggagaaatat cgacagtata tggcaggact tctggctcct 480
ccttatggtg ttatggaaac gggctctaac aatgacagga ttcctgacaa ggagaacaca 540
cctctcattg aacctcacgt tcctcttcgt cctgctaaca ccattaccaa ggtcccttca 600
gagaagatcc tcagagctgg aaaaatttta cgaaatgcca ttctctctcg agcacctcac 660
atgataagag atagaaaata ccacctaaag acatacagac aatgctgtgt gggaactgaa 720
ctggtggact ggatgatgca gcagacacca tgtgttcact cccggactca agctgttggc 780
atgtggcaag tcctgttaga agatggtgtt ctcaaccacg tggaccagga gcaccatttc 840
caagacaaat atttattcta tcgatttctg gatgatgagc acgaggatgc ccctttgcct 900
actgaggagg agaagaagga gtgtgatgag gagctccagg acaccatgct gctgctgtca 960
cagatgggcc ccgacgccca catgaggatg atccttcgca aaccacctgg ccagaggact 1020
gtggatgacc tagagattat ctatgaggag cttcttcata ttaaagcctt atcccatctt 1080
tctaccacag tgaaacgaga gttagcaggt gttctcattt ttgagtctca cgccaaagga 1140
gggactgtgt tgtttaacca gggggaagaa ggtacctcct ggtacattat tctaaaagga 1200
tcagtgaatg tagtcattta cggcaagggt gtggtctgca ccctgcatga aggagatgac 1260
ttcggcaagt tagcactagt gaatgatgcc ccacgagctg cctctatcgt cttacgagaa 1320
gataactgcc atttcttaag agtagacaag gaggatttca accggatcct aagggacgtg 1380
gaggcgaata cagtcagact taaagaacat gaccaagatg tcttggtgct ggagaaggtc 1440
ccagcaggga acagagcttc taatcaagga aactcacagc ctcagcaaaa gtatactgtg 1500
atgtcaggaa cacctgaaaa aattttagag cattttctag aaacaatacg ccttgaggca 1560
actttaaatg aagcaacaga ttctgtttta aatgacttta ttatgatgca ctgtgttttt 1620
atgccaaata cccagctttg cccggcactg gtggcccact accacgcaca gccttcacaa 1680
ggtacagaac aggagaaaat ggattatgcc ctcaacaata agaggcgagt catccgcctg 1740
gttctacagt gggctgccat gtatggagac ctcctgcaag aggatgacgt gtctatggcc 1800

```
ttcctggagg agttttatgt atctgtatca gatgatgccc ggatgattgc tgccctcaag   1860
gagcaactgc cagagttgga gaagattgtc aagcaaatct cagaagatgc aaaggcacca   1920
caaaagaagc acaaggttct tttgcaacag ttcaatacgg gcgatgagag agcccagaag   1980
cgccagccta tccgcggctc tgatgaagtt ctgtttaagg tctattgcat ggacccccacc   2040
tacacaacca ttcgggtgcc agtggccact tcggtgaagg aagtcatcag tgcagttgcc   2100
gacaagctgg gctccgggga gggcctgatc atagtcaaga tgagttccgg aggagaaaag   2160
gtggtgctca aacctaatga tgtttcagta tttatgacgc tcaccattaa tggacgcctg   2220
tttgcttgcc cgcgagagca attcgattca ctgactccct taccagaaca ggaaggccca   2280
actgttggaa cagtgggaac ttttgaactg atgagctcca aagatttagc ataccagatg   2340
acaatttatg attgggaact cttcaactgc gtgcatgagc tggagctaat ctatcacaca   2400
tttggaaggc ataattttaa aaagaccaca gcaaacttgg atttgttcct gaggagattt   2460
aatgaaattc agttttgggt cgtcactgag atctgccttt gttctcagct cagcaagcgt   2520
gttcagctat taaaaaaatt tattaagata gcagcccact gtaaggagta taaaaatctg   2580
aattcctttt ttgccatcgt catgggacta agtaacgttg ctgtgagccg cttggcacta   2640
acgtgggaga aactgccaag caagttcaag aagttctatg cggagtttga aagtttaatg   2700
gacccttcaa ggaaccacag ggcctacagg ctgacagtag ctaagctgga acctcctctc   2760
atccccttca tgcctttgct cattaaagat atgacattta ctcatgaggg gaacaagacg   2820
ttcattgaca atctagtaaa ctttgaaaaa atgcgcatga ttgcaaatac ggccagaaca   2880
gtgagatact acaggagcca acccttcaat cctgatgcag ctcaagctaa taagaaccat   2940
caggatgtcc ggagttatgt acggcaatta aatgtgattg acaaccagag aactttatca   3000
cagatgtcac acagattaga gcctcgtcga ccactcgaga acgtctatat caaggccgac   3060
aagcagaaga acggcatcaa ggcgaacttc aagatccgcc acaacatcga ggacggcggc   3120
gtgcagctcg cctaccacta ccagcagaac acccccatcg gcgacggccc cgtgctgctg   3180
cccgacaacc actacctgag cgtgcagtcc atactttcga aagaccccaa cgagaagcgc   3240
gatcacatgg tcctgctgga gttcgtgacc gccgccggga tcactctcgg catggacgag   3300
ctgtacaagg gcggtaccgg agggagcatg gtgagcaagg gcgaggagct gttcaccggg   3360
gtggtgccca tccaggtcga gctggacggc gacgtaaacg gccacaagtt cagcgtgtcc   3420
ggcgagggtg agggcgatgc cacctacggc aagctgaccc tgaagttcat ctgcaccacc   3480
ggcaagctgc ccgtgccctg gcccaccctc gtgaccaccc tgacctacgg cgtgcagtgc   3540
ttcagccgct accccgacca catgaagcag cacgacttct tcaagtccgc catgcccgaa   3600
ggctacatcc aggagcgcac catcttcttc aaggacgacg gcaactacaa gacccgcgcc   3660
gaggtgaagt tcgagggcga caccctggtg aaccgcatcg agctgaaggg catcgacttc   3720
aaggaggacg gcaacatcct ggggcacaag ctggagtaca acacgcgtcg tgagtataag   3780
ctagtcgttc ttggctcagg aggcgttgga aagtctgctt tgactgtaca atttgttcaa   3840
ggaatttttg tagaaaaata cgatcctacg atagaagatt cttatagaaa gcaagttgaa   3900
gtagatgcac aacagtgtat gcttgaaatc ttggatactg caggaacgga gcaatttaca   3960
gcaatgaggg atttatacat gaaaaatgga caaggatttg cattagttta ttccatcaca   4020
gcacagtcca catttaacga tttacaagac ctgagagaac agattcttcg agttaaagac   4080
actgatgatg ttccaatgat tcttgttggt aataagtgtg acttggaaga tgaaagagtt   4140
gtagggaagg aacaaggtca aaatctagca agacaatgga acaactgtgc attcttagaa   4200
```

tcttctgcaa aatcaaaaat aaatgttaat gagatctttt atgacctagt gcggcaaatt 4260
aacagaaaaa ctccagtgcc tgggaaggct cgcaaaaagt catcatgtca gctgctt 4317

<210> SEQ ID NO 68
<211> LENGTH: 3768
<212> TYPE: DNA
<213> ORGANISM: Artificial Sequence
<220> FEATURE:
<223> OTHER INFORMATION: Synthetic

<400> SEQUENCE: 68
atggtcgctg cgcacgctgc ccattcttcc tcctctgccg agtggatcgc ctgcctggat 60
aaaagaccac tggagcgatc cagcgaagat gtggatataa tcttcactcg actgaaagaa 120
gttaaagctt ttgagaaatt tcacccaaat ctccttcatc agatttgctt atgtggttat 180
tatgagaatc tggaaaaggg aataacatta tttcgccagg gtgatattgg aacaaactgg 240
tatgctgtcc tggcagggtc tttggatgtt aaagtatctg agaccagcag tcaccaggat 300
gctgtgacca tctgtaccct gggaattggg acggcctttg gagagtccat tctggacaac 360
acaccccgcc atgcaaccat cgttaccagg gagagcagtg aactgctccg catcgagcag 420
aaggacttca aggcactatg ggagaaatat cgacagtata tggcaggact tctggctcct 480
ccttatggtg ttatggaaac gggctctaac aatgacagga ttcctgacaa ggagaacaca 540
cctctcattg aacctcacgt tcctcttcgt cctgctaaca ccattaccaa ggtcccttca 600
gagaagatcc tcagagctgg aaaaatttta cgaaatgcca ttctctctcg agcacctcac 660
atgataagag atagaaaata ccacctaaag acatacagac aatgctgtgt gggaactgaa 720
ctggtggact ggatgatgca gcagacacca tgtgttcact cccggactca agctgttggc 780
atgtggcaag tcctgttaga agatggtgtt ctcaaccacg tggaccagga gcaccatttc 840
caagacaaat atttattcta tcgatttctg gatgatgagc acgaggatgc cccttgcct 900 actgaggagg agaagaagga gtgtgatgag gagctccagg acaccatgct gctgctgtca 960
cagatgggcc ccgacgccca catgaggatg atccttcgca aaccacctgg ccagaggact 1020
gtggatgacc tagagattat ctatgaggag cttcttcata ttaaagcctt atcccatctt 1080
tctaccacag tgaaacgaga gttagcaggt gttctcattt ttgagtctca cgccaaagga 1140
gggactgtgt tgtttaacca gggggaagaa ggtacctcct ggtacattat tctaaaagga 1200
tcagtgaatg tagtcattta cggcaagggt gtggtctgca ccctgcatga aggagatgac 1260
ttcggcaagt tagcactagt gaatgatgcc ccacgagctg cctctatcgt cttacgagaa 1320
gataactgcc atttcttaag agtagacaag gaggatttca accggatcct aagggacgtg 1380
gagctcgaga acgtctatat caaggccgac aagcagaaga acggcatcaa ggcgaacttc 1440
aagatccgcc acaacatcga ggacggcggc gtgcagctcg cctaccacta ccagcagaac 1500
acccccatcg gcgacggccc cgtgctgctg cccgacaacc actacctgag cgtgcagtcc 1560
atactttcga aagaccccaa cgagaagcgc gatcacatgg tcctgctgga gttcgtgacc 1620
gccgccggga tcactctcgg catggacgag ctgtacaagg gcggtaccgg agggagcatg 1680
gtgagcaagg gcgaggagct gttcaccggg gtggtgccca tccaggtcga gctggacggc 1740
gacgtaaacg gccacaagtt cagcgtgtcc ggcgagggtg agggcgatgc cacctacggc 1800
aagctgaccc tgaagttcat ctgcaccacc ggcaagctgc ccgtgccctg gcccaccctc 1860
gtgaccaccc tgacctacgg cgtgcagtgc ttcagccgct accccgacca catgaagcag 1920

```
cacgacttct tcaagtccgc catgcccgaa ggctacatcc aggagcgcac catcttcttc   1980

aaggacgacg gcaactacaa gacccgcgcc gaggtgaagt tcgagggcga caccctggtg   2040

aaccgcatcg agctgaaggg catcgacttc aaggaggacg gcaacatcct ggggcacaag   2100

ctggagtaca acacgcgtgc gaatacagtc agacttaaag aacatgacca agatgtcttg   2160

gtgctggaga aggtcccagc agggaacaga gcttctaatc aaggaaactc acagcctcag   2220

caaaagtata ctgtgatgtc aggaacacct gaaaaaattt tagagcattt tctagaaaca   2280

atacgccttg aggcaacttt aaatgaagca acagattctg ttttaaatga ctttattatg   2340

atgcactgtg tttttatgcc aaatacccag ctttgcccgg cactggtggc ccactaccac   2400

gcacagcctt cacaaggtac agaacaggag aaaatggatt atgccctcaa caataagagg   2460

cgagtcatcc gcctggttct acagtgggct gccatgtatg gagacctcct gcaagaggat   2520

gacgtgtcta tggccttcct ggaggagttt tatgtatctg tatcagatga tgcccggatg   2580

attgctgccc tcaaggagca actgccagag ttggagaaga ttgtcaagca aatctcagaa   2640

gatgcaaagg caccacaaaa gaagcacaag gttcttttgc aacagttcaa tacgggcgat   2700

gagagagccc agaagcgcca gcctatccgc ggctctgatg aagttctgtt taaggtctat   2760

tgcatggacc ccacctacac aaccattcgg gtgccagtgg ccacttcggt gaaggaagtc   2820

atcagtgcag ttgccgacaa gctgggctcc ggggagggcc tgatcatagt caagatgagt   2880

tccggaggag aaaaggtggt gctcaaacct aatgatgttt cagtatttat gacgctcacc   2940

attaatggac gcctgtttgc ttgcccgcga gagcaattcg attcactgac tcccttacca   3000

gaacaggaag gcccaactgt tggaacagtg ggaacttttg aactgatgag ctccaaagat   3060

ttagcatacc agatgacaat ttatgattgg gaactcttca actgcgtgca tgagctggag   3120

ctaatctatc acacatttgg aaggcataat tttaaaaaga ccacagcaaa cttggatttg   3180

ttcctgagga gatttaatga aattcagttt tgggtcgtca ctgagatctg cctttgttct   3240

cagctcagca agcgtgttca gctattaaaa aaatttatta agatagcagc ccactgtaag   3300

gagtataaaa atctgaattc ctttttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca                3768
```

<210> SEQ ID NO 69
<211> LENGTH: 3768
<212> TYPE: DNA
<213> ORGANISM: Artificial Sequence
<220> FEATURE:
<223> OTHER INFORMATION: Synthetic

<400> SEQUENCE: 69

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240
```

```
tatgctgtcc tggcagggtc tttggatgtt aaagtatctg agaccagcag tcaccaggat    300
gctgtgacca tctgtaccct gggaattggg acggcctttg gagagtccat tctggacaac    360
acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
gaggcgaata cagtcagact taaagaacat gaccaagatg tcttggtgct ggagaaggtc   1440
ccagcaggga acagagcttc taatcaagga aactcacagc ctcagcaaaa gtatactgtg   1500
atgtcaggaa cacctgaaaa aattttagag cattttctag aaacaatacg ccttctcgag   1560
aacgtctata tcaaggccga caagcagaag aacggcatca aggcgaactt caagatccgc   1620
cacaacatcg aggacggcgg cgtgcagctc gcctaccact accagcagaa cacccccatc   1680
ggcgacggcc ccgtgctgct gcccgacaac cactacctga gcgtgcagtc catactttcg   1740
aaagacccca acgagaagcg cgatcacatg gtcctgctgg agttcgtgac cgccgccggg   1800
atcactctcg gcatggacga gctgtacaag ggcggtaccg gagggagcat ggtgagcaag   1860
ggcgaggagc tgttcaccgg ggtggtgccc atccaggtcg agctggacgg cgacgtaaac   1920
ggccacaagt tcagcgtgtc cggcgagggt gagggcgatg ccacctacgg caagctgacc   1980
ctgaagttca tctgcaccac cggcaagctg cccgtgccct ggcccaccct cgtgaccacc   2040
ctgacctacg gcgtgcagtg cttcagccgc taccccgacc acatgaagca gcacgacttc   2100
ttcaagtccg ccatgcccga aggctacatc caggagcgca ccatcttctt caaggacgac   2160
ggcaactaca agacccgcgc cgaggtgaag ttcgagggcg acaccctggt gaaccgcatc   2220
gagctgaagg gcatcgactt caaggaggac ggcaacatcc tggggcacaa gctggagtac   2280
aacacgcgtg aggcaacttt aaatgaagca acagattctg ttttaaatga ctttattatg   2340
atgcactgtg tttttatgcc aaatacccag ctttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg gagacctcct gcaagaggat   2520
gacgtgtcta tggccttcct ggaggagttt tatgtatctg tatcagatga tgcccggatg   2580
```

```
attgctgccc tcaaggagca actgccagag ttggagaaga ttgtcaagca aatctcagaa   2640

gatgcaaagg caccacaaaa gaagcacaag gttcttttgc aacagttcaa tacgggcgat   2700

gagagagccc agaagcgcca gcctatccgc ggctctgatg aagttctgtt taaggtctat   2760

tgcatggacc ccacctacac aaccattcgg gtgccagtgg ccacttcggt gaaggaagtc   2820

atcagtgcag ttgccgacaa gctgggctcc ggggagggcc tgatcatagt caagatgagt   2880

tccggaggag aaaaggtggt gctcaaacct aatgatgttt cagtatttat gacgctcacc   2940

attaatggac gcctgtttgc ttgcccgcga gagcaattcg attcactgac tcccttacca   3000

gaacaggaag gcccaactgt tggaacagtg ggaacttttg aactgatgag ctccaaagat   3060

ttagcatacc agatgacaat ttatgattgg gaactcttca actgcgtgca tgagctggag   3120

ctaatctatc acacatttgg aaggcataat tttaaaaaga ccacagcaaa cttggatttg   3180

ttcctgagga gatttaatga aattcagttt tgggtcgtca ctgagatctg cctttgttct   3240

cagctcagca agcgtgttca gctattaaaa aaatttatta agatagcagc ccactgtaag   3300

gagtataaaa atctgaattc cttttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca                3768
```

<210> SEQ ID NO 70
<211> LENGTH: 3768
<212> TYPE: DNA
<213> ORGANISM: Artificial Sequence
<220> FEATURE:
<223> OTHER INFORMATION: Synthetic

<400> SEQUENCE: 70

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc ccctttgcct    900
```

```
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct actcgagaac   1380
gtctatatca aggccgacaa gcagaagaac ggcatcaagg cgaacttcaa gatccgccac   1440
aacatcgagg acggcggcgt gcagctcgcc taccactacc agcagaacac ccccatcggc   1500
gacggccccg tgctgctgcc cgacaaccac tacctgagcg tgcagtccat actttcgaaa   1560
gaccccaacg agaagcgcga tcacatggtc ctgctggagt tcgtgaccgc cgccgggatc   1620
actctcggca tggacgagct gtacaagggc ggtaccggag ggagcatggt gagcaagggc   1680
gaggagctgt tcaccggggt ggtgcccatc caggtcgagc tggacggcga cgtaaacggc   1740
cacaagttca gcgtgtccgg cgagggtgag ggcgatgcca cctacggcaa gctgaccctg   1800
aagttcatct gcaccaccgg caagctgccc gtgccctggc ccaccctcgt gaccaccctg   1860
acctacggcg tgcagtgctt cagccgctac cccgaccaca tgaagcagca cgacttcttc   1920
aagtccgcca tgcccgaagg ctacatccag gagcgcacca tcttcttcaa ggacgacggc   1980
aactacaaga cccgcgccga ggtgaagttc gagggcgaca ccctggtgaa ccgcatcgag   2040
ctgaagggca tcgacttcaa ggaggacggc aacatcctgg ggcacaagct ggagtacaac   2100
acgcgtaggg acgtggaggc gaatacagtc agacttaaag aacatgacca agatgtcttg   2160
gtgctggaga aggtcccagc agggaacaga gcttctaatc aaggaaactc acagcctcag   2220
caaaagtata ctgtgatgtc aggaacacct gaaaaaattt tagagcattt tctagaaaca   2280
atacgccttg aggcaacttt aaatgaagca acagattctg ttttaaatga ctttattatg   2340
atgcactgtg tttttatgcc aaatacccag ctttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg gagacctcct gcaagaggat   2520
gacgtgtcta tggccttcct ggaggagttt tatgtatctg tatcagatga tgcccggatg   2580
attgctgccc tcaaggagca actgccagag ttggagaaga ttgtcaagca aatctcagaa   2640
gatgcaaagg caccacaaaa gaagcacaag gttcttttgc aacagttcaa tacgggcgat   2700
gagagagccc agaagcgcca gcctatccgc ggctctgatg aagttctgtt taaggtctat   2760
tgcatggacc ccacctacac aaccattcgg gtgccagtgg ccacttcggt gaaggaagtc   2820
atcagtgcag ttgccgacaa gctgggctcc ggggagggcc tgatcatagt caagatgagt   2880
tccggaggag aaaaggtggt gctcaaacct aatgatgttt cagtatttat gacgctcacc   2940
attaatggac gcctgtttgc ttgcccgcga gagcaattcg attcactgac tcccttacca   3000
gaacaggaag gcccaactgt tggaacagtg ggaacttttg aactgatgag ctccaaagat   3060
ttagcatacc agatgacaat ttatgattgg gaactcttca actgcgtgca tgagctggag   3120
ctaatctatc acacatttgg aaggcataat tttaaaaaga ccacagcaaa cttggatttg   3180
ttcctgagga gatttaatga aattcagttt tgggtcgtca ctgagatctg cctttgttct   3240
```

```
cagctcagca agcgtgttca gctattaaaa aaatttatta agatagcagc ccactgtaag   3300

gagtataaaa atctgaattc ctttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca                3768
```

<210> SEQ ID NO 71
<211> LENGTH: 3768
<212> TYPE: DNA
<213> ORGANISM: Artificial Sequence
<220> FEATURE:
<223> OTHER INFORMATION: Synthetic

<400> SEQUENCE: 71

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480

ccttatggtg ttatggaaac gggctctaac aatgacagga ttcctgacaa ggagaacaca    540

cctctcattg aacctcacgt tcctcttcgt cctgctaaca ccattaccaa ggtcccttca    600

gagaagatcc tcagagctgg aaaaatttta cgaaatgcca ttctctctcg agcacctcac    660

atgataagag atagaaaata ccacctaaag acatacagac aatgctgtgt gggaactgaa    720

ctggtggact ggatgatgca gcagacacca tgtgttcact cccggactca agctgttggc    780

atgtggcaag tcctgttaga agatggtgtt ctcaaccacg tggaccagga gcaccatttc    840

caagacaaat atttattcta tcgatttctg gatgatgagc acgaggatgc ccctttgcct    900

actgaggagg agaagaagga gtgtgatgag gagctccagg acaccatgct gctgctgtca    960

cagatgggcc ccgacgccca catgaggatg atccttcgca aaccacctgg ccagaggact   1020

gtgctcgaga acgtctatat caaggccgac aagcagaaga acggcatcaa ggcgaacttc   1080

aagatccgcc acaacatcga ggacggcggc gtgcagctcg cctaccacta ccagcagaac   1140

acccccatcg gcgacggccc cgtgctgctg cccgacaacc actacctgag cgtgcagtcc   1200

atactttcga aagaccccaa cgagaagcgc gatcacatgg tcctgctgga gttcgtgacc   1260

gccgccggga tcactctcgg catggacgag ctgtacaagg gcggtaccgg agggagcatg   1320

gtgagcaagg gcgaggagct gttcaccggg gtggtgccca tccaggtcga gctggacggc   1380

gacgtaaacg gccacaagtt cagcgtgtcc ggcgagggtg agggcgatgc cacctacggc   1440

aagctgaccc tgaagttcat ctgcaccacc ggcaagctgc ccgtgccctg gcccaccctc   1500

gtgaccaccc tgacctacgg cgtgcagtgc ttcagccgct accccgacca catgaagcag   1560
```

```
cacgacttct tcaagtccgc catgcccgaa ggctacatcc aggagcgcac catcttcttc   1620

aaggacgacg gcaactacaa gacccgcgcc gaggtgaagt tcgagggcga caccctggtg   1680

aaccgcatcg agctgaaggg catcgacttc aaggaggacg gcaacatcct ggggcacaag   1740

ctggagtaca acacgcgtga tgacctagag attatctatg aggagcttct tcatattaaa   1800

gccttatccc atctttctac cacagtgaaa cgagagttag caggtgttct catttttgag   1860

tctcacgcca aaggagggac tgtgttgttt aaccaggggg aagaaggtac ctcctggtac   1920

attattctaa aaggatcagt gaatgtagtc atttacggca agggtgtggt ctgcaccctg   1980

catgaaggag atgacttcgg caagttagca ctagtgaatg atgccccacg agctgcctct   2040

atcgtcttac gagaagataa ctgccatttc ttaagagtag acaaggagga tttcaaccgg   2100

atcctaaggg acgtggaggc gaatacagtc agacttaaag aacatgacca agatgtcttg   2160

gtgctggaga aggtcccagc agggaacaga gcttctaatc aaggaaactc acagcctcag   2220

caaaagtata ctgtgatgtc aggaacacct gaaaaaattt tagagcattt tctagaaaca   2280

atacgccttg aggcaacttt aaatgaagca acagattctg ttttaaatga ctttattatg   2340

atgcactgtg tttttatgcc aaatacccag ctttgcccgg cactggtggc ccactaccac   2400

gcacagcctt cacaaggtac agaacaggag aaaatggatt atgccctcaa caataagagg   2460

cgagtcatcc gcctggttct acagtgggct gccatgtatg gagacctcct gcaagaggat   2520

gacgtgtcta tggccttcct ggaggagttt tatgtatctg tatcagatga tgcccggatg   2580

attgctgccc tcaaggagca actgccagag ttggagaaga ttgtcaagca aatctcagaa   2640

gatgcaaagg caccacaaaa gaagcacaag gttcttttgc aacagttcaa tacgggcgat   2700

gagagagccc agaagcgcca gcctatccgc ggctctgatg aagttctgtt taaggtctat   2760

tgcatggacc ccacctacac aaccattcgg gtgccagtgg ccacttcggt gaaggaagtc   2820

atcagtgcag ttgccgacaa gctgggctcc ggggagggcc tgatcatagt caagatgagt   2880

tccggaggag aaaaggtggt gctcaaacct aatgatgttt cagtatttat gacgctcacc   2940

attaatggac gcctgtttgc ttgcccgcga gagcaattcg attcactgac tcccttacca   3000

gaacaggaag gcccaactgt tggaacagtg ggaacttttg aactgatgag ctccaaagat   3060

ttagcatacc agatgacaat ttatgattgg gaactcttca actgcgtgca tgagctggag   3120

ctaatctatc acacatttgg aaggcataat tttaaaaaga ccacagcaaa cttggatttg   3180

ttcctgagga gatttaatga aattcagttt tgggtcgtca ctgagatctg cctttgttct   3240

cagctcagca agcgtgttca gctattaaaa aaatttatta agatagcagc ccactgtaag   3300

gagtataaaa atctgaattc ctttttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca               3768
```

<210> SEQ ID NO 72
<211> LENGTH: 3768
<212> TYPE: DNA

<213> ORGANISM: Artificial Sequence
<220> FEATURE:
<223> OTHER INFORMATION: Synthetic

<400> SEQUENCE: 72

```
atggtcgctg cgcacgctgc ccattcttcc tcctctgccg agtggatcgc ctgcctggat     60
aaaagaccac tggagcgatc cagcgaagat gtggatataa tcttcactcg actgaaagaa    120
gttaaagctt ttgagaaatt tcacccaaat ctccttcatc agatttgctt atgtggttat    180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg gagagtccat tctggacaac    360
acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
gaggcgaata cagtcagact taaagaacat gaccaagatg tcttggtgct ggagaaggtc   1440
ccagcaggga acagagctct cgagaacgtc tatatcaagg ccgacaagca gaagaacggc   1500
atcaaggcga acttcaagat ccgccacaac atcgaggacg gcggcgtgca gctcgcctac   1560
cactaccagc agaacacccc catcggcgac ggccccgtgc tgctgcccga caaccactac   1620
ctgagcgtgc agtccatact ttcgaaagac cccaacgaga agcgcgatca catggtcctg   1680
ctggagttcg tgaccgccgc cgggatcact ctcggcatgg acgagctgta caagggcggt   1740
accggaggga gcatggtgag caagggcgag gagctgttca ccggggtggt gcccatccag   1800
gtcgagctgg acggcgacgt aaacggccac aagttcagcg tgtccggcga gggtgagggc   1860
gatgccacct acggcaagct gaccctgaag ttcatctgca ccaccggcaa gctgcccgtg   1920
ccctggccca ccctcgtgac caccctgacc tacggcgtgc agtgcttcag ccgctacccc   1980
gaccacatga agcagcacga cttcttcaag tccgccatgc ccgaaggcta catccaggag   2040
cgcaccatct tcttcaagga cgacggcaac tacaagaccc gcgccgaggt gaagttcgag   2100
ggcgacaccc tggtgaaccg catcgagctg aagggcatcg acttcaagga ggacggcaac   2160
atcctggggc acaagctgga gtacaacacg cgttctaatc aaggaaactc acagcctcag   2220
```

```
caaaagtata ctgtgatgtc aggaacacct gaaaaaattt tagagcattt tctagaaaca   2280

atacgccttg aggcaacttt aaatgaagca acagattctg ttttaaatga ctttattatg   2340

atgcactgtg tttttatgcc aaatacccag ctttgcccgg cactggtggc ccactaccac   2400

gcacagcctt cacaaggtac agaacaggag aaaatggatt atgccctcaa caataagagg   2460

cgagtcatcc gcctggttct acagtgggct gccatgtatg gagacctcct gcaagaggat   2520

gacgtgtcta tggccttcct ggaggagttt tatgtatctg tatcagatga tgcccggatg   2580

attgctgccc tcaaggagca actgccagag ttggagaaga ttgtcaagca aatctcagaa   2640

gatgcaaagg caccacaaaa gaagcacaag gttcttttgc aacagttcaa tacgggcgat   2700

gagagagccc agaagcgcca gcctatccgc ggctctgatg aagttctgtt taaggtctat   2760

tgcatggacc ccacctacac aaccattcgg gtgccagtgg ccacttcggt gaaggaagtc   2820

atcagtgcag ttgccgacaa gctgggctcc ggggagggcc tgatcatagt caagatgagt   2880

tccggaggag aaaaggtggt gctcaaacct aatgatgttt cagtatttat gacgctcacc   2940

attaatggac gcctgtttgc ttgcccgcga gagcaattcg attcactgac tcccttacca   3000

gaacaggaag gcccaactgt tggaacagtg ggaacttttg aactgatgag ctccaaagat   3060

ttagcatacc agatgacaat ttatgattgg gaactcttca actgcgtgca tgagctggag   3120

ctaatctatc acacatttgg aaggcataat tttaaaaaga ccacagcaaa cttggatttg   3180

ttcctgagga gatttaatga aattcagttt tgggtcgtca ctgagatctg cctttgttct   3240

cagctcagca agcgtgttca gctattaaaa aaatttatta agatagcagc ccactgtaag   3300

gagtataaaa atctgaattc ctttttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca                 3768
```

<210> SEQ ID NO 73
<211> LENGTH: 3768
<212> TYPE: DNA
<213> ORGANISM: Artificial Sequence
<220> FEATURE:
<223> OTHER INFORMATION: Synthetic

<400> SEQUENCE: 73

```
atggtcgctg cgcacgctgc ccattcttcc tcctctgccg agtggatcgc ctgcctggat     60

aaaagaccac tggagcgatc cagcgaagat gtggatataa tcttcactcg actgaaagaa    120

gttaaagctt ttgagaaatt tcacccaaat ctccttcatc agatttgctt atgtggttat    180

tatgagaatc tggaaaaggg aataacatta tttcgccagg gtgatattgg aacaaactgg    240

tatgctgtcc tggcagggtc tttggatgtt aaagtatctg agaccagcag tcaccaggat    300

gctgtgacca tctgtaccct gggaattggg acggcctttg gagagtccat tctggacaac    360

acaccccgcc atgcaaccat cgttaccagg gagagcagtg aactgctccg catcgagcag    420

aaggacttca aggcactatg ggagaaatat cgacagtata tggcaggact tctggctcct    480
```

```
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
gaggcgaata cagtcagact taaagaacat gaccaagatg tcttggtgct ggagaaggtc   1440
ccagcaggga acagagcttc taatcaagga aactcacagc ctcagcaaaa gtatactgtg   1500
atgtcaggaa cacctgaaaa aattttagag cattttctag aaacaatacg ccttgaggca   1560
ctcgagaacg tctatatcaa ggccgacaag cagaagaacg gcatcaaggc gaacttcaag   1620
atccgccaca acatcgagga cggcggcgtg cagctcgcct accactacca gcagaacacc   1680
cccatcggcg acggccccgt gctgctgccc gacaaccact acctgagcgt gcagtccata   1740
ctttcgaaag accccaacga gaagcgcgat cacatggtcc tgctggagtt cgtgaccgcc   1800
gccgggatca ctctcggcat ggacgagctg tacaagggcg gtaccggagg gagcatggtg   1860
agcaagggcg aggagctgtt caccggggtg gtgcccatcc aggtcgagct ggacggcgac   1920
gtaaacggcc acaagttcag cgtgtccggc gagggtgagg gcgatgccac ctacggcaag   1980
ctgaccctga agttcatctg caccaccggc aagctgcccg tgccctggcc caccctcgtg   2040
accaccctga cctacggcgt gcagtgcttc agccgctacc ccgaccacat gaagcagcac   2100
gacttcttca agtccgccat gcccgaaggc tacatccagg agcgcaccat cttcttcaag   2160
gacgacggca actacaagac ccgcgccgag gtgaagttcg agggcgacac cctggtgaac   2220
cgcatcgagc tgaagggcat cgacttcaag gaggacggca acatcctggg gcacaagctg   2280
gagtacaaca cgcgtacttt aaatgaagca acagattctg ttttaaatga ctttattatg   2340
atgcactgtg tttttatgcc aaatacccag ctttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg gagacctcct gcaagaggat   2520
gacgtgtcta tggccttcct ggaggagttt tatgtatctg tatcagatga tgcccggatg   2580
attgctgccc tcaaggagca actgccagag ttggagaaga ttgtcaagca aatctcagaa   2640
gatgcaaagg caccacaaaa gaagcacaag gttcttttgc aacagttcaa tacgggcgat   2700
gagagagccc agaagcgcca gcctatccgc ggctctgatg aagttctgtt taaggtctat   2760
tgcatggacc ccacctacac aaccattcgg gtgccagtgg ccacttcggt gaaggaagtc   2820
atcagtgcag ttgccgacaa gctgggctcc ggggagggcc tgatcatagt caagatgagt   2880
```

```
tccggaggag aaaaggtggt gctcaaacct aatgatgttt cagtatttat gacgctcacc   2940

attaatggac gcctgtttgc ttgcccgcga gagcaattcg attcactgac tcccttacca   3000

gaacaggaag gcccaactgt tggaacagtg ggaacttttg aactgatgag ctccaaagat   3060

ttagcatacc agatgacaat ttatgattgg gaactcttca actgcgtgca tgagctggag   3120

ctaatctatc acacatttgg aaggcataat tttaaaaaga ccacagcaaa cttggatttg   3180

ttcctgagga gatttaatga aattcagttt tgggtcgtca ctgagatctg cctttgttct   3240

cagctcagca agcgtgttca gctattaaaa aaatttatta agatagcagc ccactgtaag   3300

gagtataaaa atctgaattc ctttttttgcc atcgtcatgg gactaagtaa cgttgctgtg   3360

agccgcttgg cactaacgtg ggagaaactg ccaagcaagt tcaagaagtt ctatgcggag   3420

tttgaaagtt taatggaccc ttcaaggaac cacagggcct acaggctgac agtagctaag   3480

ctggaacctc ctctcatccc cttcatgcct ttgctcatta aagatatgac atttactcat   3540

gaggggaaca agacgttcat tgacaatcta gtaaactttg aaaaaatgcg catgattgca   3600

aatacggcca gaacagtgag atactacagg agccaaccct tcaatcctga tgcagctcaa   3660

gctaataaga accatcagga tgtccggagt tatgtacggc aattaaatgt gattgacaac   3720

cagagaactt tatcacagat gtcacacaga ttagagcctc gtcgacca               3768
```

<210> SEQ ID NO 74
<211> LENGTH: 881
<212> TYPE: PRT
<213> ORGANISM: Homo sapiens

<400> SEQUENCE: 74

```
Met Val Leu Arg Arg Met His Arg Pro Arg Ser Cys Ser Tyr Gln Leu
1               5                   10                  15

Leu Leu Glu His Gln Arg Pro Ser Cys Ile Gln Gly Leu Arg Trp Thr
            20                  25                  30

Pro Leu Thr Asn Ser Glu Glu Ser Leu Asp Phe Ser Glu Ser Leu Glu
        35                  40                  45

Gln Ala Ser Thr Glu Arg Val Leu Arg Ala Gly Arg Gln Leu His Arg
    50                  55                  60

His Leu Leu Ala Thr Cys Pro Asn Leu Ile Arg Asp Arg Lys Tyr His
65                  70                  75                  80

Leu Arg Leu Tyr Arg Gln Cys Cys Ser Gly Arg Glu Leu Val Asp Gly
                85                  90                  95

Ile Leu Ala Leu Gly Leu Gly Val His Ser Arg Ser Gln Val Val Gly
            100                 105                 110

Ile Cys Gln Val Leu Leu Asp Glu Gly Ala Leu Cys His Val Lys His
        115                 120                 125

Asp Trp Ala Phe Gln Asp Arg Asp Ala Gln Phe Tyr Arg Phe Pro Gly
    130                 135                 140

Pro Glu Pro Glu Pro Val Gly Thr His Glu Met Glu Glu Glu Leu Ala
145                 150                 155                 160

Glu Ala Val Ala Leu Leu Ser Gln Arg Gly Pro Asp Ala Leu Leu Thr
                165                 170                 175

Val Ala Leu Arg Lys Pro Pro Gly Gln Arg Thr Asp Glu Glu Leu Asp
            180                 185                 190

Leu Ile Phe Glu Glu Leu Leu His Ile Lys Ala Val Ala His Leu Ser
        195                 200                 205

Asn Ser Val Lys Arg Glu Leu Ala Ala Val Leu Leu Phe Glu Pro His
```

```
    210                 215                 220

Ser Lys Ala Gly Thr Val Leu Phe Ser Gln Gly Asp Lys Gly Thr Ser
225                 230                 235                 240

Trp Tyr Ile Ile Trp Lys Gly Ser Val Asn Val Val Thr His Gly Lys
                245                 250                 255

Gly Leu Val Thr Thr Leu His Glu Gly Asp Asp Phe Gly Gln Leu Ala
            260                 265                 270

Leu Val Asn Asp Ala Pro Arg Ala Ala Thr Ile Ile Leu Arg Glu Asp
        275                 280                 285

Asn Cys His Phe Leu Arg Val Asp Lys Gln Asp Phe Asn Arg Ile Ile
    290                 295                 300

Lys Asp Val Glu Ala Lys Thr Met Arg Leu Glu Glu His Gly Lys Val
305                 310                 315                 320

Val Leu Val Leu Glu Arg Ala Ser Gln Gly Ala Gly Pro Ser Arg Pro
                325                 330                 335

Pro Thr Pro Gly Arg Asn Arg Tyr Thr Val Met Ser Gly Thr Pro Glu
            340                 345                 350

Lys Ile Leu Glu Leu Leu Leu Glu Ala Met Gly Pro Asp Ser Ser Ala
        355                 360                 365

His Asp Pro Thr Glu Thr Phe Leu Ser Asp Phe Leu Leu Thr His Arg
    370                 375                 380

Val Phe Met Pro Ser Ala Gln Leu Cys Ala Ala Leu Leu His His Phe
385                 390                 395                 400

His Val Glu Pro Ala Gly Gly Ser Glu Gln Glu Arg Ser Thr Tyr Val
                405                 410                 415

Cys Asn Lys Arg Gln Gln Ile Leu Arg Leu Val Ser Gln Trp Val Ala
            420                 425                 430

Leu Tyr Gly Ser Met Leu His Thr Asp Pro Val Ala Thr Ser Phe Leu
        435                 440                 445

Gln Lys Leu Ser Asp Leu Val Gly Arg Asp Thr Arg Leu Ser Asn Leu
    450                 455                 460

Leu Arg Glu Gln Trp Pro Glu Arg Arg Arg Cys His Arg Leu Glu Asn
465                 470                 475                 480

Gly Cys Gly Asn Ala Ser Pro Gln Met Lys Ala Arg Asn Leu Pro Val
                485                 490                 495

Trp Leu Pro Asn Gln Asp Glu Pro Leu Pro Gly Ser Ser Cys Ala Ile
            500                 505                 510

Gln Val Gly Asp Lys Val Pro Tyr Asp Ile Cys Arg Pro Asp His Ser
        515                 520                 525

Val Leu Thr Leu Gln Leu Pro Val Thr Ala Ser Val Arg Glu Val Met
    530                 535                 540

Ala Ala Leu Ala Gln Glu Asp Gly Trp Thr Lys Gly Gln Val Leu Val
545                 550                 555                 560

Lys Val Asn Ser Ala Gly Asp Ala Ile Gly Leu Gln Pro Asp Ala Arg
                565                 570                 575

Gly Val Ala Thr Ser Leu Gly Leu Asn Glu Arg Leu Phe Val Val Asn
            580                 585                 590

Pro Gln Glu Val His Glu Leu Ile Pro His Pro Asp Gln Leu Gly Pro
        595                 600                 605

Thr Val Gly Ser Ala Glu Gly Leu Asp Leu Val Ser Ala Lys Asp Leu
    610                 615                 620

Ala Gly Gln Leu Thr Asp His Asp Trp Ser Leu Phe Asn Ser Ile His
625                 630                 635                 640
```

```
Gln Val Glu Leu Ile His Tyr Val Leu Gly Pro Gln His Leu Arg Asp
                645                 650                 655

Val Thr Thr Ala Asn Leu Glu Arg Phe Met Arg Arg Phe Asn Glu Leu
            660                 665                 670

Gln Tyr Trp Val Ala Thr Glu Leu Cys Leu Cys Pro Val Pro Gly Pro
        675                 680                 685

Arg Ala Gln Leu Leu Arg Lys Phe Ile Lys Leu Ala Ala His Leu Lys
    690                 695                 700

Glu Gln Lys Asn Leu Asn Ser Phe Phe Ala Val Met Phe Gly Leu Ser
705                 710                 715                 720

Asn Ser Ala Ile Ser Arg Leu Ala His Thr Trp Glu Arg Leu Pro His
                725                 730                 735

Lys Val Arg Lys Leu Tyr Ser Ala Leu Glu Arg Leu Leu Asp Pro Ser
            740                 745                 750

Trp Asn His Arg Val Tyr Arg Leu Ala Leu Ala Lys Leu Ser Pro Pro
        755                 760                 765

Val Ile Pro Phe Met Pro Leu Leu Leu Lys Asp Met Thr Phe Ile His
    770                 775                 780

Glu Gly Asn His Thr Leu Val Glu Asn Leu Ile Asn Phe Glu Lys Met
785                 790                 795                 800

Arg Met Met Ala Arg Ala Ala Arg Met Leu His His Cys Arg Ser His
                805                 810                 815

Asn Pro Val Pro Leu Ser Pro Leu Arg Ser Arg Val Ser His Leu His
            820                 825                 830

Glu Asp Ser Gln Val Ala Arg Ile Ser Thr Cys Ser Glu Gln Ser Leu
        835                 840                 845

Ser Thr Arg Ser Pro Ala Ser Thr Trp Ala Tyr Val Gln Gln Leu Lys
    850                 855                 860

Val Ile Asp Asn Gln Arg Glu Leu Ser Arg Leu Ser Arg Glu Leu Glu
865                 870                 875                 880

Pro
```

<210> SEQ ID NO 75
<211> LENGTH: 381
<212> TYPE: PRT
<213> ORGANISM: Homo sapiens

<400> SEQUENCE: 75

```
Met Glu Ser Gly Ser Thr Ala Ala Ser Glu Glu Ala Arg Ser Leu Arg
1               5                   10                  15

Glu Cys Glu Leu Tyr Val Gln Lys His Asn Ile Gln Ala Leu Leu Lys
            20                  25                  30

Asp Ser Ile Val Gln Leu Cys Thr Ala Arg Pro Glu Arg Pro Met Ala
        35                  40                  45

Phe Leu Arg Glu Tyr Phe Glu Arg Leu Glu Lys Glu Glu Ala Lys Gln
    50                  55                  60

Ile Gln Asn Leu Gln Lys Ala Gly Thr Arg Thr Asp Ser Arg Glu Asp
65                  70                  75                  80

Glu Ile Ser Pro Pro Pro Pro Asn Pro Val Val Lys Gly Arg Arg Arg
                85                  90                  95

Arg Gly Ala Ile Ser Ala Glu Val Tyr Thr Glu Glu Asp Ala Ala Ser
            100                 105                 110

Tyr Val Arg Lys Val Ile Pro Lys Asp Tyr Lys Thr Met Ala Ala Leu
        115                 120                 125
```

```
Ala Lys Ala Ile Glu Lys Asn Val Leu Phe Ser His Leu Asp Asp Asn
    130                 135                 140

Glu Arg Ser Asp Ile Phe Asp Ala Met Phe Ser Val Ser Phe Ile Ala
145                 150                 155                 160

Gly Glu Thr Val Ile Gln Gln Gly Asp Glu Gly Asp Asn Phe Tyr Val
                165                 170                 175

Ile Asp Gln Gly Glu Thr Asp Val Tyr Val Asn Asn Glu Trp Ala Thr
            180                 185                 190

Ser Val Gly Glu Gly Gly Ser Phe Gly Glu Leu Ala Leu Ile Tyr Gly
        195                 200                 205

Thr Pro Arg Ala Ala Thr Val Lys Ala Lys Thr Asn Val Lys Leu Trp
    210                 215                 220

Gly Ile Asp Arg Asp Ser Tyr Arg Arg Ile Leu Met Gly Ser Thr Leu
225                 230                 235                 240

Arg Lys Arg Lys Met Tyr Glu Glu Phe Leu Ser Lys Val Ser Ile Leu
                245                 250                 255

Glu Ser Leu Asp Lys Trp Glu Arg Leu Thr Val Ala Asp Ala Leu Glu
            260                 265                 270

Pro Val Gln Phe Glu Asp Gly Gln Lys Ile Val Val Gln Gly Glu Pro
        275                 280                 285

Gly Asp Glu Phe Phe Ile Ile Leu Glu Gly Ser Ala Ala Val Leu Gln
    290                 295                 300

Arg Arg Ser Glu Asn Glu Glu Phe Val Glu Val Gly Arg Leu Gly Pro
305                 310                 315                 320

Ser Asp Tyr Phe Gly Glu Ile Ala Leu Leu Met Asn Arg Pro Arg Ala
                325                 330                 335

Ala Thr Val Val Ala Arg Gly Pro Leu Lys Cys Val Lys Leu Asp Arg
            340                 345                 350

Pro Arg Phe Glu Arg Val Leu Gly Pro Cys Ser Asp Ile Leu Lys Arg
        355                 360                 365

Asn Ile Gln Gln Tyr Asn Ser Phe Val Ser Leu Ser Val
    370                 375                 380


<210> SEQ ID NO 76
<211> LENGTH: 184
<212> TYPE: PRT
<213> ORGANISM: Homo sapiens

<400> SEQUENCE: 76

Met Arg Glu Tyr Lys Leu Val Phe Leu Gly Ser Gly Gly Val Gly Lys
1               5                   10                  15

Ser Ala Leu Thr Val Gln Phe Val Gln Gly Ile Phe Val Glu Lys Tyr
            20                  25                  30

Asp Pro Thr Ile Glu Asp Ser Tyr Arg Lys Gln Val Glu Val Asp Ala
        35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Asp Asp Val Pro Met Ile
            100                 105                 110

Leu Val Gly Asn Lys Cys Asp Leu Glu Asp Glu Arg Val Val Gly Lys
```

-continued

```
        115                 120                 125

Glu Gln Gly Gln Asn Leu Ala Arg Gln Trp Asn Asn Cys Ala Phe Leu
    130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Pro Gly Lys Ala Arg
                165                 170                 175

Lys Lys Ser Ser Cys Gln Leu Leu
            180


<210> SEQ ID NO 77
<211> LENGTH: 239
<212> TYPE: PRT
<213> ORGANISM: Artificial Sequence
<220> FEATURE:
<223> OTHER INFORMATION: Synthetic

<400> SEQUENCE: 77

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```